(12) United States Patent
Cuny et al.

(10) Patent No.: US 11,135,209 B2
(45) Date of Patent: Oct. 5, 2021

(54) COMPOSITIONS AND METHODS FOR INHIBITING PROTEIN KINASES

(71) Applicants: UNIVERSITY OF HOUSTON SYSTEM, Houston, TX (US); TRUSTEES OF TUFTS COLLEGE, Medford, MA (US)

(72) Inventors: Gregory Cuny, Houston, TX (US); Chalada Suebsuwong, Houston, TX (US); Alexei Degterev, Brookline, MA (US)

(73) Assignees: University of Houston System, Houston, TX (US); Trustees of Tufts College, Medford, MA (US)

( * ) Notice: Subject to any disclaimer, the term of this patent is extended or adjusted under 35 U.S.C. 154(b) by 29 days.

(21) Appl. No.: 16/496,503

(22) PCT Filed: Mar. 29, 2018

(86) PCT No.: PCT/US2018/025077
§ 371 (c)(1),
(2) Date: Sep. 23, 2019

(87) PCT Pub. No.: WO2018/183633
PCT Pub. Date: Oct. 4, 2018

(65) Prior Publication Data
US 2020/0030303 A1  Jan. 30, 2020

Related U.S. Application Data

(60) Provisional application No. 62/478,277, filed on Mar. 29, 2017.

(51) Int. Cl.
*C07D 213/00* (2006.01)
*A61K 31/444* (2006.01)

(52) U.S. Cl.
CPC .................... *A61K 31/444* (2013.01)

(58) Field of Classification Search
CPC ........ A61K 31/444; A61K 31/44; A61P 19/00
USPC ............................................. 546/329
See application file for complete search history.

(56) References Cited

FOREIGN PATENT DOCUMENTS

WO   2015/148654   10/2015

OTHER PUBLICATIONS

Notification of Transmittal of the International Search Report and Written Opinion of the International Search Authority—European Patent Office—dated Jun. 8, 2018 for International Application No. PCT/US2018/025077, 13 pages.
Canning, et al., "Chemistry & Biology—Inflammatory Signaling by NOD-RIPK2 is Inhibited by Clinically Relevant Type II Kinase Inhibitors", Chemistry & Biology 22, Sep. 17, 2015, pp. 1174-1184.
Notification of Transmittal of the International Preliminary Report on Patentability dated Oct. 10, 2019 for International Application No. PCT/US2018/025077, 7 pages.

*Primary Examiner* — Taylor V Oh
(74) *Attorney, Agent, or Firm* — Jackson Walker LLP

(57) ABSTRACT

Identified compounds demonstrate protein kinase inhibitory activity and inhibition of dependent cell signaling pathways, such as NOD2 cell signaling. More specifically, the compounds are demonstrated to inhibit receptor interacting kinase 2 (RIPK2) and/or Activin-like kinase 2 (ALK2). Compounds that are either dual RIPK2/ALK2 inhibitors or that preferentially inhibit RIPK2 or ALK2 could provide therapeutic benefit.

8 Claims, 49 Drawing Sheets

FIG. 3

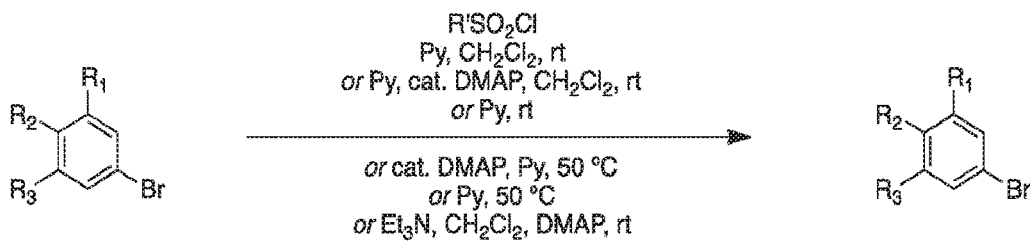

R'SO₂Cl
Py, CH₂Cl₂, rt
or Py, cat. DMAP, CH₂Cl₂, rt
or Py, rt or cat. DMAP, Py, 50 °C
or Py, 50 °C
or Et₃N, CH₂Cl₂, DMAP, rt 3aa : $R_1$ = OCH₂CH₃ ; $R_2$ = H ; $R_3$ = NH₂
3ab : $R_1$ = OCH(CH₃)₂ ; $R_2$ = H ; $R_3$ = NH₂
3b  : $R_1$ = Cl ; $R_2$ = OCH₃ ; $R_3$ = NH₂
3ca : $R_1$ = $R_2$ = OCH₃ ; $R_3$ = NH₂
3cb : $R_1$ = $R_2$ = OCH₂CH₃ ; $R_3$ = NH₂
3cc : $R_1$–$R_2$ = OCH₂CH₂O ; $R_3$ = NH₂
3d  : $R_1$ = OCH₂CH₃ ; $R_2$ = OCH₃ ; $R_3$ = NH₂
3e  : $R_1$ = H ; $R_2$–$R_3$ = OCH₂CH₂NH
3f  : $R_1$ = F ; $R_2$–$R_3$ = OCH₂CH₂NH
3h  : $R_1$ = OCH₃ ; $R_2$ = CH₃ ; $R_3$ = NH₂
3i  : $R_1$ = OCH₂CH₃ ; $R_2$ = CH₃ ; $R_3$ = NH₂
3k  : $R_1$ = OCH₃ ; $R_2$ = NH₂ ; $R_3$ = H
3l  : $R_1$ = OCH₃ ; $R_2$ = H ; $R_3$ = NH₂
3m  : $R_1$ = H ; $R_2$ = OCH₃ ; $R_3$ = NH₂
3n  : $R_1$ = H ; $R_2$ = CH₃ ; $R_3$ = NH₂
3o  : $R_1$ = H ; $R_2$ = OCH₃ ; $R_3$ = CH₂NH₂
3p  : $R_1$ = F ; $R_2$ = OCH₃ ; $R_3$ = NH₂
3q  : $R_1$ = F ; $R_2$ = H ; $R_3$ = NH₂
3r  : $R_1$ = Cl ; $R_2$ = H ; $R_3$ = NH₂
3s  : $R_1$ = Cl ; $R_2$ = CH₃ ; $R_3$ = NH₂
3t  : $R_1$ = F ; $R_2$ = CH₃ ; $R_3$ = NH₂
3u  : $R_1$ = $R_2$ = CH₃ ; $R_3$ = NH₂
3v  : $R_1$ = CH₃ ; $R_2$ = OCH₃ ; $R_3$ = NH₂
3w  : $R_1$ = H ; $R_2$–$R_3$ = CH₂CH₂NH
6aa : $R_1$ = OCH₂CH₃ ; $R_2$ = H ; $R_3$ = NHSO₂CH(CH₃)₂
6ab : $R_1$ = OCH(CH₃)₂ ; $R_2$ = H ; $R_3$ = NHSO₂CH(CH₃)₂
6b  : $R_1$ = Cl ; $R_2$ = OCH₃ ; $R_3$ = NHSO₂CH₂CH₂CH₃
6ca : $R_1$ = $R_2$ = OCH₃ ; $R_3$ = NHSO₂CH₂CH₂CH₃
6cb : $R_1$ = $R_2$ = OCH₂CH₃ ; $R_3$ = NHSO₂CH₂CH₂CH₃
6cc : $R_1$–$R_2$ = OCH₂CH₂O ; $R_3$ = NHSO₂CH₂CH₂CH₃
6d  : $R_1$ = OCH₂CH₃ ; $R_2$ = OCH₃ ; $R_3$ = NHSO₂CH₂CH₂CH₃
6e  : $R_1$ = H ; $R_2$–$R_3$ = OCH₂CH₂NSO₂CH₂CH₂CH₃
6f  : $R_1$ = F ; $R_2$–$R_3$ = OCH₂CH₂NSO₂CH₂CH₂CH₃
6ha : $R_1$ = OCH₃ ; $R_2$ = CH₃ ; $R_3$ = NHSO₂CH₂CH₂CH₃
6hb : $R_1$ = OCH₃ ; $R_2$ = CH₃ ; $R_3$ = NHSO₂CH₃
6hc : $R_1$ = OCH₃ ; $R_2$ = CH₃ ; $R_3$ = NHSO₂CH(CH₃)₂
6hd : $R_1$ = OCH₃ ; $R_2$ = CH₃ ; $R_3$ = NHSO₂Bn
6i  : $R_1$ = OCH₂CH₃ ; $R_2$ = CH₃ ; $R_3$ = NHSO₂Bn
6k  : $R_1$ = OCH₃ ; $R_2$ = NHSO₂CH₂CH₂CH₃ ; $R_3$ = H
6la : $R_1$ = OCH₃ ; $R_2$ = H ; $R_3$ = NHSO₂CH₃
6lb : $R_1$ = OCH₃ ; $R_2$ = H ; $R_3$ = NHSO₂CH₂CH₃
6lc : $R_1$ = OCH₃ ; $R_2$ = H ; $R_3$ = NHSO₂CH₂CH₂CH₃
6ld : $R_1$ = OCH₃ ; $R_2$ = H ; $R_3$ = NHSO₂CH(CH₃)₂
6le : $R_1$ = OCH₃ ; $R_2$ = H ; $R_3$ = NHSO₂CH(CH₃)₂
6lf : $R_1$ = OCH₃ ; $R_2$ = H ; $R_3$ = NHSO₂CH₂CH(CH₃)₂
6lg : $R_1$ = OCH₃ ; $R_2$ = H ; $R_3$ = NHSO₂Ph
6lh : $R_1$ = OCH₃ ; $R_2$ = H ; $R_3$ = NHSO₂Bn
6ma : $R_1$ = H ; $R_2$ = OCH₃ ; $R_3$ = NHSO₂CH₂CH₂CH₃
6mb : $R_1$ = H ; $R_2$ = OCH₃ ; $R_3$ = NHSO₂CH(CH₃)₂
6n  : $R_1$ = H ; $R_2$ = CH₃ ; $R_3$ = NHSO₂CH₂CH₂CH₃
6o  : $R_1$ = H ; $R_2$ = OCH₃ ; $R_3$ = CH₂NHSO₂CH₂CH₂CH₃
6p  : $R_1$ = F ; $R_2$ = OCH₃ ; $R_3$ = NHSO₂CH₂CH₂CH₃
6q  : $R_1$ = F ; $R_2$ = H ; $R_3$ = NHSO₂CH₂CH₂CH₃
6r  : $R_1$ = Cl ; $R_2$ = H ; $R_3$ = NHSO₂CH₂CH₂CH₃
6s  : $R_1$ = Cl ; $R_2$ = CH₃ ; $R_3$ = NHSO₂CH₂CH₂CH₃
6t  : $R_1$ = F ; $R_2$ = CH₃ ; $R_3$ = NHSO₂CH₂CH₂CH₃
6u  : $R_1$ = $R_2$ = CH₃ ; $R_3$ = NHSO₂CH₂CH₂CH₃
6v  : $R_1$ = CH₃ ; $R_2$ = OCH₃ ; $R_3$ = NHSO₂CH₂CH₂CH₃
6w  : $R_1$ = H ; $R_2$–$R_3$ = CH₂CH₂NSO₂CH₂CH₂CH₃

FIG. 5

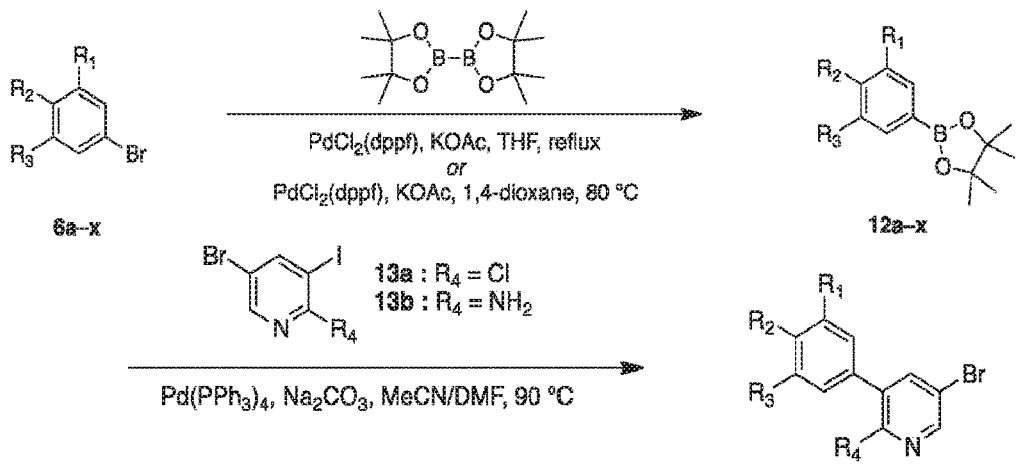

- 14aa : $R_1 = OCH_2CH_3$ ; $R_2 = H$ ; $R_3 = NHSO_2CH(CH_3)_2$ ; $R_4 = NH_2$
- 14ab : $R_1 = OCH(CH_3)_2$ ; $R_2 = H$ ; $R_3 = NHSO_2CH(CH_3)_2$ ; $R_4 = NH_2$
- 14b : $R_1 = Cl$ ; $R_2 = OCH_3$ ; $R_3 = NHSO_2CH_2CH_2CH_3$ ; $R_4 = NH_2$
- 14ca : $R_1 = R_2 = OCH_3$ ; $R_3 = NHSO_2CH_2CH_2CH_3$ ; $R_4 = NH_2$
- 14cb : $R_1 = R_2 = OCH_2CH_3$ ; $R_3 = NHSO_2CH_2CH_2CH_3$ ; $R_4 = NH_2$
- 14cc : $R_1-R_2 = OCH_2CH_2O$ ; $R_3 = NHSO_2CH_2CH_2CH_3$ ; $R_4 = NH_2$
- 14d : $R_1 = OCH_2CH_3$ ; $R_2 = OCH_3$ ; $R_3 = NHSO_2CH_2CH_2CH_3$ ; $R_4 = NH_2$
- 14e : $R_1 = H$ ; $R_2-R_3 = OCH_2CH_2NSO_2CH_2CH_2CH_3$ ; $R_4 = NH_2$
- 14f : $R_1 = F$ ; $R_2-R_3 = OCH_2CH_2NSO_2CH_2CH_2CH_3$ ; $R_4 = NH_2$
- 14ha : $R_1 = OCH_3$ ; $R_2 = CH_3$ ; $R_3 = NHSO_2CH_2CH_2CH_3$ ; $R_4 = NH_2$
- 14hb : $R_1 = OCH_3$ ; $R_2 = CH_3$ ; $R_3 = NHSO_2CH_3$ ; $R_4 = NH_2$
- 14hc : $R_1 = OCH_3$ ; $R_2 = CH_3$ ; $R_3 = NHSO_2CH(CH_3)_2$ ; $R_4 = NH_2$
- 14hd : $R_1 = OCH_3$ ; $R_2 = CH_3$ ; $R_3 = NHSO_2Bn$ ; $R_4 = NH_2$
- 14he : $R_1 = OCH_3$ ; $R_2 = CH_3$ ; $R_3 = NHSO_2Ph$ ; $R_4 = NH_2$
- 14i : $R_1 = OCH_2CH_3$ ; $R_2 = CH_3$ ; $R_3 = NHSO_2Bn$ ; $R_4 = NH_2$
- 14k : $R_1 = OCH_3$ ; $R_2 = NHSO_2CH_2CH_2CH_3$ ; $R_3 = H$ ; $R_4 = Cl$
- 14laa : $R_1 = OCH_3$ ; $R_2 = H$ ; $R_3 = NHSO_2CH_3$ ; $R_4 = Cl$
- 14lab : $R_1 = OCH_3$ ; $R_2 = H$ ; $R_3 = NHSO_2CH_3$ ; $R_4 = NH_2$
- 14lba : $R_1 = OCH_3$ ; $R_2 = H$ ; $R_3 = NHSO_2CH_2CH_3$ ; $R_4 = Cl$
- 14lbb : $R_1 = OCH_3$ ; $R_2 = H$ ; $R_3 = NHSO_2CH_2CH_3$ ; $R_4 = NH_2$
- 14lca : $R_1 = OCH_3$ ; $R_2 = H$ ; $R_3 = NHSO_2CH_2CH_2CH_3$ ; $R_4 = Cl$
- 14lcb : $R_1 = OCH_3$ ; $R_2 = H$ ; $R_3 = NHSO_2CH_2CH_2CH_3$ ; $R_4 = NH_2$
- 14lda : $R_1 = OCH_3$ ; $R_2 = H$ ; $R_3 = NHSO_2CH(CH_3)_2$ ; $R_4 = Cl$
- 14ldb : $R_1 = OCH_3$ ; $R_2 = H$ ; $R_3 = NHSO_2CH(CH_3)_2$ ; $R_4 = NH_2$
- 14lea : $R_1 = OCH_3$ ; $R_2 = H$ ; $R_3 = NHSO_2CH(CH_2)_2$ ; $R_4 = Cl$
- 14leb : $R_1 = OCH_3$ ; $R_2 = H$ ; $R_3 = NHSO_2CH(CH_2)_2$ ; $R_4 = NH_2$
- 14lfa : $R_1 = OCH_3$ ; $R_2 = H$ ; $R_3 = NHSO_2CH_2CH(CH_3)_2$ ; $R_4 = Cl$
- 14lfb : $R_1 = OCH_3$ ; $R_2 = H$ ; $R_3 = NHSO_2CH_2CH(CH_3)_2$ ; $R_4 = NH_2$
- 14lg : $R_1 = OCH_3$ ; $R_2 = H$ ; $R_3 = NHSO_2Ph$ ; $R_4 = NH_2$
- 14lh : $R_1 = OCH_3$ ; $R_2 = H$ ; $R_3 = NHSO_2Bn$ ; $R_4 = NH_2$
- 14ma : $R_1 = H$ ; $R_2 = OCH_3$ ; $R_3 = NHSO_2CH_2CH_2CH_3$ ; $R_4 = NH_2$
- 14mb : $R_1 = H$ ; $R_2 = OCH_3$ ; $R_3 = NHSO_2CH(CH_3)_2$ ; $R_4 = NH_2$
- 14mc : $R_1 = H$ ; $R_2 = OCH_3$ ; $R_3 = NHSO_2CF_3$ ; $R_4 = NH_2$
- 14n : $R_1 = H$ ; $R_2 = CH_3$ ; $R_3 = NHSO_2CH_2CH_2CH_3$ ; $R_4 = NH_2$
- 14o : $R_1 = H$ ; $R_2 = OCH_3$ ; $R_3 = CH_2NHSO_2CH_2CH_2CH_3$ ; $R_4 = NH_2$
- 14pa : $R_1 = F$ ; $R_2 = OCH_3$ ; $R_3 = NHSO_2CH_2CH_2CH_3$ ; $R_4 = Cl$
- 14pb : $R_1 = F$ ; $R_2 = OCH_3$ ; $R_3 = NHSO_2CH_2CH_2CH_3$ ; $R_4 = NH_2$
- 14q : $R_1 = F$ ; $R_2 = H$ ; $R_3 = NHSO_2CH_2CH_2CH_3$ ; $R_4 = NH_2$
- 14r : $R_1 = Cl$ ; $R_2 = H$ ; $R_3 = NHSO_2CH_2CH_2CH_3$ ; $R_4 = NH_2$
- 14s : $R_1 = Cl$ ; $R_2 = CH_3$ ; $R_3 = NHSO_2CH_2CH_2CH_3$ ; $R_4 = NH_2$
- 14t : $R_1 = F$ ; $R_2 = CH_3$ ; $R_3 = NHSO_2CH_2CH_2CH_3$ ; $R_4 = NH_2$
- 14u : $R_1 = CH_3$ ; $R_2 = OCH_3$ ; $R_3 = NHSO_2CH_2CH_2CH_3$ ; $R_4 = NH_2$
- 14v : $R_1 = R_2 = CH_3$ ; $R_3 = NHSO_2CH_2CH_2CH_3$ ; $R_4 = NH_2$
- 14w : $R_1 = H$ ; $R_2-R_3 = CH_2CH_2NSO_2CH_2CH_2CH_3$ ; $R_4 = NH_2$
- 14x : $R_1 = H$ ; $R_2 = OH$ ; $R_3 = NHSO_2CH_2CH_2CH_3$ ; $R_4 = NH_2$

COMPOSITIONS AND METHODS FOR INHIBITING PROTEIN KINASES

This application claims priority to U.S. Provisional Patent Application No. 62/478,277, filed Mar. 29, 2017, entitled "Compositions and Methods for Inhibiting Protein Kinases," the entire contents of which are hereby incorporated by reference.

This invention was made with U.S. government support under grant CA190542 awarded by the National Institutes of Health. The U.S. government has certain rights in the invention.

BACKGROUND

This disclosure pertains to compounds that demonstrate protein kinase inhibitory activity.

Protein kinases are important enzymes in cellular signal transduction. In many pathological conditions aberrant signal transduction occurs. Therefore, protein kinase inhibitors can be used as therapeutic agents for the treatment of various diseases.

SUMMARY

The present disclosure relates generally to compounds that demonstrate protein kinase inhibitory activity and inhibition of dependent cell signaling pathways, such as NOD2 cell signaling. More specifically, the compounds can inhibit receptor interacting kinase 2 (RIPK2) and/or Activin-like kinase 2 (ALK2). RIPK2 mediates pro-inflammatory signaling and is an emerging therapeutic target in autoimmune and inflammatory diseases, such as inflammatory bowel disease (IBD) and multiple sclerosis. RIPK2 inhibitors could provide therapeutic benefit in the treatment of these and other conditions. Activin-like kinase 2 (ALK2) has been implicated in a number of diseases, such as bone disease (e.g. fibrodysplasia ossificans progressiva, ankylosing spondylitis), cardiovascular diseases (e.g. atherosclerosis and vascular calcification), some cancers (e.g. diffuse intrinsic pontine gliomas) and burns. Many of these maladies also have an inflammatory component that could exacerbate the condition and/or worsen the clinical outcome. Compounds that are either dual RIPK2/ALK2 inhibitors or that preferentially inhibit RIPK2 or ALK2 could provide therapeutic benefit in the treatment of these and other conditions.

BRIEF DESCRIPTION OF THE DRAWINGS

FIG. 3 shows a scheme for the synthesis of exemplary intermediate compounds.

FIG. 5 shows a scheme for the synthesis of exemplary intermediate compounds.

DETAILED DESCRIPTION OF PREFERRED EMBODIMENTS

The present disclosure relates to protein kinase inhibitors and uses thereof.

The following figure depicts a general structure of preferred embodiments of compounds that inhibit protein kinases, including RIPK2 and/or ALK2.

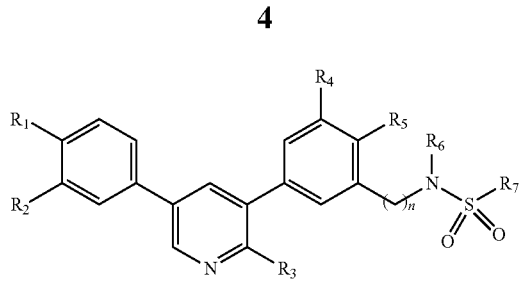

In the above structure, $R_1$ can generally be H or any amine that imparts aqueous solubility. Preferably, when it is not H, $R_1$ should be attached to the benzene ring through N, O, or C. $R_2$ can generally be H or it can be a sulfone group that may (without being bound by theory) have an impact on RIPK2 selectivity. $R_1$ and $R_2$ can be located at any suitable positions on the benzene ring and are not limited to the positions shown in the figure above. $R_3$ can be H, Cl, Me, $NH_2$, $NHCH_3$, $N(CH_3)_2$, or other suitable groups. $R_4$ and $R_5$ can generally be any of a wide variety of suitable electron donating and electron withdrawing groups. $R_6$ can be H, methyl, or ethyl. $R_7$ can broadly be any of a number of suitable alkyl, aryl, aralkyl, and similar groups. In the figure, n is 0 or 1.

Additional preferred embodiments of compounds that inhibit protein kinases, including RIPK2 and/or ALK2, are depicted below.

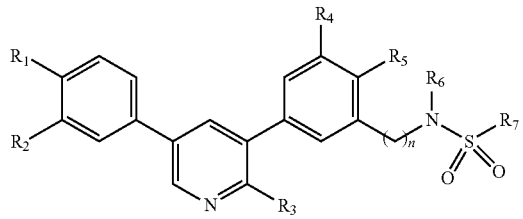

wherein $R_1$ is H,

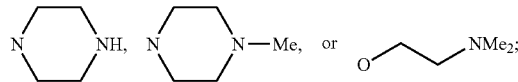

$R_2$ is H, $SO_2Me$, $SO_2i$-Pr, $SO_2CF_3$, or

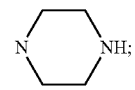

$R_3$ is H, Cl, Me, $NH_2$, NHMe, or $NMe_2$;
$R_4$ is H, F, Cl, OMe, OEt, O-n-Pr, O-i-Pr, OPh, or $OCF_3$;
$R_5$ is H, Me, Et, Pr, i-Pr, OMe, OEt, O-n-Pr, O-i-Pr, $OCF_3$, Cl, or F;
$R_6$ is H, Me, or Et;
$R_7$ is Me, Et, n-Pr, i-Pr, $CF_3$, $CF_2Et$, $CH_2Ph$, or Ph; and n is 0 or 1.

In the present disclosure, "Me" may refer to methyl, "Et" may refer to ethyl, "Pr" may refer to propyl, "n-Pr" or "nPr" may refer to linear propyl, "i-Pr" may refer to isopropyl, "Ph" may refer to phenyl, and OMe, OEt, O-n-Pr, O-i-Pr, OPh, and $OCF_3$ refer to ethers. In further preferred embodiments, $R_5$ is Me or other alkyls and/or $R_7$ is benzyl or other aralkyls. These preferred embodiments have demonstrated particular inhibitory activity against RIPK2 and ALK2, respectively.

Figure 1:
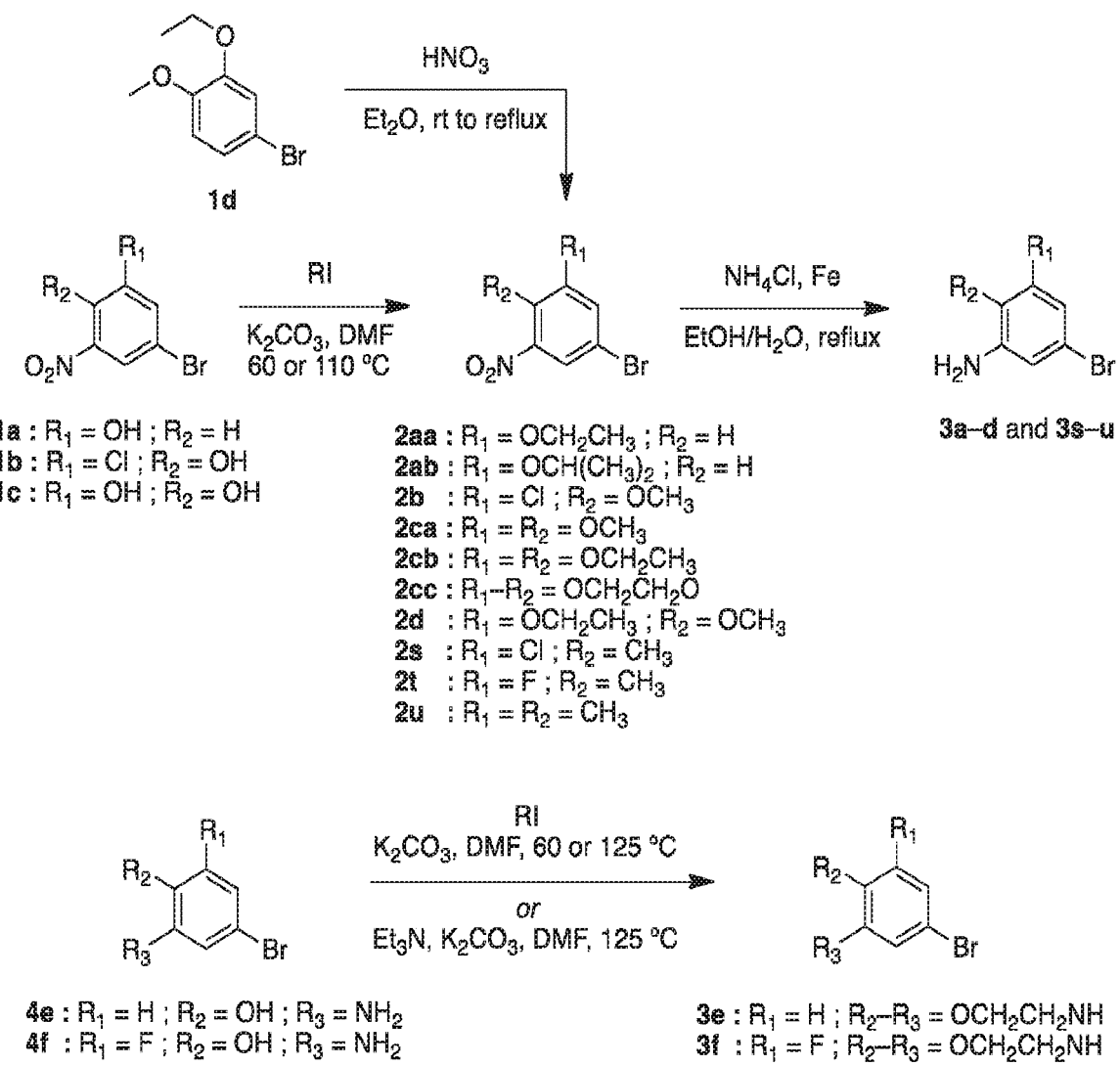
FIG. 1 shows a scheme for the synthesis of exemplary intermediate compounds.
Figure 2:
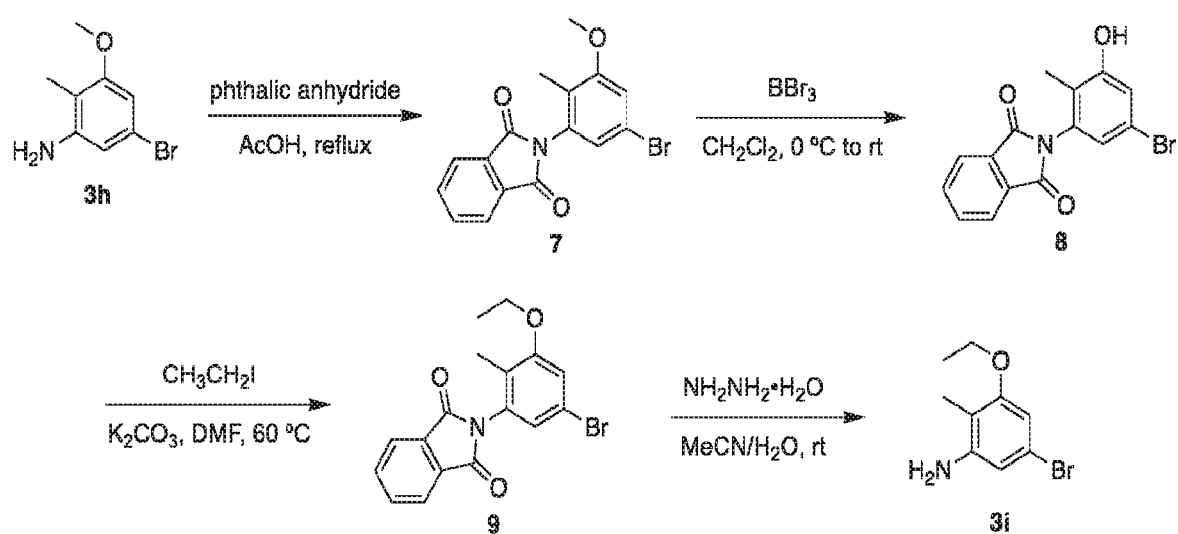
FIG. 2 shows a scheme for the synthesis of exemplary intermediate compounds.
Figure 4:
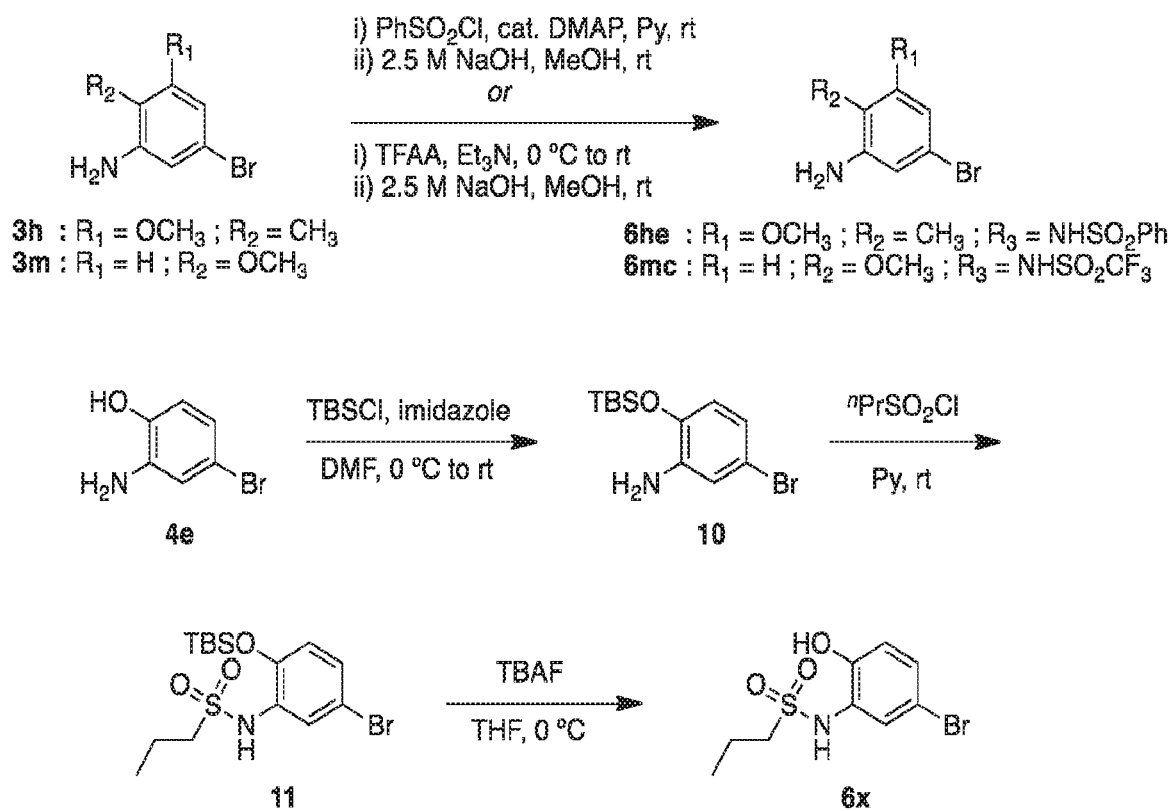
FIG. 4 shows a scheme for the synthesis of exemplary intermediate compounds.
Figure 6:
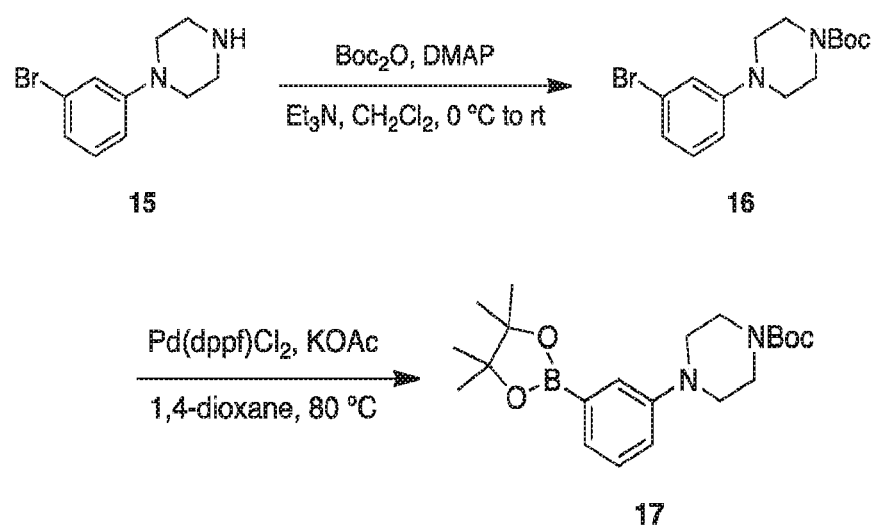
FIG. 6 shows a scheme for the synthesis of exemplary intermediate compounds.
Figure 7:
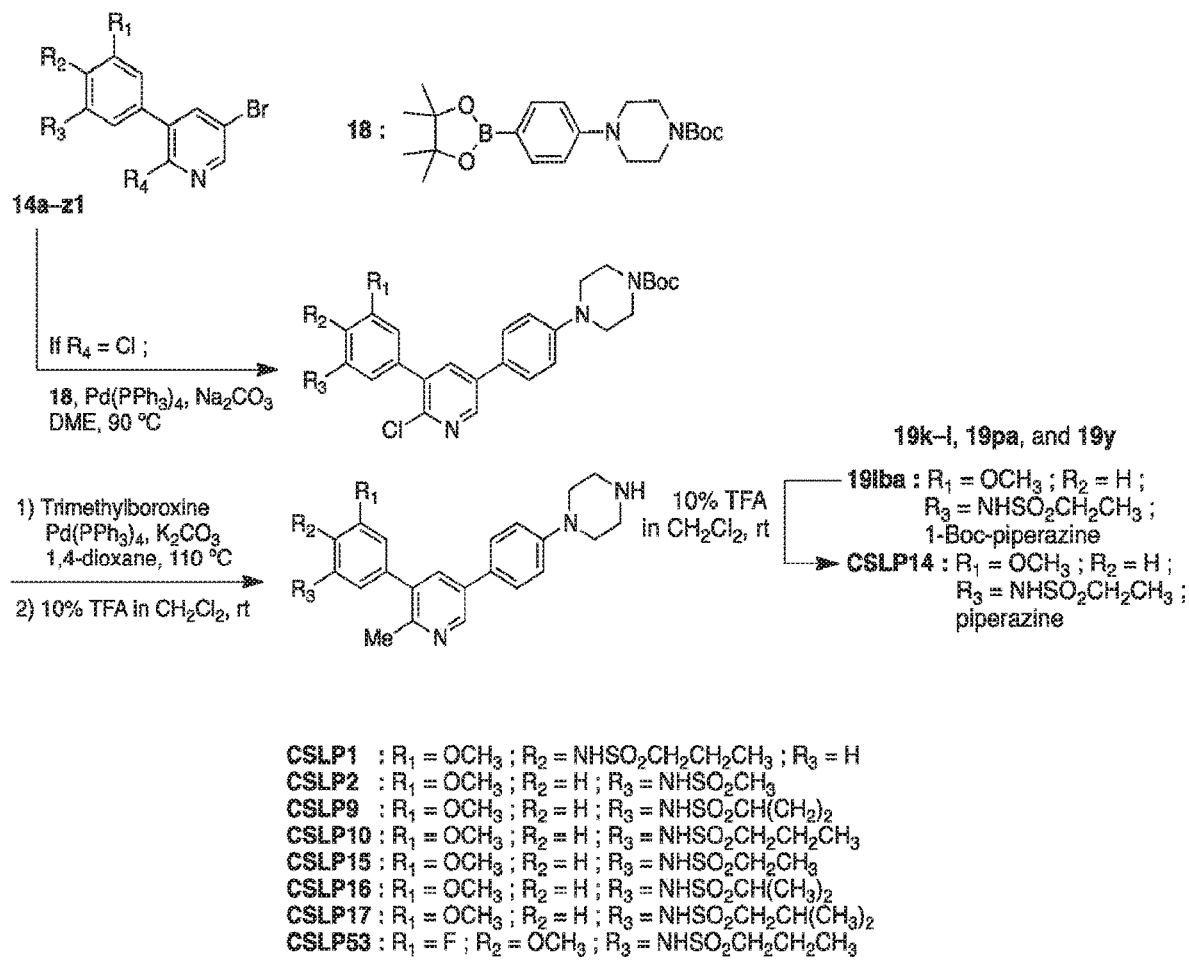
FIG. 7 shows a scheme for the synthesis of exemplary representative compounds in accordance with preferred embodiments disclosed herein.
Figure 8:
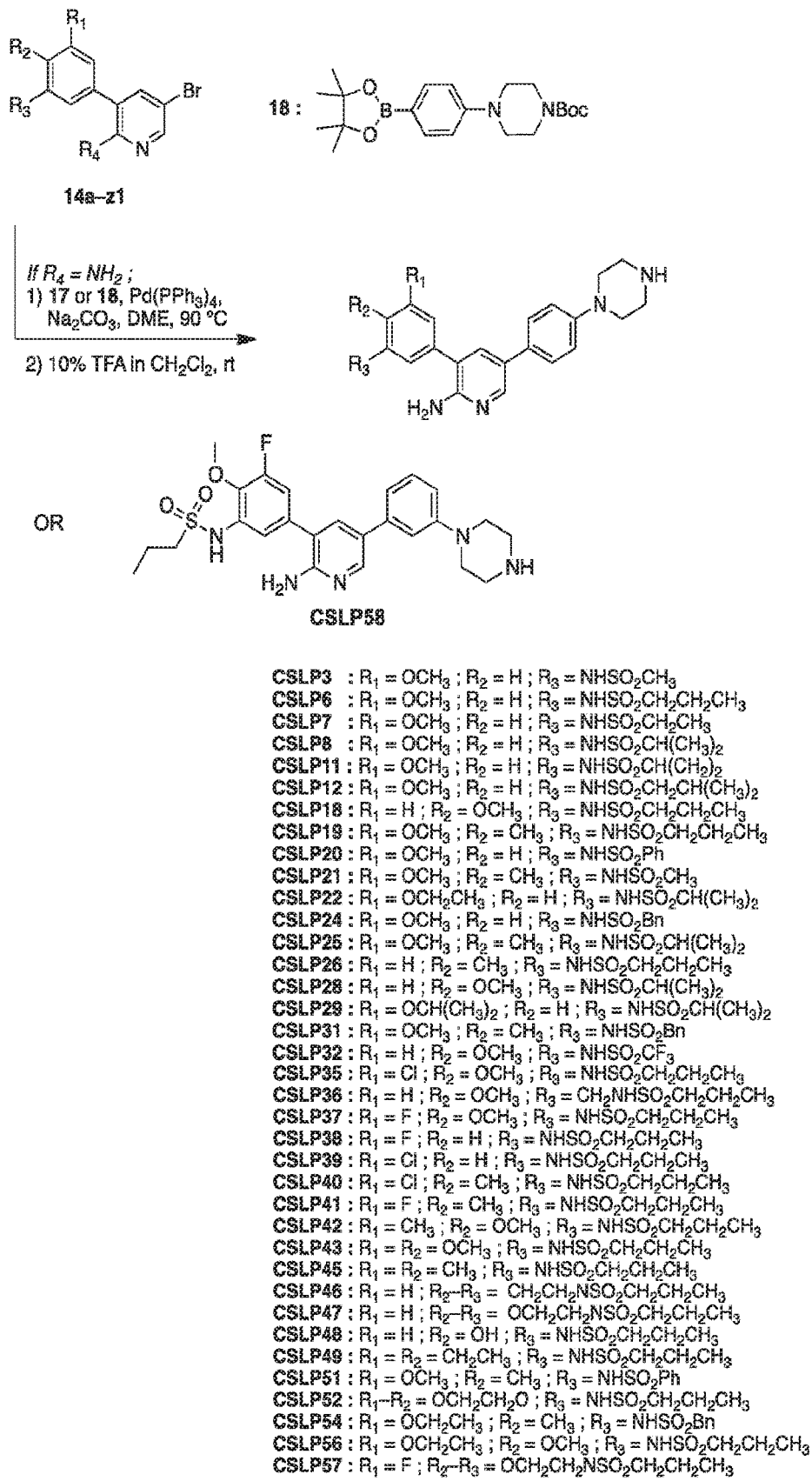
FIG. 8 shows a scheme for the synthesis of exemplary representative compounds in accordance with preferred embodiments disclosed herein.
Figure 9:
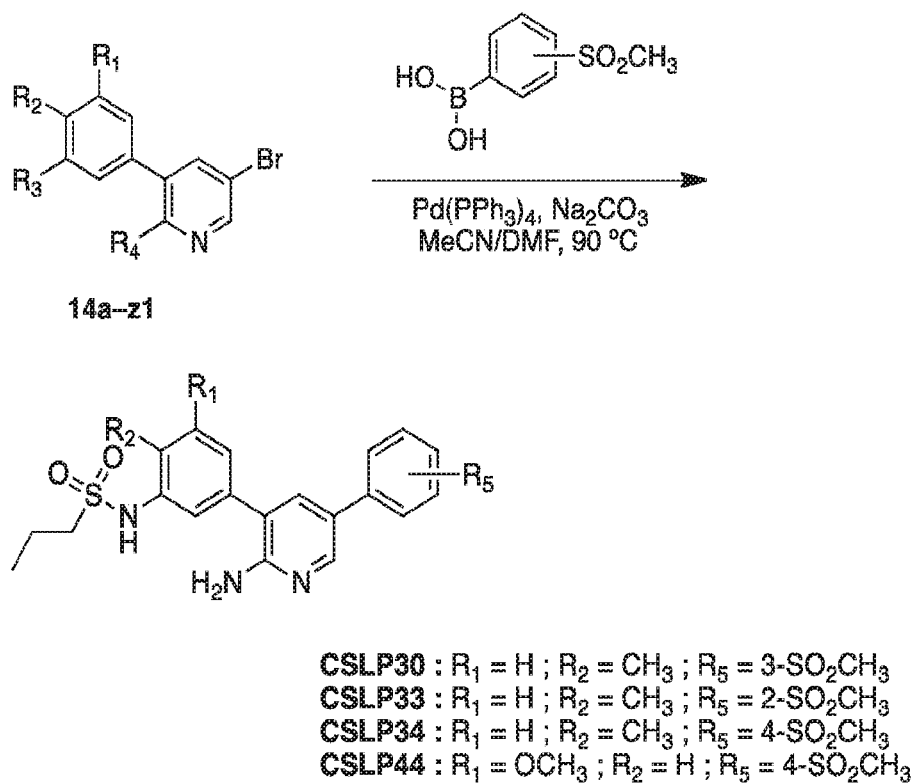
FIG. 9 shows a scheme for the synthesis of exemplary representative compounds in accordance with preferred embodiments disclosed herein.

FIGS. 1-9 illustrate a general scheme for synthesis of representative compounds of the present disclosure. FIGS. 1-6 illustrate general schemes for step-wise synthesis of intermediate compounds, while FIGS. 7-9 illustrate general schemes for the steps in synthesis of representative compounds of the present disclosure. FIGS. 10-49 depict steps in the synthesis of either intermediate compounds or representative compounds of the present disclosure. Additional preferred embodiments of compounds that inhibit protein kinases, including RIPK2 and/or ALK2, and that demonstrate NOD2 cellular signaling inhibitory activity, include those depicted in FIGS. 7-9 and in FIGS. 39-49. In further preferred embodiments, the compounds that demonstrate protein kinase inhibitory activity or NOD2 cellular signaling inhibitory activity include CSLP37, CSLP43, or CSLP58.

The exemplary compounds that inhibit protein kinases described herein may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

The current invention also pertains to methods of prevention or therapy for diseases involving protein kinase activity, including the step of administering a compound that inhibits protein kinase activity in accordance with preferred embodiments disclosed herein.

In another aspect of the present invention there is provided a pharmaceutical composition including a therapeutically effective amount of a compound that inhibits protein kinase as defined above and a pharmaceutically acceptable excipient, adjuvant, carrier, buffer or stabiliser. A "therapeutically effective amount" is to be understood as an amount of an exemplary protein kinase inhibitor compound that is sufficient to show inhibitory effects on protein kinase activity. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilisers, buffers, antioxidants and/or other additives may be included as required.

In another aspect, there is provided the use in the manufacture of a medicament of a therapeutically effective amount of protein kinase inhibitor compound as defined above for administration to a subject.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Further aspects of the present invention will become apparent from the following description given by way of example only and with reference to the accompanying synthetic schemes.

EXAMPLE 1

Synthesis

All reactions involving air-sensitive reagents were carried out with magnetic stirring and in oven-dried glassware with rubber septa under argon unless otherwise stated. All commercially available chemicals and reagent grade solvents were used directly without further purification unless otherwise specified. Reactions were monitored by thin-layer chromatography (TLC) on Baker-flex® silica gel plates (IB2-F) using UV-light (254 and 365 nm) detection or visualizing agents (ninhydrin or phosphomolybdic acid stain). Flash chromatography was conducted on silica gel (230-400 mesh) using Teledyne Isco CombiFlash® Rf. NMR spectra were recorded at room temperature using a JEOL ECA ($^1$H NMR at 400, 500 or 600 MHz and $^{13}$C NMR at 100, 125 or 150 MHz) with tetramethylsilane (TMS) as an internal standard. Chemical shifts (δ) are given in parts per million (ppm) with reference to solvent signals [$^1$H-NMR: CDCl$_3$ (7.26 ppm), CD$_3$OD (3.30 ppm), DMSO-d$_6$ (2.49 ppm); $^{13}$C-NMR: CDCl$_3$ (77.0 ppm), CD$_3$OD (49.0 ppm), DMSO-d$_6$ (39.5 ppm)]. Signal patterns are reported as s (singlet), d (doublet), t (triplet), q (quartet), quin (quintet), sex (sextet), sep (septet), m (multiplet), br (broad), dd (doublet of doublets), dt (doublet of triplets), td (triplet of doublets) and tt (triplet of triplets). Coupling constants (J) are given in Hz. The C—F coupling patterns labeled in $^{13}$C-NMR indicate visible patterns in spectra. High resolution mass spectral (HRMS) were carried out using AccuTOF by the Department of Chemistry, The University of Texas at Austin. The spectra were measured using TOF-MS with an ESI ionization source and reported as m/z (relative intensity) for the molecular ion [M]. All test compounds reported had a purity ≥95% as determined by high-performance liquid chromatography (HPLC) analyses using a Waters 1525 instrument equipped with a quaternary pump and a Proteo-C12 column (250 mm×1 mm, 4 μm). UV absorption was monitored at λ=220 nm. HPLC gradient went from 0% (method A) or 2% (method B) MeCN in $H_2O$ to 90% MeCN in $H_2O$ (both solvents contain 0.1% trifluoroacetic acid) with a total run time of 30 min and a flow rate of 0.5 mL/min.

Figure 10:
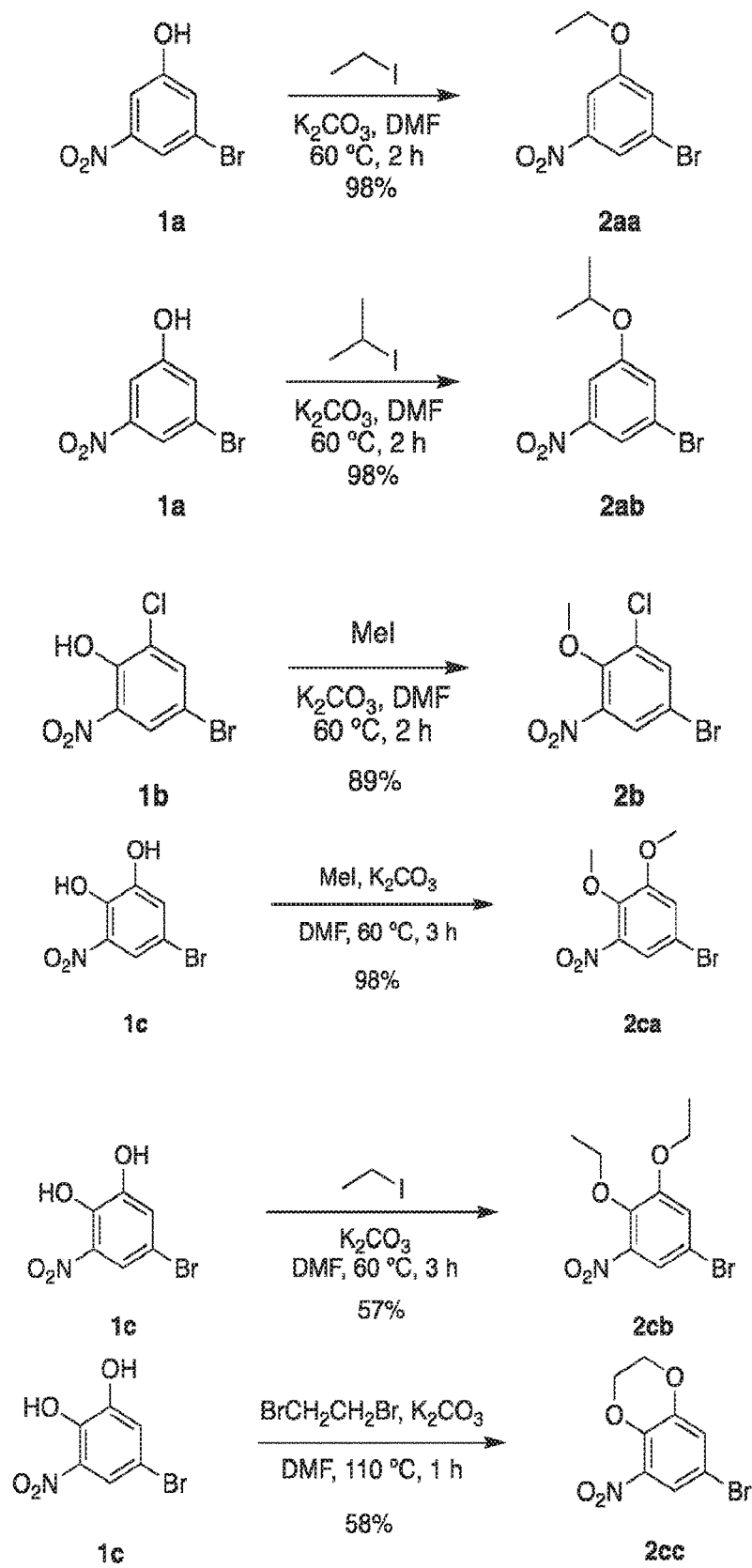
FIG. 10 shows steps in the synthesis of specific exemplary intermediate compounds described in Example 1 in accordance with preferred embodiments disclosed herein.
Figure 11:
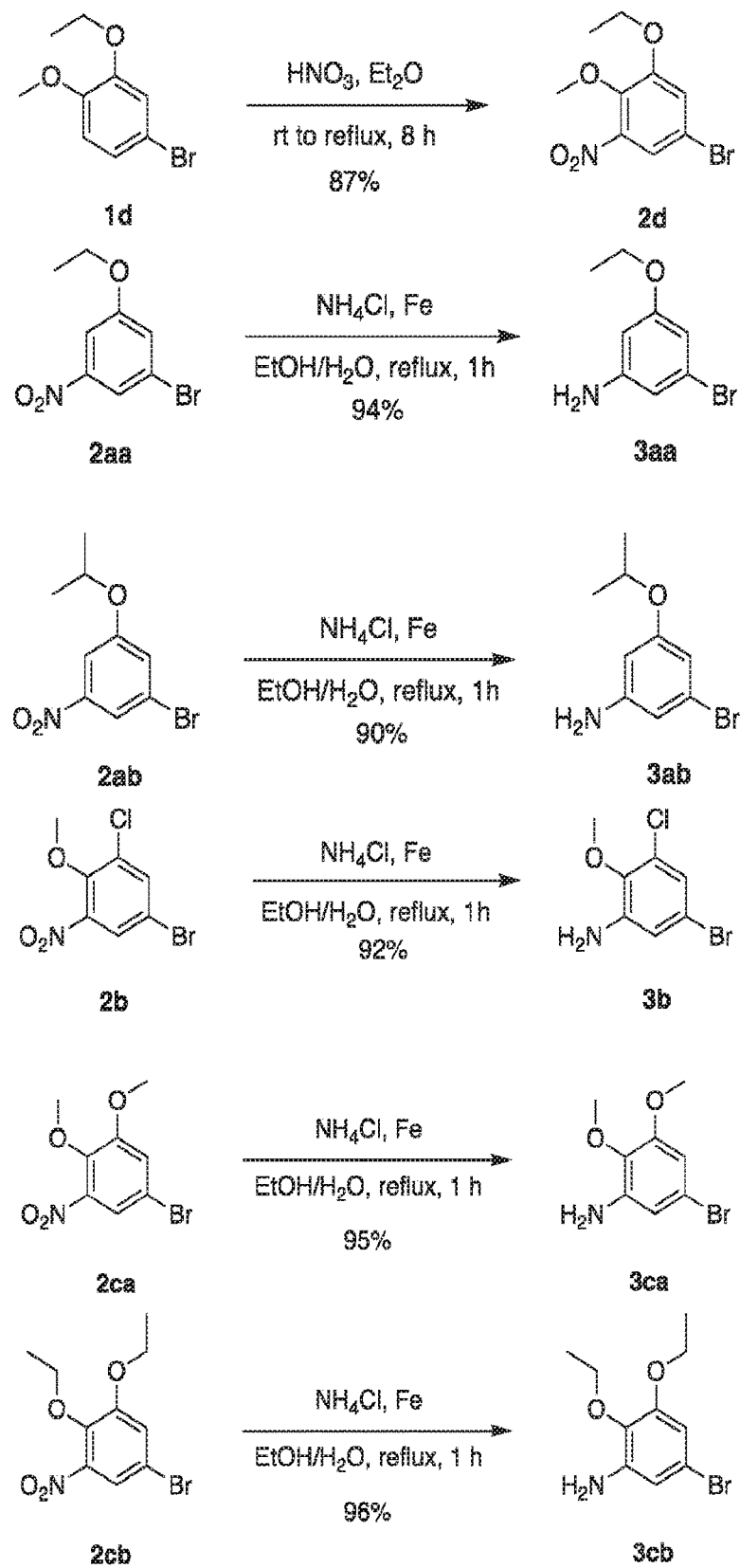
FIG. 11 shows steps in the synthesis of specific exemplary intermediate compounds described in Example 1 in accordance with preferred embodiments disclosed herein.
Figure 12:
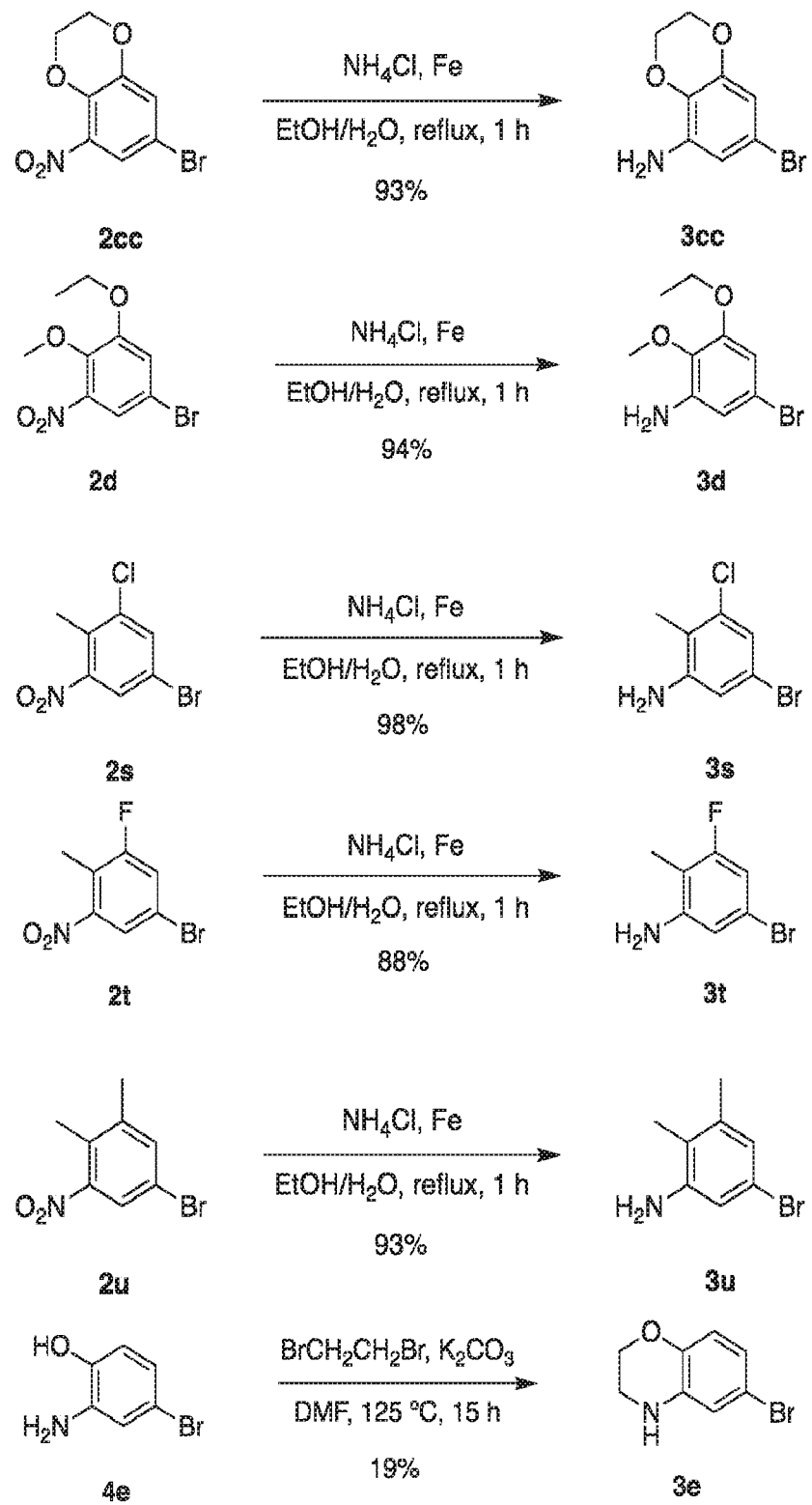
FIG. 12 shows steps in the synthesis of specific exemplary intermediate compounds described in Example 1 in accordance with preferred embodiments disclosed herein.
Figure 13:
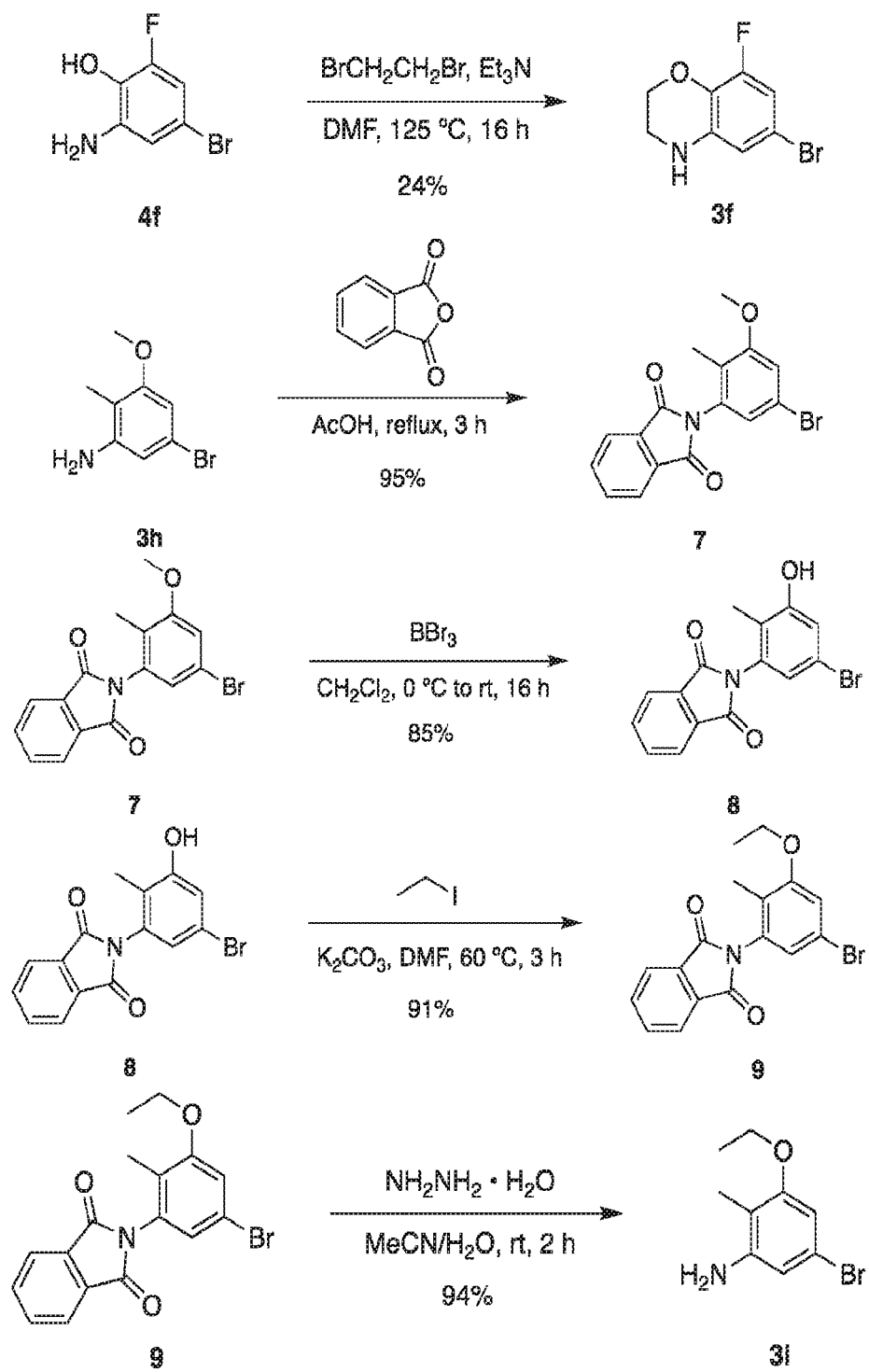
FIG. 13 shows steps in the synthesis of specific exemplary intermediate compounds described in Example 1 in accordance with preferred embodiments disclosed herein.
Figure 14:
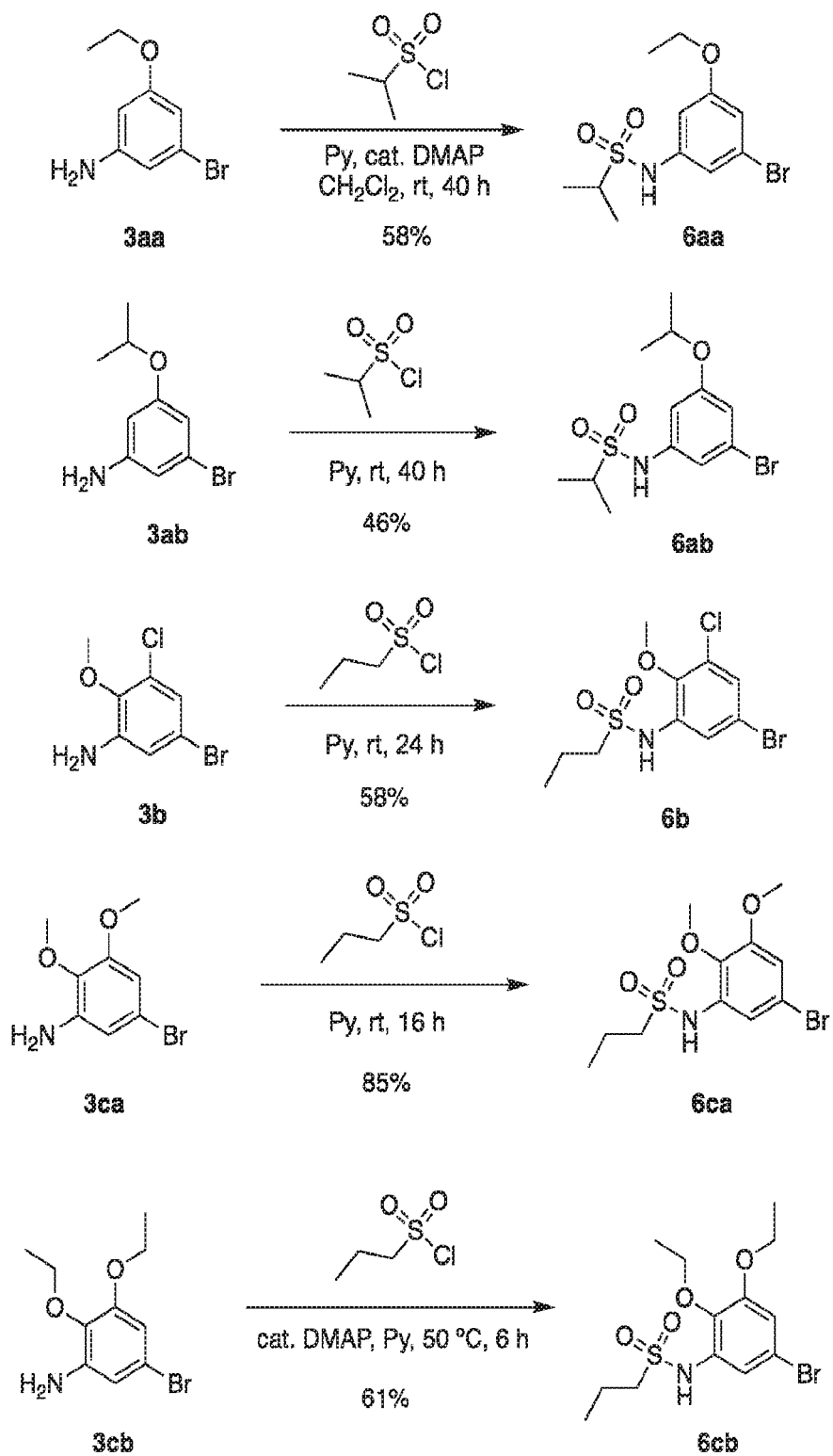
FIG. 14 shows steps in the synthesis of specific exemplary intermediate compounds described in Example 1 in accordance with preferred embodiments disclosed herein.
Figure 15:
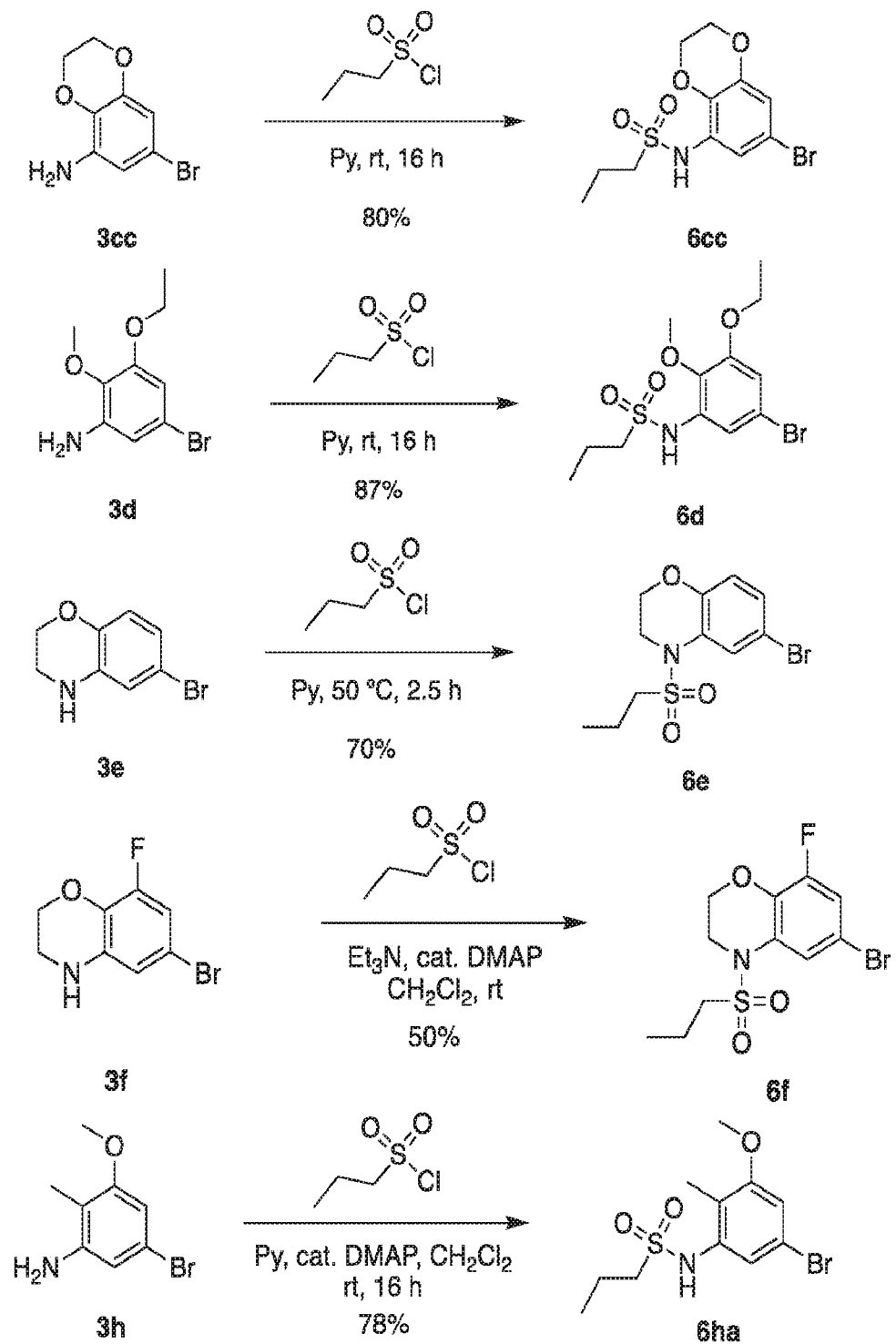
FIG. 15 shows steps in the synthesis of specific exemplary intermediate compounds described in Example 1 in accordance with preferred embodiments disclosed herein.
Figure 16:
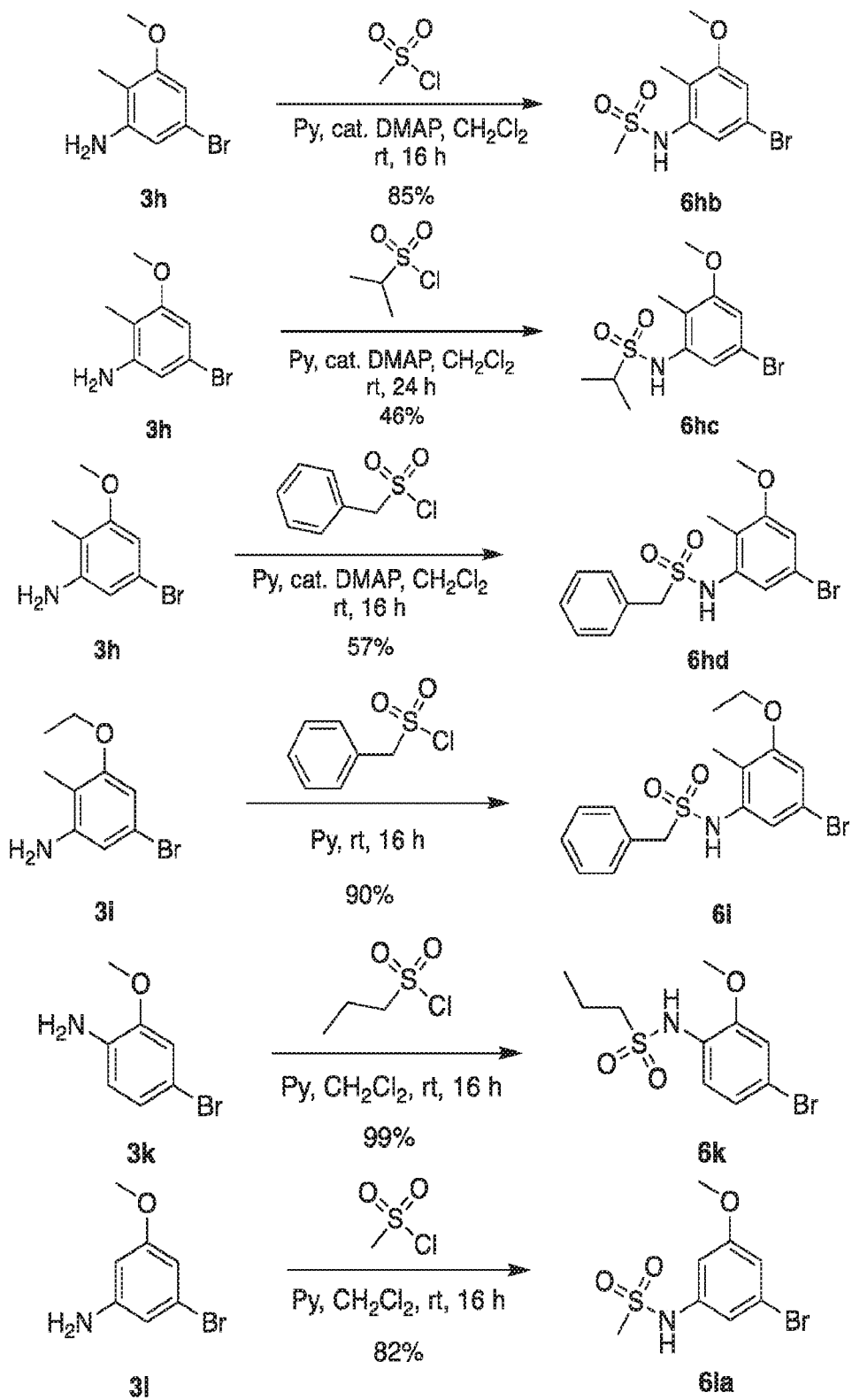
FIG. 16 shows steps in the synthesis of specific exemplary intermediate compounds described in Example 1 in accordance with preferred embodiments disclosed herein.
Figure 17:
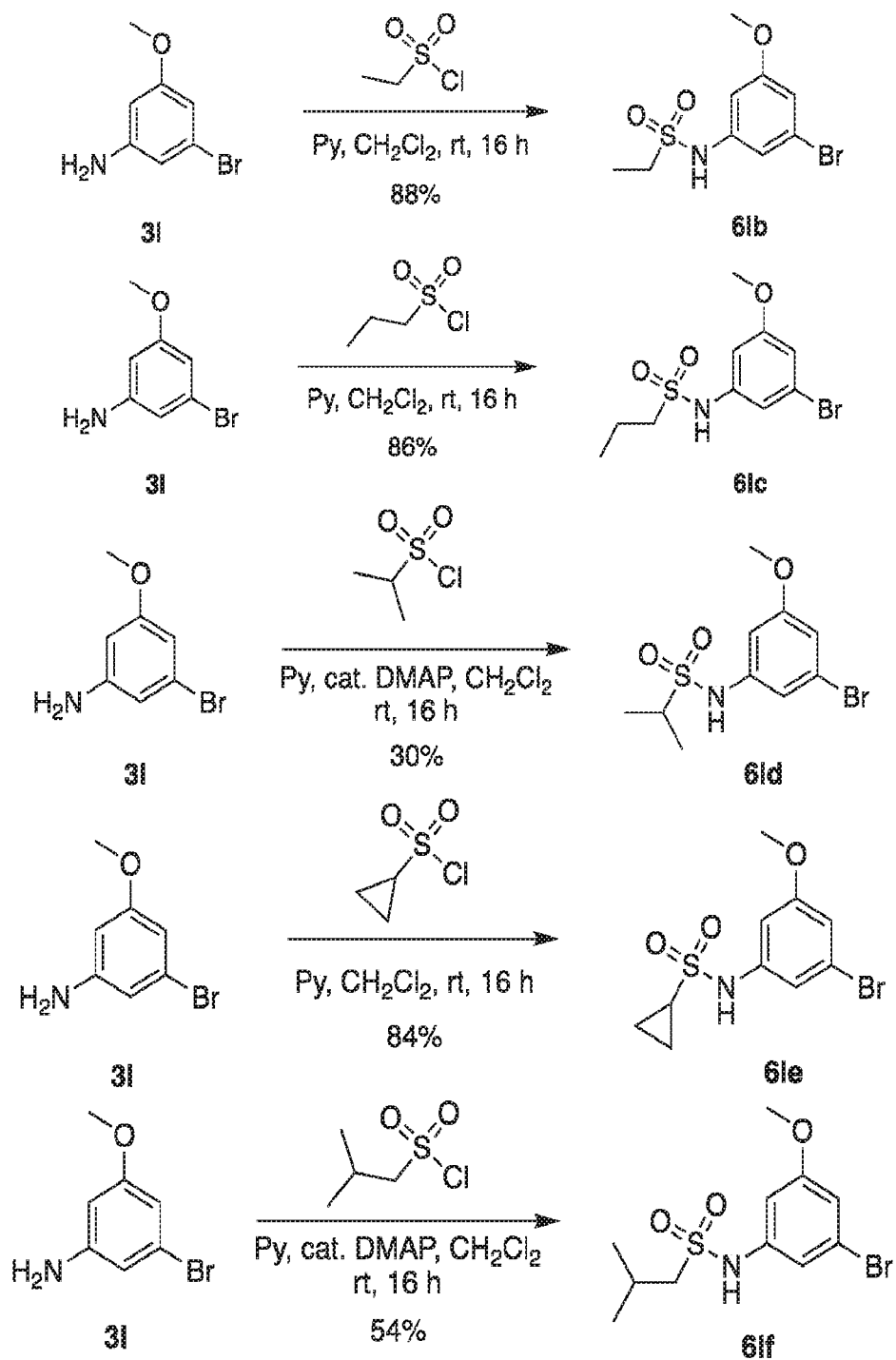
FIG. 17 shows steps in the synthesis of specific exemplary intermediate compounds described in Example 1 in accordance with preferred embodiments disclosed herein.
Figure 18:
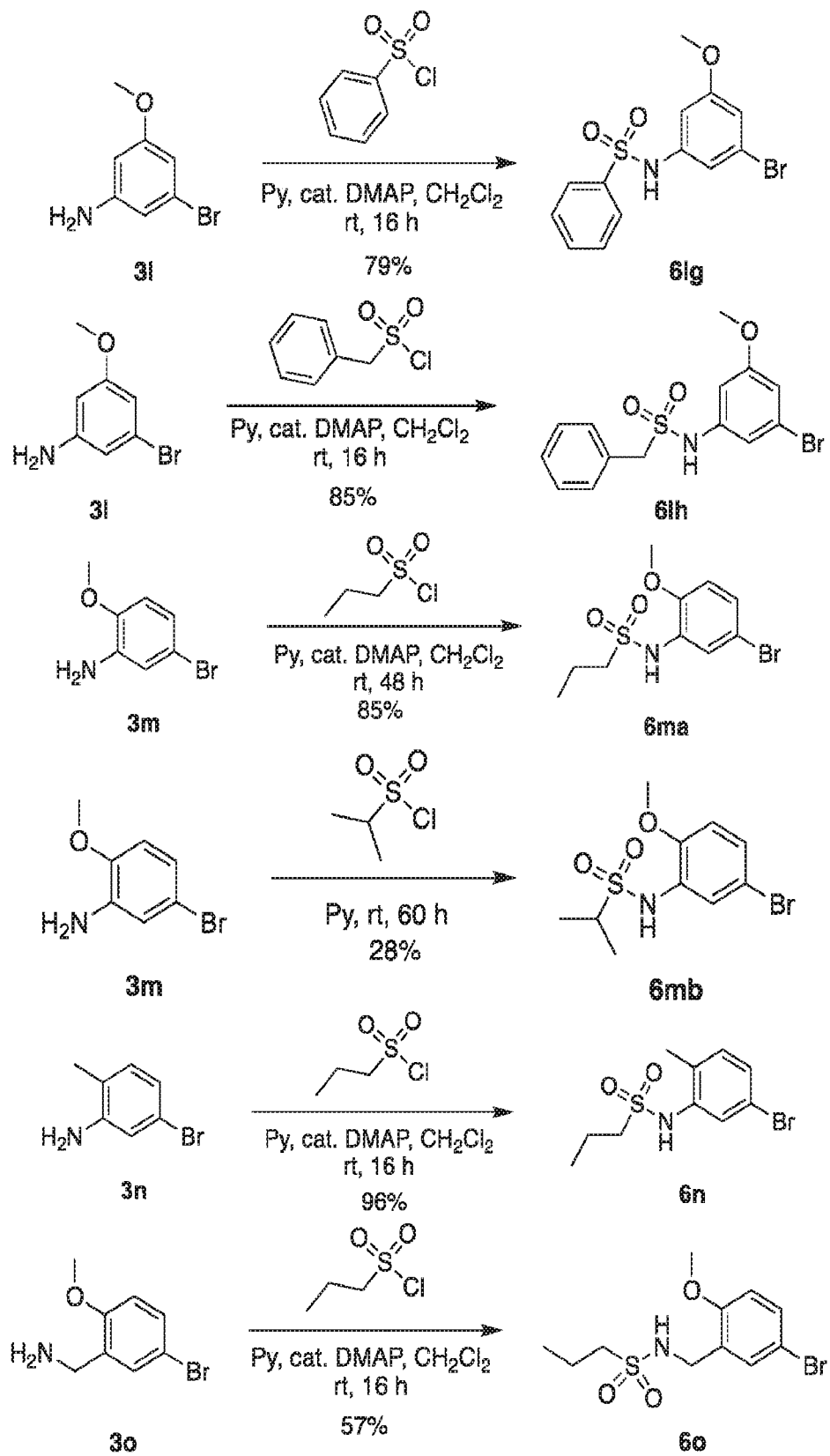
FIG. 18 shows steps in the synthesis of specific exemplary intermediate compounds described in Example 1 in accordance with preferred embodiments disclosed herein.
Figure 19:
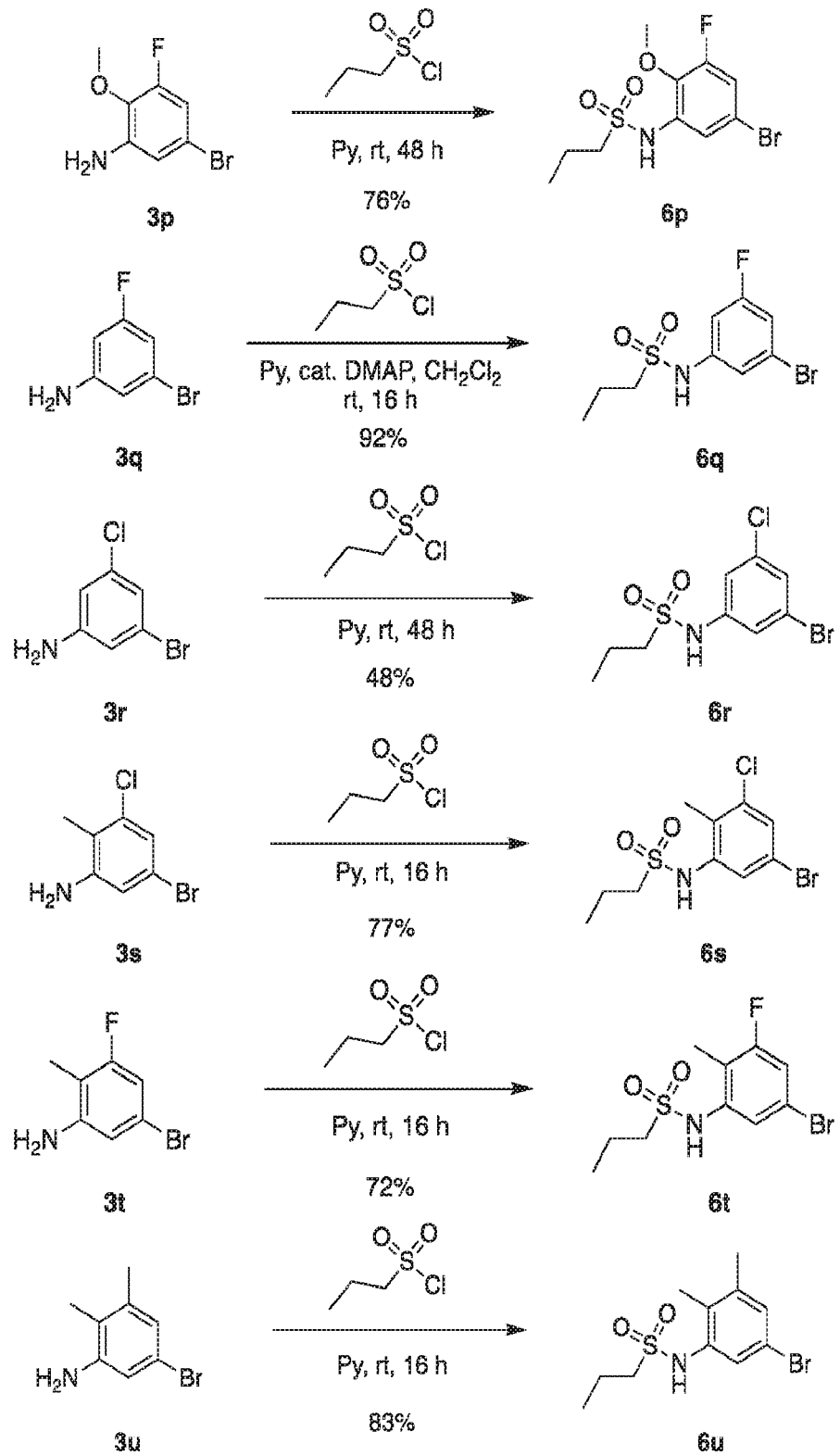
FIG. 19 shows steps in the synthesis of specific exemplary intermediate compounds described in Example 1 in accordance with preferred embodiments disclosed herein.
Figure 20:
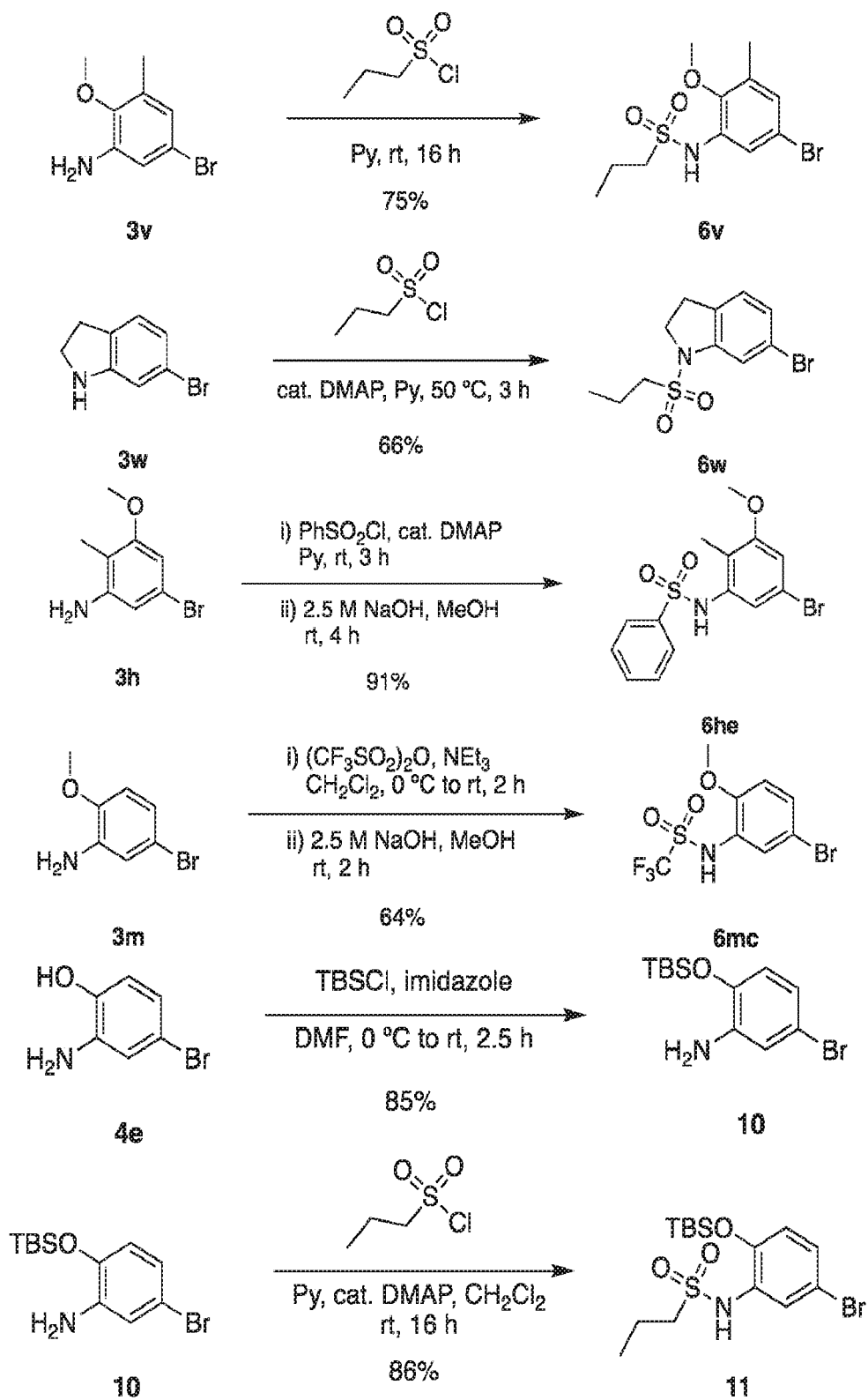
FIG. 20 shows steps in the synthesis of specific exemplary intermediate compounds described in Example 1 in accordance with preferred embodiments disclosed herein.
Figure 21:
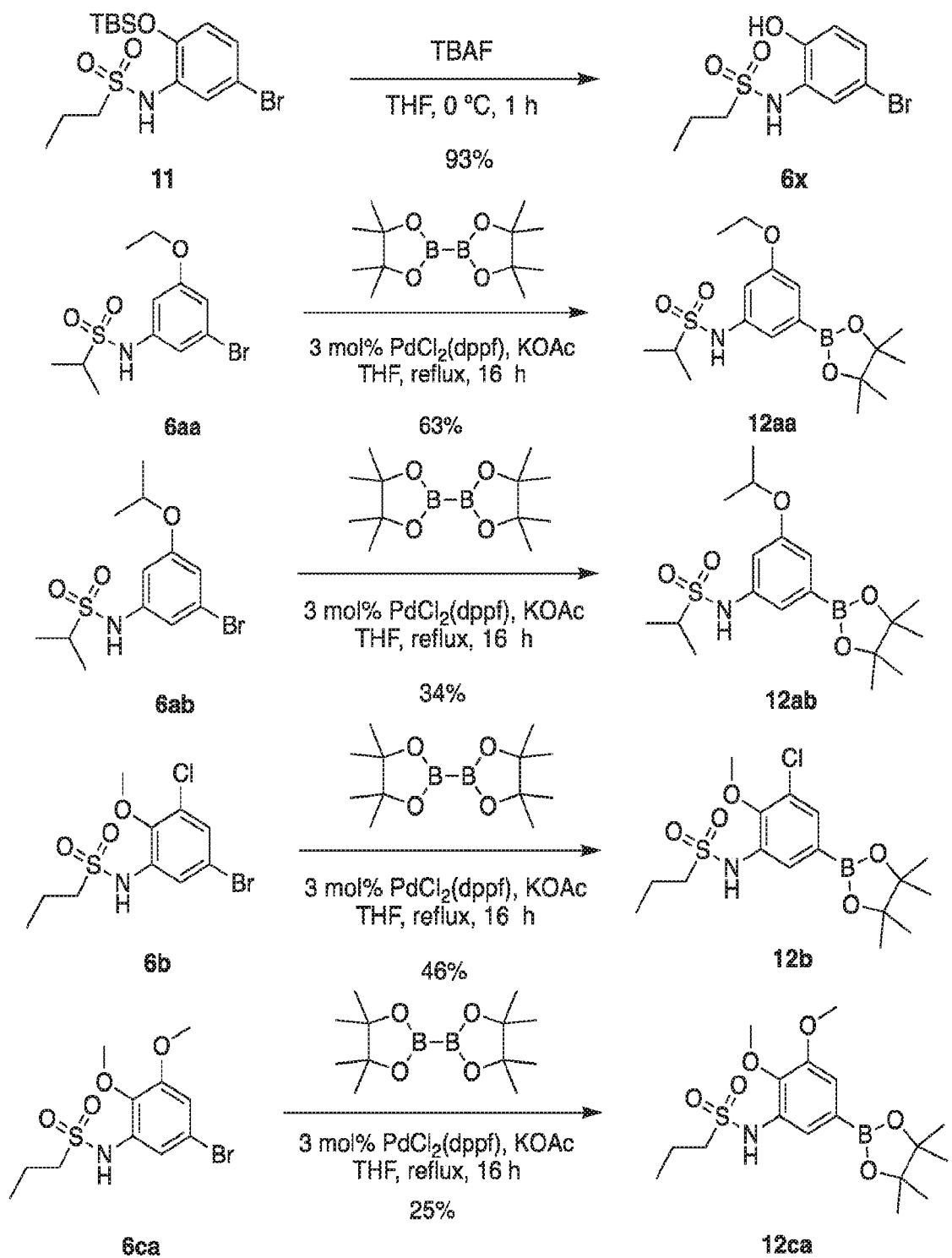
FIG. 21 shows steps in the synthesis of specific exemplary intermediate compounds described in Example 1 in accordance with preferred embodiments disclosed herein.
Figure 22:
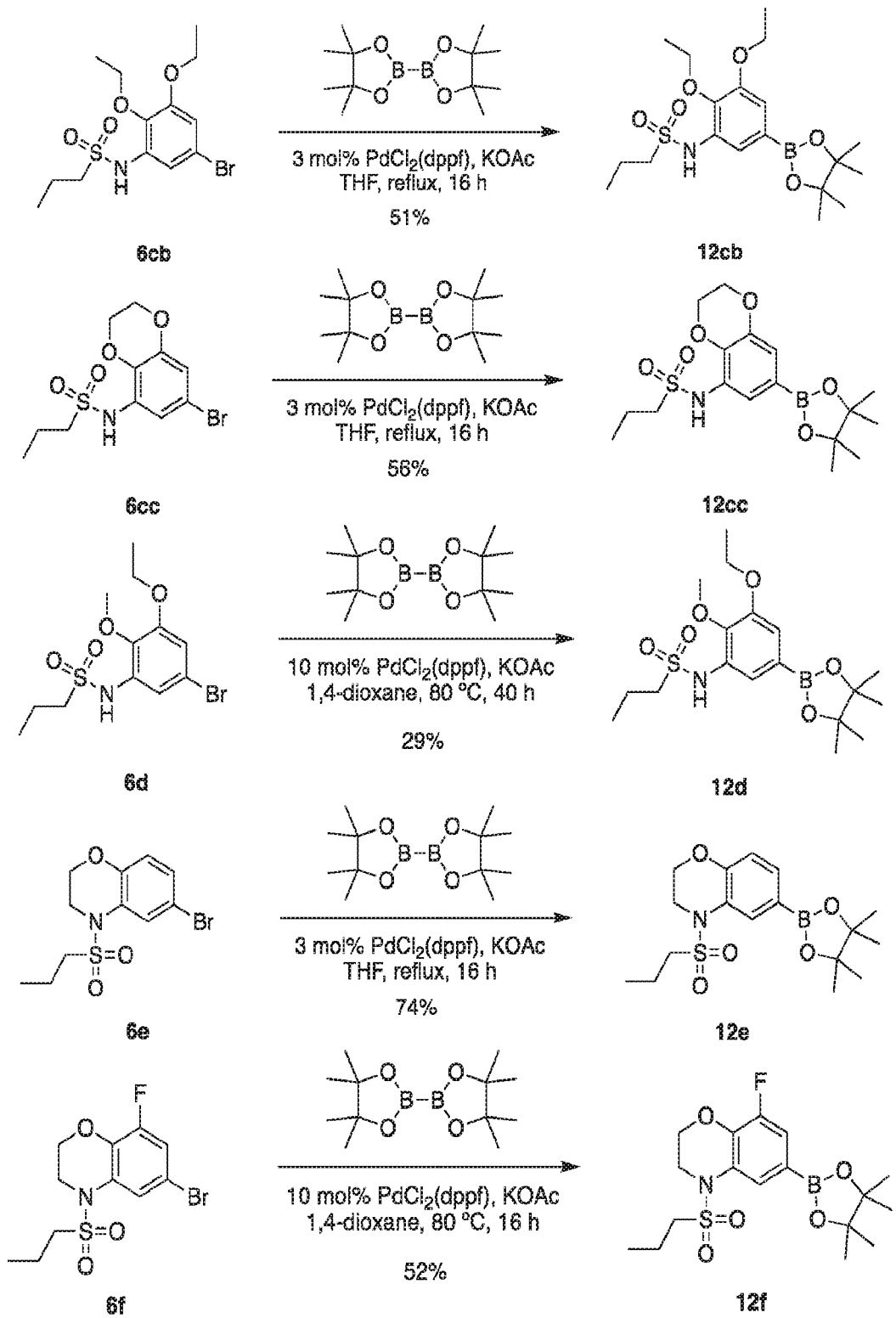
FIG. 22 shows steps in the synthesis of specific exemplary intermediate compounds described in Example 1 in accordance with preferred embodiments disclosed herein.
Figure 23:
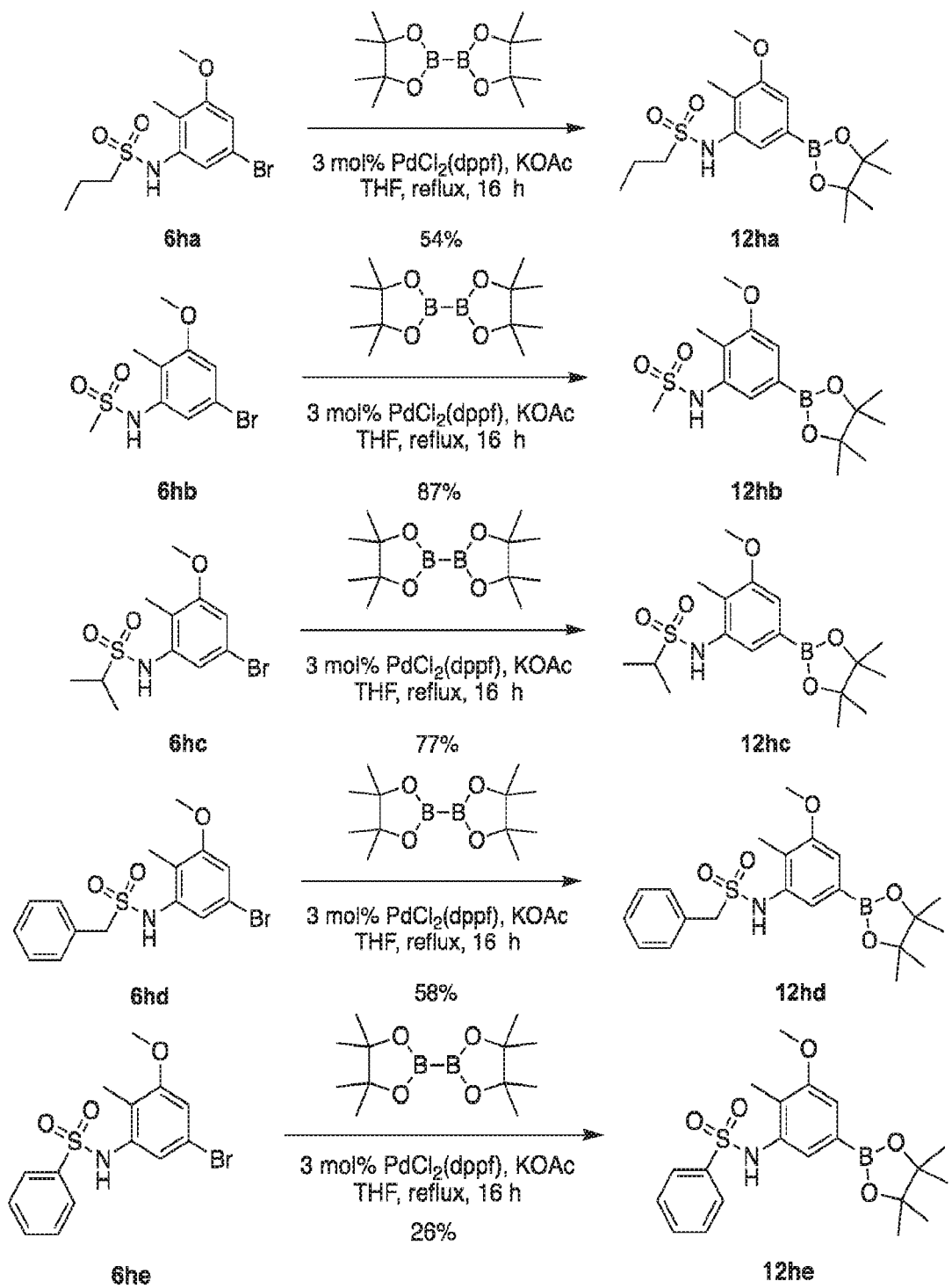
FIG. 23 shows steps in the synthesis of specific exemplary intermediate compounds described in Example 1 in accordance with preferred embodiments disclosed herein.
Figure 24:
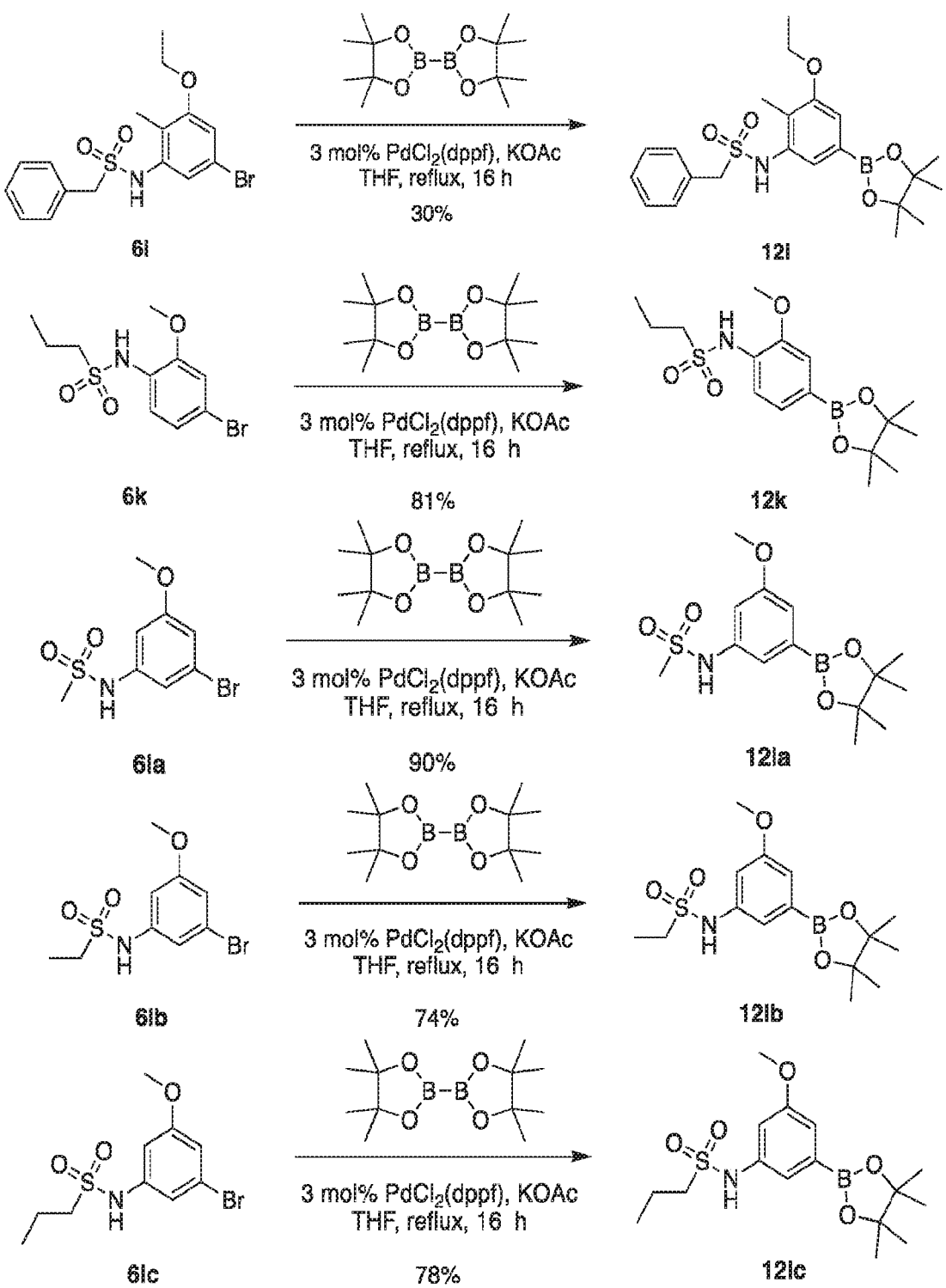
FIG. 24 shows steps in the synthesis of specific exemplary intermediate compounds described in Example 1 in accordance with preferred embodiments disclosed herein.
Figure 25:
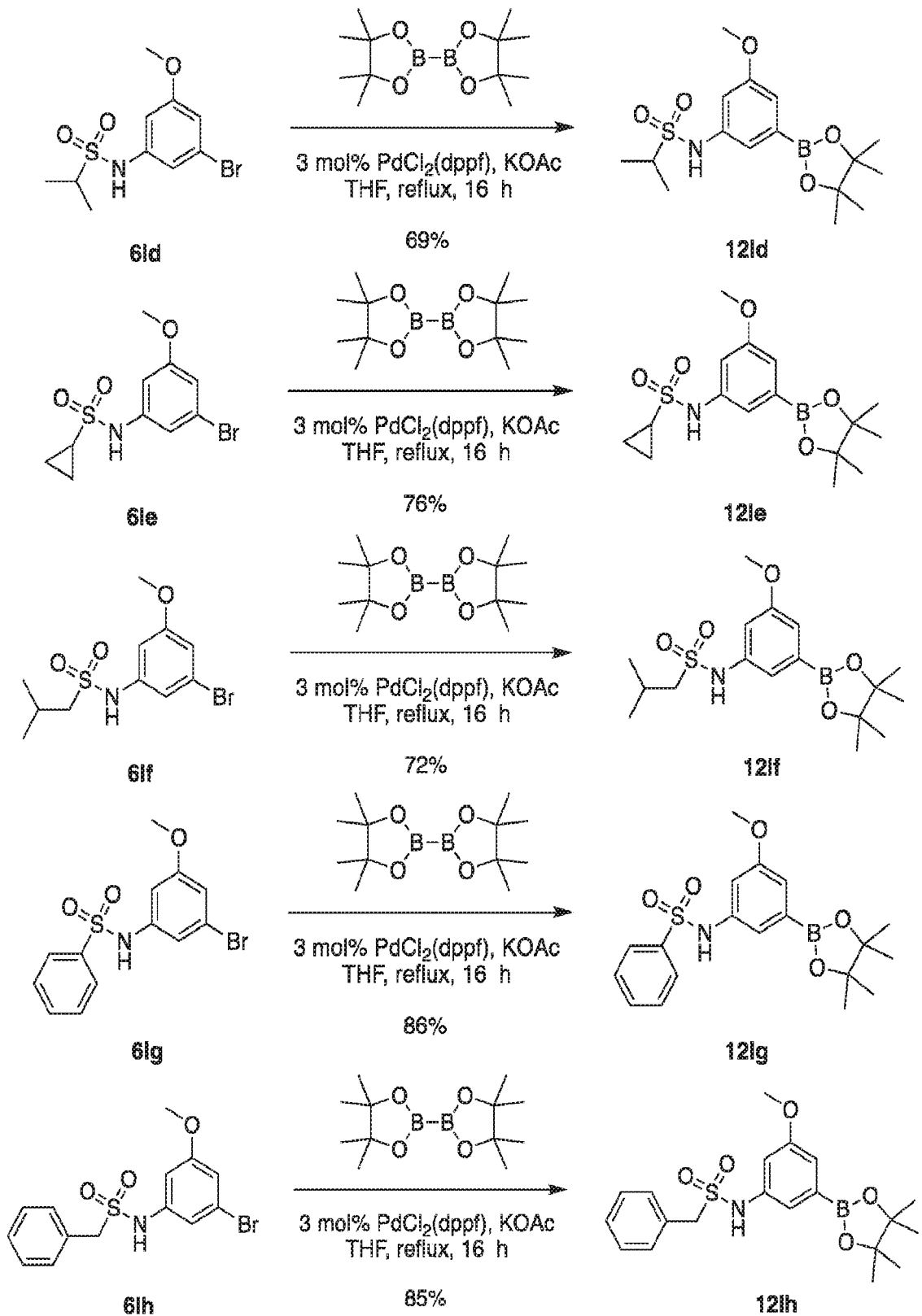
FIG. 25 shows steps in the synthesis of specific exemplary intermediate compounds described in Example 1 in accordance with preferred embodiments disclosed herein.
Figure 26:
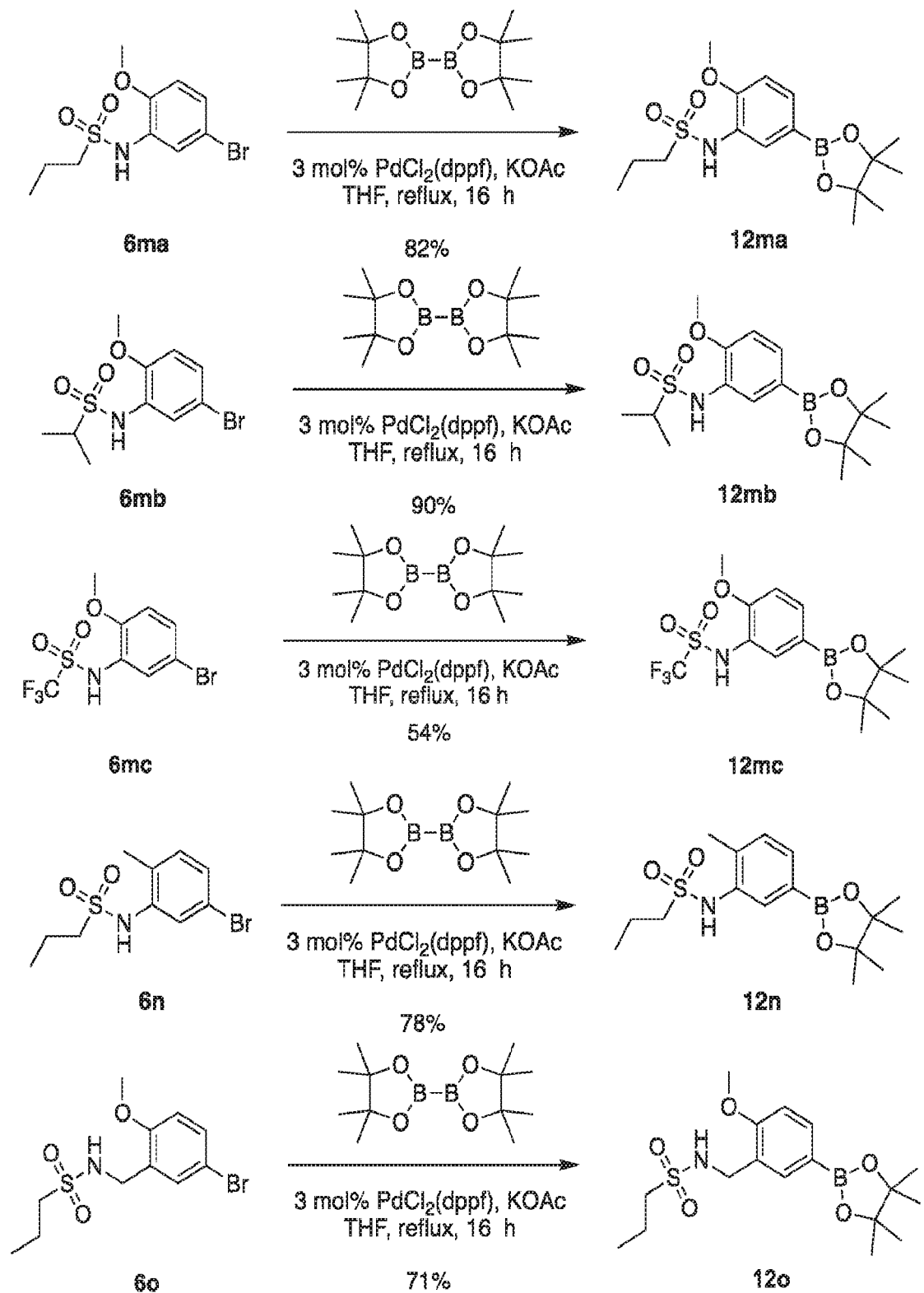
FIG. 26 shows steps in the synthesis of specific exemplary intermediate compounds described in Example 1 in accordance with preferred embodiments disclosed herein.
Figure 27:
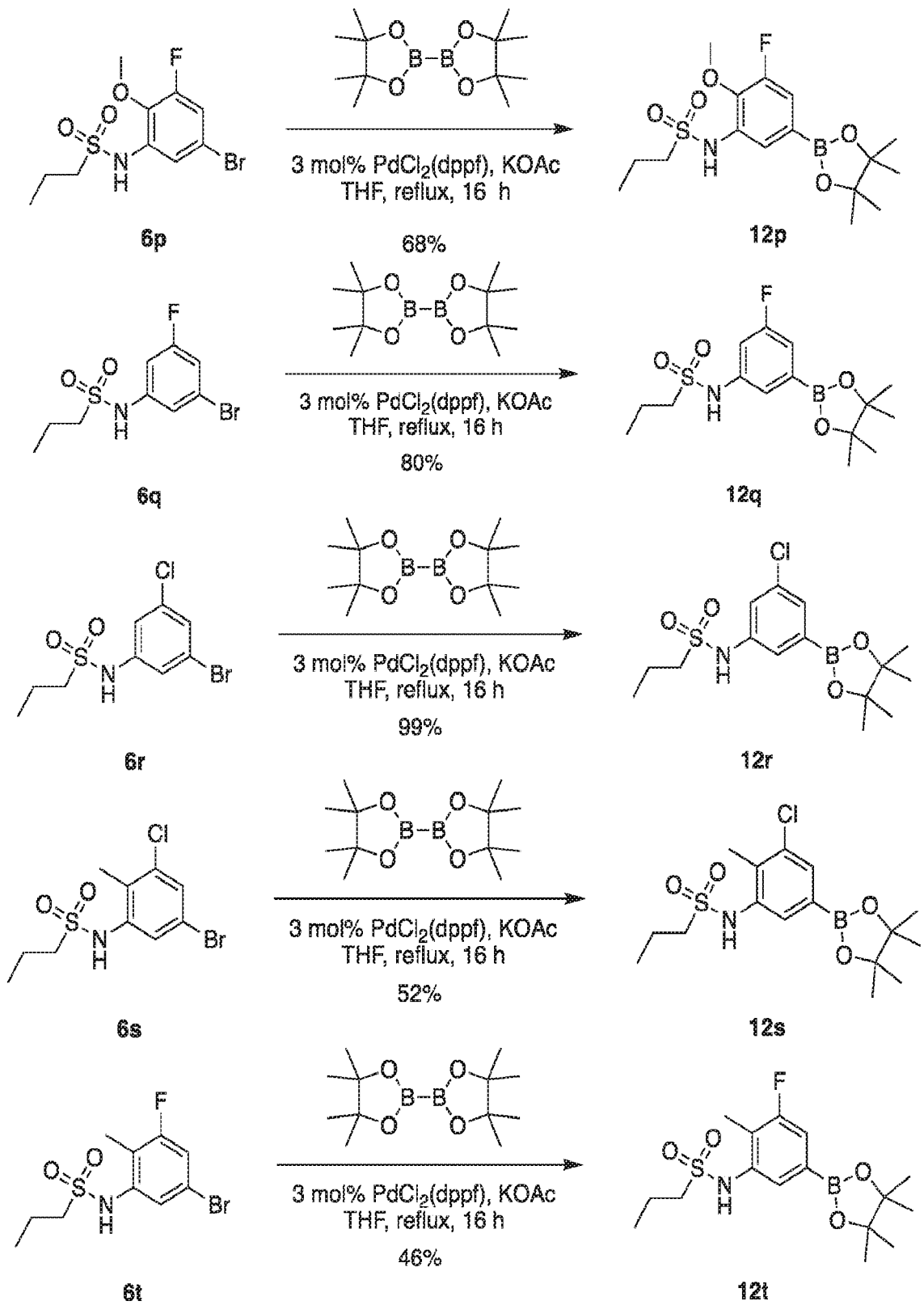
FIG. 27 shows steps in the synthesis of specific exemplary intermediate compounds described in Example 1 in accordance with preferred embodiments disclosed herein.
Figure 28:
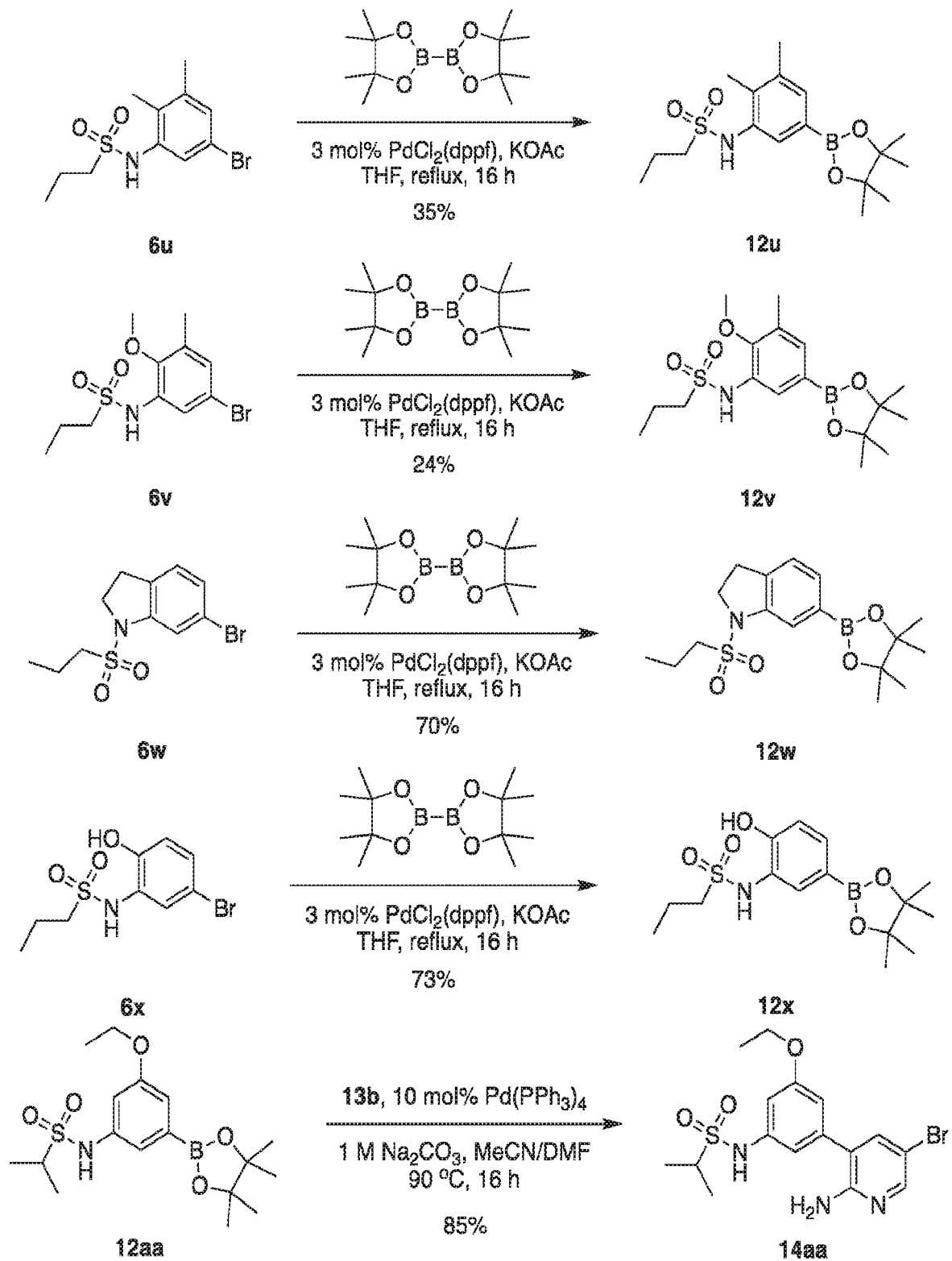
FIG. 28 shows steps in the synthesis of specific exemplary intermediate compounds described in Example 1 in accordance with preferred embodiments disclosed herein.
Figure 29:
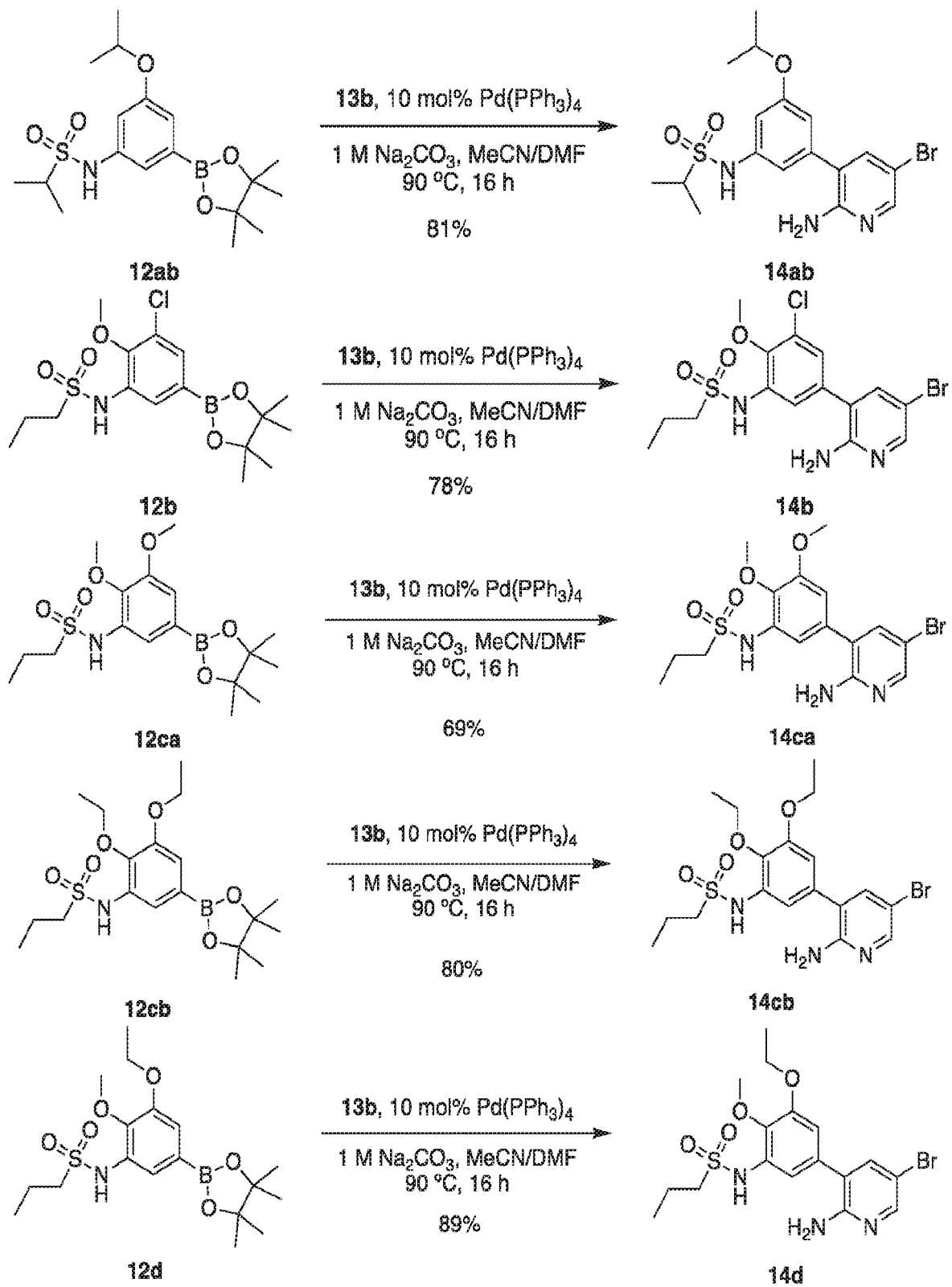
FIG. 29 shows steps in the synthesis of specific exemplary intermediate compounds described in Example 1 in accordance with preferred embodiments disclosed herein.
Figure 30:
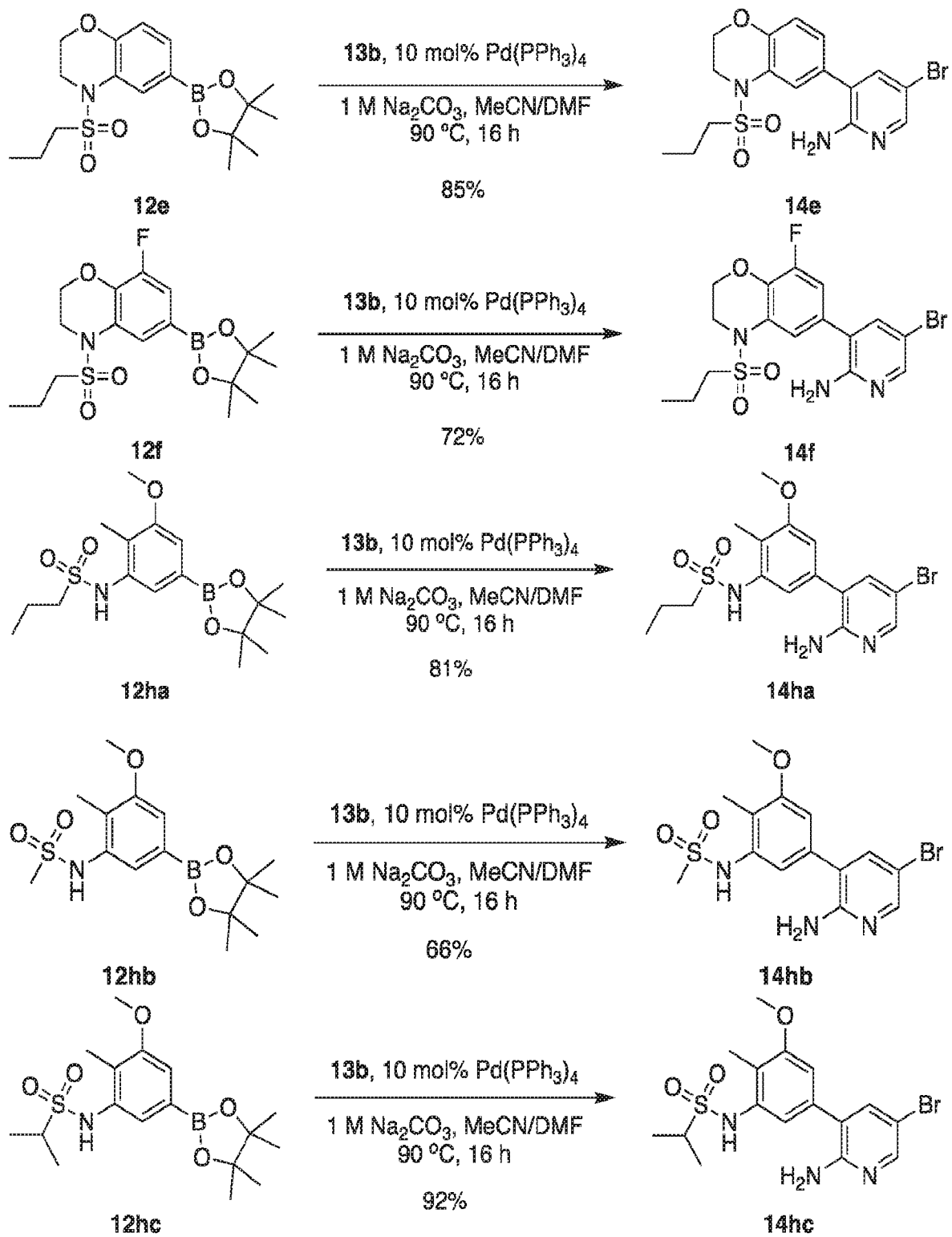
FIG. 30 shows steps in the synthesis of specific exemplary intermediate compounds described in Example 1 in accordance with preferred embodiments disclosed herein.
Figure 31:
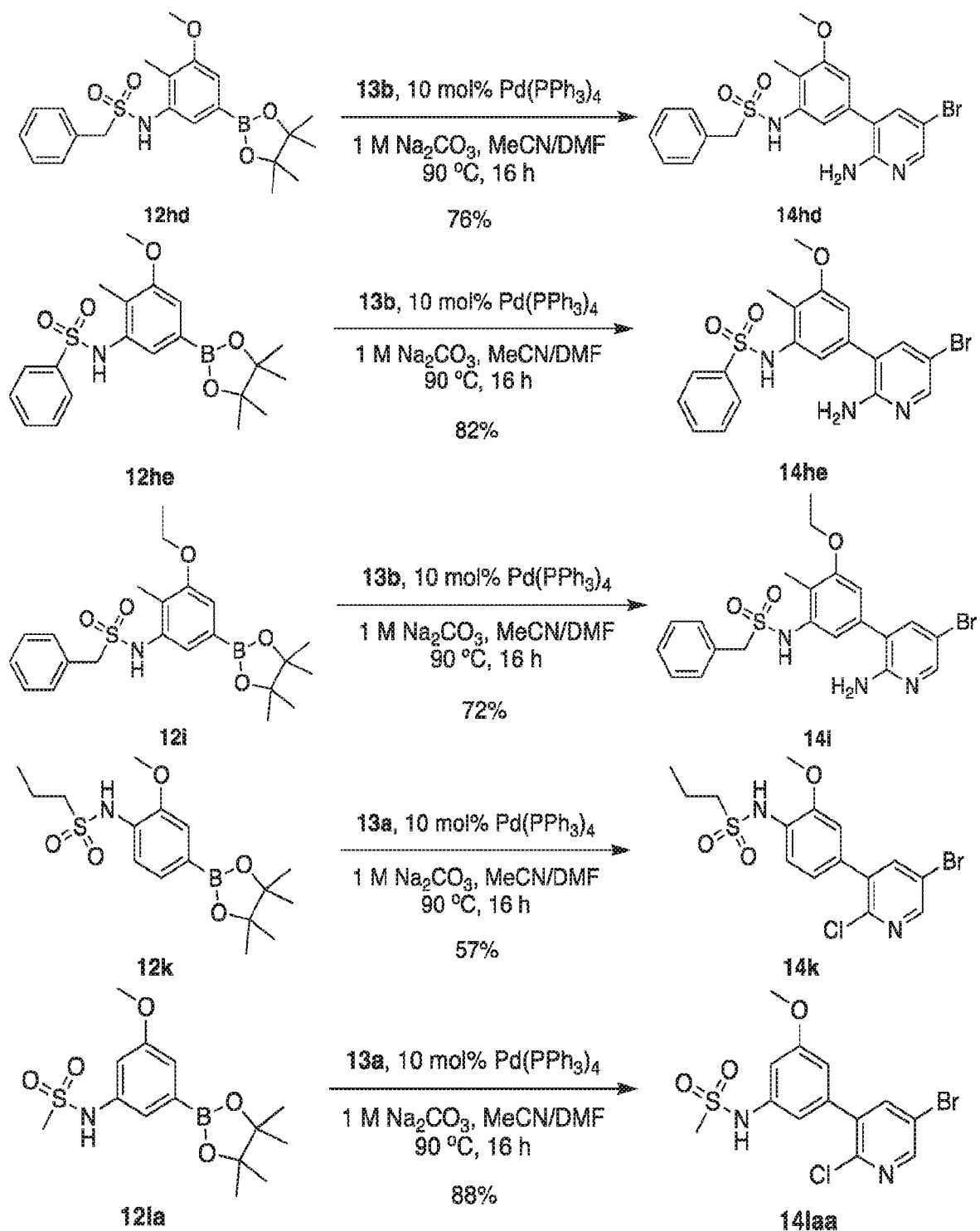
FIG. 31 shows steps in the synthesis of specific exemplary intermediate compounds described in Example 1 in accordance with preferred embodiments disclosed herein.
Figure 32:
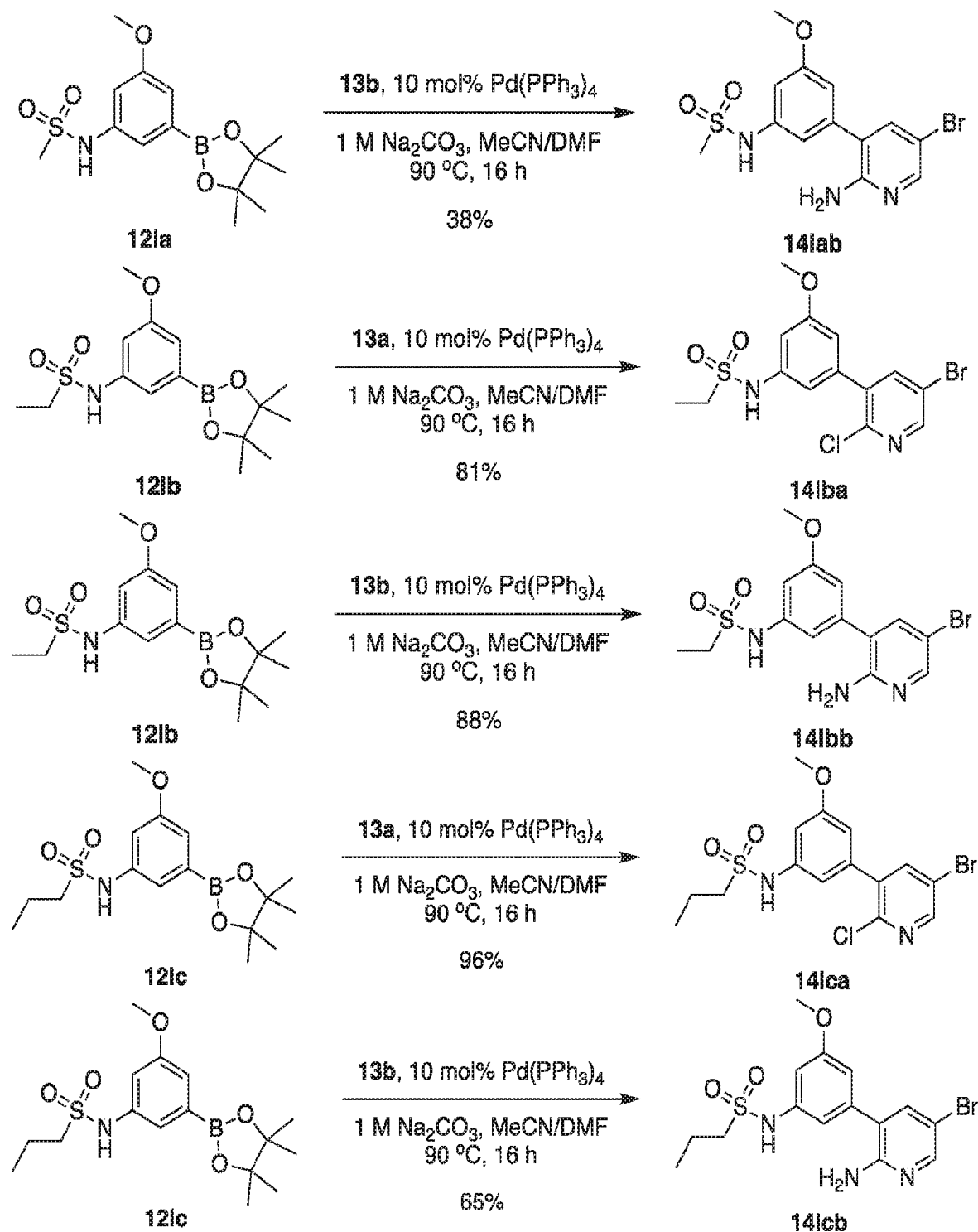
FIG. 32 shows steps in the synthesis of specific exemplary intermediate compounds described in Example 1 in accordance with preferred embodiments disclosed herein.
Figure 33:
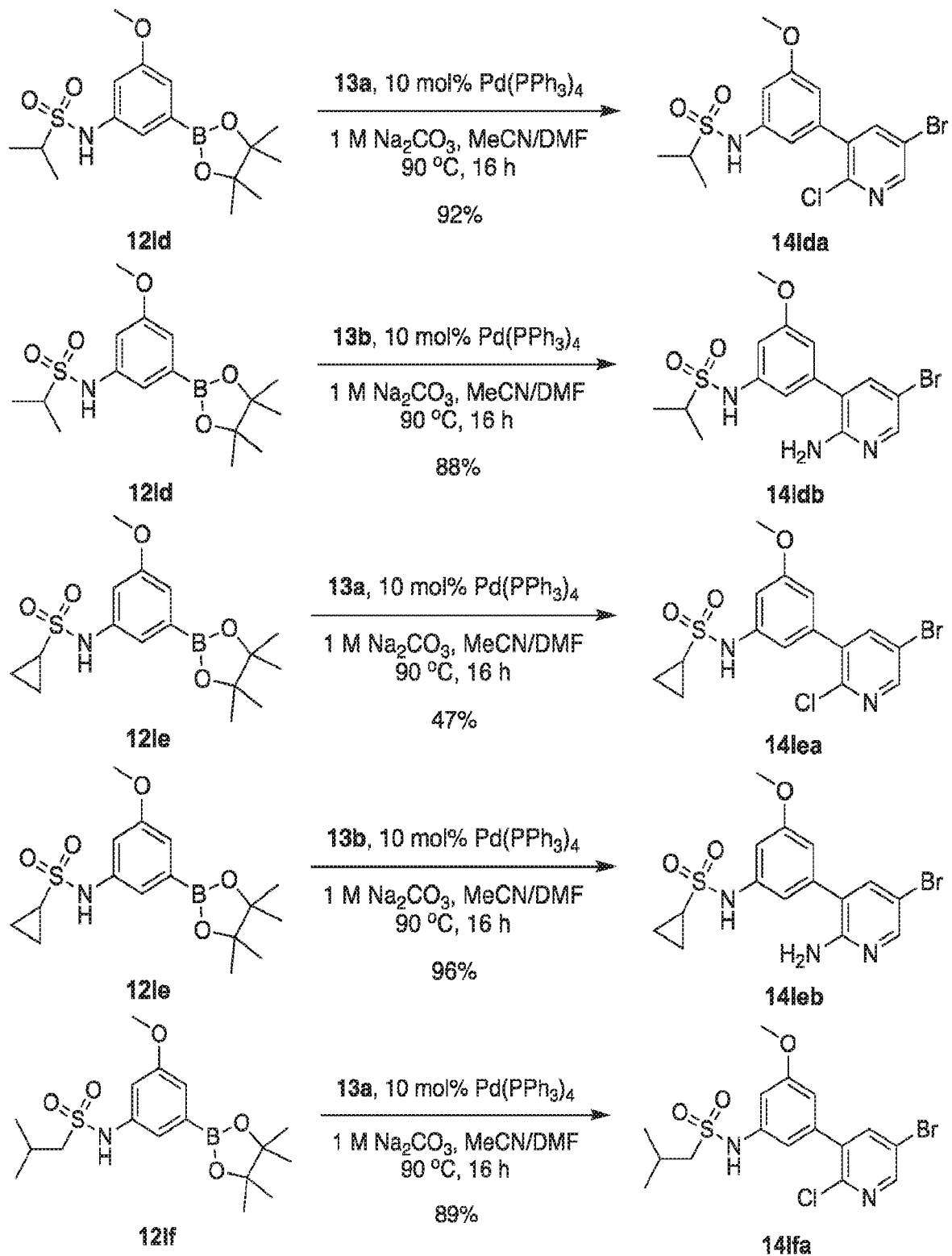
FIG. 33 shows steps in the synthesis of specific exemplary intermediate compounds described in Example 1 in accordance with preferred embodiments disclosed herein.
Figure 34:
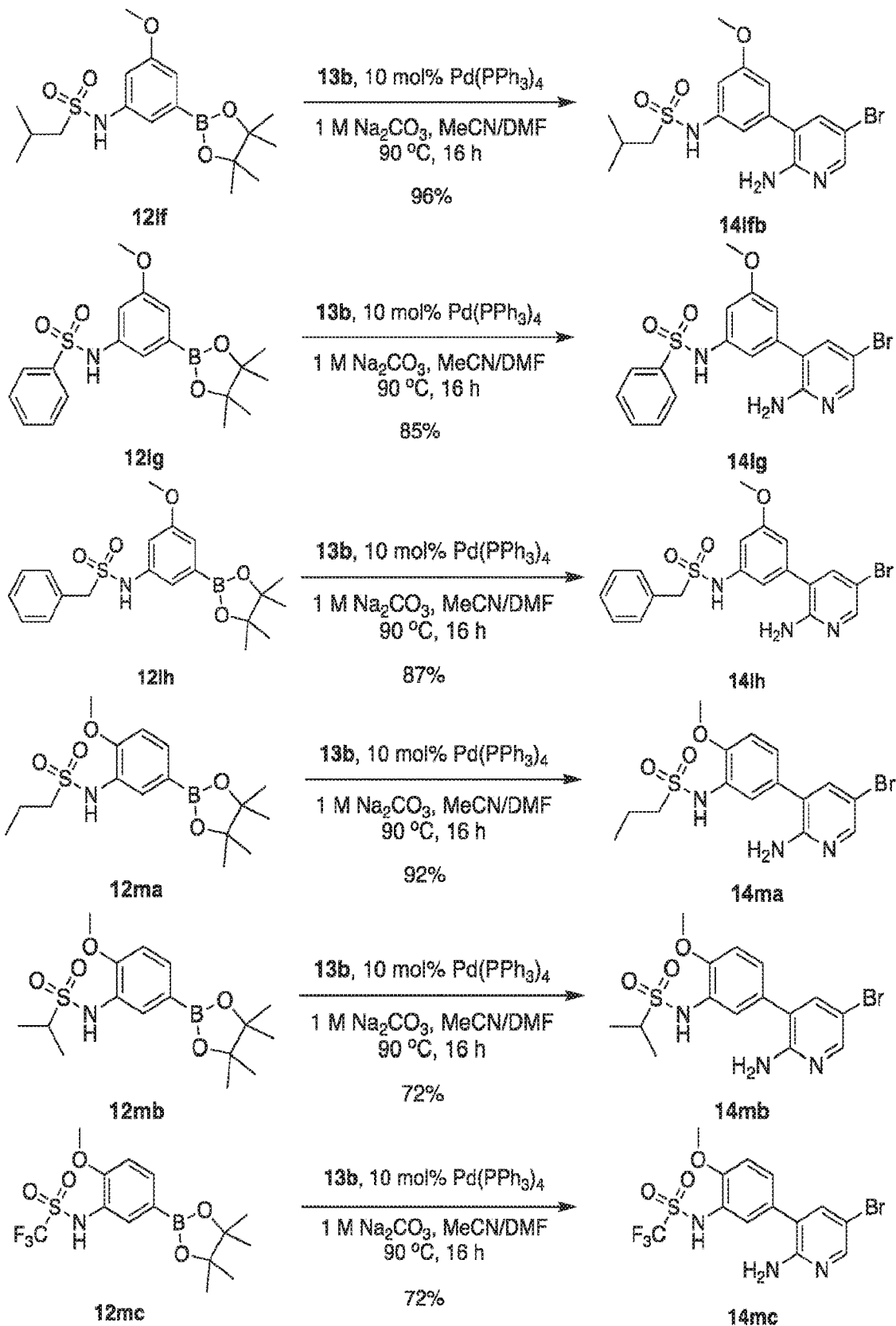
FIG. 34 shows steps in the synthesis of specific exemplary intermediate compounds described in Example 1 in accordance with preferred embodiments disclosed herein.
Figure 35:
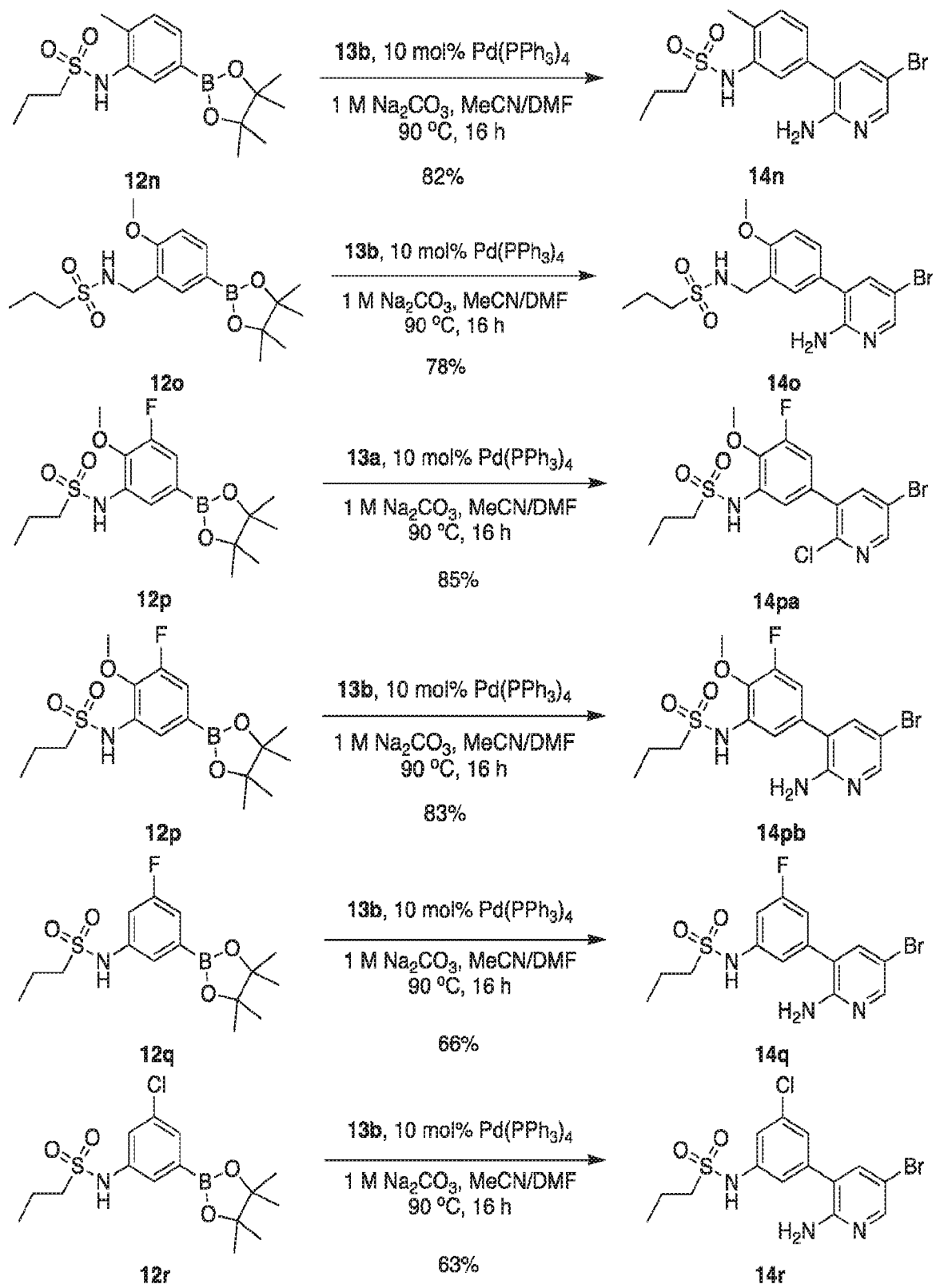
FIG. 35 shows steps in the synthesis of specific exemplary intermediate compounds described in Example 1 in accordance with preferred embodiments disclosed herein.
Figure 36:
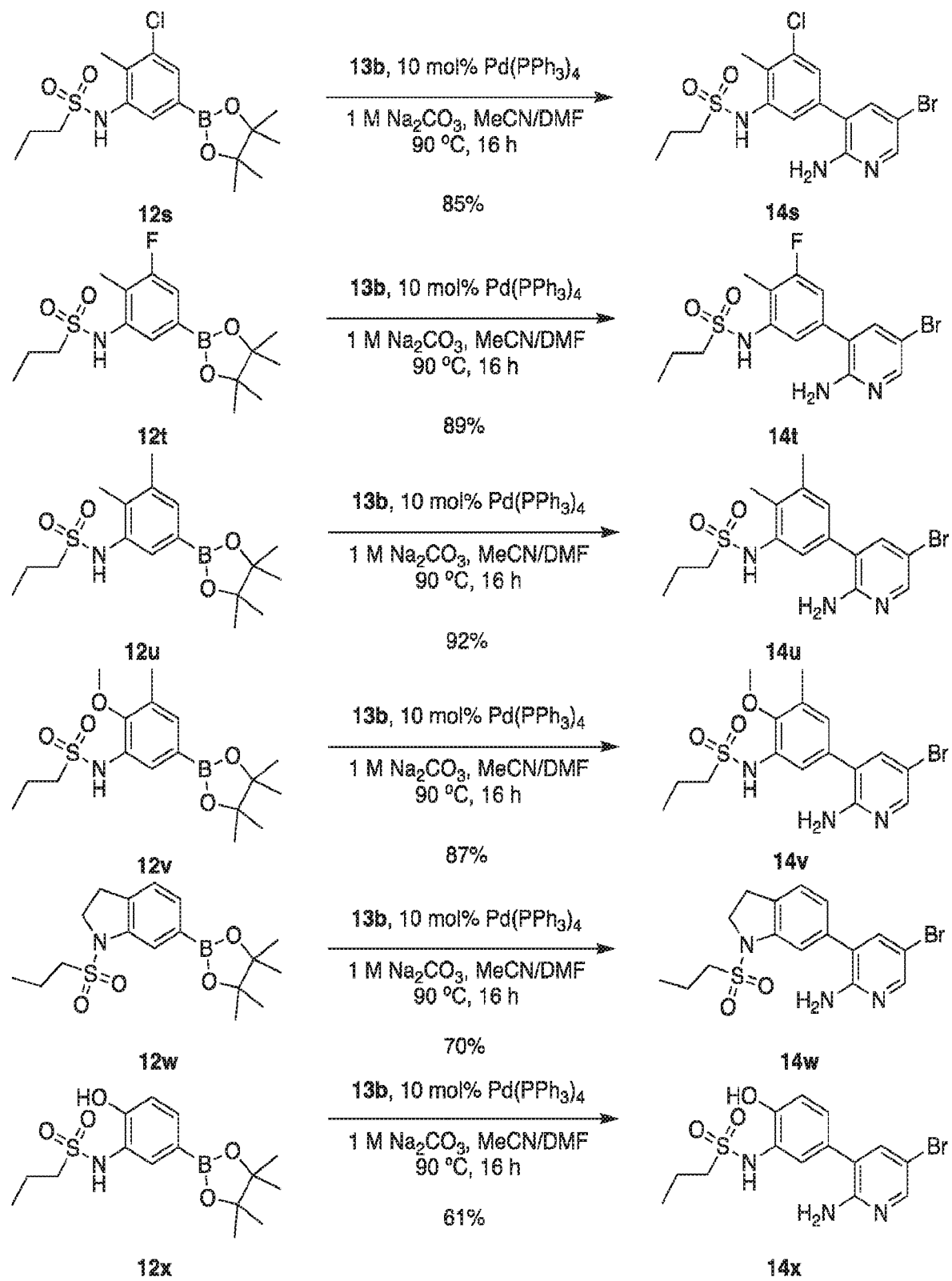
FIG. 36 shows steps in the synthesis of specific exemplary intermediate compounds described in Example 1 in accordance with preferred embodiments disclosed herein.
Figure 37:
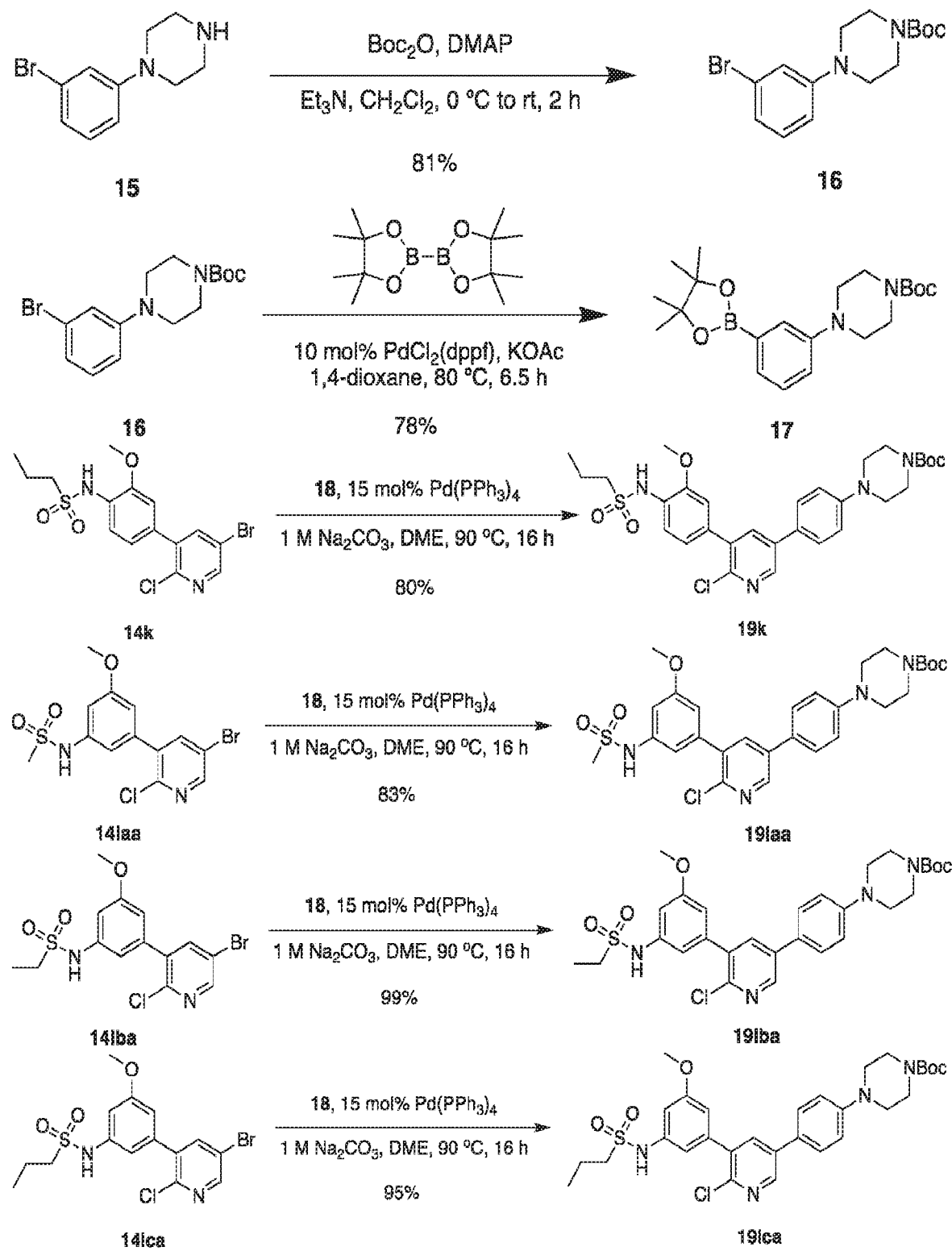
FIG. 37 shows steps in the synthesis of specific exemplary intermediate compounds described in Example 1 in accordance with preferred embodiments disclosed herein.
Figure 38:
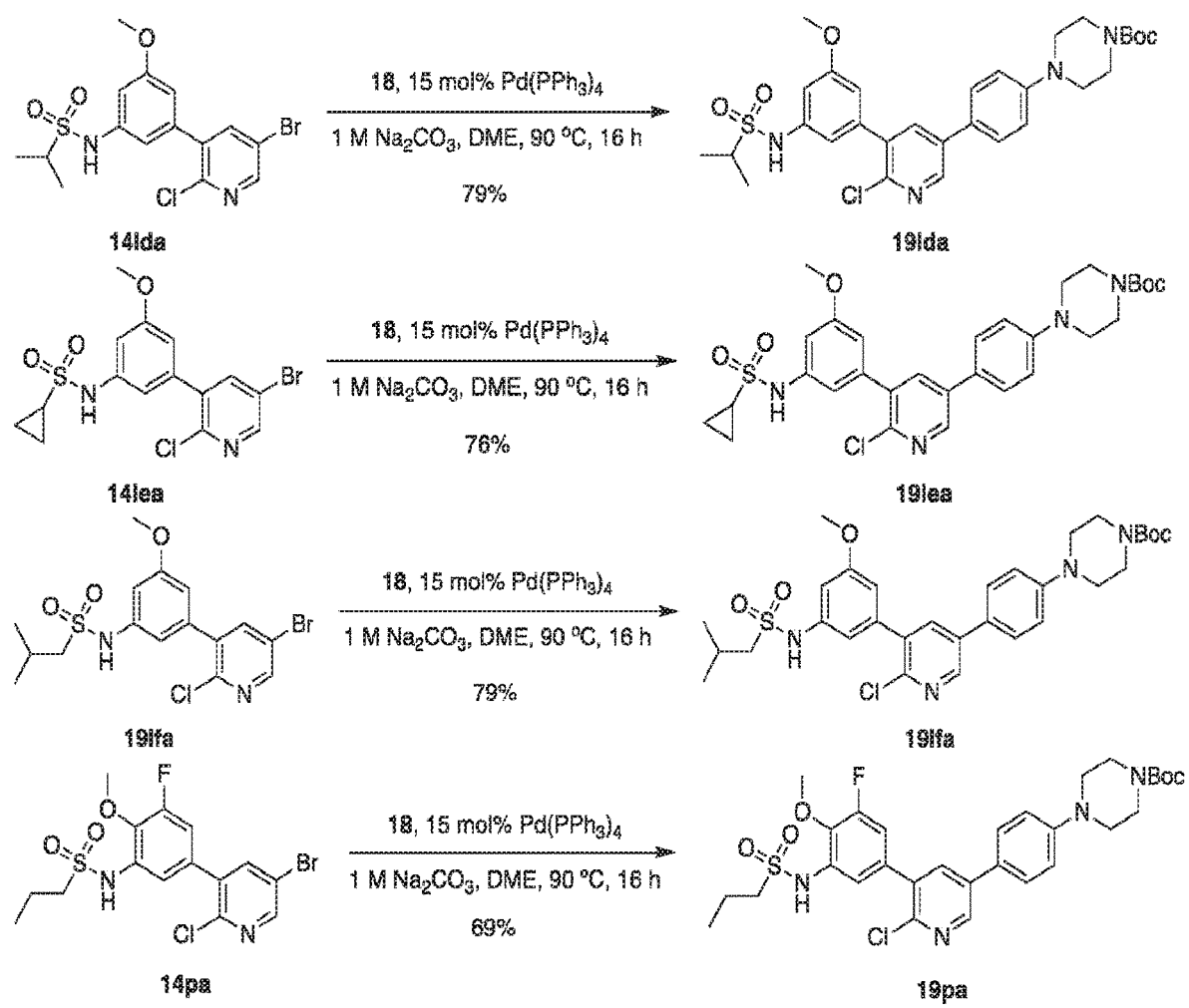
FIG. 38 shows steps in the synthesis of specific exemplary intermediate compounds described in Example 1 in accordance with preferred embodiments disclosed herein.
Figure 39:
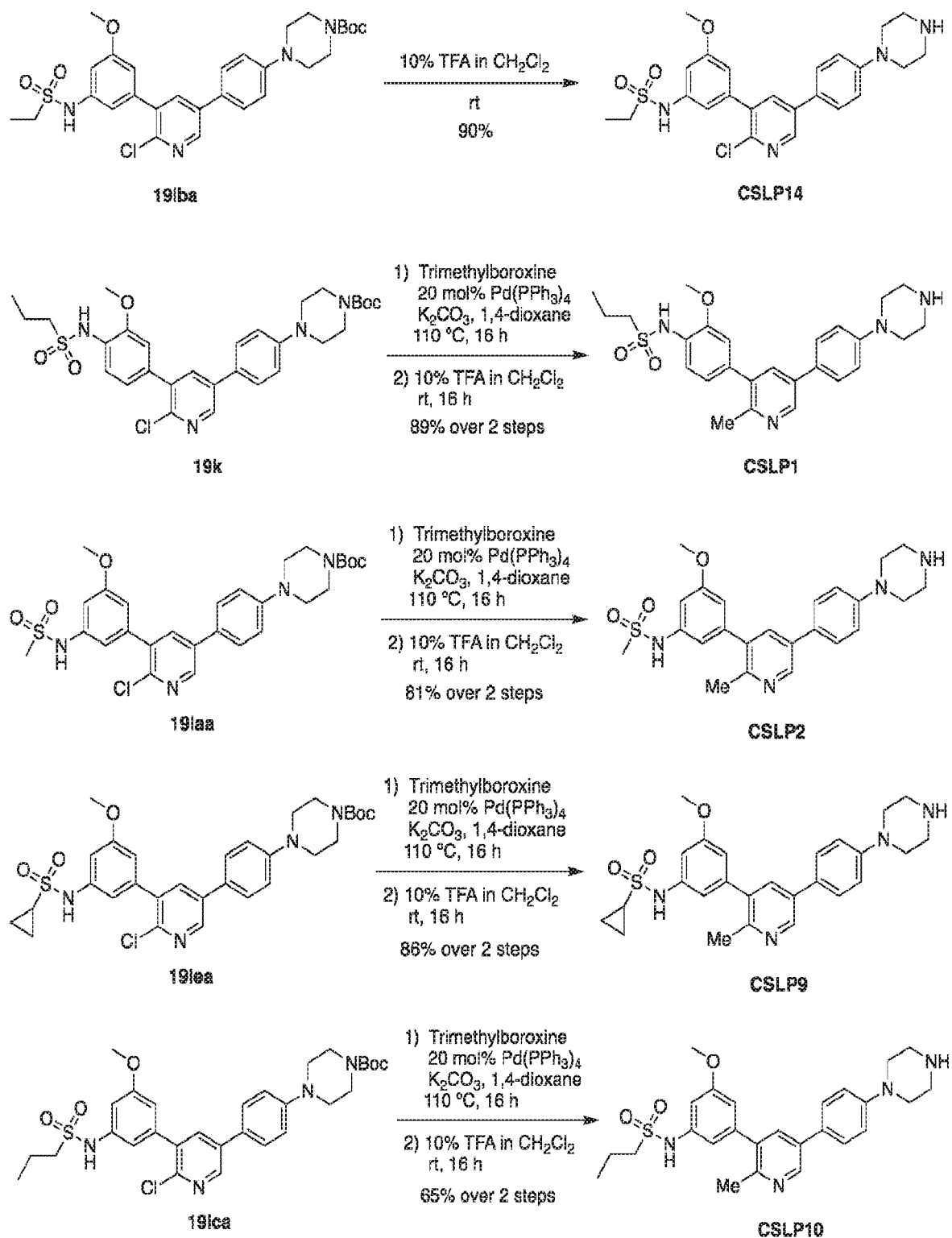
FIG. 39 shows steps in the synthesis of specific exemplary representative compounds described in Example 1 in accordance with preferred embodiments disclosed herein.
Figure 40:
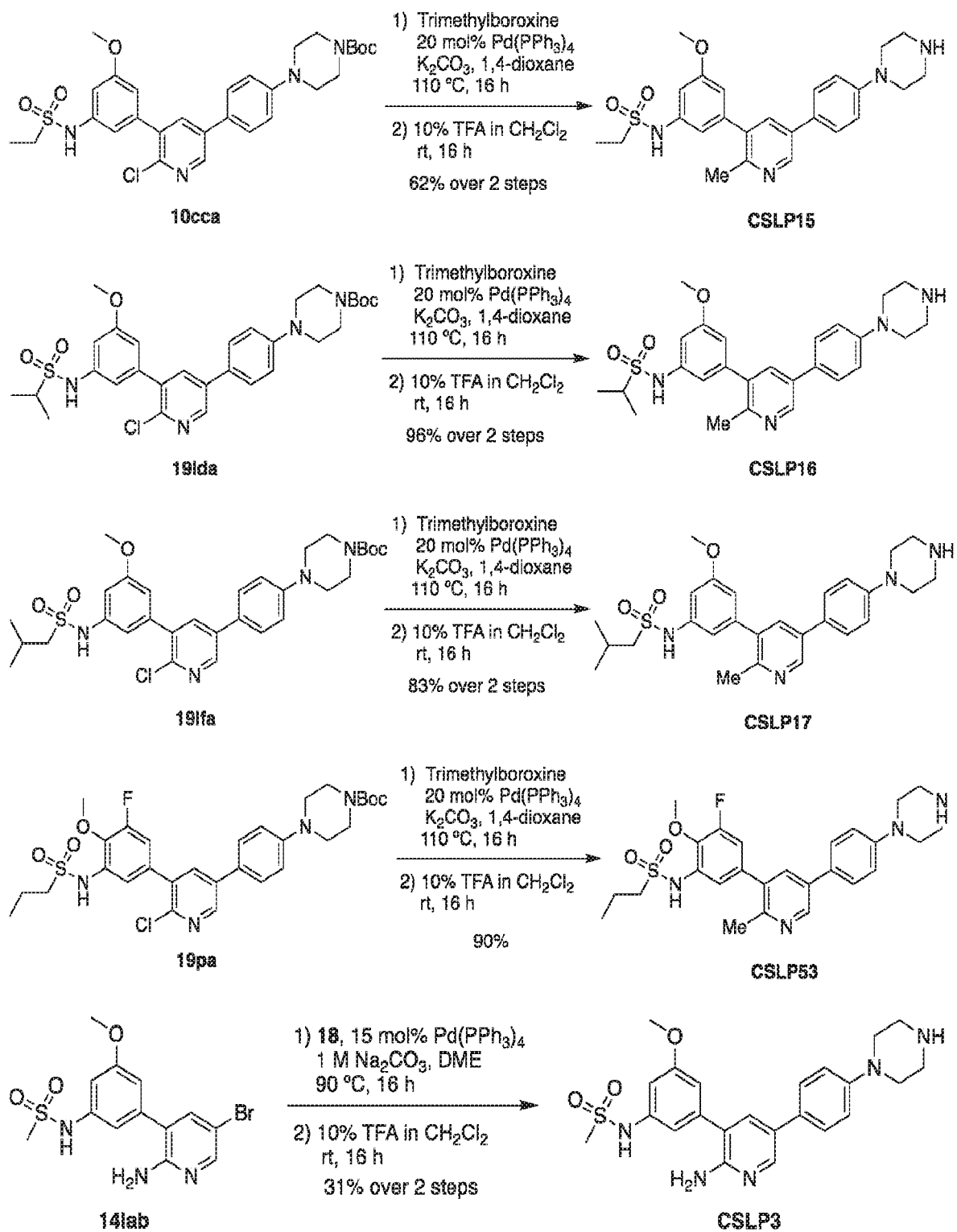
FIG. 40 shows steps in the synthesis of specific exemplary representative compounds described in Example 1 in accordance with preferred embodiments disclosed herein.
Figure 41:
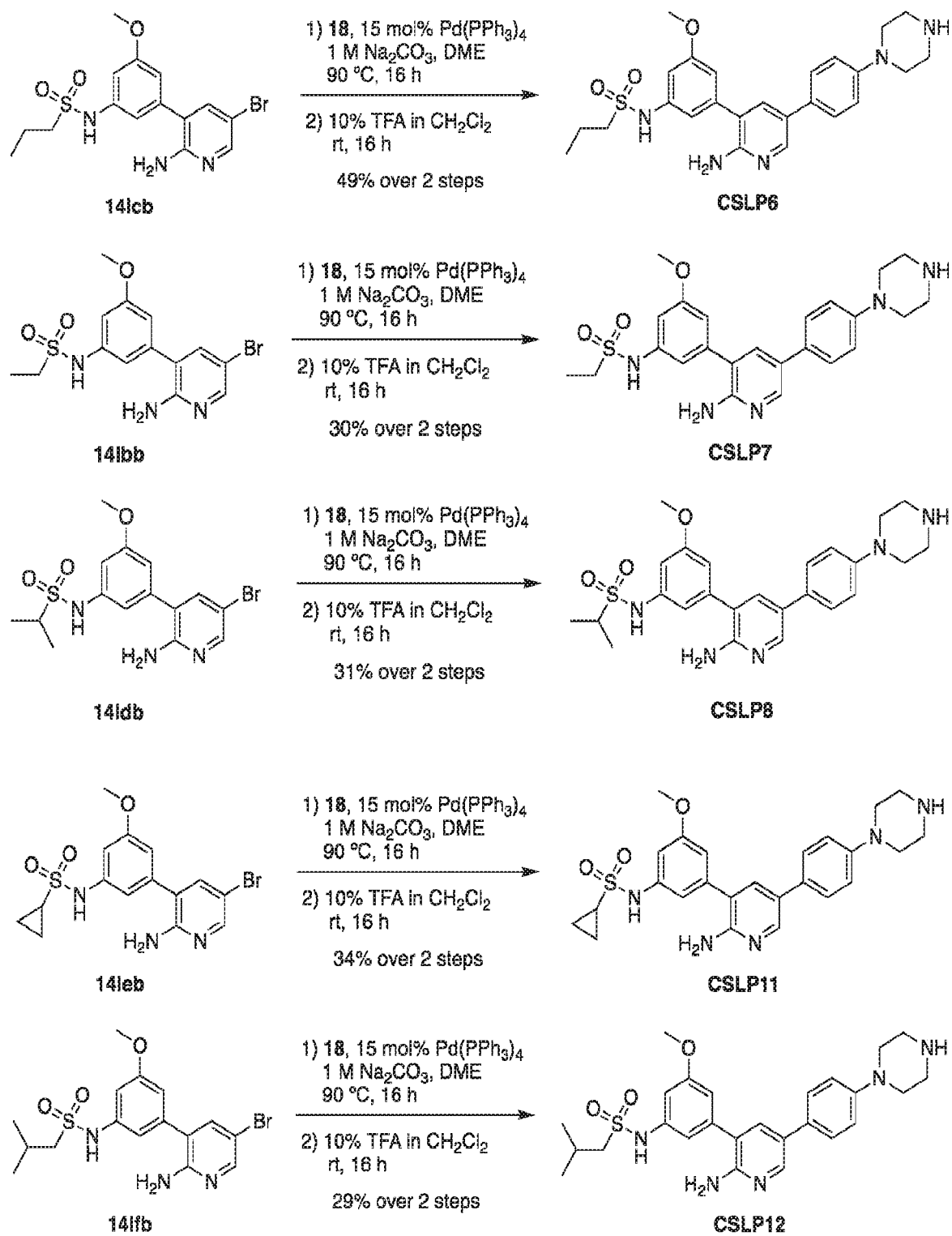
FIG. 41 shows steps in the synthesis of specific exemplary representative compounds described in Example 1 in accordance with preferred embodiments disclosed herein.
Figure 42:
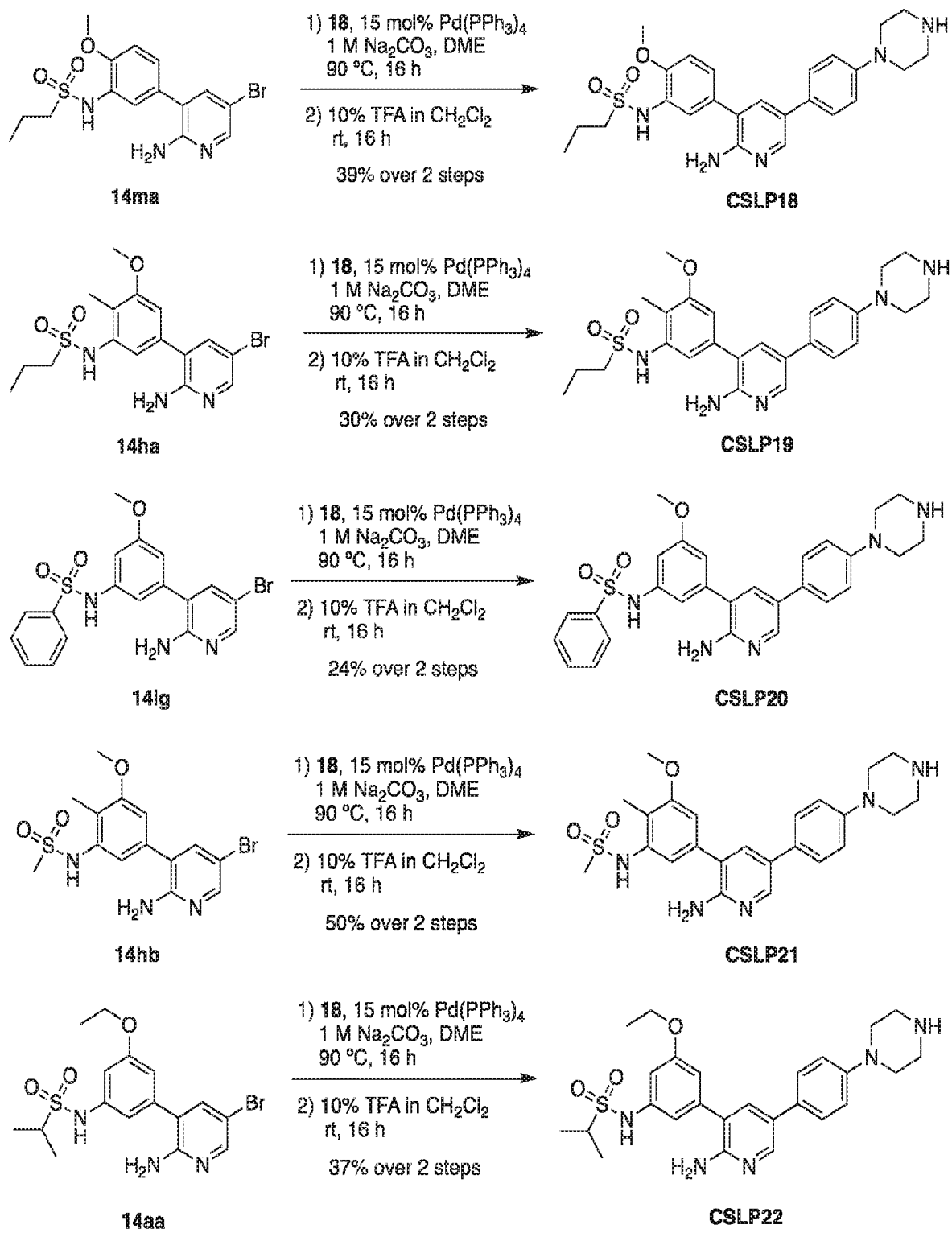
FIG. 42 shows steps in the synthesis of specific exemplary representative compounds described in Example 1 in accordance with preferred embodiments disclosed herein.
Figure 43:
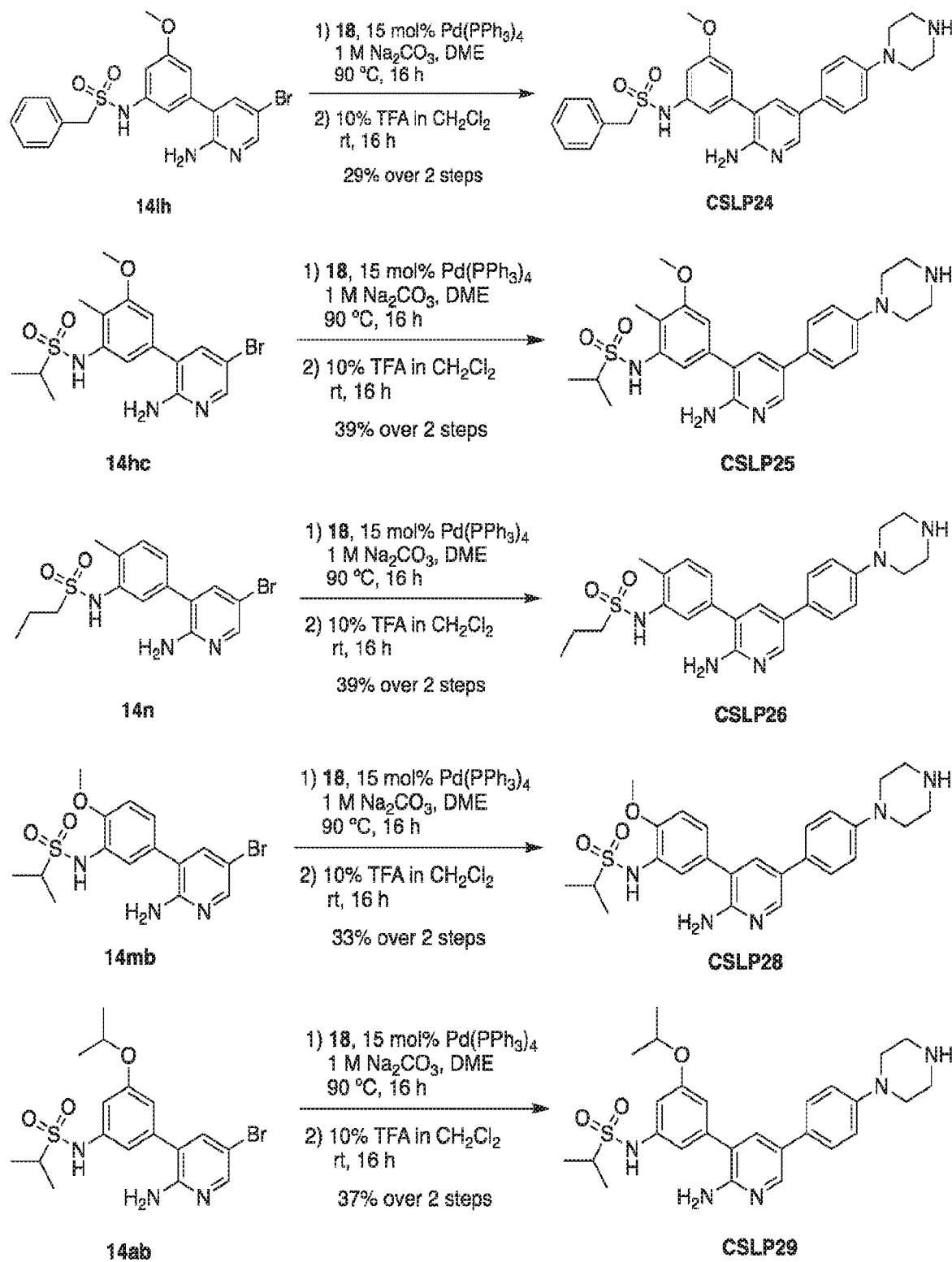
FIG. 43 shows steps in the synthesis of specific exemplary representative compounds described in Example 1 in accordance with preferred embodiments disclosed herein.
Figure 44:
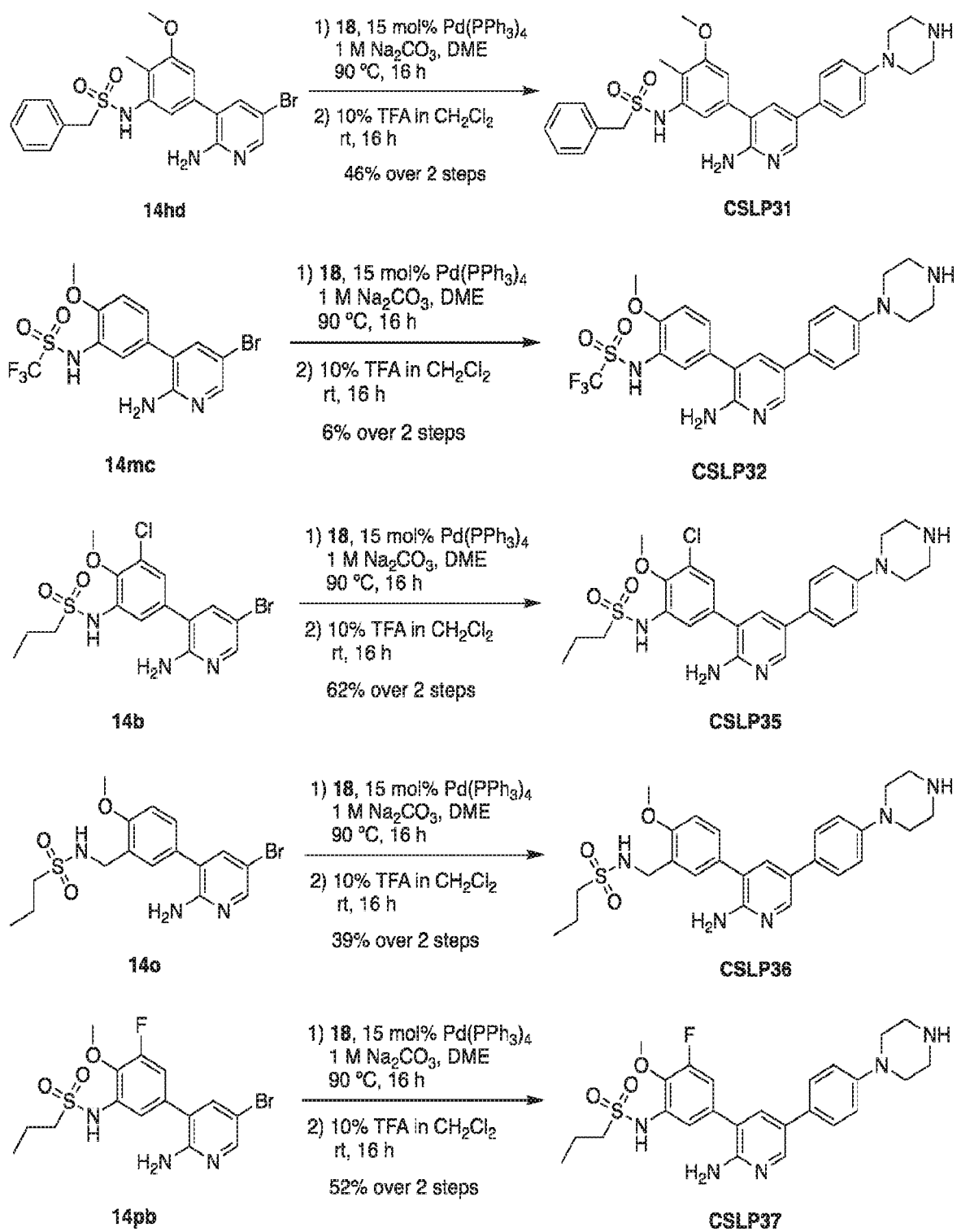
FIG. 44 shows steps in the synthesis of specific exemplary representative compounds described in Example 1 in accordance with preferred embodiments disclosed herein.
Figure 45:
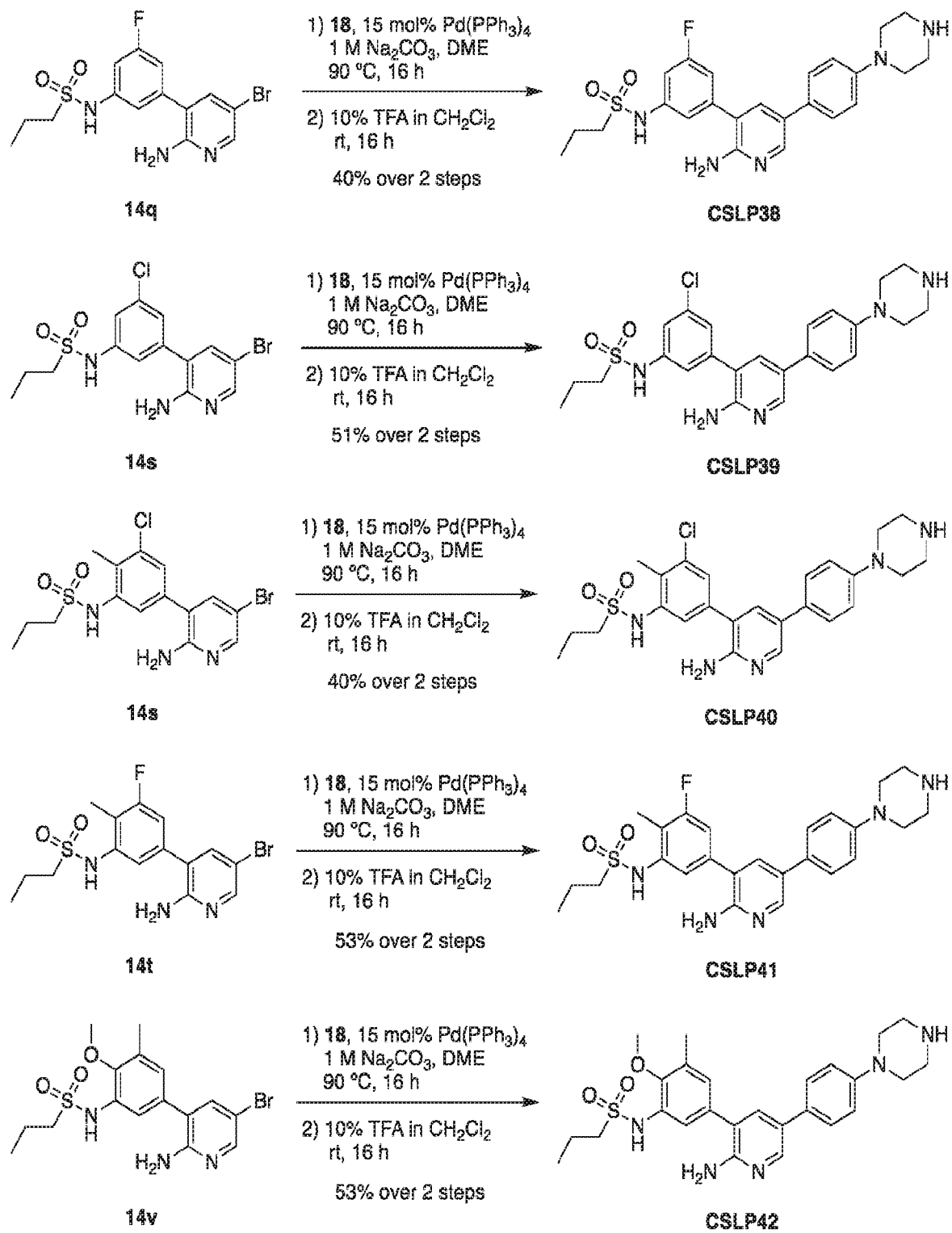
FIG. 45 shows steps in the synthesis of specific exemplary representative compounds described in Example 1 in accordance with preferred embodiments disclosed herein.
Figure 46:
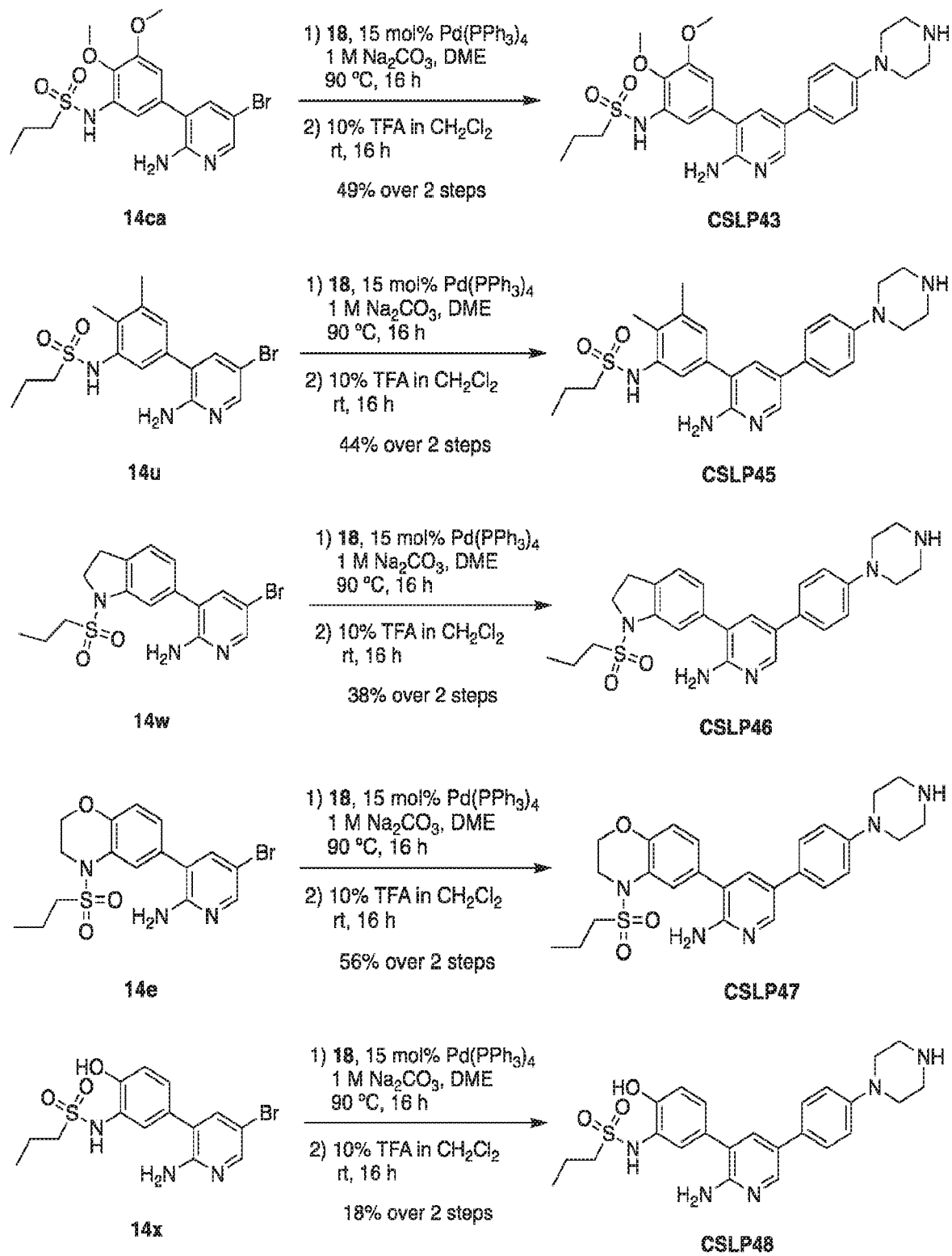
FIG. 46 shows steps in the synthesis of specific exemplary representative compounds described in Example 1 in accordance with preferred embodiments disclosed herein.
Figure 47:
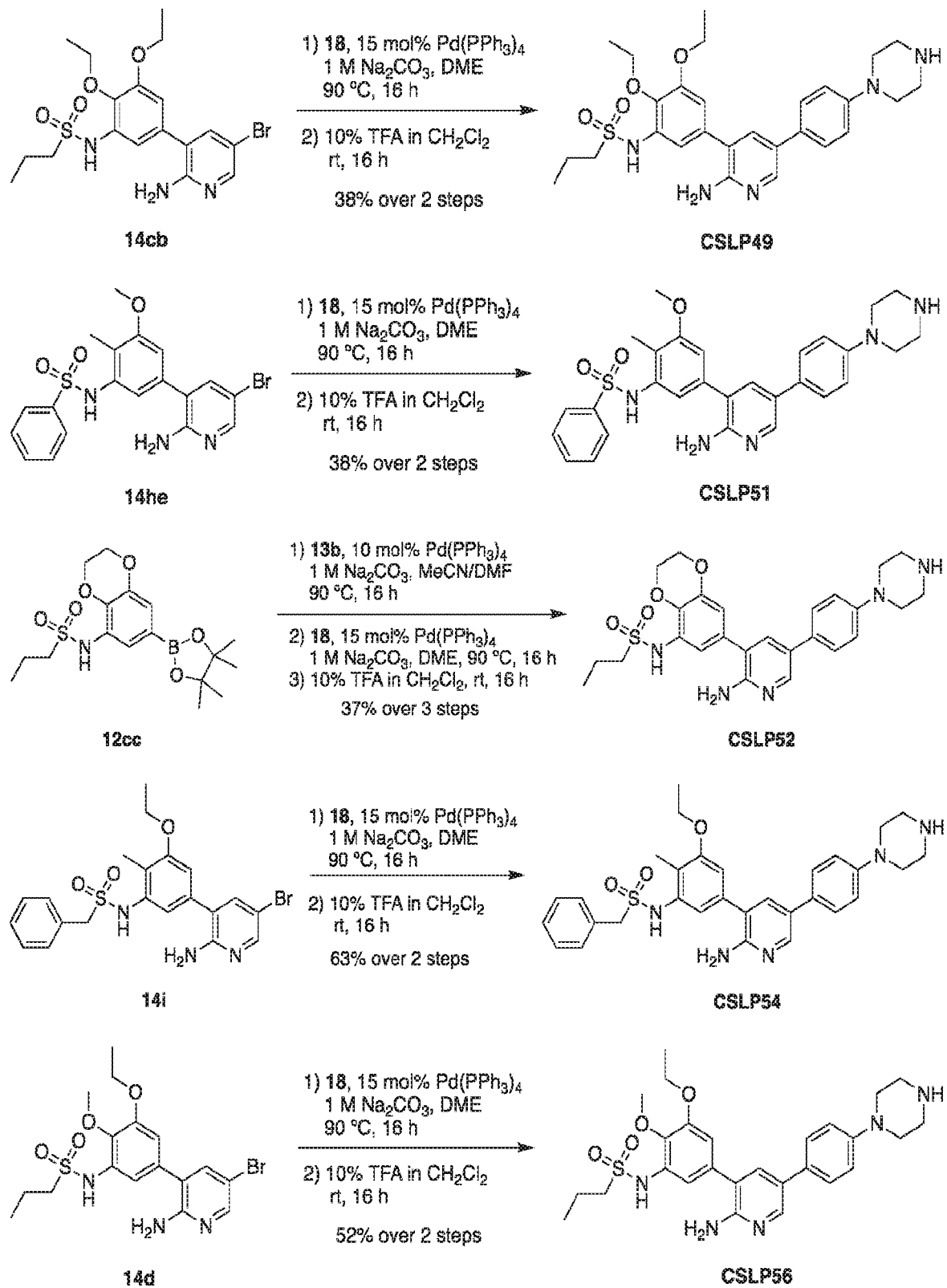
FIG. 47 shows steps in the synthesis of specific exemplary representative compounds described in Example 1 in accordance with preferred embodiments disclosed herein.
Figure 48:
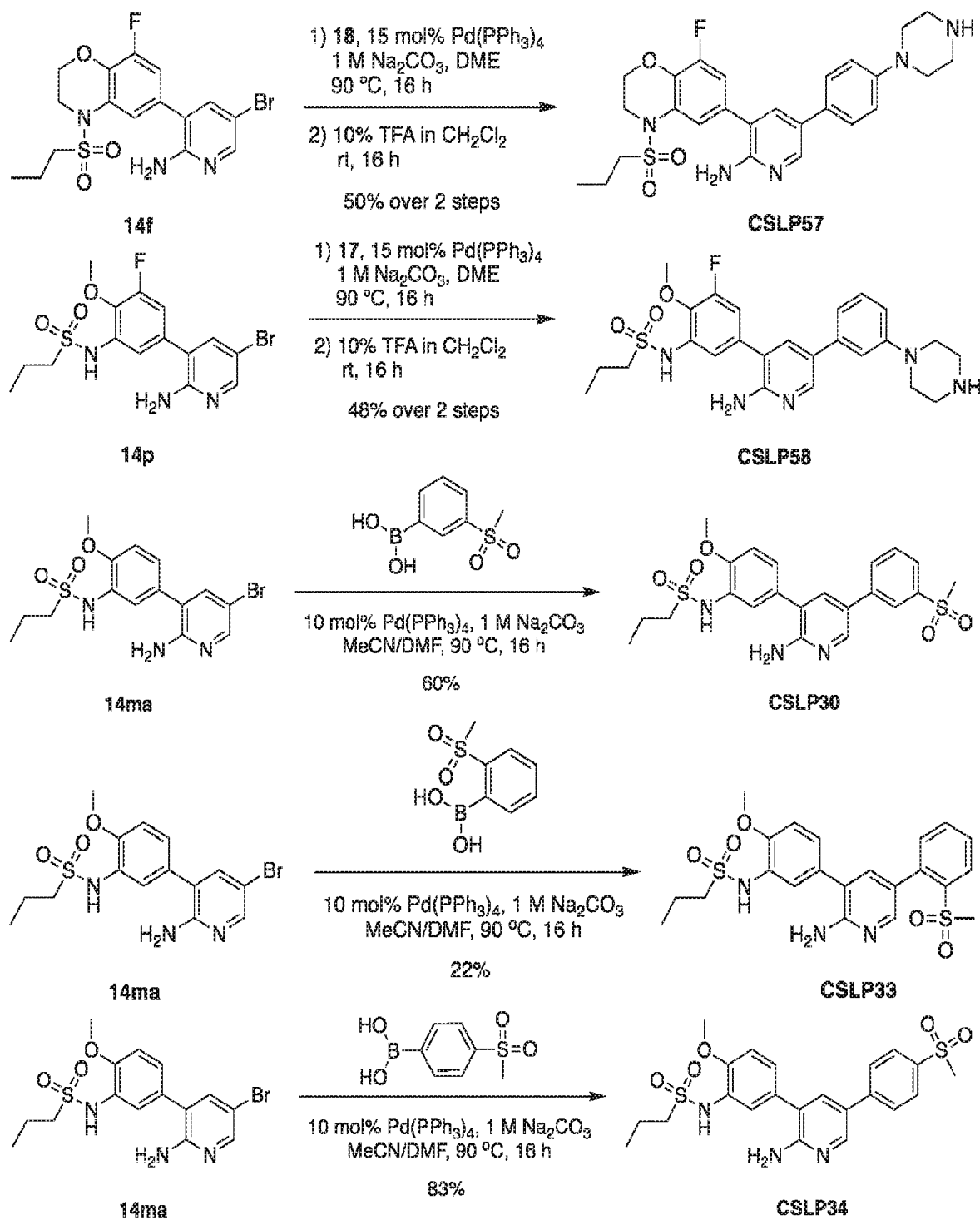
FIG. 48 shows steps in the synthesis of specific exemplary representative compounds described in Example 1 in accordance with preferred embodiments disclosed herein.
Figure 49:
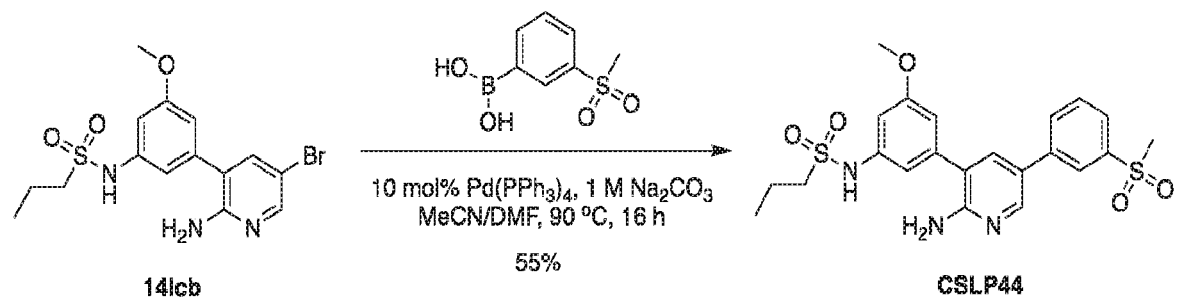
FIG. 49 shows steps in the synthesis of specific exemplary representative compounds described in Example 1 in accordance with preferred embodiments disclosed herein.

Compounds in the paragraphs below are referred to by compound number. Steps in the synthesis of each compound, as designated by compound number, are illustrated in FIGS. 10-49. For example, steps in the synthesis of 1-bromo-3-ethoxy-5-nitrobenzene (2aa), as well as compounds 2ab, 2b, 2ca, 2cb, and 2cc, are depicted in FIG. 10.

General Procedure for the Preparation of Bromo-alkoxy-5-nitrobenzenes; 1-bromo-3-ethoxy-5-nitrobenzene (2aa), Method A To a solution of 3-bromo-5-nitrophenol (1a) (100.0 mg, 0.46 mmol) and $K_2CO_3$ (126.7 mg, 0.92 mmol) in anhydrous DMF (2 mL) was added iodoethane (0.07 mL, 0.92 mmol) under argon. The resulting mixture was stirred at 60° C. for 2 h. After being quenched with $H_2O$ (5 mL), the aqueous layer was extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 2.5:97.5 to 10:90) to afford 2aa (111 mg, 98%) as a pale yellow solid; $^1H$ NMR ($CDCl_3$, 500 MHz) 7.92 (1H, s), 7.64 (1H, s), 7.33 (1H, s), 4.09 (1H, q, J=7.4 Hz), 1.44 (1H, t, J=6.9 Hz); $^{13}C$ NMR ($CDCl_3$, 125 MHz) 159.9, 149.4, 124.2, 122.9, 118.6, 108.1, 64.7, 14.4.

1-Bromo-3-isopropoxy-5-nitrobenzene (2ab)

Method A; purified by column chromatography on silica gel (EtOAc/hexane, 2.5:97.5 to 5:95) to give 2ab (98%) as a yellow oil; $^1H$ NMR ($CDCl_3$, 400 MHz) 7.90 (1H, t, J=1.4 Hz), 7.63 (1H, t, J=2.3 Hz), 7.32 (1H, t, J=1.4 Hz), 4.61 (1H, sep, J=6.0 Hz), 1.36 (6H, d, J=6.0 Hz); $^{13}C$ NMR ($CDCl_3$, 100 MHz) 158.9, 149.4, 125.2, 122.9, 118.4, 109.1, 71.4, 21.6.

5-Bromo-1-chloro-2-methoxy-3-nitrobenzene (2b)

Method A; purified by column chromatography on silica gel (EtOAc/hexane, 2.5:97.5 to 5:95) to give 2b (89%) as a yellow solid; $^1H$ NMR ($CDCl_3$, 600 MHz) 7.85 (1H, d, J=2.8 Hz), 7.77 (1H, d, J=2.8 Hz), 4.02 (3H, s); $^{13}C$ NMR ($CDCl_3$, 100 MHz) 149.1, 145.5, 137.1, 131.7, 126.4, 116.1, 62.6.

5-Bromo-1,2-dimethoxy-3-nitrobenzene (2ca)

Method A; purified by column chromatography on silica gel (EtOAc/hexane, 5:95 to 10:90) to give 2ca (98%) as a yellow solid; $^1H$ NMR ($CDCl_3$, 400 MHz) 7.46 (1H, d, J=2.3 Hz), 7.20 (1H, d, J=2.3 Hz), 3.95 (3H, s), 3.92 (3H, s); $^{13}C$ NMR ($CDCl_3$, 100 MHz) 154.7, 145.1, 142.1, 119.2, 118.6, 115.7, 62.0, 56.7.

5-Bromo-1,2-diethoxy-3-nitrobenzene (2cb)

Method A; purified by column chromatography on silica gel (EtOAc/hexane, 5:95) to give 2cb (57%) as a yellow oil; $^1H$ NMR ($CDCl_3$, 600 MHz) 7.42 (1H, d, J=2.1 Hz), 7.16 (1H, d, J=2.1 Hz), 4.19 (2H, q, J=7.6 Hz), 4.08 (2H, q, J=6.9 Hz), 1.48 (3H, t, J=6.9 Hz), 1.38 (3H, t, J=6.9 Hz); $^{13}C$ NMR ($CDCl_3$, 150 MHz) 154.2, 145.4, 141.5, 119.9, 118.4, 115.3, 70.6, 65.4, 15.3, 14.6.

7-Bromo-5-nitro-2,3-dihydrobenzo[b][1,4]dioxine (2cc)

To a solution of 5-bromo-3-nitrobenzene-1,2-diol (1c) (60.0 mg, 0.26 mmol) and $K_2CO_3$ (106.1 mg, 0.77 mmol) in anhydrous DMF (2 mL) was added 1,2-dibromoethane (0.03 mL, 0.31 mmol) under argon. The resulting mixture was stirred at 110° C. for 1 h. After being quenched with $H_2O$ (5 mL), the aqueous layer was extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 10:90) to afford 2cc (38.6 mg, 58%) as a yellow solid; $^1H$ NMR ($CDCl_3$, 500 MHz) 7.61 (1H, d, J=2.3 Hz), 7.24 (1H, d, J=2.3 Hz), 4.40-4.38 (2H, m), 4.36-4.34 (2H, m); $^{13}C$ NMR ($CDCl_3$, 125 MHz) 145.6, 139.2, 138.2, 124.8, 120.4, 111.5, 64.7, 63.9.

5-Bromo-1-ethoxy-2-methoxy-3-nitrobenzene (2d)

To a solution of 4-bromo-2-ethoxy-1-methoxybenzene (1d) (100.0 mg, 0.43 mmol) in diethyl ether (4.0 mL) was added fuming nitric acid (0.15 mL, 2.16 mmol) dropwise. The reaction mixture was stirred room temperature for 10 min then refluxed for 8 h. After being quenched with saturated aqueous $NaHCO_3$ (5 mL), the aqueous layer was extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 5:95) to afford 2d (104.5 mg, 87%) as a yellow solid; $^1H$ NMR ($CDCl_3$, 500 MHz) 7.55 (1H, s), 7.09 (1H, s), 4.16 (1H, q, J=6.9 Hz), 3.92 (3H, s), 1.50 (1H, t, J=6.9 Hz); $^{13}C$ NMR ($CDCl_3$, 125 MHz) 152.2, 148.2, 141.4, 117.1, 109.0, 107.4, 65.3, 56.4, 14.4.

General Procedure for the Preparation of Bromo-5-alkoxyanilines; 3-Bromo-5-ethoxyaniline (3aa), Method B To a solution of 2aa (96.9 mg, 0.39 mmol) and $NH_4Cl$ (109.5 mg, 2.05 mmol) in a mixture of $EtOH/H_2O$ (5:1, 5 mL) was added iron (Fe) powder (110 mg) and vigorously stirred at 85° C. for 1 h. After the mixture was allowed to cool to room temperature, the solid was removed by filtration through a Celite pad, and the filtrate was concentrated. The residue was purified by column chromatography (EtOAc/hexane, 10:90) to afford 3aa (80.4 mg, 94%) as a yellow solid; $^1H$ NMR ($CDCl_3$, 500 MHz) 6.45 (1H, s), 6.42 (1H, s), 6.12, 6.11 (1H, t, J=2.3 Hz), 3.94 (2H, q, J=6.9 Hz), 3.70 (2H, br), 1.37 (3H, t, J=6.9 Hz); $^{13}C$ NMR ($CDCl_3$, 125 MHz) 160.5, 148.5, 123.2, 110.7, 107.8, 100.2, 63.5, 14.7.

3-Bromo-5-isopropoxyaniline (3ab)

Method B; purified by column chromatography on silica gel (EtOAc/hexane, 5:95 to 10:90) to give 3ab (90%) as a yellow oil; $^1$H NMR (CDCl$_3$, 500 MHz) 6.45 (1H, t, J=1.7 Hz), 6.41 (1H, t, J=1.7 Hz), 6.12 (1H, t, J=1.7 Hz), 4.45 (1H, sep, J=6.3 Hz), 3.69 (2H, br), 1.30 (6H, d, J=6.3 Hz); $^{13}$C NMR (CDCl$_3$, 125 MHz) 159.5, 148.5, 123.2, 110.6, 109.0, 101.6, 70.0, 22.0, 21.9.

5-Bromo-3-chloro-2-methoxyaniline (3b)

Method B; purified by column chromatography on silica gel (EtOAc/hexane, 2:98) to give 3b (92%) as a yellow oil; $^1$H NMR (CDCl$_3$, 400 MHz) 6.86 (1H, s), 6.75 (1H, s), 3.99 (2H, br), 3.81 (3H, s); $^{13}$C NMR (CDCl$_3$, 100 MHz) 142.3, 142.1, 128.4, 121.4, 116.9, 116.8, 59.6.

5-Bromo-2,3-dimethoxyaniline (3ca)

Method B; purified by column chromatography on silica gel (EtOAc/hexane, 10:90) to give 3ca (95%) as a yellow oil; $^1$H NMR (CDCl$_3$, 400 MHz) 6.52 (1H, d, J=1.8 Hz), 6.44 (1H, d, J=1.8 Hz), 3.88 (2H, br), 3.81 (3H, s), 3.78 (3H, s); $^{13}$C NMR (CDCl$_3$, 100 MHz) 153.3, 141.6, 134.6, 116.6, 111.4, 105.6, 59.8, 55.8.

5-Bromo-2,3-diethoxyaniline (3cb)

Method B; purified by column chromatography on silica gel (EtOAc/hexane, 10:90) to give 3cb (96%) as a yellow oil; $^1$H NMR (CDCl$_3$, 500 MHz) 6.51 (1H, d, J=2.3 Hz), 6.43 (1H, d, J=2.3 Hz), 4.05-3.98 (4H, m), 3.87 (2H, br), 1.41 (3H, t, J=6.9 Hz), 1.35 (3H, t, J=6.9 Hz); $^{13}$C NMR (CDCl$_3$, 125 MHz) 152.7, 141.9, 133.9, 116.2, 111.2, 106.6, 68.0, 64.2, 15.7, 14.8.

7-Bromo-2,3-dihydrobenzo[b][1,4]dioxin-5-amine (3cc)

Method B; purified by column chromatography on silica gel (EtOAc/hexane, 10:90 to 20:80) to give 3cc (93%) as a yellow oil; $^1$H NMR (CDCl$_3$, 500 MHz) 6.46 (1H, d, J=2.3 Hz), 6.44 (1H, d, J=2.3 Hz), 4.27-4.25 (2H, m), 4.24-4.22 (2H, m), 3.79 (2H, br); $^{13}$C NMR (CDCl$_3$, 125 MHz) 144.2, 137.2, 130.4, 112.8, 110.5, 110.0, 64.4, 64.2.

5-Bromo-3-ethoxy-2-methoxyaniline (3d)

Method B; purified by column chromatography on silica gel (EtOAc/hexane, 10:90 to 15:85) to give 3d (94%) as a yellow oil; $^1$H NMR (CDCl$_3$, 500 MHz) 6.90 (1H, s), 6.34 (1H, s), 3.95 (2H, q, J=6.9 Hz), 3.76 (5H, s), 1.38 (3H, t, J=6.9 Hz); $^{13}$C NMR (CDCl$_3$, 125 MHz) 149.8, 141.3, 138.1, 117.7, 100.5, 98.4, 65.3, 55.8, 14.7.

5-Bromo-3-chloro-2-methylaniline (3s)

Method B; purified by column chromatography on silica gel (EtOAc/hexane, 5:95) to give 3s (98%) as a yellow oil; $^1$H NMR (CDCl$_3$, 400 MHz) 6.94 (1H, d, J=1.8 Hz), 6.70 (1H, s), 3.76 (2H, br), 2.14 (3H, s); $^{13}$C NMR (CDCl$_3$, 100 MHz) 146.7, 135.4, 121.5, 119.3, 119.0, 115.9, 12.4.

5-Bromo-3-fluoro-2-methylaniline (3t)

Method B; purified by column chromatography on silica gel (EtOAc/hexane, 5:95) to give 3t (88%) as a brown oil; $^1$H NMR (CDCl$_3$, 400 MHz) 6.63 (1H, dd, J=8.9, 1.4 Hz), 6.59 (1H, s), 1.99 (3H, d, J=1.4 Hz); $^{13}$C NMR (CDCl$_3$, 100 MHz) 162.5, 160.1, 147.2 (d, $J_{CF}$=7.8 Hz), 119.0 (d, $J_{CF}$=13.7 Hz), 113.1, 108.4 (d, $J_{CF}$=27.4 Hz), 108.1, 8.2 (d, $J_{CF}$=5.9 Hz).

5-Bromo-2,3-dimethylaniline (3u)

Method B; purified by column chromatography on silica gel (EtOAc/hexane, 10:90) to give 3u (93%) as a yellow oil; $^1$H NMR (CDCl$_3$, 500 MHz) 6.77 (1H, s), 6.70 (1H, s), 3.62 (2H, br), 2.24 (3H, s), 2.01 (3H, s); $^{13}$C NMR (CDCl$_3$, 125 MHz) 145.7, 138.9, 122.9, 119.5, 119.0, 115.4, 20.2, 13.4.

General Procedure for the Preparation of 6-Bromo-3,4-dihydro-2H-benzo[b][1,4]oxazine; 6-Bromo-3,4-dihydro-2H-benzo[b][1,4]oxazine (3e); Method C To a solution of 2-amino-4-bromophenol (4e) (200.0 mg, 1.06 mmol) and K$_2$CO$_3$ (735.3 mg, 5.32 mmol) in anhydrous DMF (3 mL) was added 1,2-dibromoethane (0.14 mL, 1.60 mmol) under argon. The resulting mixture was stirred at 125° C. for 15 h. After being quenched with H$_2$O (5 mL), the aqueous layer was extracted with EtOAc (2×15 mL). The combined organic extracts were washed with brine, dried over anhydrous Na$_2$SO$_4$, filtered, and concentrated. The residue was purified by column chromatography on silica gel (EtOAc/hexane, 10:90 to 20:80) to afford 3e (44.0 mg, 19%) as a brown oil; $^1$H NMR (CDCl$_3$, 400 MHz) 6.74-6.69 (2H, m), 6.64 (1H, d, J=8.7 Hz), 4.22-4.20 (2H, m), 3.89 (2H, br), 3.04-3.38 (2H, m); $^{13}$C NMR (CDCl$_3$, 100 MHz) 142.9, 135.0, 121.0, 118.0, 117.6, 113.1, 64.9, 40.5.

6-Bromo-8-fluoro-3,4-dihydro-2H-benzo[b][1,4]oxazine (3f)

Method C; purified by column chromatography on silica gel (EtOAc/hexane, 10:90 to 20:80) to give 3f (24%) as a brown oil; $^1$H NMR (CDCl$_3$, 600 MHz) 6.61 (1H, dd, J=10.0, 2.1 Hz), 6.50 (1H, t, J=2.1 Hz), 4.27 (2H, t, J=4.1 Hz), 3.97 (1H, br), 3.44 (2H, t, J=4.1 Hz); $^{13}$C NMR (CDCl$_3$, 150 MHz) 151.6 (d, $J_{CF}$=246.9 Hz), 136.4 (d, $J_{CF}$=4.4 Hz), 131.2 (d, $J_{CF}$=13.3 Hz), 113.1 (d, $J_{CF}$=3.0 Hz), 111.7 (d, $J_{CF}$=11.8 Hz), 108.9 (d, $J_{CF}$=22.2 Hz), 65.1, 40.4.

2-(5-Bromo-3-methoxy-2-methylphenyl)isoindoline-1,3-dione (7)

To a solution of 5-bromo-3-methoxy-2-methylaniline (3h) (102.0 mg, 0.47 mmol) in acetic acid (5 mL) was added phthalic anhydride (69.9 mg, 0.92 mmol). The resulting mixture was refluxed for 3 h. After being quenched with saturated aqueous NaHCO$_3$ to pH 7, the aqueous layer was extracted with EtOAc (2×15 mL). The combined organic extracts were washed with brine, dried over anhydrous Na$_2$SO$_4$, filtered, and concentrated yielding the product 7 (155.3 mg, 95%) as a light brown solid; $^1$H NMR (CDCl$_3$, 400 MHz) 7.97-7.93 (2H, m), 7.82-7.78 (2H, m), 7.24 (1H, d, J=2.8 Hz), 6.74 (1H, d, J=2.8 Hz), 3.78 (3H, s), 2.16 (3H, s); $^{13}$C NMR (CDCl$_3$, 100 MHz) 166.9, 158.0, 134.5, 131.7, 128.6, 126.1, 123.9, 119.5, 114.1, 55.6, 17.7.

2-(5-Bromo-3-hydroxy-2-methylphenyl)isoindoline-1,3-dione (8)

To a solution of 7 (117.5 mg, 0.34 mmol) in anhydrous CH$_2$Cl$_2$ (12 mL) was added 1 M BBr$_3$ in CH$_2$Cl$_2$ (1.29 mL, 1.29 mmol) dropwise under argon at 0° C. The temperature was slowly increased to room temperature and the reaction was stirred for 16 h. After being quenched with ice-water, the aqueous layer was extracted with $CH_2Cl_2$ (2×20 mL). The combined organic extracts were washed with brine, dried over anhydrous $Na_2SO_4$, filtered, and concentrated. The residue was purified by column chromatography on silica gel (EtOAc/hexane, 20:80) to afford 8 (96.1 mg, 85%) as a pale yellow solid; $^1H$ NMR ($CD_3OD$, 500 MHz) 7.96-7.93 (2H, m), 7.89-7.86 (2H, m), 7.15 (1H, d, J=2.3 Hz), 6.70 (1H, d, J=2.3 Hz), 2.09 (3H, s); $^{13}C$ NMR ($CD_3OD$, 125 MHz) 168.5, 157.6, 135.9, 133.6, 133.2, 128.1, 126.4 121.5, 116.9, 17.7.

2-(5-Bromo-3-ethoxy-2-methylphenyl)isoindoline-1,3-dione (9)

Method A; purified by column chromatography on silica gel (EtOAc/hexane, 15:85) to give 9 (91%) as a yellow oil; $^1H$ NMR ($CDCl_3$, 500 MHz) 7.97-7.93 (2H, m), 7.82-7.78 (2H, m), 7.24 (1H, d, J=2.9 Hz), 6.72 (1H, d, J=2.9 Hz), 3.99 (2H, q, J=6.9 Hz), 2.16 (3H, s), 1.39 (3H, t, J=6.9 Hz); $^{13}C$ NMR ($CDCl_3$, 125 MHz) 166.9, 157.4, 134.5, 131.7, 131.6, 128.4, 126.1, 123.9, 120.0, 114.6, 64.0, 17.7, 14.6.

5-Bromo-3-ethoxy-2-methylaniline (3i)

To a solution of 9 (39.0 mg, 0.11 mmol) in mixture of acetonitrile (2.0 mL) and $H_2O$ (0.7 mL) was added hydrazine hydrate (0.07 mL, 1.08 mmol). The reaction mixture was stirred room temperature for 2 h. The reaction was diluted and extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 10:90) to afford 3i (23.3 mg, 94%) as a yellow solid; $^1H$ NMR ($CDCl_3$, 500 MHz) 6.58 (1H, d, J=2.3 Hz), 6.19 (1H, d, J=2.9 Hz), 3.94 (2H, q, J=6.9 Hz), 3.70 (2H, br), 2.19 (3H, s), 1.37 (3H, t, J=6.9 Hz); $^{13}C$ NMR ($CDCl_3$, 125 MHz) 157.8, 146.1, 125.7, 114.4, 108.7, 101.0, 63.5, 16.0, 14.8.

General Procedure for the Preparation of N-(Bromophenyl)alkylsulfonamides; N-(3-bromo-5-ethoxyphenyl)propane-2-sulfonamide (6aa), Method D To a solution of 3aa (62 mg, 0.29 mmol) and a catalytic amount of DMAP in anhydrous $CH_2Cl_2$ (2 mL) was added pyridine (0.05 mL, 0.58 mmol) and 2-propanesulfonyl chloride (0.07 mL, 0.58 mmol) under argon, and the mixture was stirred at room temperature for 40 h. After being quenched with 1 N $HCl_{(aq)}$ (0.5 mL) and water, $CH_2Cl_2$ were added, and the layers were separated. The combined organic phases were washed with brine, dried over anhydrous $Na_2SO_4$, filtered, and concentrated. The residue was purified by column chromatography on silica gel (EtOAc/hexane, 5:95 to 10:90) to give 6aa (54.5 mg, 58%) as a yellow solid; $^1H$ NMR ($CDCl_3$, 500 MHz) 7.21 (1H, br), 6.95 (1H, s), 6.79 (1H, s), 6.76 (1H, s), 3.98 (2H, q, J=7.4 Hz), 3.35 (1H, sep, J=7.4 Hz), 1.40-1.37 (9H, m); $^{13}C$ NMR ($CDCl_3$, 125 MHz) 160.4, 139.3, 123.3, 114.4, 113.7, 104.9, 64.0, 52.7, 16.4, 14.6.

General Procedure for the Preparation of N-(Bromophenyl)alkylsulfonamides; N-(3-Bromo-5-isopropoxyphenyl)propane-2-sulfonamide (6ab), Method E To a solution of 3ab (108.5 mg, 0.47 mmol) in pyridine (2.5 mL) was added 2-propanesulfonyl chloride (0.08 mL, 0.71 mmol) under argon, and the mixture was stirred at room temperature for 40 h. After being quenched with 1 N $HCl_{(aq)}$ (1 mL) and water, EtOAc were added, and the layers were separated. The combined organic phases were washed with brine, dried over anhydrous $Na_2SO_4$, filtered, and concentrated. The residue was purified by column chromatography on silica gel (EtOAc/hexane, 10:90 to 15:85) to give 6ab (73.1 mg, 46%) as a yellow solid; $^1H$ NMR ($CDCl_3$, 500 MHz) 7.31 (1H, s), 6.94 (1H, t, J=1.7 Hz), 6.78 (1H, t, J=1.7 Hz), 6.75 (1H, t, J=1.7 Hz), 4.49 (1H, sep, J=5.7 Hz), 3.35(1H, sep, J=6.9 Hz), 1.39 (6H, d, J=6.9 Hz), 1.31 (6H, d, J=5.7 Hz); $^{13}C$ NMR ($CDCl_3$, 125 MHz) 159.4, 139.4, 123.3, 114.9, 114.3, 105.9, 70.5, 52.7, 21.8, 16.4.

N-(5-Bromo-3-chloro-2-methoxyphenyl)propane-1-sulfonamide (6b)

Method E; the mixture was stirred at room temperature for 24 h and purified by column chromatography on silica gel (EtOAc/hexane, 10:90 to 15:85) to give 6b (58%) as a yellow solid; $^1H$ NMR ($CDCl_3$, 500 MHz) 7.61 (1H, d, J=2.3 Hz), 7.25 (1H, d, J=2.3 Hz), 7.10 (1H, br), 3.90 (3H, s), 3.14-3.11 (2H, m), 1.88-1.83 (2H, m), 1.04 (3H, t, J=7.4 Hz); $^{13}C$ NMR ($CDCl_3$, 125 MHz) 144.1, 133.2, 128.4, 127.8, 119.4, 117.4, 61.2, 53.9, 17.2, 12.8.

N-(5-Bromo-2,3-dimethoxyphenyl)propane-1-sulfonamide (6ca)

Method E; purified by column chromatography on silica gel (EtOAc/hexane, 10:90 to 15:85) to give 6ca (85%) as a yellow solid; $^1H$ NMR ($CDCl_3$, 400 MHz) 7.33 (1H, d, J=1.8 Hz), 7.01 (1H, br), 6.80 (1H, d, J=2.3 Hz), 3.86 (3H, s), 3.10-3.06 (2H, m), 1.86-1.80 (2H, m), 1.02 (3H, t, J=7.3 Hz); $^{13}C$ NMR ($CDCl_3$, 100 MHz) 152.8, 136.6, 131.9, 116.8, 113.3, 111.3, 60.9, 56.0, 53.3, 17.1, 12.7.

General Procedure for the Preparation of N-(Bromophenyl)alkylsulfonamides; N-(5-Bromo-2,3-diethoxyphenyl)propane-1-sulfonamide (6cb), Method F To a solution of 3cb (48.0 mg, 0.18 mmol) and catalytic amount of DMAP in pyridine (1 mL) was added 1-propanesulfonyl chloride (0.03 mL, 0.28 mmol) under argon. The mixture was stirred at 50° C. for 6 h. After being quenched with 1 N $HCl_{(aq)}$ (1 mL) and water, EtOAc were added, and the layers were separated. The combined organic phases were washed with brine, dried over anhydrous $Na_2SO_4$, filtered, and concentrated. The residue was purified by column chromatography on silica gel (EtOAc/hexane, 10:90 to 15:85) to give 6cb (41.2 mg, 61%) as a yellow oil; $^1H$ NMR ($CDCl_3$, 400 MHz) 7.31 (1H, d, J=1.8 Hz), 6.96 (1H, br), 6.78 (1H, d, J=1.8 Hz), 4.13 (2H, q, J=7.3 Hz), 4.04 (2H, q, J=6.9 Hz), 3.10-3.06 (2H, m), 1.88-1.78 (2H, m), 1.45 (3H, t, J=6.9 Hz), 1.36 (3H, t, J=7.3 Hz), 1.02 (3H, t, J=7.3 Hz); $^{13}C$ NMR ($CDCl_3$, 100 MHz) 152.1, 135.5, 132.2, 116.7, 112.9, 112.1, 69.2, 64.6, 53.4, 17.2, 15.6, 14.7, 12.8.

N-(7-Bromo-2,3-dihydrobenzo[b][1,4]dioxin-5-yl)propane-1-sulfonamide (6cc)

Method E; the mixture was stirred at room temperature for 16 h and purified by column chromatography on silica gel (EtOAc/hexane, 10:90 to 20:80) to give 6cc (80%) as a yellow oil; $^1H$ NMR ($CDCl_3$, 400 MHz) 7.25 (1H, d, J=2.3 Hz), 6.82 (1H, d, J=1.8 Hz), 6.67 (1 H br), 4.31-4.29 (2H, m), 4.28-4.26 (2H, m), 3.10-3.06 (2H, m), 1.88-1.79 (2H, m), 1.03 (3H, t, J=7.8 Hz); $^{13}$C NMR (CDCl$_3$, 100 MHz) 144.2, 132.3, 127.3, 116.0, 114.3, 113.2, 64.6, 64.2, 53.4, 17.2, 12.8.

N-(5-Bromo-3-ethoxy-2-methoxyphenyl)propane-1-sulfonamide (6d)

Method E; the mixture was stirred at room temperature for 16 h and purified by column chromatography on silica gel (EtOAc/hexane, 15:85) to give 6d (87%) as a pale yellow solid; $^1$H NMR (CDCl$_3$, 400 MHz) 7.22 (1H, s), 6.98 (1H, s), 6.51 (1H, s), 4.04 (2H, q, J=7.3 Hz), 3.84 (3H, s), 3.01-2.97 (2H, m), 1.88-1.78 (2H, m), 1.44 (3H, t, J=6.9 Hz), 0.99 (3H, t, J=7.3 Hz); $^{13}$C NMR (CDCl$_3$, 100 MHz) 149.3, 146.8, 127.7, 115.8, 107.6, 105.9, 64.8, 56.1, 53.6, 17.1, 14.6, 12.9.

6-Bromo-4-(propylsulfonyl)-3,4-dihydro-2H-benzo[b][1,4]oxazine (6e)

To a solution of 3e (44.0 mg, 0.22 mmol) in pyridine (1 mL) was added 1-propanesulfonyl chloride (0.04 mL, 0.33 mmol) under argon, and the mixture was stirred at 50° C. for 2.5 h. After being quenched with 1 N HCl$_{(aq)}$ (1.0 mL) and water, EtOAc were added, and the layers were separated. The combined organic phases were washed with brine, dried over anhydrous Na$_2$SO$_4$, filtered, and concentrated. The residue was purified by column chromatography on silica gel (EtOAc/hexane, 10:90 to 20:80) to give 6e (49.6 mg, 70%) as a brown solid; $^1$H NMR (CDCl$_3$, 500 MHz) 7.76 (1H, d, J=2.3 Hz), 7.13 (1H, dd, J=8.6, 2.3 Hz), 6.79 (1H, d, J=8.6 Hz), 4.26 (2H, t, J=4.6 Hz), 3.85 (2H, t, J=4.6 Hz), 3.09-3.06 (2H, m), 1.92-1.85 (2H, m), 1.06 (3H, t, J=7.4 Hz); $^{13}$C NMR (CDCl$_3$, 125 MHz) 145.0, 128.1, 125.6, 124.3, 119.2, 113.0, 64.7, 54.0, 44.0, 17.0, 12.9.

6-Bromo-8-fluoro-4-(propylsulfonyl)-3,4-dihydro-2H-benzo[b][1,4]oxazine (6f)

To a solution of 3f (55.1 mg, 0.24 mmol) and catalytic amount of DMAP in anhydrous CH$_2$Cl$_2$ (2 mL) was added 1-propanesulfonyl chloride (0.04 mL, 0.36 mmol) and triethylamine (0.05 mL, 0.35 mmol) under argon, and the mixture was stirred at room temperature for 6 h. After being quenched with water, CH$_2$Cl$_2$ were added, and the layers were separated. The combined organic phases were washed with brine, dried over anhydrous Na$_2$SO$_4$, filtered, and concentrated. The residue was purified by column chromatography on silica gel (EtOAc/hexane, 10:90 to 15:85) to give 6f (46.0 mg, 50%) as a pale yellow solid; $^1$H NMR (CDCl$_3$, 400 MHz) 7.58 (1H, t, J=2.3 Hz), 7.04 (1H, dd, J=9.6, 2.3 Hz), 4.33 (2H, t, J=4.6 Hz), 3.89 (2H, t, J=4.6 Hz), 3.12-3.08 (2H, m), 1.94-1.84 (2H, m), 1.07 (3H, t, J=7.3 Hz); $^{13}$C NMR (CDCl$_3$, 100 MHz) 151.7 (d, J$_{CF}$=249.4 Hz), 134.2 (d, J$_{CF}$=12.7 Hz), 127.2 (d, J$_{CF}$=3.9 Hz), 119.5 (d, J$_{CF}$=3.9 Hz), 115.3 (d, J$_{CF}$=21.5 Hz), 111.5 (d, J$_{CF}$=10.8 Hz), 65.0, 54.2, 44.0, 17.0, 12.9.

N-(5-Bromo-3-methoxy-2-methylphenyl)propane-1-sulfonamide (6ha)

Method D; purified by column chromatography on silica gel (EtOAc/hexane, 10:90) to give 6ha (78%) as a yellow oil; $^1$H NMR (CDCl$_3$, 400 MHz) 7.05 (1H, d, J=2.8 Hz), 6.97 (1H, d, J=2.8 Hz), 6.71 (1H, br), 3.76 (3H, s), 3.09-3.05 (2H, m), 2.33 (3H, s), 1.86-1.81 (2H, m), 1.02 (3H, t, J=7.8 Hz); $^{13}$C NMR (CDCl$_3$, 100 MHz) 158.2, 136.2, 125.9, 121.6, 115.2, 107.9, 55.6, 53.8, 17.2, 17.1, 12.8.

N-(5-Bromo-3-methoxy-2-methylphenyl)methanesulfonamide (6hb)

Method D; purified by column chromatography on silica gel (EtOAc/hexane, 15:85 to 20:80) to give 6hb (85%) as a white solid; $^1$H NMR (CDCl$_3$, 400 MHz) 7.04 (1H, d, J=2.8 Hz), 7.02 (1H, d, J=2.8 Hz), 6.50 (1H, br), 3.78 (3H, s), 3.02(3H, s), 2.34 (3H, s); $^{13}$C NMR (CDCl$_3$, 100 MHz) 158.3, 135.9, 126.0, 122.2, 115.9, 108.6, 55.6, 39.9, 17.2.

N-(5-Bromo-3-methoxy-2-methylphenyl)propane-2-sulfonamide (6hc)

Method D; the mixture was stirred at room temperature for 24 h and purified by column chromatography on silica gel (EtOAc/hexane, 20:80) to give 6hc (46%) as a pale yellow solid; $^1$H NMR (CDCl$_3$, 400 MHz) 7.12 (1H, d, J=2.3 Hz), 6.94 (1H, d, J=2.3 Hz), 6.56 (1H, br), 3.76 (3H, s), 3.34 (1H, sep, J=6.9 Hz), 2.34 (3H, s), 1.38 (6H, d, J=6.9 Hz); $^{13}$C NMR (CDCl$_3$, 100 MHz) 158.2, 136.7, 125.9, 120.6, 114.7, 106.9, 55.5, 53.1, 17.0, 16.5.

N-(5-Bromo-3-methoxy-2-methylphenyl)-1-phenylmethanesulfonamide (6hd)

Method D; purified by column chromatography on silica gel (EtOAc/hexane, 10:90 to 20:80) to give 6hd (57%) as a yellow solid; $^1$H NMR (CDCl$_3$, 400 MHz) 7.39-7.31 (3H, m), 7.20 (2H, dd, J=8.0, 1.8 Hz), 7.12 (1H, d, J=2.3 Hz), 6.96 (1H, d, J=2.8 Hz), 6.20 (1H, s), 4.38 (2H, s), 3.77 (3H, s), 2.10 (3H, s); $^{13}$C NMR (CDCl$_3$, 100 MHz) 158.4, 136.6, 130.6, 129.1, 128.9, 128.1, 125.9, 119.7, 114.6, 105.4, 57.6, 55.6, 16.5.

N-(5-Bromo-3-ethoxy-2-methylphenyl)-1-phenylmethanesulfonamide (6i)

Method E; the mixture was stirred at room temperature for 16 h and purified by column chromatography on silica gel (EtOAc/hexane, 10:90) to give 6i (90%) as a yellow oil; $^1$H NMR (CDCl$_3$, 400 MHz) 7.37-7.31 (3H, m), 7.20 (2H, d, J=7.8, 1.4 Hz), 7.12 (1H, d, J=2.3 Hz), 6.96 (1H, d, J=2.8 Hz), 6.22 (1H, br), 4.38 (2H, s), 3.98 (2H, q, J=6.9 Hz), 2.00 (3H, s), 1.41 (3H, t, J=7.3 Hz); $^{13}$C NMR (CDCl$_3$, 100 MHz) 157.8, 136.5, 130.6, 129.0, 128.9, 128.2, 125.9, 119.6, 115.2, 105.9, 63.9, 57.6, 16.5, 14.6.

General Procedure for the Preparation of N-(Bromophenyl)alkylsulfonamides; N-(4-bromo-2-methoxyphenyl)propane-1-sulfonamide (6k), Method G To a solution of 3k (300 mg, 1.48 mmol) in anhydrous CH$_2$Cl$_2$ (15 mL) was added pyridine (0.24 mL, 2.97 mmol) and 1-propanesulfonyl chloride (0.18 mL, 1.63 mmol) under argon, and the mixture was stirred at room temperature for 16 h. After being quenched with 1 N HCl$_{(aq)}$ (1.0 mL), water, and CH$_2$Cl$_2$ were added, the layers were separated. The combined organic phases were washed with brine, dried over anhydrous Na$_2$SO$_4$, filtered, and concentrated. The residue was purified by column chromatography on silica gel (EtOAc/hexane, 10:90 to 15:85) to give 6k (490.1 mg, 99%) as a light yellow oil; $^1$H NMR (CDCl$_3$, 500 MHz) 7.41 (1H, d, J=8.6 Hz), 7.08 (1H, dd, J=8.3, 2.3 Hz), 7.03 (1H, d, J=2.5 Hz), 6.74 (1H, br), 3.88 (3H, s), 3.02-2.98 (2H, m), 1.83-1.79 (2H, m), 1.00 (3H, t, J=7.4 Hz); $^{13}$C NMR (CDCl$_3$, 125 MHz) 149.5, 125.5, 124.2, 121.0, 117.5, 114.3, 56.1, 53.1, 17.1, 12.8.

N-(3-Bromo-5-methoxyphenyl)methanesulfonamide (61a)

Method G; purified by column chromatography on silica gel (EtOAc/hexane, 10:90 to 20:80) to give 61a (82%) as a yellow solid; $^1$H NMR (CDCl$_3$, 400 MHz) 6.96-6.95 (2H, m), 6.86 (1H, s), 6.75-6.74 (1H, m), 3.79 (3H, s), 3.05 (3H, s); $^{13}$C NMR (CDCl$_3$, 100 MHz) 161.1, 137.8, 123.5, 115.1, 113.8, 105.0, 55.7, 39.5.

N-(3-Bromo-5-methoxyphenyl)ethanesulfonamide (61b)

Method G; purified by column chromatography on silica gel (EtOAc/hexane, 10:90 to 20:80) to give 61b (88%) as a yellow oil; $^1$H NMR (CDCl$_3$, 400 MHz) 7.34 (1H, br), 6.96 (1H, t, J=1.8 Hz), 6.82 (1H, t, J=1.8 Hz), 6.75 (1H, t, J=1.8 Hz), 3.78 (3H, s), 3.18 (2H, q, J=7.3 Hz), 1.36 (3H, t, J=7.3 Hz); $^{13}$C NMR (CDCl$_3$, 100 MHz) 161.0, 139.0, 123.4, 114.7, 113.5, 104.5, 55.6, 46.0, 8.1.

N-(3-Bromo-5-methoxyphenyl)propane-1-sulfonamide (61c)

Method G; purified by column chromatography on silica gel (EtOAc/hexane, 10:90 to 20:80) to give 61c (86%) as a yellow oil; $^1$H NMR (CDCl$_3$, 400 MHz) 7.34 (1H, br), 6.96 (1H, t, J=1.8 Hz), 6.82 (1H, t, J=1.8 Hz), 6.75 (1H, d, J=2.3 Hz), 3.78 (3H, s), 3.13-3.09 (2H, m), 1.90-1.79 (2H, m), 1.02 (3H, t, J=7.3 Hz); $^{13}$C NMR (CDCl$_3$, 100 MHz) 161.0, 139.0, 123.4, 114.6, 113.4, 104.5, 55.6, 53.3, 17.1, 12.8.

N-(3-Bromo-5-methoxyphenyl)propane-2-sulfonamide (61d)

Method D; purified by column chromatography on silica gel (EtOAc/hexane, 10:90 to 20:80) to give 61d (30%) as a yellow oil; $^1$H NMR (CDCl$_3$, 600 MHz) 7.12 (1H, br), 6.96 (1H, t, J=2.1 Hz), 6.81 (1H, t, J=2.1 Hz), 6.76 (1H, t, J=2.1 Hz), 3.78 (3H, s), 3.35 (1H, sep, J=6.9 Hz), 1.40 (6H, d, J=6.9 Hz); $^{13}$C NMR (CDCl$_3$, 150 MHz) 161.0, 139.4, 123.4, 114.6, 113.3, 104.5, 55.6, 52.8, 16.4.

N-(3-Bromo-5-methoxyphenyl)cyclopropanesulfonamide (61e)

Method G; purified by column chromatography on silica gel (EtOAc/hexane, 10:90 to 15:85) to give 61e (84%) as a brown solid; $^1$H NMR (CDCl$_3$, 600 MHz) 7.21 (1H, br), 7.00 (1H, s), 6.84 (1H, s), 6.78 (1H, t, J=2.1 Hz), 3.78 (3H, s), 2.54 (1H, tt, J=8.2, 4.8 Hz), 1.21-1.85 (2H, m), 1.02-0.98 (2H, m); $^{13}$C NMR (CDCl$_3$, 150 MHz) 160.9, 139.0, 123.1, 116.0, 113.8, 105.7, 55.6, 29.9, 5.7.

N-(3-Bromo-5-methoxyphenyl)-2-methylpropane-1-sulfonamide (61f)

Method D; purified by column chromatography on silica gel (EtOAc/hexane, 10:90 to 15:85) to give 61f (54%) as a yellow oil; $^1$H NMR (CDCl$_3$, 400 MHz) 7.43 (1H, br), 6.95 (1H, s), 6.82-6.81 (1H, m), 6.74 (1H, d, J=1.8 Hz), 3.77 (3H, s), 3.02 (2H, d, J=6.4 Hz), 2.29 (1H, sep, J=6.9 Hz), 1.07 (6H, d, J=6.9 Hz); $^{13}$C NMR (CDCl$_3$, 100 MHz) 161.0, 139.1, 123.4, 114.7, 113.4, 104.4, 59.2, 55.6, 24.7, 22.4.

N-(3-Bromo-5-methoxyphenyl)benzenesulfonamide (61g)

Method D; purified by column chromatography on silica gel (EtOAc/hexane, 10:90 to 15:85) to give 61g (79%) as a light brown solid; $^1$H NMR (CDCl$_3$, 400 MHz) 7.83 (2H, d, J=7.3 Hz), 7.57 (1H, t, J=7.8 Hz), 7.48 (2H, t, J=7.8 Hz), 7.14 (1H, br), 6.81 (1H, s), 6.77 (1H, s), 6.64 (1H, t, J=1.8 Hz), 3.71 (3H, s); $^{13}$C NMR (CDCl$_3$, 100 MHz) 160.7, 138.5, 138.5, 133.4, 129.2, 127.2, 123.0, 115.9, 113.9, 105.5, 55.6.

N-(3-Bromo-5-methoxyphenyl)-1-phenylmethanesulfonamide (61h)

Method D; purified by column chromatography on silica gel (EtOAc/hexane, 10:90 to 15:85) to give 61h (85%) as a brown solid; $^1$H NMR (CDCl$_3$, 500 MHz) 7.35-7.31 (3H, m), 7.24-7.22 (2H, m), 6.93 (1H, br), 6.83-6.82 (2H, m), 6.63 (1H, t, J=1.7 Hz), 4.32 (2H, s), 3.76 (3H, s); $^{13}$C NMR (CDCl$_3$, 125 MHz) 161.0, 139.1, 130.8, 129.1, 128.9, 128.0, 123.4, 114.4, 113.4, 104.1, 57.7, 55.6.

N-(5-Bromo-2-methoxyphenyl)propane-1-sulfonamide (6ma)

Method D; the mixture was stirred at room temperature for 48 h and purified by column chromatography on silica gel (EtOAc/hexane, 20:80 to 30:70) to give 6ma (85%) as a yellow solid; $^1$H NMR (CDCl$_3$, 500 MHz) 7.65 (1H, d, J=2.3 Hz), 7.18 (1H, dd, J=8.6, 2.3 Hz), 6.86 (1H, br), 6.76 (1H, d, J=8.6 Hz), 3.86 (3H, s), 3.05-3.02 (2H, m), 1.83-1.79 (2H, m), 1.00 (3H, t, J=7.4 Hz); $^{13}$C NMR (CDCl$_3$, 125 MHz) 147.7, 127.6, 127.3, 122.0, 113.3, 112.0, 56.0, 53.2, 17.1, 12.7.

N-(5-Bromo-2-methoxyphenyl)propane-2-sulfonamide (6mb)

Method E; purified by column chromatography on silica gel (EtOAc/hexane, 5:95 to 15:85) to give 6mb (28%) as a brown solid; $^1$H NMR (CDCl$_3$, 500 MHz) 7.70 (1H, d, J=2.3 Hz), 7.17 (1H, dd, J=8.6, 2.3 Hz), 6.78 (1H, br), 6.75 (1H, d, J=8.6 Hz), 3.87 (3H, s), 3.26 (1H, sep, J=6.9 Hz), 1.37 (6H, d, J=6.9 Hz); $^{13}$C NMR (CDCl$_3$, 125 MHz) 147.4, 128.0, 127.0, 121.7, 113.5, 112.0, 56.0, 52.6, 16.4.

N-(5-Bromo-2-methylphenyl)propane-1-sulfonamide (6n)

Method D; purified by column chromatography on silica gel (EtOAc/hexane, 10:90 to 15:85) to give 6n (96%) as a white solid; $^1$H NMR (CDCl$_3$, 500 MHz) 7.64 (1H, d, J=2.3 Hz), 7.22 (1H, dd, J=8.0, 1.7 Hz), 7.07 (1H, d, J=8.0 Hz), 6.42 (1H, br), 3.13-3.10 (2H, m), 2.25 (3H, s), 1.90-1.82 (2H, m), 1.05 (3H, t, J=7.4 Hz); $^{13}$C NMR (CDCl$_3$, 125 MHz) 136.3, 132.3, 128.2, 127.7, 123.8, 120.3, 54.0, 17.6, 17.2, 12.9.

N-(5-Bromo-2-methoxybenzyl)propane-1-sulfonamide (6o)

Method D; purified by column chromatography on silica gel (EtOAc/hexane, 10:90 to 15:85) to give 6o (57%) as a clear oil; ${}^1$H NMR (CDCl$_3$, 500 MHz) 7.39-7.38 (2H, m), 6.77-675 (1H, m), 5.06 (1H, br), 4.22 (2H, d, J=6.3 Hz), 3.83 (3H, s), 2.84-2.81(2H, m), 1.72-1.65 (2H, m), 0.92 (3H, t, J=7.4 Hz); ${}^{13}$C NMR (CDCl$_3$, 125 MHz) 156.4, 132.1, 132.0, 127.4, 112.7, 112.0, 55.6, 54.8, 43.0, 17.2, 12.8.

N-(5-Bromo-3-fluoro-2-methoxyphenyl)propane-1-sulfonamide (6p)

Method E; the mixture was stirred at room temperature for 48 h and purified by column chromatography on silica gel (EtOAc/hexane, 10:90 to 15:85) to give 6p (76%) as a pale yellow solid; ${}^1$H NMR (CDCl$_3$, 400 MHz) 7.49 (1H, s), 7.04-7.00 (2H, m), 3.99 (3H, d, J=2.3 Hz), 3.12-3.08 (2H, m), 1.89-1.80 (2H, m), 1.04 (3H, t, J=7.3 Hz); ${}^{13}$C NMR (CDCl$_3$, 100 MHz) 154.6 (d, $J_{CF}$=251.4 Hz), 135.7 (d, $J_{CF}$=12.7 Hz), 132.1 (d, $J_{CF}$=5.9 Hz), 116.7 (d, $J_{CF}$=2.9 Hz), 115.7 (d, $J_{CF}$=22.5 Hz), 115.4 (d, $J_{CF}$=10.8 Hz), 61.6 (d, $J_{CF}$=6.8 Hz), 53.6, 17.2, 12.8.

N-(3-Bromo-5-fluorophenyl)propane-1-sulfonamide (6q)

Method D; purified by column chromatography on silica gel (EtOAc/hexane, 10:90 to 15:85) to give 6q (92%) as a pale yellow solid; ${}^1$H NMR (CDCl$_3$, 400 MHz) 7.64 (1H, br), 7.14 (1H, s), 7.02-6.97 (2H, m), 3.15 (2H, m), 1.86 (2H, sex, J=7.8 Hz), 1.04 (3H, t, J=7.3 Hz); ${}^{13}$C NMR (CDCl$_3$, 100 MHz) 163.0 (d, $J_{CF}$=251.4 Hz), 139.5 (d, $J_{CF}$=11.7 Hz), 123.3 (d, $J_{CF}$=10.8 Hz), 117.8 (d, $J_{CF}$=2.9 Hz), 115.1 (d, $J_{CF}$=24.4 Hz), 105.4 (d, $J_{CF}$=26.4 Hz), 53.7, 17.1, 12.8.

N-(3-Bromo-5-chlorophenyl)propane-1-sulfonamide (6r)

Method E; the mixture was stirred at room temperature for 48 h and purified by column chromatography on silica gel (EtOAc/hexane, 5:95 to 10:90) to give 6r (48%) as a yellow solid; 41 NMR (CDCl$_3$, 500 MHz) 7.57 (1H, d, J=3.4 Hz), 7.56 (1H, d, J=3.4 Hz), 7.40 (1H, dd, J=9.2, 2.3 Hz), 6.79 (1H, br), 3.99 (3H, d, J=2.3 Hz), 3.12-3.08 (2H, m), 1.89-1.80 (2H, m), 1.04 (3H, t, J=7.3 Hz); ${}^{13}$C NMR (CDCl$_3$, 125 MHz) 133.0, 132.1, 131.3, 125.0, 122.5, 117.8, 54.0, 17.2, 12.8.

N-(5-Bromo-3-chloro-2-methylphenyl)propane-1-sulfonamide (6s)

Method E; the mixture was stirred at room temperature for 16 h and purified by column chromatography on silica gel (EtOAc/hexane, 5:95 to 10:90) to give 6s (77%) as a yellow solid; ${}^1$H NMR (CDCl$_3$, 500 MHz) 7.56 (1H, d, J=2.3 Hz), 7.38 (1H, d, J=2.3 Hz), 6.81 (1H, br), 3.12-3.09 (2H, m), 2.32 (3H, s), 1.89-1.82 (2H, m), 1.05 (3H, t, J=7.4 Hz); ${}^{13}$C NMR (CDCl$_3$, 125 MHz) 137.0, 136.1, 129.1, 127.4, 123.5, 119.7, 54.2, 17.2, 14.7, 12.8.

N-(5-Bromo-3-fluoro-2-methylphenyl)propane-1-sulfonamide (6t)

Method E; the mixture was stirred at room temperature for 16 h and purified by column chromatography on silica gel (EtOAc/hexane, 5:95 to 10:90) to give 6t (72%) as a pale yellow solid; ${}^1$H NMR (CDCl$_3$, 500 MHz) 7.46 (1H, s), 7.06 (2H, dd, J=8.6, 1.7 Hz), 6.78(1H, br), 3.14-3.10 (2H, m), 2.16(3H, d, J=1.7 Hz), 1.89-1.81 (2H, m), 1.05 (3H,); ${}^{13}$C NMR (CDCl$_3$, 125 MHz) 161.0 (d, $J_{CF}$=248.6 Hz), 137.5 (d, $J_{CF}$=6.2 Hz), 119.7, 119.6, 116.0 (d, $J_{CF}$=19.7 Hz), 115.7 (d, $J_{CF}$=25.8 Hz), 54.1, 17.2, 12.8, 9.2 (d, $J_{CF}$=4.9 Hz).

N-(5-Bromo-2,3-dimethylphenyl)propane-1-sulfonamide (6u)

Method E; the mixture was stirred at room temperature for 16 h and purified by column chromatography on silica gel (EtOAc/hexane, 15:85) to give 6u (83%) as a yellow solid; ${}^1$H NMR (CDCl$_3$, 400 MHz) 7.46 (1H, s), 7.18 (1H, s), 6.51 (1H, s), 3.10-3.06 (2H, m), 2.28 (3H, s), 2.18 (3H, s), 1.89-1.82 (2H, m), 1.05 (3H, t, J=7.3 Hz); ${}^{13}$C NMR (CDCl$_3$, 100 MHz) 140.0, 135.8, 130.4, 128.4, 123.4, 119.2, 53.9, 20.6, 17.2, 13.8, 12.9.

N-(5-Bromo-2-methoxy-3-methylphenyl)propane-1-sulfonamide (6v)

Method E; the mixture was stirred at room temperature for 16 h and purified by column chromatography on silica gel (EtOAc/hexane, 10:90 to 15:85) to give 6v (75%) as a yellow solid; ${}^1$H NMR (CDCl$_3$, 500 MHz) 7.51 (1H, d, J=2.3 Hz), 7.13 (1H, br), 7.04 (1H, d, J=1.7 Hz), 3.74 (3H, s), 3.12-3.09 (2H, m), 2.26 (3H, s), 1.86-1.81 (2H, m), 1.02(3H, t, J=7.4 Hz); ${}^{13}$C NMR (CDCl$_3$, 125 MHz) 146.2, 133.1, 131.8, 128.9, 118.4, 117.2, 60.6, 53.5, 17.1, 15.9, 12.7.

6-Bromo-1-(propylsulfonyl)indoline (6w)

Method F; the mixture was stirred at 50° C. for 3 h and purified by column chromatography on silica gel (EtOAc/hexane, 10:90 to 15:85) to give 6w (66%) as a white solid; ${}^1$H NMR (CDCl$_3$, 500 MHz) 7.50 (1H, d, J=1.7 Hz), 7.10 (1H, dd, J=8.0, 1.7 Hz), 7.03 (1H, d, J=8.0 Hz), 4.02 (2H, t, J=8.6 Hz), 3.08 (2H, t, J=8.0 Hz), 3.04-3.00 (2H, m), 1.92-1.84 (2H, m), 1.05 (3H, t, J=7.4 Hz); ${}^{13}$C NMR (CDCl$_3$, 125 MHz) 143.4, 130.0, 126.4, 126.1, 121.2, 116.4, 51.0, 50.6, 27.5, 16.7, 13.0.

N-(5-Bromo-3-methoxy-2-methylphenyl)benzenesulfonamide (6he)

To a solution of 3h (63.0 mg, 0.29 mmol) and a catalytic amount of DMAP in pyridine (1 mL) was added benzenesulfonyl chloride (0.06 mL, 0.44 mmol) added under argon. The mixture was stirred at room temperature for 3 h. A solution of 2.5 M NaOH (0.6 mL, 1.46 mmol) in MeOH (1.2 mL) was added. The mixture was stirred at room temperature for 4 h, then it was adjusted to pH 6 by 1 N HCl. The mixture was extracted with CH$_2$Cl$_2$ (2×15 mL). The combined organic extracts were washed with brine, dried over anhydrous Na$_2$SO$_4$, filtered and concentrated. The residue was purified by column chromatography (EtOAc/hexane, 10:90 to 20:80) to afford 6he (94.3 mg, 91%) as a yellow solid; ${}^1$H NMR (CDCl$_3$, 500 MHz) 7.75 (1H, d, J=7.4 Hz), 7.58 (1H, t, J=7.4 Hz), 7.47 (1H, t, J=7.4 Hz), 6.96 (1H, d, J=2.9 Hz), 6.86 (1H, d, J=2.3 Hz), 6.57 (1H, br), 3.71 (3H, s), 2.00(3H, s); ${}^{13}$C NMR (CDCl$_3$, 125 MHz) 158.0, 139.1, 135.5, 133.2, 129.1, 127.1, 125.6, 123.4, 116.6, 109.8, 55.5, 16.7.

N-(5-Bromo-2-methoxyphenyl)-1,1,1-trifluoromethanesulfonamide (6mc)

To a solution of 3m (500.0 mg, 2.47 mmol) in anhydrous CH$_2$Cl$_2$ (5 mL) was added triethylamine (0.69 mL, 4.95 mmol) added under argon at 0° C., then a solution of trifluoromethanesulfonic anhydride (0.61 mL, 3.71 mmol) in $CH_2Cl_2$ (2.5 mL) was added dropwise. The temperature was slowly increased to room temperature over 2 h. A solution of 2.5 M NaOH (5 mL, 12.5 mmol) in MeOH (10 mL) was added. The mixture was stirred at room temperature for 2 h, then it was adjusted to pH 6 by 1 N HCl. The mixture was extracted with $CH_2Cl_2$ (2×20 mL). The combined organic extracts were washed with brine, dried over anhydrous $Na_2SO_4$, filtered and concentrated. The residue was purified by column chromatography (EtOAc/hexane, 10:90 to 20:80) to afford 6mc (526.6 mg, 64%) as a light brown solid; $^1H$ NMR ($CDCl_3$, 500 MHz) 7.64 (1H, d, J=2.3 Hz), 7.32 (1H, dd, J=8.6, 2.3 Hz), 6.81(1H, d, J=9.2 Hz), 3.90 (3H, s); $^{13}C$ NMR ($CDCl_3$, 125 MHz) 148.9, 129.7, 124.7, 124.2, 199.6 (q, $J_{CF}$=322.4 Hz), 113.1, 112.2, 56.2.

5-Bromo-2-((tert-butyldimethylsilyl)oxy)aniline (10)

To a solution of 2-amino-4-bromophenol (4e) (200.0 mg, 1.06 mmol) and imidazole (109.8 mg, 1.60 mmol) in anhydrous DMF (3 mL) was added tert-butyldimethylsilyl chloride (192.4 mg, 1.28 mmol) under argon. The resulting mixture was stirred at 0° C. to room temperature for 2.5 h. After being quenched with $H_2O$ (5 mL), the aqueous layer was extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 5:95 to 10:90) to afford 10 (274.6 mg, 85%) as a brown oil; $^1H$ NMR ($CDCl_3$, 400 MHz) 6.83 (1H, d, J=2.8 Hz), 6.72 (1H, dd, J=8.2, 2.3 Hz), 6.60 (1H, d, J=8.2 Hz), 3.76 (2H, br), 1.02 (9H, s), 0.24 (6H, s); $^{13}C$ NMR ($CDCl_3$, 100 MHz) 141.9, 139.7, 120.6, 119.5, 117.9, 113.8, 25.7, 18.1, −4.37.

N-(5-Bromo-2-((tert-butyldimethylsilyl)oxy)phenyl) propane-1-sulfonamide (11)

Method D; purified by column chromatography on silica gel (EtOAc/hexane, 5:95 to 10:90) to give 11 (86%) as a brown oil; $^1H$ NMR ($CDCl_3$, 400 MHz) 7.65 (1H, d, J=2.3 Hz), 7.08 (1H, dd, J=8.5, 2.3 Hz), 6.72 (1H, d, J=8.2 Hz), 6.75 (1H, br), 3.08-3.04 (2H, m), 1.86-1.77 (2H, m), 1.03-0.99 (12H, m), 0.27 (6H, s); $^{13}C$ NMR ($CDCl_3$, 100 MHz) 143.5, 129.8, 127.0, 121.4, 119.1, 114.0, 53.3, 25.6, 18.1, 17.2, 12.7, −4.30.

N-(5-Bromo-2-hydroxyphenyl)propane-1-sulfonamide (6x)

To a solution of 11 (35.0 mg, 0.09 mmol) in anhydrous THF (1 mL) were added 1 M tetrabutylammonium fluoride in THF (0.17 mL, 0.17 mmol) at 0° C. The mixture was stirred at 0° C. for 1 h. After being quenched with saturated aqueous $NH_4Cl$ (5 mL), EtOAc were added, and the layers were separated. The combined organic phases were washed with brine, dried over anhydrous $Na_2SO_4$, filtered, and concentrated. The residue was purified by column chromatography on silica gel (EtOAc/hexane, 30:70) to give 6x (23.6 mg, 93%) as a brown oil; $^1H$ NMR ($CDCl_3$, 500 MHz) 7.46 (1H, d, J=2.3 Hz), 7.21 (1H, dd, J=8.6, 2.3 Hz), 6.82 (1H, d, J=8.6 Hz), 6.47 (1H, br), 3.09-3.06 (2H, m), 1.90-1.86 (2H, m), 1.05 (3H, t, J=7.4 Hz); $^{13}C$ NMR ($CDCl_3$, 100 MHz) 147.1, 129.3, 125.3, 125.2, 117.6, 112.6, 53.1, 17.0, 12.8.

General Procedure for the Preparation of N-((4,4,5,5-tetramethyl-1,3,2-dioxaborolan-2-yl)phenyl)alkylsulfonamides; N-(3-ethoxy-5-(4,4,5,5-tetramethyl-1,3,2-dioxaborolan-2-yl)phenyl)propane-2-sulfonamide (12aa), Method H To a mixture of 6aa (50.0 mg, 0.16 mmol), bis(pinacolato) diboron (47.3 mg, 0.19 mmol), KOAc (45.6 mg, 0.46 mmol), and $PdCl_2$(dppf) (3.4 mg, 0.005 mmol) was added anhydrous THF (2 mL) under argon. The reaction was stirred at room temperature for 10 min then was refluxed for 16 h. After being quenched by the addition of water, the aqueous layer was extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 10:90 to 20:80) to afford 12aa (36.2 mg, 63%) as a white solid; $^1H$ NMR ($CDCl_3$, 500 MHz) 7.09-7.08 (1H, m), 7.05-7.04 (2H, m), 6.63 (1H, br), 4.04 (2H, q, J=6.9 Hz), 3.32 (1H, sep, J=6.9 Hz), 1.40-1.37 (9H, m), 1.32 (12H, s); $^{13}C$ NMR ($CDCl_3$, 125 MHz) 159.5, 137.8, 118.2, 116.0, 109.9, 84.0, 63.6, 52.3, 24.8, 16.5, 14.7.

N-(3-Isopropoxy-5-(4,4,5,5-tetramethyl-1,3,2-dioxaborolan-2-yl)phenyl)propane-2-sulfonamide (12ab)

Method H; purified by column chromatography on silica gel (EtOAc/hexane, 2.5:97.5) to give 12ab (34%) as a yellow solid; $^1H$ NMR ($CDCl_3$, 500 MHz) 7.09 (1H, d, J=2.3 Hz), 7.04 (1H, t, J=2.3 Hz), 7.00 (1H, d, J=1.7 Hz), 4.59(1H, sep, J=5.7 Hz), 3.32 (1H, sep, J=6.9 Hz), 1.38 (6H, d, J=6.9 Hz), 1.32-1.31 (18H, m); $^{13}C$ NMR ($CDCl_3$, 125 MHz) 158.4, 137.8, 118.0, 117.7, 111.0, 84.0, 70.0, 52.3, 24.8, 22.0, 16.5.

N-(3-Chloro-2-methoxy-5-(4,4,5,5-tetramethyl-1,3,2-dioxaborolan-2-yl)phenyl)propane-1-sulfonamide (12b)

Method H; purified by column chromatography on silica gel (EtOAc/hexane, 2.5:97.5) to give 12b (46%) as a white solid; $^1H$ NMR ($CDCl_3$, 500 MHz) 7.79 (1H, d, J=1.2 Hz), 7.56 (1H, d, J=1.2 Hz), 6.96 (1H, br), 3.92 (3H, s), 3.15-3.12 (2H, m), 1.88-1.83 (2H, m), 1.32 (12H, s), 1.03 (3H, t, J=8.0 Hz); $^{13}C$ NMR ($CDCl_3$, 125 MHz) 147.6, 132.1, 131.8, 127.1, 122.9, 84.3, 61.1, 53.7, 24.8, 17.2, 12.8.

N-(2,3-Dimethoxy-5-(4,4,5,5-tetramethyl-1,3,2-dioxaborolan-2-yl)phenyl)propane-1-sulfonamide (12ca)

Method H; purified by column chromatography on silica gel (EtOAc/hexane, 10:90 to 20:80) to give 12ca (25%) as a clear oil; $^1H$ NMR ($CDCl_3$, 400 MHz) 7.56 (1H, d, J=0.9 Hz), 7.12 (1H, d, J=1.4 Hz), 6.92 (1H, br), 3.91 (3H, s), 3.90 (3H, s), 3.11-3.07 (2H, m), 1.88-1.78 (2H, m), 1.32 (12H, s), 1.00 (3H, t, J=7.3 Hz); $^{13}C$ NMR ($CDCl_3$, 100 MHz) 151.6, 140.3, 130.5, 117.3, 113.9, 84.0, 60.9, 55.9, 53.2, 24.8, 17.2, 12.8.

N-(2,3-Diethoxy-5-(4,4,5,5-tetramethyl-1,3,2-dioxaborolan-2-yl)phenyl)propane-1-sulfonamide (12cb)

Method H; purified by column chromatography on silica gel (EtOAc/hexane, 10:90) to give 12cb (51%) as a white solid; $^1H$ NMR ($CDCl_3$, 500 MHz) 7.54 (1H, d, J=1.2 Hz), 7.10 (1H, d, J=1.2 Hz), 6.92 (1H, s), 4.20 (2H, q, J=6.9 Hz), 4.12 (2H, q, J=6.9 Hz), 3.10-3.07 (2H, m), 1.87-1.80 (2H, m), 1.44 (3H, t, J=6.9 Hz), 1.36 (3H, t, J=6.9 Hz), 1.31 (12H, s), 1.00 (3H, t, J=7.4 Hz); $^{13}$C NMR (CDCl$_3$, 125 MHz) 150.9, 139.3, 130.8, 117.0, 114.8, 83.9, 69.1, 64.3, 53.2, 24.8, 17.2, 15.7, 14.9, 12.8.

N-(7-(4,4,5,5-Tetramethyl-1,3,2-dioxaborolan-2-yl)-2,3-dihydrobenzo[b][1,4]dioxin-5-yl)propane-1-sulfonamide (12cc)

Method H; purified by column chromatography on silica gel (EtOAc/hexane, 10:90 to 25:75) to give 12cc (56%) as a white solid; $^1$H NMR (CDCl$_3$, 600 MHz) 7.48 (1H, s), 7.13 (1H, s), 6.57 (1H, s), 4.33-4.32 (2H, m), 4.26-4.-.24 (2H, m), 3.08-3.06 (2H, m), 1.84 (2H, sex, J=8.2 Hz), 1.30 (12H, s), 1.01 (3H, t, J=7.6 Hz); $^{13}$C NMR (CDCl$_3$, 150 MHz) 143.1, 136.3, 125.8, 119.9, 118.7, 83.8, 64.9, 63.9, 53.2, 24.8, 17.2, 12.8.

General Procedure for the Preparation of N-((4,4,5,5-tetramethyl-1,3,2-dioxaborolan-2-yl)phenyl)alkylsulfonamides; N-(3-Ethoxy-2-methoxy-5-(4,4,5,5-tetramethyl-1,3,2-dioxaborolan-2-yl)phenyl)propane-1-sulfonamide (12d); Method I To a mixture of 6d (60.0 mg, 0.17 mmol), bis(pinacolato)diboron (64.9 mg, 0.26 mmol), KOAc (50.0 mg, 0.51 mmol), and PdCl$_2$(dppf) (12.4 mg, 0.017 mmol) was added anhydrous 1,4-dioxane (0.9 mL) under argon. The reaction was put into a preheated oil bath (80° C.), and stirred for 40 h. After being quenched by the addition of water, the aqueous layer was extracted with EtOAc (2×15 mL). The combined organic extracts were washed with brine, dried over anhydrous Na$_2$SO$_4$, filtered, and concentrated. The residue was purified by column chromatography on silica gel (EtOAc/hexane, 10:90) to afford 12d (19.8 mg, 29%) as a yellow oil; $^1$H NMR (CDCl$_3$, 500 MHz) 8.24 (1H, s), 7.26 (1H, s), 7.18 (1H, s), 4.10 (2H, q, J=6.9 Hz), 3.89 (3H, s), 2.98-2.95 (2H, m), 1.82-1.74 (2H, m), 1.45 (3H, t, J=6.9 Hz), 1.34 (12H, s), 0.95 (3H, t, J=7.4 Hz); $^{13}$C NMR (CDCl$_3$, 125 MHz) 153.0, 144.7, 138.7, 119.0, 103.4, 84.4, 64.5, 55.9, 52.5, 24.8. 17.0, 14.8, 12.9.

4-(Propylsulfonyl)-6-(4,4,5,5-tetramethyl-1,3,2-dioxaborolan-2-yl)-3,4-dihydro-2H-benzo[b][1,4]oxazine (12e)

Method H; purified by column chromatography on silica gel (EtOAc/hexane, 10:90) to give 12e (74%) as a yellow oil; $^1$H NMR (CDCl$_3$, 500 MHz) 7.95 (1H, d, J=1.2 Hz), 7.48 (1H, dd, J=8.3, 1.2 Hz), 6.90 (1H, d, J=8.6 Hz), 4.30 (2H, t, J=4.6 Hz), 3.86 (2H, t, J=4.6 Hz), 3.13-3.09 (2H, m), 1.93-1.85 (2H, m), 1.31 (12H, s), 1.05 (3H, t, J=7.4 Hz); $^{13}$C NMR (CDCl$_3$, 125 MHz) 148.7, 132.2, 129.0, 124.0, 117.2, 83.7, 65.1, 54.4, 44.0, 24.8, 17.0, 13.0.

8-Fluoro-4-(propylsulfonyl)-6-(4,4,5,5-tetramethyl-1,3,2-dioxaborolan-2-yl)-3,4-dihydro-2H-benzo[b][1,4]oxazine (12f)

Method I; the reaction was stirred for 16 h and purified by column chromatography on silica gel (EtOAc/hexane, 15:85) to give 12f (52%) as a yellow oil; $^1$H NMR (CDCl$_3$, 600 MHz) 7.73 (1H, s), 7.30 (1H, d, J=10.3 Hz), 4.37 (2H, t, J=4.8 Hz), 3.88 (2H, t, J=4.8 Hz), 3.14-3.12 (2H, m), 1.93-1.86 (2H, m), 1.31 (12H, s), 1.06 (3H, t, J=7.6 Hz); $^{13}$C NMR (CDCl$_3$, 150 MHz) 151.5 (d, J$_{CF}$=246.9 Hz), 137.6 (d, J$_{CF}$=13.3 Hz), 125.8, 123.7 (d, J$_{CF}$=3.0 Hz), 117.6 (d, J$_{CF}$=16.3 Hz), 84.0, 65.4, 54.6, 43.7, 24.8, 17.0, 12.9.

N-(3-Methoxy-2-methyl-5-(4,4,5,5-tetramethyl-1,3,2-dioxaborolan-2-yl)phenyl)propane-1-sulfonamide (12ha)

Method H; purified by column chromatography on silica gel (EtOAc/hexane, 10:90) to give 12ha (54%) as a white solid; $^1$H NMR (CDCl$_3$, 500 MHz) 7.20 (1H, d, J=2.7 Hz), 7.14 (1H, d, J=2.7 Hz), 6.31 (1H, br), 3.80 (3H, s), 3.06-3.03 (2H, m), 2.42 (3H, s), 1.87-1.79 (2H, m), 1.34 (12H, s), 1.01 (3H, t, J=7.4 Hz); $^{13}$C NMR (CDCl$_3$, 125 MHz) 157.7, 135.9, 126.4, 117.5, 110.1, 83.9, 55.4, 53.6, 24.8, 17.2, 15.5, 12.9.

N-(3-Methoxy-2-methyl-5-(4,4,5,5-tetramethyl-1,3,2-dioxaborolan-2-yl)phenyl)methanesulfonamide (12hb)

Method H; purified by column chromatography on silica gel (EtOAc/hexane, 20:80) to give 12hb (87%) as a white solid; $^1$H NMR (CDCl$_3$, 500 MHz) 7.17 (2H, s), 6.41 (1H, br), 3.80 (3H, s), 2.96 (3H, s), 2.42 (3H, s), 1.34 (12H, s); $^{13}$C NMR (CDCl$_3$, 125 MHz) 157.7, 135.6, 127.5, 118.3, 111.3, 83.9, 55.4, 39.5, 24.8, 15.6.

N-(3-Methoxy-2-methyl-5-(4,4,5,5-tetramethyl-1,3,2-dioxaborolan-2-yl)phenyl)propane-2-sulfonamide (12hc)

Method H; purified by column chromatography on silica gel (EtOAc/hexane, 20:80) to give 12hc (77%) as a yellow solid; $^1$H NMR (CDCl$_3$, 500 MHz) 7.25 (1H, d, J=2.3 Hz), 7.10 (1H, d, J=2.3 Hz), 6.17 (1H, br), 3.80(3H, s), 3.33 (1H, sep, J=6.9 Hz), 2.42 (3H, s), 1.37 (6H, d, J=6.9 Hz), 1.34 (12H, s); $^{13}$C NMR (CDCl$_3$, 125 MHz) 157.7, 136.4, 125.5, 116.8, 109.1, 83.9, 55.4, 52.6, 24.8, 16.6, 15.4.

N-(3-Methoxy-2-methyl-5-(4,4,5,5-tetramethyl-1,3,2-dioxaborolan-2-yl)phenyl)-1-phenylmethanesulfonamide (12hd)

Method H; purified by column chromatography on silica gel (EtOAc/hexane, 20:80) to give 12hd (58%) as a yellow oil; $^1$H NMR (CDCl$_3$, 500 MHz) 7.37-7.30 (3H, m), 7.26 (1H, d, J=2.3 Hz), 7.20-7.19 (2H, m), 7.13 (1H, d, J=2.9 Hz), 6.14 (1H, s), 4.36 (2H, s), 3.81 (3H, s), 2.14 (3H, s), 1.36 (12H, s); $^{13}$C NMR (CDCl$_3$, 125 MHz) 157.8, 136.2, 130.6, 128.9, 128.8, 128.4, 125.4, 116.9, 108.3, 83.9, 57.3, 55.4, 24.8, 15.1.

N-(3-Methoxy-2-methyl-5-(4,4,5,5-tetramethyl-1,3,2-dioxaborolan-2-yl)phenyl)benzenesulfonamide (12he)

Method H; purified by column chromatography on silica gel (EtOAc/hexane, 10:90) to give 12he (26%) as a white solid; $^1$H NMR (CDCl$_3$, 500 MHz) 7.75 (2H, d, J=7.4 Hz), 7.54 (1H, t, J=7.4 Hz), 7.43 (2H, t, J=7.4 Hz), 7.11 (1H, d, J=2.9 Hz), 7.03 (1H, d, J=2.9 Hz), 6.39 (1H, s), 3.75 (3H, s), 2.11 (3H, s), 1.30 (12H, s); $^{13}$C NMR (CDCl$_3$, 125 MHz) 157.4, 139.5, 135.2, 132.9, 129.0, 128.3, 127.1, 118.8, 111.9, 83.8, 55.4, 24.8, 15.2.

N-(3-Ethoxy-2-methyl-5-(4,4,5,5-tetramethyl-1,3,2-dioxaborolan-2-yl)phenyl)-1-phenylmethanesulfonamide (12i)

Method H; purified by column chromatography on silica gel (EtOAc/hexane, 10:90) to give 12i (30%) as a yellow oil; $^1$H NMR (CDCl$_3$, 500 MHz) 7.35-7.29 (3H, m), 7.26 (2H, d, J=2.9 Hz), 7.19 (2H, d, J=6.3 Hz), 7.13 (1H, d, J=2.3 Hz), 6.13 (1H, s), 4.35 (2H, s), 4.03 (3H, q, J=6.9 Hz), 2.13 (3H, s), 1.40 (3H, t, J=6.9 Hz), 1.35 (12H, s); $^{13}$C NMR (CDCl$_3$, 125 MHz) 157.2, 136.1, 130.6, 128.8, 128.7, 128.4, 125.2, 117.8, 108.7, 83.8, 63.6, 57.3, 24.8, 15.0, 14.8.

N-(2-Methoxy-4-(4,4,5,5-tetramethyl-1,3,2-dioxaborolan-2-yl)phenyl)propane-1-sulfonamide (12k)

Method H; purified by column chromatography on silica gel (EtOAc/hexane, 20:80) to give 12k (81%) as a white solid; $^1$H NMR (CDCl$_3$, 400 MHz) 7.53 (1H, d, J=7.8 Hz), 7.41 (1H, d, J=7.8 Hz), 7.29 (1H, s), 6.99 (1H, br), 3.91 (3H, s), 3.04-3.00 (2H, m), 1.82-1.74 (2H, m), 1.33 (12H, s), 0.97 (1H, t, J=7.3 Hz); $^{13}$C NMR (CDCl$_3$, 100 MHz) 147.6, 129.2, 128.3, 117.8, 116.0, 83.9, 55.8, 52.9, 24.8, 17.1, 12.8.

N-(3-methoxy-5-(4,4,5,5-tetramethyl-1,3,2-dioxaborolan-2-yl)phenyl)methane sulfonamide (12la)

Method H; purified by column chromatography on silica gel (EtOAc/hexane, 30:70 to 50:50) to give 12la (90%) as a white solid; $^1$H NMR (CDCl$_3$, 500 MHz) 7.37 (1H, br), 7.14 (1H, d, J=1.7 Hz), 7.10 (1H, d, J=2.9 Hz), 6.99, (1H, t, J=2.3 Hz), 3.78 (3H, s), 2.98 (3H, s), 1.30 (12H, s); $^{13}$C NMR (CDCl$_3$, 125 MHz) 159.9, 137.6, 118.8, 115.8, 110.0, 84.0, 55.3, 39.0, 24.6.

N-(3-Methoxy-5-(4,4,5,5-tetramethyl-1,3,2-dioxaborolan-2-yl)phenyl)ethanesulfonamide (12lb)

Method H; purified by column chromatography on silica gel (EtOAc/hexane, 15:85 to 20:80) to give 12lb (74%) as a pale yellow solid; $^1$H NMR (CDCl$_3$, 500 MHz) 7.10-7.09 (2H, m), 7.01 (1H, t, J=2.3 Hz), 6.93 (1H, br), 7.02 (1H, s), 3.81 (3H, s), 3.13 (2H, q, J=7.4 Hz), 1.36-1.32 (15H, m); $^{13}$C NMR (CDCl$_3$, 125 MHz) 160.1, 137.6, 118.5, 115.5, 109.6, 84.1, 55.4, 45.8, 24.8, 8.2.

N-(3-Methoxy-5-(4,4,5,5-tetramethyl-1,3,2-dioxaborolan-2-yl)phenyl)propane-1-sulfonamide (12lc)

Method H; purified by column chromatography on silica gel (EtOAc/hexane, 15:85) to give 12lc (78%) as a pale yellow solid; $^1$H NMR (CDCl$_3$, 400 MHz) 7.11-7.10 (1H, m), 7.06 (1H, s), 7.02 (1H, s), 6.68 (1H, br), 3.82 (3H, s), 3.09-3.05 (2H, m), 1.89-1.79 (2H, m), 1.33 (12H, s), 1.00 (3H, t, J=7.3 Hz); $^{13}$C NMR (CDCl$_3$, 100 MHz) 160.1, 137.6, 118.4, 115.5, 109.5, 84.1, 55.5, 53.2, 24.8, 17.2, 12.8.

N-(3-Methoxy-5-(4,4,5,5-tetramethyl-1,3,2-dioxaborolan-2-yl)phenyl)propane-2-sulfonamide (12ld)

Method H; purified by column chromatography on silica gel (EtOAc/hexane, 15:85 to 20:80) to give 12ld (69%) as a pale yellow solid; $^1$H NMR (CDCl$_3$, 500 MHz) 7.09-7.07 (2H, m), 7.06-7.05 (1H, m), 6.76 (1H, br), 3.81 (3H, s), 3.32 (1H, sep, J=6.9 Hz), 1.38 (6H, d, J=6.9 Hz), 1.33 (12H, s); $^{13}$C NMR (CDCl$_3$, 125 MHz) 160.1, 137.9, 118.2, 115.2, 109.4, 84.1, 55.4, 52.4, 24.8, 16.5.

N-(3-Methoxy-5-(4,4,5,5-tetramethyl-1,3,2-dioxaborolan-2-yl)phenyl)cyclopropanesulfonamide (12le)

Method H; purified by column chromatography on silica gel (EtOAc/hexane, 10:90 to 15:85) to give 12le (76%) as a white solid; $^1$H NMR (CDCl$_3$, 500 MHz) 7.14-7.12 (2H, m), 7.04 (1H, t, J=1.7 Hz), 6.70 (1H, br), 3.81 (3H, s), 2.50 (1H, tt, J=8.0, 5.2 Hz), 1.33 (12H, s), 1.18-1.15 (2H, m), 0.96-0.92 (2H, m); $^{13}$C NMR (CDCl$_3$, 125 MHz) 160.0, 137.5, 119.7, 116.0, 110.8, 84.1, 55.4, 52.4, 29.8, 24.8, 5.6.

N-(3-Methoxy-5-(4,4,5,5-tetramethyl-1,3,2-dioxaborolan-2-yephenyl)-2-methylpropane-1-sulfonamide (12lf)

Method H; purified by column chromatography on silica gel (EtOAc/hexane, 10:90 to 20:80) to give 12lf (72%) as a pale yellow solid; $^1$H NMR (CDCl$_3$, 500 MHz) 7.10 (1H, s), 7.08 (1H, s), 7.01 (1H, s), 6.93 (1H, br), 3.81 (3H, s), 2.97 (2H, d, J=6.3 Hz), 2.28 (1H, sep, J=6.3 Hz), 1.32 (12H, s), 1.06 (6H, d, J=6.9 Hz); $^{13}$C NMR (CDCl$_3$, 125 MHz) 160.1, 137.6, 118.6, 115.5, 109.6, 84.1, 59.1, 55.4, 24.8, 22.4.

N-(3-Methoxy-5-(4,4,5,5-tetramethyl-1,3,2-dioxaborolan-2-yl)phenyl)benzenesulfonamide (12lg)

Method H; purified by column chromatography on silica gel (EtOAc/hexane, 10:90 to 15:85) to give 12lg (86%) as a white solid; $^1$H NMR (CDCl$_3$, 400 MHz) 7.79 (2H, d, J=7.3 Hz), 7.51 (1H, t, J=7.3 Hz), 7.42 (2H, t, J=7.3 Hz), 7.04 (1H, s), 6.93-6.92 (3H, m), 3.75 (3H, s), 1.29 (12H, s); $^{13}$C NMR (CDCl$_3$, 100 MHz) 159.8, 138.9, 137.1, 133.0, 129.0, 127.2, 119.5, 115.8, 110.2, 84.0, 55.4, 24.8.

N-(3-Methoxy-5-(4,4,5,5-tetramethyl-1,3,2-dioxaborolan-2-yl)phenyl)-1-phenylmethanesulfonamide (12lh)

Method H; purified by column chromatography on silica gel (EtOAc/hexane, 15:85 to 20:80) to give 12lh (85%) as a white solid; $^1$H NMR (CDCl$_3$, 500 MHz) 7.35-7.34 (3H, m), 7.28-7.26 (2H, m), 7.12 (1H, d, J=2.3 Hz), 7.03 (1H, s), 6.93 (1H, s), 4.33 (2H, s), 3.82 (3H, s), 1.35 (12H, s); $^{13}$C NMR (CDCl$_3$, 125 MHz) 160.1, 137.6, 130.9, 128.9, 128.8, 128.5, 118.4, 115.5, 109.2, 84.1, 57.4, 55.5, 24.8.

N-(2-Methoxy-5-(4,4,5,5-tetramethyl-1,3,2-dioxaborolan-2-yl)phenyl)propane-1-sulfonamide (12ma)

Method H; purified by column chromatography on silica gel (EtOAc/hexane, 10:90 to 20:80) to give 12ma (82%) as a white solid; $^1$H NMR (CDCl$_3$, 500 MHz) 7.90 (1H, s), 7.58 (1H, d, J=8.0 Hz), 6.89 (1H, d, J=8.0 Hz), 6.72 (1H, br), 3.90 (3H, s), 3.04-3.03 (2H, t, J=8.0 Hz), 1.82 (2H, sex, J=7.4 Hz), 1.32 (12H, s), 0.99 (3H, t, J=6.7 Hz); $^{13}$C NMR (CDCl$_3$, 125 MHz) 151.6, 132.4, 126.4, 125.7, 109.9, 83.8, 55.8, 53.0, 24.8, 17.2, 12.8.

N-(2-Methoxy-5-(4,4,5,5-tetramethyl-1,3,2-dioxaborolan-2-yl)phenyl)propane-2-sulfonamide (12mb)

Method H; purified by column chromatography on silica gel (EtOAc/hexane, 10:90 to 20:80) to give 12mb (90%) as a light brown solid; $^1$H NMR (CDCl$_3$, 500 MHz) 7.92 (1H, s), 7.55 (1H, dd, J=8.0, 1.2 Hz), 6.88 (1H, d, J=8.0 Hz), 6.70 (1H, br), 3.89 (3H, s), 3.26 (1H, sep, J=6.9 Hz), 1.36 (6H, d, J=6.9 Hz), 1.31 (12H, s); $^{13}$C NMR (CDCl$_3$, 125 MHz) 151.2, 132.1, 126.0, 125.9, 109.9, 83.7, 55.7, 52.1, 24.8, 16.4.

1,1,1-Trifluoro-N-(2-methoxy-5-(4,4,5,5-tetramethyl-1,3,2-dioxaborolan-2-yl)phenyl)methanesulfonamide (12*mc*)

Method H; purified by column chromatography on silica gel (EtOAc/hexane, 10:90 to 15:85) to give 12*mc* (54%) as a yellow oil; $^1$H NMR (CDCl$_3$, 500 MHz) 7.87 (1H, d, J=1.2 Hz), 7.68 (1H, dd, J=8.3, 1.5 Hz), 7.08 (1H, br), 6.90 (1H, d, J=8.0 Hz), 3.90 (3H, s), 1.32 (12H, s); $^{13}$C NMR (CDCl$_3$, 125 MHz) 153.2, 134.8, 129.4, 122.8, 119.8 (d, J$_{CF}$=322.4 Hz), 110.2, 83.9, 55.9, 24.8.

N-(2-Methyl-5-(4,4,5,5-tetramethyl-1,3,2-dioxaborolan-2-yl)phenyl)propane-1-sulfonamide (12*n*)

Method H; purified by column chromatography on silica gel (EtOAc/hexane, 10:90 to 15:85) to give 12*n* (78%) as a white solid; $^1$H NMR (CDCl$_3$, 500 MHz) 7.77 (1H, s), 7.56 (1H, d, J=7.4 Hz), 7.23 (1H, d, J=7.4 Hz), 6.43 (1H, br), 3.13-3.10 (2H, m), 2.36 (3H, s), 1.88 (2H, sex, J=8.0 Hz), 1.32 (12H, s), 1.04 (3H, J=7.4 Hz); $^{13}$C NMR (CDCl$_3$, 125 MHz) 135.0, 134.4, 132.6, 130.7, 129.4, 83.9, 53.9, 24.8, 18.5, 17.3, 12.9.

N-(2-Methoxy-5-(4,4,5,5-tetramethyl-1,3,2-dioxaborolan-2-yl)benzyl)propane-1-sulfonamide (12*o*)

Method H; purified by column chromatography on silica gel (EtOAc/hexane, 2.5:97.5) to give 12*o* (71%) as a clear oil; $^1$H NMR (CDCl$_3$, 500 MHz) 7.77 (1H, dd, J=8.0, 1.7 Hz), 7.68 (1H, d, J=1.7 Hz), 6.89 (1H, d, J=8.6 Hz), 4.28 (2H, d, J=6.9 Hz), 3.88 (3H, s), 2.82-2.79 (2H, m), 1.68-1.60 (2H, m), 1.33 (12H, s), 0.87 (3H, t, J=7.4 Hz); $^{13}$C NMR (CDCl$_3$, 125 MHz) 160.0, 136.8, 136.2, 124.4, 109.8, 83.7, 55.4, 54.6, 43.7, 24.8, 17.2, 12.8.

N-(3-Fluoro-2-methoxy-5-(4,4,5,5-tetramethyl-1,3,2-dioxaborolan-2-yl)phenyl)propane-1-sulfonamide (12*p*)

Method H; purified by column chromatography on silica gel (EtOAc/hexane, 10:90 to 15:85) to give 12*p* (68%) as a white solid; $^1$H NMR (CDCl$_3$, 500 MHz) 7.67 (1H, s), 7.29 (1H, dd, J=12.0, 1.2 Hz), 6.90 (1H, s), 4.03 (3H, d, J=2.9 Hz), 3.10-3.07 (2H, m), 1.87-1.80 (2H, m), 1.31 (12H, s), 1.02 (3H, t, J=7.4 Hz); $^{13}$C NMR (CDCl$_3$, 125 MHz) 153.8 (d, J$_{CF}$=248.6 Hz), 139.2 (d, J$_{CF}$=12.3 Hz), 130.4 (d, J$_{CF}$=3.7 Hz), 120.6 (d, J$_{CF}$=2.5 Hz), 118.7 (d, J$_{CF}$=17.2 Hz), 84.2, 61.4 (d, J$_{CF}$=8.6 Hz), 53.3, 24.8, 17.2, 12.8.

N-(3-Fluoro-5-(4,4,5,5-tetramethyl-1,3,2-dioxaborolan-2-yl)phenyl)propane-1-sulfonamide (12*q*)

Method H; purified by column chromatography on silica gel (EtOAc/hexane, 15:85 to 20:80) to give 12*q* (80%) as a white solid; $^1$H NMR (CDCl$_3$, 500 MHz) 7.50 (1H, s), 7.30 (1H, d, J=1.7 Hz), 7.26 (1H, dd, J=8.6, 2.3 Hz), 7.22 (1H, dt, J=9.7, 2.3 Hz), 3.13-3.10 (2H, m), 1.90-1.82 (2H, m), 1.34 (12H, s), 1.02 (3H, t, J=7.4 Hz); $^{13}$C NMR (CDCl$_3$, 125 MHz) 162.8 (d, J$_{CF}$=248.6 Hz), 138.2 (d, J$_{CF}$=9.8 Hz), 121.2, 117.1 (d, J$_{CF}$=18.5 Hz), 109.8 (d, J$_{CF}$=25.8 Hz), 84.2, 53.4, 24.7, 17.1, 12.7.

N-(3-Chloro-5-(4,4,5,5-tetramethyl-1,3,2-dioxaborolan-2-yl)phenyl)propane-1-sulfonamide (12*r*)

Method H; purified by column chromatography on silica gel (EtOAc/hexane, 5:95 to 10:90) to give 12*r* (99%) as a clear oil; $^1$H NMR (CDCl$_3$, 500 MHz) 7.82 (1H, s), 7.69-7.65 (2H, m), 6.92 (1H, br), 3.09-3.06 (2H, m), 1.85-1.80 (2H, m), 1.33 (12H, s), 1.00 (3H, t, J=8.0); $^{13}$C NMR (CDCl$_3$, 125 MHz) 136.2, 135.9, 134.6, 123.0, 119.0, 84.2, 53.7, 24.8, 17.2, 12.8.

N-(3-Chloro-2-methyl-5-(4,4,5,5-tetramethyl-1,3,2-dioxaborolan-2-yl)phenyl)propane-1-sulfonamide (12*s*)

Method H; purified by column chromatography on silica gel (EtOAc/hexane, 10:90 to 15:85) to give 12*s* (52%) as a pale yellow solid; $^1$H NMR (CDCl$_3$, 600 MHz) 7.68 (1H, s), 7.66 (1H, s), 6,52 (1H, s), 3.11-3.09 (2H, m), 2.42 (3H, s), 1.90-1.86 (2H, m), 13.2 (12H, s), 1.05 (3H, t, J=7.6 Hz); $^{13}$C NMR (CDCl$_3$, 150 MHz) 135.5, 135.4, 134.1, 133.4, 128.6, 84.2, 54.1, 24.8, 17.2, 15.6, 12.9.

N-(3-Fluoro-2-methyl-5-(4,4,5,5-tetramethyl-1,3,2-dioxaborolan-2-yl)phenyl)propane-1-sulfonamide (12*t*)

Method H; purified by column chromatography on silica gel (EtOAc/hexane, 15:85 to 20:80) to give 12*t* (46%) as a white solid; $^1$H NMR (CDCl$_3$, 500 MHz) 7.57 (1H, s), 7.33 (1H, d, J=9.2 Hz), 6.43 (1H, s), 3.13-3.10 (2H, m), 2.27 (3H, d, J=1.7 Hz), 1.92-1.84 (2H, m), 1.32 (12H, s), 1.05 (3H, t, J=7.4 Hz); $^{13}$C NMR (CDCl$_3$, 125 MHz) 161.1 (d, J$_{CF}$=247.3 Hz), 135.9 (d, J$_{CF}$=4.9 Hz), 124.8, 122.6 (d, J$_{CF}$=18.5 Hz), 118.6 (d, J$_{CF}$=22.2 Hz), 84.2, 54.0. 24.8, 17.2, 12.9, 10.0 (d, J$_{CF}$=4.9 Hz).

N-(2,3-Dimethyl-5-(4,4,5,5-tetramethyl-1,3,2-dioxaborolan-2-yl)phenyl)propane-1-sulfonamide (12*u*)

Method H; purified by column chromatography on silica gel (EtOAc/hexane, 10:90 to 15:85) to give 12*u* (35%) as a white solid; $^1$H NMR (CDCl$_3$, 500 MHz) 7.58 (1H, s), 7.50 (1H, s), 6.31 (1H, s), 3.10-3.07 (2H, m), 2.30 (3H, s), 2.29 (3H, s), 1.93-1.85 (2H, m), 1.33 (12H, s), 1.05 (3H, t, J=7.4 Hz); $^{13}$C NMR (CDCl$_3$, 125 MHz) 137.8, 135.7, 134.7, 134.0, 128.9, 83.8, 53.8, 24.8, 20.4, 17.2, 14.7, 12.9.

N-(2-Methoxy-3-methyl-5-(4,4,5,5-tetramethyl-1,3,2-dioxaborolan-2-yl)phenyl)propane-1-sulfonamide (12*v*)

Method H; purified by column chromatography on silica gel (EtOAc/hexane, 15:85 to 20:80) to give 12*v* (24%) as a pale yellow solid; $^1$H NMR (CDCl$_3$, 400 MHz) 7.73 (1H, s), 7.39 (1H, s), 6.89 (1H, s), 3.77 (3H, s), 3.15-3.11 (2H, m), 2.30 (3H, s), 1.90-1.80 (2H, m), 1.00 (3H, t, J=7.3 Hz); $^{13}$C NMR (CDCl$_3$, 100 MHz) 150.0, 133.5, 130.4, 130.1, 122.2, 83.9, 60.5, 53.4, 24.8, 17.2, 16.0, 12.8.

1-(Propylsulfonyl)-6-(4,4,5,5-tetramethyl-1,3,2-dioxaborolan-2-yl)indoline (12*w*)

Method H; purified by column chromatography on silica gel (EtOAc/hexane, 10:90) to give 12*w* (70%) as a yellow oil; $^1$H NMR (CDCl$_3$, 500 MHz) 7.74 (1H, s), 7.46 (1H, d, J=7.4 Hz), 7.20 (1H, d, J=7.4 Hz), 4.02 (2H, t, J=8.6 Hz), 3.14 (2H, t, J=8.6 Hz), 3.05-3.02 (2H, m), 1.92-1.84 (2H, m), 1.32 (12H, s), 1.03 (3H, t, J=7.4 Hz); $^{13}$C NMR (CDCl$_3$, 125 MHz) 141.7, 134.5, 130.2, 124.8, 118.9, 83.8, 50.9, 50.2, 28.2, 24.8, 16.7, 13.1.

N-(2-Hydroxy-5-(4,4,5,5-tetramethyl-1,3,2-dioxaborolan-2-yl)phenyl)propane-1-sulfonamide (12x)

Method H; purified by column chromatography on silica gel (EtOAc/hexane, 20:80) to give 12x (73%) as a clear oil; $^1$H NMR (CDCl$_3$, 500 MHz) 7.67 (1H, d, J=1.2 Hz), 7.56 (1H, dd, J=8.0, 1.2 Hz), 6.94 (1H, d, J=8.0 Hz), 6.60 (1H, s), 3.06-3.03 (2H, m), 1.90-1.83 (2H, m), 1.32 (12H, s), 1.00 (3H, t, J=7.4 Hz); $^{13}$C NMR (CDCl$_3$, 125 MHz) 152.6, 134.6, 131.0, 123.0, 116.4, 83.9, 52.5, 24.8, 17.0, 12.8.

General Procedure for the Preparation of 3-Bromo-5-phenylpyridines; N-(3-(2-amino-5-bromopyridin-3-yl)-5-ethoxyphenyl)propane-2-sulfonamide (14aa), Method J To a mixture of 12a (36.2 mg, 0.10 mmol), 13b (29.3 mg, 0.10 mmol), and Pd(PPh$_3$)$_4$ (11.6 mg, 0.01 mmol) was added anhydrous acetonitrile (1 mL) and anhydrous DMF (0.5 mL) under argon. The reaction was stirred at room temperature for 10 min then 1 M Na$_2$CO$_3$ (0.2 mL, 0.20 mmol) was added. The mixture was put into a preheated oil bath (90° C.), and stirred for 16 h. After being quenched by the addition of water, the aqueous layer was extracted with EtOAc (2×10 mL). The combined organic extracts were washed with brine, dried over anhydrous Na$_2$SO$_4$, filtered, and concentrated. The residue was purified by column chromatography on silica gel (EtOAc/hexane, 30:70 to 35:65) to afford 14aa (34.4 mg, 85%) as a yellow solid; $^1$H NMR (CDCl$_3$, 400 MHz) 8.07 (1H, d, J=2.3 Hz), 7.80 (1H, br), 7.45 (1H, d, J=2.3 Hz), 6.85 (1H, s), 6.82 (1H, br), 6.68(1H, s), 4.84 (2H, br), 4.03 (2H, q, J=6.9 Hz), 3.36 (1H, sep, J=6.9 Hz), 1.43-1.40 (9H, m); $^{13}$C NMR (CDCl$_3$, 100 MHz) 160.5, 154.5, 147.6, 139.7, 139.4, 138.8, 122.8, 111.7, 110.6, 108.1, 105.9, 63.9, 52.9, 24.8, 16.5, 14.6.

N-(3-(2-Amino-5-bromopyridin-3-yl)-5-isopropoxyphenyl)propane-2-sulfonamide (14ab)

Method J; purified by column chromatography on silica gel (EtOAc/hexane, 30:70 to 50:50) to give 14ab (81%) as a yellow solid; $^1$H NMR (CDCl$_3$, 500 MHz) 8.08 (1H, s), 7.68 (1H, s), 7.45 (1H, d, J=2.3 Hz), 6.84 (1H, t, J=2.3 Hz), 6.80 (1H, s), 6.68 (1H, s), 4.84 (2H, br), 4.56 (1H, sep, J=5.7 Hz), 3.36 (1H, sep, J=6.9 Hz), 1.41 (6H, d, J=6.9 Hz), 1.34 (6H, d, J=6.3 Hz); $^{13}$C NMR (CDCl$_3$, 125 MHz) 159.5, 154.5, 147.6, 139.7, 139.5, 138.9, 122.8, 111.7, 111.6, 108.1, 107.0, 70.3, 52.9, 21.9, 16.5.

N-(5-(2-Amino-5-bromopyridin-3-yl)-3-chloro-2-methoxyphenyl)propane-1-sulfonamide (14b)

Method J; purified by column chromatography on silica gel (EtOAc/hexane, 30:70) to give 14b (78%) as a yellow solid; $^1$H NMR (CDCl$_3$, 500 MHz) 8.11 (1H, d, J=2.3 Hz), 7.50 (1H, d, J=1.7 Hz), 7.44 (1H, d, J=2.3 Hz), 7.19 (1H, d, J=2.3 Hz), 7.13 (1H, br), 4.68 (2H, br), 3.97 (3H, s), 3.16-3.13 (2H, m), 1.93-1.86 (2H, m), 1.06 (3H, t, J=7.4 Hz); $^{13}$C NMR (CDCl$_3$, 125 MHz) 154.3, 148.4, 144.9, 130.7, 134.0, 132.9, 128.3, 125.5, 121.0, 116.9, 108.4, 61.3, 54.5, 17.3, 12.8.

N-(5-(2-Amino-5-bromopyridin-3-yl)-2,3-dimethoxyphenye)propane-1-sulfonamide (14ca)

Method J; purified by column chromatography on silica gel (EtOAc/hexane, 30:70) to give 14ca (69%) as a yellow solid; $^1$H NMR (CDCl$_3$, 500 MHz) 8.09 (1H, d, J=2.3 Hz), 7.46 (1H, d, J=2.3 Hz), 7.20 (1H, d, J=1.7 Hz), 7.12 (1H, br), 6.72(1H, d, J=2.3 Hz), 4.72 (2H, br), 3.93 (3H, s), 3.90 (3H, s), 3.12-3.09 (2H, m), 1.90-1.83 (2H, m), 1.03 (3H, t, J=7.4 Hz); $^{13}$C NMR (CDCl$_3$, 125 MHz) 154.5, 152.8, 147.8, 139.6, 137.5, 132.9, 131.6, 122.6, 110.8, 108.2, 61.0, 56.0, 54.0, 17.2, 12.8.

N-(5-(2-Amino-5-bromopyridin-3-yl)-2,3-diethoxyphenyl)propane-1-sulfonamide (14cb)

Method J; purified by column chromatography on silica gel (EtOAc/hexane, 30:70 to 40:60) to give 14cb (80%) as a brown solid; $^1$H NMR (CDCl$_3$, 500 MHz) 8.08 (1H, d, J=2.3 Hz), 7.45 (1H, d, J=2.3 Hz), 7.18 (1H, d, J=1.7 Hz), 7.06 (1H, s), 6.70 (1H, d, J=1.7 Hz), 4.71 (2H, br), 4.21 (2H, q, J=7.4 Hz), 4.08 (2H, q, J=6.9 Hz), 3.11-3.08 (2H, m), 1.90-1.83 (2H, m), 1.47 (3H, t, J=6.9 Hz), 1.40 (3H, t, J=6.9 Hz), 1.30 (3H, t, J=7.4 Hz); $^{13}$C NMR (CDCl$_3$, 125 MHz) 154.5, 152.0, 147.8, 139.6, 136.6, 132.5, 131.8, 122.7, 110.5, 109.0, 108.2, 69.3, 64.5, 53.9, 17.2, 15.7, 14.8, 12.9.

N-(5-(2-Amino-5-bromopyridin-3-yl)-3-ethoxy-2-methoxyphenye)propane-1-sulfonamide (14d)

Method J; purified by column chromatography on silica gel (EtOAc/hexane, 30:70 to 40:60) to give 14d (89%) as a yellow solid; $^1$H NMR (CDCl$_3$, 400 MHz) 8.19 (1H, d, J=2.3 Hz), 7.50 (1H, d, J=2.3 Hz), 7.21 (1H, s), 6.88 (1H, s), 6.70(1H, s), 4.52(2H, br), 4.14-4.02 (2H, m), 3.92 (3H, s), 2.76-2.69 (1H, m), 2.60-2.53 (1H, m), 1.60-1.51 (1H, m), 1.47 (3H, t, J=6.9 Hz), 1.29-1.20 (1H, m), 0.84 (3H, t, J=7.3 Hz); $^{13}$C NMR (CDCl$_3$, 100 MHz) 154.2, 150.2, 148.8, 147.3, 140.8, 127.2, 121.5, 121.0, 113.8, 110.0, 109.5, 64.8, 56.2, 53.8, 17.1, 14.7, 12.9.

5-Bromo-3-(4-(propylsulfonyl)-3,4-dihydro-2H-benzo[b][1,4]oxazin-6-yl)pyridin-2-amine (14e)

Method J; purified by column chromatography on silica gel (EtOAc/hexane, 30:70 to 40:60) to give 14e (85%) as a yellow solid; $^1$H NMR (CDCl$_3$, 400 MHz) 8.07 (1H, s), 7.60 (1H, d, J=1.8 Hz), 7.45 (1H, d, J=1.4 Hz), 7.08 (1H, d, J=8.7, 1.8 Hz), 7.00 (1H, d, J=8.7 Hz), 7.24 (1H, s), 4.72 (2H, br), 4.33 (2H, t, J=4.1 Hz), 3.87 (2H, t, J=4.6 Hz), 3.15-3.11 (2H, m), 1.91 (2H, sex, J=7.8 Hz), 1.07 (3H, t, J=7.3 Hz); $^{13}$C NMR (CDCl$_3$, 100 MHz) 154.7, 147.5, 146.0, 139.6, 129.2, 125.6, 124.6, 122.3, 118.6, 65.0, 54.8, 44.0, 17.1, 12.9.

5-Bromo-3-(8-fluoro-4-(propylsulfonyl)-3,4-dihydro-2H-benzo[b][1,4]oxazin-6-yl)pyridin-2-amine (14f)

Method J; purified by column chromatography on silica gel (EtOAc/hexane, 30:70 to 40:60) to give 14f (72%) as a pale yellow solid; $^1$H NMR (CDCl$_3$, 500 MHz) 8.08 (1H, d, J=2.3 Hz), 7.44 (1H, d, J=2.3 Hz), 7.40(1H, t, J=1.7 Hz), 6.96 (1H, dd, J=10.9, 2.3 Hz), 4.74 (2H, s), 4.40 (2H, t, J=4.6

Hz), 3.90 (2H, t, J=4.6 Hz), 3.16-3.13 (2H, m), 1.95-1.87 (2H, m), 1.08 (3H, t, J=7.45 Hz); $^{13}$C NMR (CDCl$_3$, 125 MHz) 154.5, 152.1 (d, J$_{CF}$=248.6 Hz), 148.0, 139.6, 135.0 (d, J$_{CF}$=13.5 Hz), 128.3 (d, J$_{CF}$=7.4 Hz), 126.4 (d, J$_{CF}$=3.7 Hz), 121.5, 117.3 (d, J$_{CF}$=3.7 Hz), 112.1 (d, J$_{CF}$=18.5 Hz), 108.3, 62.3, 55.0, 43.9, 17.1, 12.9.

N-(5-(2-amino-5-Bromopyridin-3-yl)-3-methoxy-2-methylphenyl)propane-1-sulfonamide (14*ha*)

Method J; purified by column chromatography on silica gel (EtOAc/hexane, 30:70 to 40:60) to give 14*ha* (81%) as a yellow solid; $^1$H NMR (CDCl$_3$, 500 MHz) 8.10 (1H, d, J=2.3 Hz), 7.37 (1H, d, J=2.8 Hz), 7.13 (1H, d, J=2.8 Hz), 6.80 (1H, br), 6.57 (1H, d, J=2.3 Hz), 4.48 (2H, br), 3.79 (3H, s), 3.16-3.12 (2H, m), 2.02 (3H, s), 1.93-1.84 (2H, m), 1.06 (3H, t, J=7.3 Hz); $^{13}$C NMR (CDCl$_3$, 125 MHz) 158.5, 154.5, 148.0, 139.7, 137.7, 137.0, 122.6, 119.8, 112.0, 107.9, 107.8, 55.5, 54.1, 17.3, 13.8, 12.9.

N-(5-(2-Amino-5-bromopyridin-3-yl)-3-methoxy-2-methylphenyl)methanesulfonamide (14*hb*)

Method J; purified by column chromatography on silica gel (EtOAc/hexane, 30:70 to 40:60) to give 14*hb* (66%) as a pale yellow solid; $^1$H NMR (CDCl$_3$, 500 MHz) 8.15 (1H, d, J=2.3 Hz), 7.38 (1H, d, J=2.3 Hz), 7.14 (1H, d, J=2.9 Hz), 6.61 (1H, d, J=2.9 Hz), 6.28 (1H, br), 4.35 (2H, br), 3.81 (3H, s), 3.10 (3H, s), 2.03 (3H, s); $^{13}$C NMR (CDCl$_3$, 125 MHz) 158.7, 154.4, 148.3, 139.6, 137.9, 136.7, 122.5, 119.7, 112.4, 108.0, 55.6, 40.2, 13.8.

N-(5-(2-Amino-5-bromopyridin-3-yl)-3-methoxy-2-methylphenyl)propane-2-sulfonamide (14*hc*)

Method J; purified by column chromatography on silica gel (EtOAc/hexane, 20:80 to 40:60) to give 14*hc* (92%) as a yellow solid; $^1$H NMR (CDCl$_3$, 500 MHz) 8.11 (1H, d, J=2.3 Hz), 7.37 (1H, d, J=2.3 Hz), 7.18 (1H, d, J=2.9 Hz), 6.56-6.54 (2H, m), 4.45 (2H, br), 3.79 (3H, s), 3.41 (1H, sep, J=6.9 Hz), 2.03 (3H, s), 1.44 (3H, d, J=6.9 Hz), 1.42 (3H, d, J=6.9 Hz); $^{13}$C NMR (CDCl$_3$, 125 MHz) 158.5, 154.5, 148.1, 139.7, 137.7, 137.4, 122.7, 119.0, 111.5, 107.8, 107.2, 55.5, 53.2, 16.8, 16.5, 13.8.

N-(5-(2-Amino-5-bromopyridin-3-yl)-3-methoxy-2-methylphenyl)-1-phenylmethanesulfonamide (14*hd*)

Method J; purified by column chromatography on silica gel (EtOAc/hexane, 20:80 to 40:60) to give 14*hd* (76%) as a yellow solid; $^1$H NMR (CDCl$_3$, 500 MHz) 8.10 (1H, d, J=2.3 Hz), 7.38-7.32 (4H, m), 7.27-7.18 (2H, m), 7.18 (1H, d, J=2.3 Hz), 6.56 (1H, d, J=2.3 Hz), 6.43 (1H, br), 4.46-4.44 (4H, m), 3.79 (3H, s), 1.71 (3H, s); $^{13}$C NMR (CDCl$_3$, 125 MHz) 158.7, 154.5, 148.0, 139.7, 137.6, 137.2, 130.6, 129.1, 128.9, 128.4, 122.6, 118.3, 111.5, 107.8, 106.0, 57.9, 55.5, 13.3.

N-(5-(2-Amino-5-bromopyridin-3-yl)-3-methoxy-2-methylphenyl)benzenesulfonamide (14*he*)

Method J; purified by column chromatography on silica gel (EtOAc/hexane, 30:70 to 50:50) to give 14*he* (82%) as a pale yellow solid; $^1$H NMR (CDCl$_3$, 500 MHz) 8.08 (1H, d, J=2.3 Hz), 7.78 (2H, d, J=6.9 Hz), 7.59 (1H, t, J=7.4 Hz), 7.47 (2H, t, J=7.4 Hz), 7.26 (1H, d, J=3.4 Hz), 7.01 (1H, d, J=2.9 Hz), 6.56-6.55 (2H, m), 4.20 (2H, br), 3.76 (3H, s), 1.69 (3H, s); $^{13}$C NMR (CDCl$_3$, 125 MHz) 158.3, 154.3, 148.1, 139.6, 139.3, 137.4, 136.3, 133.2, 129.1, 127.2, 122.5, 121.2, 113.5, 109.8, 107.8, 55.5, 13.4.

N-(5-(2-Amino-5-bromopyridin-3-yl)-3-methoxy-2-methylphenyl)-1-phenylmethanesulfonamide (14*i*)

Method J; purified by column chromatography on silica gel (EtOAc/hexane, 20:80 to 30:70) to give 14*i* (72%) as a yellow solid; $^1$H NMR (CDCl$_3$, 500 MHz) 8.10 (1H, d, J=1.7 Hz), 7.36-7.31 (4H, m), 7.25 (1H, d, J=1.2 Hz), 7.23 (1H, d, J=1.7 Hz), 7.19 (1H, d, J=2.9 Hz), 6.54 (1H, d, J=2.3 Hz), 6.30 (1H, br), 4.44 (4H, s), 4.00 (2H, q, J=7.4 Hz), 1.69 (3H, s), 1.41 (3H, t, J=6.9 Hz); $^{13}$C NMR (CDCl$_3$, 125 MHz) 158.1, 154.5, 145.0, 139.7, 137.6, 137.2, 130.6, 129.1, 128.9, 128.4, 122.7, 117.9, 112.1, 107.8, 106.3, 63.8, 57.8, 14.7, 13.3.

N-(4-(5-Bromo-2-chloropyridin-3-yl)-2-methoxyphenyl)propane-1-sulfonamide (14*k*)

Method J; purified by column chromatography on silica gel (EtOAc/hexane, 10:90 to 20:80) to give 14k (57%) as a white solid; $^1$H NMR (CDCl$_3$, 500 MHz) 8.44 (1H, d, J=2.3 Hz), 7.81 (1H, d, J=2.3 Hz), 7.61 (1H, d, J=8.0 Hz), 7.02-6.99 (2H, m), 6.94 (1H, br), 3.92 (3H, s), 3.11-3.08 (2H, m), 1.89-1.84 (2H, m), 1.03 (3H, t, J=7.4 Hz); $^{13}$C NMR (CDCl$_3$, 125 MHz) 149.1, 148.2, 148.1, 141.7, 137.6, 132.4, 127.1, 122.3, 119.0, 118.8, 111.6, 56.0, 53.5, 24.8, 17.2, 12.8.

N-(3-(5-Bromo-2-chloropyridin-3-yl)-5-methoxyphenyemethanesulfonamide (14*laa*)

Method J; purified by column chromatography on silica gel (EtOAc/hexane, 20:80 to 30:70) to give 14*laa* (88%) as a yellow solid; 41 NMR (CDCl$_3$, 400 MHz) 8.45 (1H, s), 7.80 (1H, s), 7.45 (1H, s), 6.88 (2H, s), 6.74 (1H, s), 3.83 (3H, s), 3.08 (3H, s); $^{13}$C NMR (CDCl$_3$, 100 MHz) 165.0, 149.5, 147.9, 141.7, 138.4, 138.2, 137.4, 119.1, 112.9, 111.6, 106.2, 55.6, 39.4.

N-(3-(2-Amino-5-bromopyridin-3-yl)-5-methoxyphenyemethanesulfonamide (14*lab*)

Method J; purified by column chromatography on silica gel (EtOAc/hexane, 20:80 to 60:40) to give 14*lab* (38%) as a yellow oil; $^1$H NMR (CDCl$_3$, 400 MHz) 8.08 (1H, s), 7.44 (1H, d, J=1.8 Hz), 6.88-6.87 (1H, m), 6.85 (1H, s), 6.72 (1H, s), 4.79 (2H, br), 3.81 (3H, s), 3.05 (3H, s); $^{13}$C NMR (CDCl$_3$, 100 MHz) 161.1, 154.4, 147.8, 139.7, 139.2, 139.0, 122.6, 112.3, 110.5, 108.2, 105.7, 55.6, 39.7.

N-(3-(5-Bromo-2-chloropyridin-3-yl)-5-methoxyphenyeethanesulfonamide (14*lba*)

Method J; purified by column chromatography on silica gel (EtOAc/hexane, 15:85 to 25:75) to give 14*lba* (81%) as a pale yellow solid; $^1$H NMR (CDCl$_3$, 500 MHz) 8.47 (1H, d, J=2.3 Hz), 7.80 (1H, d, J=2.9 Hz), 7.00 (1H, br), 6.87 (1H, t, J=1.7 Hz), 6.86 (1H, t, J=1.7 Hz), 6.72 (1H, t, J=2.3 Hz), 3.84 (3H, s), 3.20 (2H, q, J=7.4 Hz), 1.40 (3H, t, J=7.4 Hz); $^{13}$C NMR (CDCl$_3$, 125 MHz) 160.6, 149.5, 148.0, 141.7, 138.5, 138.3, 137.4, 119.1, 112.6, 111.3, 105.9, 55.6, 46.1, 8.3.

N-(3-(2-Amino-5-bromopyridin-3-yl)-5-methoxyphenyeethanesulfonamide (141*bb*)

Method J; purified by column chromatography on silica gel (EtOAc/hexane, 30:70 to 45:55) to give 141*bb* (88%) as a pale yellow solid; $^1$H NMR (CD$_3$OD, 500 MHz) 7.98 (1H, d, J=2.3 Hz), 7.49 (1H, d, J=2.3 Hz), 6.87 (1H, t, J=1.7 Hz), 6.85 (1H, t, J=1.7 Hz), 6.73 (1H, t, J=1.7 Hz), 3.81 (3H, s), 3.14 (2H, q, J=7.4 Hz), 1.31 (3H, t, J=2.3 Hz), 1.02 (3H, t, J=7.4 Hz); $^{13}$C NMR (CD$_3$OD, 125 MHz) 162.6, 156.7, 148.2, 141.6, 141.0, 140.2, 124.6, 112.8, 110.6, 108.1, 106.3, 56.0, 46.6, 8.4.

N-(3-(5-Bromo-2-chloropyridin-3-yl)-5-methoxyphenyl)propane-1-sulfonamide (141*ca*)

Method J; purified by column chromatography on silica gel (EtOAc/hexane, 20:80) to give 141*ca* (96%) as a yellow solid; $^1$H NMR (CDCl$_3$, 500 MHz) 8.46 (1H, d, J=2.3 Hz), 7.80 (1H, d, J=2.9 Hz), 7.28 (1H, s), 6.87 (1H, t, J=1.7 Hz), 6.86 (1H, t, J=1.7 Hz), 6.72 (1H, t, J=1.7 Hz), 3.84 (3H, s), 3.16-3.13 (2H, m), 1.91-1.82 (2H, m), 1.03 (3H, t, J=7.4 Hz); $^{13}$C NMR (CDCl$_3$, 125 MHz) 160.5, 149.5, 148.0, 141.7, 138.4, 138.3, 137.4, 119.1, 112.6, 111.3, 105.8, 55.6, 53.4, 17.2, 12.8.

N-(3-(2-Amino-5-bromopyridin-3-yl)-5-methoxyphenyl)propane-1-sulfonamide (141*cb*)

Method J; purified by column chromatography on silica gel (EtOAc/hexane, 30:70 to 45:55) to give 141*cb* (65%) as a pale yellow solid; $^1$H NMR (CD$_3$OD, 500 MHz) 7.98 (1H, d, J=2.3 Hz), 7.50 (1H, d, J=2.3 Hz), 6.87 (1H, t, J=1.7 Hz), 6.84 (1H, t, J=1.7 Hz), 6.74 (1H, t, J=1.7 Hz), 3.82 (3H, s), 3.13-3.10 (2H, m), 1.81 (2H, sex, J=7.4 Hz), 1.02 (3H, t, J=7.4 Hz); $^{13}$C NMR (CD$_3$OD, 125 MHz) 162.6, 148.2, 141.6, 141.0, 140.2, 124.7, 112.9, 110.6, 108.1, 107.9, 106.4, 56.0, 54.0, 18.4, 13.1.

N-(3-(5-Bromo-2-chloropyridin-3-yl)-5-methoxyphenyl)propane-2-sulfonamide (141*da*)

Method J; purified by column chromatography on silica gel (EtOAc/hexane, 10:90 to 20:80) to give 141*da* (92%) as a yellow solid; $^1$H NMR (CDCl$_3$, 500 MHz) 8.46 (1H, d, J=2.9 Hz), 7.80 (1H, d, J=2.3 Hz), 7.19 (1H, br), 6.90 (1H, t, J=2.3 Hz), 6.88 (1H, t, J=1.7 Hz), 6.70 (1H, t, J=1.7 Hz), 3.84 (3H, s), 3.38 (1H, sep, J=6.9 Hz), 1.42 (6H, d, J=6.9 Hz); $^{13}$C NMR (CDCl$_3$, 125 MHz) 160.5, 149.5, 148.0, 141.7, 138.6, 138.4, 137.5, 119.0, 112.5, 111.1, 105.8, 55.6, 52.8, 16.5.

N-(3-(2-Amino-5-bromopyridin-3-yl)-5-methoxyphenyl)propane-2-sulfonamide (141*db*)

Method J; purified by column chromatography on silica gel (EtOAc/hexane, 30:70 to 45:55) to give 141*db* (88%) as a pale yellow solid; $^1$H NMR (CDCl$_3$, 500 MHz) 8.08 (1H, d, J=1.7 Hz), 7.76 (1H, br), 7.45 (1H, d, J=2.3 Hz), 6.85 (1H, t, J=1.7 Hz), 6.84 (1H, t, J=1.7 Hz), 6.69 (1H, t, J=2.3 Hz), 4.82 (2H, br), 3.82 (3H, s), 3.36 (1H, sep, J=6.9 Hz), 1.41 (6H, d, J=6.9 Hz); $^{13}$C NMR (CDCl$_3$, 125 MHz) 161.2, 154.5, 147.8, 139.7, 139.5, 138.9, 122.7, 111.9, 110.1, 108.1, 105.5, 55.6, 53.0, 16.5.

N-(3-(5-Bromo-2-chloropyridin-3-yl)-5-methoxyphenyecyclopropanesulfonamide (141*ea*)

Method J; purified by column chromatography on silica gel (EtOAc/hexane, 20:80 to 30:70) to give 141*ea* (47%) as a pale yellow solid; $^1$H NMR (CDCl$_3$, 500 MHz) 8.47 (1H, d, J=2.3 Hz), 7.80 (1H, d, J=2.9 Hz), 6.90-6.89 (2H, m), 6.75 (1H, t, J=2.3 Hz) 6.67 (1H, br), 3.85 (3H, s), 2.55 (1H, tt, J=8.0, 5.2 Hz), 1.25-1.21 (2H, m), 1.04-1.00 (2H, m); $^{13}$C NMR (CDCl$_3$, 125 MHz) 160.4, 149.5, 148.0, 141.7, 138.3, 138.2, 137.4, 119.1, 114.0, 111.8, 107.2, 55.6, 30.1, 5.8.

N-(3-(2-Amino-5-bromopyridin-3-yl)-5-methoxyphenyecyclopropanesulfonamide (141*eb*)

Method J; purified by column chromatography on silica gel (EtOAc/hexane, 30:70 to 40:60) to give 141*eb* (96%) as a pale yellow solid; $^1$H NMR (CD$_3$OD, 500 MHz) 7.97 (1H, d, J=2.3 Hz), 7.50 (1H, d, J=2.3 Hz), 6.90 (1H, t, J=1.7 Hz), 6.89 (1H, t, J=1.7 Hz), 6.75 (1H, t, J=1.7 Hz), 3.81 (3H, s), 2.62 (1H, tt, J=8.0, 4.6 Hz), 1.10-1.06 (2H, m), 1.00-0.95 (2H, m); $^{13}$C NMR (CD$_3$OD, 125 MHz) 162.4, 156.7, 148.2, 141.5, 141.0, 140.0, 124.6, 113.9, 110.9, 108.0, 107.4, 56.0, 30.6, 5.8.

N-(3-(5-Bromo-2-chloropyridin-3-yl)-5-methoxyphenyl)-2-methylpropane-1-sulfonamide (141*fa*)

Method J; purified by column chromatography on silica gel (EtOAc/hexane, 10:90 to 15:85) to give 141*fa* (89%) as a yellow solid; $^1$H NMR (CDCl$_3$, 500 MHz) 8.46 (1H, d, J=2.3 Hz), 7.80 (1H, d, J=2.3 Hz), 7.30 (1H, br), 6.86-6.86 (2H, m), 6.71 (1H, t, J=1.7 Hz), 3.84 (3H, s), 3.06 (2H, d, J=6.9 Hz), 2.32 (1H, sep, J=6.3 Hz), 1.08 (6H, d, J=6.9 Hz); $^{13}$C NMR (CDCl$_3$, 125 MHz) 160.5, 149.5, 148.0, 141.7, 138.4, 138.4, 137.4, 119.1, 112.4, 111.2, 105.7, 59.4, 55.6, 24.8, 22.4.

N-(3-(2-Amino-5-bromopyridin-3-yl)-5-methoxyphenyl)-2-methylpropane-1-sulfonamide (141*fb*)

Method J; purified by column chromatography on silica gel (EtOAc/hexane, 30:70 to 50:8505) to give 141*fb* (96%) as a yellow solid; $^1$H NMR (CD$_3$OD, 500 MHz) 7.98 (1H, d, J=2.3 Hz), 7.50 (1H, d, J=2.3 Hz), 6.86 (1H, t, J=1.7 Hz), 6.83 (1H, t, J=1.7 Hz), 6.73 (1H, t, J=1.2 Hz), 3.81 (3H, s), 3.03 (2H, d, J=6.9 Hz), 2.23 (1H, sep, J=6.9 Hz), 1.06 (6H, d, J=6.9 Hz); $^{13}$C NMR (CD$_3$OD, 125 MHz) 162.6, 156.7, 148.2, 141.6, 141.0, 140.2, 124.6, 112.8, 110.6, 108.5, 106.3, 59.9, 56.0, 26.0, 22.7.

N-(3-(2-Amino-5-bromopyridin-3-yl)-5-methoxyphenyebenzenesulfonamide (141*g*)

Method J; purified by column chromatography on silica gel (EtOAc/hexane, 40:60) to give 141*g* (85%) as a pale yellow solid; $^1$H NMR (CDCl$_3$, 500 MHz) 7.98 (1H, s), 7.79 (2H, d, J=8.0 Hz), 7.53 (1H, t, J=7.4 Hz), 7.43 (2H, t, J=7.4 Hz), 7.30 (1H, d, J=2.3 Hz), 6.72 (1H, s), 6.62 (1H, s), 6.58 (1H, s), 3.73 (3H, s); $^{13}$C NMR (CDCl$_3$, 125 MHz) 160.8, 154.3, 147.3, 139.8, 139.0, 139.0, 138.2, 133.0, 129.0, 127.1, 122.8, 112.5, 110.4, 107.9, 106.2, 55.4.

N-(3-(2-Amino-5-bromopyridin-3-yl)-5-methoxyphenyl)-1-phenylmethanesulfonamide (141*h*)

Method J; purified by column chromatography on silica gel (EtOAc/hexane, 40:60) to give 141*h* (87%) as a pale yellow oil; $^1$H NMR (CDCl$_3$, 500 MHz) 7.95 (1H, d, J=2.3 Hz), 7.67 (1H, br), 7.42 (1H, d, J=2.3 Hz), 7.35-7.31 (3H, m), 7.29-7.27 (2H, m), 6.76 (1H, t, J=1.7 Hz), 6.68 (1H, t, J=2.3 Hz), 6.64(1H, t, J=1.7 Hz), 4.69 (2H, s), 4.39 (2H, s), 3.81 (3H, s); $^{13}$C NMR (CDCl$_3$, 125 MHz) 161.1, 154.3, 147.6, 139.7, 139.3, 138.8, 130.9, 129.1, 128.8, 128.4, 122.6, 111.6, 110.1, 108.1, 105.0, 58.1, 55.6.

N-(5-(2-Amino-5-bromopyridin-3-yl)-2-methoxyphenyl)propane-1-sulfonamide (14*ma*)

Method J; purified by column chromatography on silica gel (EtOAc/hexane, 30:70 to 50:50) to give **14*ma*** (92%) as a pale yellow solid; $^1$H NMR (CDCl$_3$, 500 MHz) 8.08 (1H, s), 7.59 (1H, d, J=1.7 Hz), 7.44 (1H, d, J=2.3 Hz), 7.17 (1H, dd, J=8.6, 2.3 Hz), 6.99 (1H, d, J=8.6 Hz), 6.89 (1H, s), 4.65 (2H, br), 3.94 (3H, s), 3.08-3.04 (2H, m), 1.90-1.83 (2H, m), 1.03 (3H, t, J=6.9 Hz); $^{13}$C NMR (CDCl$_3$, 125 MHz) 154.6, 148.8, 147.6, 139.7, 132.0, 129.8, 128.4, 127.0, 125.1, 119.9, 111.3, 56.0, 53.8, 17.2, 12.9.

N-(5-(2-Amino-5-bromopyridin-3-yl)-2-methoxyphenyl)propane-2-sulfonamide (14*mb*)

Method J; purified by column chromatography on silica gel (EtOAc/hexane, 30:70 to 50:50) to give **14*mb*** (72%) as a light brown solid; $^1$H NMR (CDCl$_3$, 500 MHz) 8.06 (1H, d, J=2.3 Hz), 7.61 (1H, d, J=2.3 Hz), 7.42 (1H, d, J=2.3 Hz), 7.13 (1H, dd, J=8.0, 2.3 Hz), 6.98-6.95 (2H, m), 4.69 (2H, s), 3.93 (3H, s), 3.26 (1H, sep, J=6.9 Hz), 1.39 (6H, d, J=6.9 Hz); $^{13}$C NMR (CDCl$_3$, 125 MHz) 154.6, 148.5, 147.5, 129.6, 127.3, 124.8, 122.5, 119.8, 119.7, 111.2, 108.3, 56.0, 53.0, 16.5.

N-(5-(2-Amino-5-bromopyridin-3-yl)-2-methoxyphenyl)-1,1,1-trifluoromethanesulfonamide (14*mc*)

Method J; purified by column chromatography on silica gel (EtOAc/hexane, 30:70 to 50:50) to give **14*mc*** (72%) as a pale yellow solid; $^1$H NMR (CDCl$_3$, 600 MHz) 8.08 (1H, d, J=2.1 Hz), 7.59 (1H, d, J=1.4 Hz), 7.44 (1H, d, J=2.1 Hz), 7.28(1H, dd, J=8.2, 1.4 Hz), 7.04 (1H, d, J=8.9 Hz), 4.67 (2H, br), 3.96 (3H, s); $^{13}$C NMR (CDCl$_3$, 150 MHz) 154.6, 150.5, 147.6, 139.9, 129.6, 127.6, 124.2, 122.8, 122.1, 119.8 (d, J$_{CF}$=322.3 Hz), 111.7, 108.3, 56.2.

N-(5-(2-Amino-5-bromopyridin-3-yl)-2-methylphenyl)propane-1-sulfonamide (14*n*)

Method J; purified by column chromatography on silica gel (EtOAc/hexane, 30:70 to 50:50) to give **14*n*** (82%) as a pale yellow solid; $^1$H NMR (CDCl$_3$, 400 MHz) 8.06 (1H, d, J=2.3 Hz), 7.51 (1H, d, J=1.4 Hz), 7.46 (1H, d, J=2.3 Hz), 7.31 (1H, d, J=7.8 Hz), 7.17 (1H, dd, J=7.8, 1.4 Hz), 6.80 (1H, br), 4.75 (2H, br), 3.15-3.11 (2H, m), 2.36 (3H, s), 1.90 (2H, sex, J=7.8 Hz), 1.06 (3H, t, J=7.8 Hz); $^{13}$C NMR (CDCl$_3$, 100 MHz) 154.6, 147.7, 139.7, 135.7, 135.7, 132.0, 129.9, 125.6, 122.4, 122.1, 108.3, 54.7, 17.8, 17.3, 12.9.

N-(5-(2-Amino-5-bromopyridin-3-yl)-2-methoxybenzyl)propane-1-sulfonamide (14*o*)

Method J; purified by column chromatography on silica gel (EtOAc/hexane, 30:70 to 50:50) to give **14*o*** (78%) as a yellow solid; $^1$H NMR (CDCl$_3$, 500 MHz) 7.98 (1H, s), 7.39-7.33 (3H, m), 6.96 (1H, d, J=8.6 Hz), 5.45 (1H, t, J=6.3 Hz), 4.72 (2H, br), 4.29 (2H, d, J=6.3 Hz), 3.90 (3H, s), 2.91-2.88 (2H, m), 1.79-1.72 (2H, m), 0.96 (3H, t, J=7.4 Hz); $^{13}$C NMR (CDCl$_3$, 125 MHz) 157.2, 154.8, 147.2, 139.6, 129.7, 129.6, 128.9, 126.3, 122.7, 111.0, 108.2, 55.6, 54.8, 43.2, 17.3, 12.9.

N-(5-(2-Amino-5-bromopyridin-3-yl)-3-fluoro-2-methoxyphenyl)propane-1-sulfonamide (14*pa*)

Method J; purified by column chromatography on silica gel (EtOAc/hexane, 10:90 to 15:85) to give **14*pa*** (85%) as a yellow oil; $^1$H NMR (CDCl$_3$, 600 MHz) 8.46 (1H, d, J=2.1 Hz), 7.78 (1H, d, J=2.1 Hz), 7.41 (1H, s), 7.06 (1H, s), 6.96 (1H, dd, J=12.4, 1.4 Hz), 4.09 (3H, d, J=2.1 Hz), 3.13 (2H, t, J=7.6 Hz), 1.87 (2H, sex, J=7.6 Hz), 1.04 (3H, t, J=7.6 Hz); $^{13}$C NMR (CDCl$_3$, 150 MHz) 153.8 (d, J$_{CF}$=246.9 Hz), 149.6, 148.0, 141.6, 136.8 (d, J$_{CF}$=11.8 Hz), 136.4, 131.4 (d, J$_{CF}$=8.9 Hz), 131.1 (d, J$_{CF}$=4.4 Hz), 119.1, 114.8, 113.3 (d, J$_{CF}$=22.2 Hz), 108.3, 61.6 (d, J$_{CF}$=7.4 Hz), 53.7, 17.2, 12.8.

N-(5-(2-amino-5-bromopyridin-3-yl)-3-fluoro-2-methoxyphenyl)propane-1-sulfonamide (14*pb*)

Method J; purified by column chromatography on silica gel (EtOAc/hexane, 30:70 to 50:50) to give **14*pb*** (83%) as a pale yellow solid; $^1$H NMR (CDCl$_3$, 600 MHz) 8.09 (1H, d, J=1.4 Hz), 7.43 (1H, d, J=1.4 Hz), 7.37 (1H, s), 7.24 (1H, s), 6.96(1H, d, J=11.7 Hz), 4.75 (2H, s), 4.06 (3H, d, J=2.1 Hz), 3.12-3.10 (2H, m), 1.87 (2H, sex, J=7.6 Hz), 1.05 (3H, t, J=6.9 Hz); $^{13}$C NMR (CDCl$_3$, 150 MHz) 154.5 (d, J$_{CF}$=248.4 Hz), 154.4, 148.2, 139.7, 136.6 (d, J$_{CF}$=11.8 Hz), 132.2 (d, J$_{CF}$=8.9 Hz), 131.7 (d, J$_{CF}$=5.9 Hz), 121.2, 114.6, 112.7 (d, J$_{CF}$=20.7 Hz), 108.3, 61.6 (d, J$_{CF}$=7.4 Hz), 54.2, 17.2, 12.8.

N-(3-(2-Amino-5-bromopyridin-3-yl)-5-fluorophenyl)propane-1-sulfonamide (14*q*)

Method J; purified by column chromatography on silica gel (EtOAc/hexane, 30:70) to give **14*q*** (66%) as a pale yellow solid; $^1$H NMR (CD$_3$OD, 500 MHz) 8.00 (1H, d, J=2.3 Hz), 7.51 (1H, d, J=2.3 Hz), 7.09-7.06 (2H, m), 6.94 (1H, dt, J=9.2, 1.7 Hz), 3.16-3.13 (2H, m), 1.82 (2H, sex, J=7.4 Hz), 1.02 (3H, t, J=7.4 Hz); $^{13}$C NMR (CD$_3$OD, 125 MHz) 164.9 (d, J$_{CF}$=246.1 Hz), 156.7, 148.7, 142.3 (d, J$_{CF}$=11.1 Hz), 141.1, 141.0, 123.4, 116.0, 111.7 (d, J$_{CF}$=23.4 Hz), 108.0, 106.9 (d, J$_{CF}$=25.8 Hz), 54.3, 18.3, 13.1.

N-(3-(2-Amino-5-bromopyridin-3-yl)-5-chlorophenyl)propane-1-sulfonamide (14*r*)

Method J; purified by column chromatography on silica gel (EtOAc/hexane, 15:85 to 30:70) to give **14*r*** (63%) as a pale yellow solid; $^1$H NMR (CDCl$_3$, 600 MHz) 8.10 (1H, d, J=2.1 Hz), 7.76 (1H, d, J=8.2 Hz), 7.51 (1H, d, J=2.1 Hz), 7.44 (1H, d, J=2.1 Hz), 7.37 (1H, d, J=8.2, 2.1 Hz), 7.06 (1H, br), 4.71 (2H, br), 3.14-3.12 (2H, m), 1.93-1.88 (2H, m), 1.06 (3H, t, J=7.6 Hz); $^{13}$C NMR (CDCl$_3$, 150 MHz) 154.4, 148.2, 139.8, 134.1, 133.8, 129.7, 128.3, 124.8, 121.7, 121.1, 108.4, 54.3, 24.8, 17.2, 12.8.

N-(5-(2-Amino-5-bromopyridin-3-yl)-3-chloro-2-methylphenyl)propane-1-sulfonamide (14*s*)

Method J; purified by column chromatography on silica gel (EtOAc/hexane, 30:70) to give **14*s*** (85%) as a yellow solid; $^1$H NMR (CDCl$_3$, 500 MHz) 8.07 (1H, br), 7.45 (2H, s), 7.33 (1H, s), 7.14 (1H, br), 4.81 (2H, br), 3.13-3.10 (2H, m), 2.42 (3H, s), 1.93-1.86 (2H, m), 1.06 (3H, t, J=7.4 Hz); $^{13}$C NMR (CDCl$_3$, 125 MHz) 154.4, 148.1, 139.7, 136.8, 136.4, 135.9, 129.4, 126.8, 121.8, 54.9, 17.3, 15.0, 12.9.

N-(5-(2-Amino-5-bromopyridin-3-yl)-3-fluoro-2-methylphenyl)propane-1-sulfonamide (14*t*)

Method J; purified by column chromatography on silica gel (EtOAc/hexane, 30:70) to give 14*t* (89%) as a pale yellow solid; $^1$H NMR (CDCl$_3$, 500 MHz) 8.08 (1H, d, J=2.3 Hz), 7.46 (1H, d, J=2.3 Hz), 7.34 (1H, s), 7.0 (1H, dd, J=9.4, 1.7 Hz), 6.96 (1H, br), 4.78 (2H, s), 3.15-3.12 (2H, m), 2.27 (3H, d, J=1.7 Hz), 1.92-1.86 (2H, m), 1.06 (3H, t, J=7.4 Hz); $^{13}$C NMR (CDCl$_3$, 125 MHz) 161.6 (d, J$_{CF}$=246.1 Hz), 154.4, 148.2, 139.7, 137.3 (d, J$_{CF}$=7.4 Hz), 136.1 (d, J$_{CF}$=9.8 Hz), 121.4, 117.6, 112.5 (d, J$_{CF}$=24.6 Hz), 108.3, 54.8, 17.3, 12.9, 9.49 (d, J$_{CF}$=3.7 Hz).

N-(5-(2-Amino-5-bromopyridin-3-yl)-2,3-dimethylphenyl)propane-1-sulfonamide (14*u*)

Method J; purified by column chromatography on silica gel (EtOAc/hexane, 30:70 to 40:60) to give 14*u* (92%) as a pale yellow solid; $^1$H NMR (CDCl$_3$, 500 MHz) 8.04 (1H, d, J=2.3 Hz), 7.44 (1H, d, J=2.3 Hz), 7.35 (1H, s), 7.10 (1H, s), 6.91 (1H, s), 4.80 (2H, br), 4.06 (3H, d, J=2.1 Hz), 3.12-3.08 (2H, m), 2.35 (3H, s), 2.29 (3H, s), 1.93-1.86 (2H, m), 1.05 (3H, t, J=7.4 Hz); $^{13}$C NMR (CDCl$_3$, 125 MHz) 154.6, 147.5, 139.6, 139.4, 135.3, 134.6, 130.4, 127.9, 122.5, 121.6, 108.2, 54.6, 20.8, 17.3, 14.0, 12.9.

N-(5-(2-Amino-5-bromopyridin-3-yl)-2-methoxy-3-methylphenyl)propane-1-sulfonamide (14*v*)

Method J; purified by column chromatography on silica gel (EtOAc/hexane, 30:70 to 40:60) to give 14*v* (87%) as a light brown solid; $^1$H NMR (CDCl$_3$, 500 MHz) 8.08 (1H, d, J=2.3 Hz), 7.44 (1H, d, J=2.3 Hz), 7.37 (1H, d, J=1.7 Hz), 7.04 (1H, br), 6.97 (1H, d, J=1.2 Hz), 4.72 (2H, br), 3.82 (3H, s), 3.15-3.12 (2H, m), 2.35 (3H, s), 1.92-1.86 (2H, m), 1.05 (3H, t, J=7.4 Hz); $^{13}$C NMR (CDCl$_3$, 125 MHz) 154.5, 147.7, 147.2, 139.7, 133.1, 132.3, 131.3, 126.6, 122.5, 116.0, 108.3, 60.7, 54.2, 17.3, 16.3, 12.9.

5-Bromo-3-(1-(propylsulfonyl)indolin-6-yl)pyridin-2-amine (14*w*)

Method J; purified by column chromatography on silica gel (EtOAc/hexane, 30:70 to 40:60) to give 14*w* (70%) as a pale yellow solid; $^1$H NMR (CDCl$_3$, 500 MHz) 8.07 (1H, d, J=2.3 Hz), 7.43 (1H, d, J=2.3 Hz), 7.39 (1H, d, J=1.2 Hz), 7.27 (1H, d, J=8.6 Hz), 7.04 (1H, dd, J=7.4, 1.2 Hz), 4.67 (2H, br), 4.08 (2H, t, J=8.6 Hz), 3.18 (2H, t, J=8.6 Hz), 3.06-3.03 (2H, m), 1.93-1.85 (2H, m), 1.04 (3H, t, J=7.4 Hz); $^{13}$C NMR (CDCl$_3$, 125 MHz) 154.5, 147.8, 143.0, 139.7, 136.6, 131.2, 126.0, 123.4, 123.0, 113.2, 108.2, 51.4, 50.4, 27.8, 16.7, 13.0.

N-(5-(2-Amino-5-bromopyridin-3-yl)-2-hydroxyphenyl)propane-1-sulfonamide (14*x*)

Method J; purified by column chromatography on silica gel (MeOH/CH$_2$Cl$_2$, 1:99 to 3:97) to give 14*x* (61%) as a brown solid; $^1$H NMR (CD$_3$OD, 500 MHz) 7.93 (1H, s), 7.46 (1H, d, J=2.3 Hz), 7.43 (1H, d, J=1.7 Hz), 7.11 (1H, dd, J=7.7, 2.9 Hz), 6.97 (1H, d, J=8.6 Hz), 3.07-3.04 (2H, m), 1.86 (2H, sex, J=8.0 Hz), 1.00 (3H, t, J=7.4 Hz); $^{13}$C NMR (CD$_3$OD, 125 MHz) 156.9, 151.4, 147.4, 141.0, 129.2, 127.8, 126.6, 126.2, 124.8, 117.1, 108.2, 25.0, 18.3, 13.2.

tert-Butyl 4-(3-bromophenyl)piperazine-1-carboxylate (16)

To a solution of 15 (100.0 mg, 0.42 mmol), triethylmine (0.17 mL, 1.24 mmol) and DMAP (15.2 mg, 0.12 mmol) in anhydrous CH$_2$Cl$_2$ (2 mL) was added di-tert-butyl dicarbonate (0.11 mL, 0.46 mmol) under argon at 0° C. The resulting mixture was stirred at 0° C. for 10 min. Then, the temperature was slowly increased to room temperature and the reaction was stirred for 2 h. After being quenched with H$_2$O (5 mL), the aqueous layer was extracted with CH$_2$Cl$_2$ (2×10 mL). The combined organic extracts were washed with brine, dried over anhydrous Na$_2$SO$_4$, filtered, and concentrated. The residue was purified by column chromatography on silica gel (EtOAc/hexane, 5:95 to 10:90) to afford 16 (114.6 mg, 81%) as a clear oil; $^1$H NMR (CDCl$_3$, 400 MHz) 7.09 (1H, t, J=7.8 Hz), 7.02-7.01 (1H, m), 6.96 (1H, d, J=7.8 Hz), 6.82-6.80 (1H, m), 3.56-3.53 (4H, m), 3.12-3.09 (4H, m), 1.47 (9H, s); $^{13}$C NMR (CDCl$_3$, 100 MHz) 154.5, 152.3, 130.3, 123.1, 122.6, 119.1, 114.8, 79.9, 48.7, 28.3.

tert-Butyl 4-(3-(4,4,5,5-tetramethyl-1,3,2-dioxaborolan-2-yl)phenyl)piperazine-1-carboxylate (17)

Method I; the reaction was stirred for 6.5 h and purified by column chromatography on silica gel (EtOAc/hexane, 10:90) to give 17 (78%) as a white solid; $^1$H NMR (CDCl$_3$, 500 MHz) 7.38 (1H, d, J=2.9 Hz), 7.34 (1H, d, J=7.4 Hz), 7.28 (1H, t, J=7.4 Hz), 7.04-7.02 (1H, m), 3.58-3.56 (4H, m), 3.15 (4H, br), 1.33 (12H, s); $^{13}$C NMR (CDCl$_3$, 125 MHz) 154.7, 150.6, 128.6, 126.7, 122.8, 119.7, 83.7, 79.8, 49.5, 28.4, 24.8.

General Procedure for the Preparation of tert-Butyl 4-(4-(6-chloro-5-phenylpyridin-3-yl)phenyl)piperazine-1-carboxylate; tert-butyl 4-(4-(6-chloro-5-(3-methoxy-4-(propylsulfonamido)phenyl)pyridin-3-yl)phenyl)piperazine-1-carboxylate (19*k*), Method K To a mixture of 14*k* (31.0 mg, 0.07 mmol), 18 (31.6 mg, 0.08 mmol), and Pd(PPh$_3$)$_4$ (12.8 mg, 0.01 mmol) was added anhydrous DME (2 mL) under argon. The reaction was stirred at room temperature for 10 min then 1 M Na$_2$CO$_3$ (0.15 mL, 0.15 mmol) was added. The mixture was refluxed for 16 h. After being quenched by the addition of water, the aqueous layer was extracted with EtOAc (2×15 mL). The combined organic extracts were washed with brine, dried over anhydrous Na$_2$SO$_4$, filtered, and concentrated. The residue was purified by column chromatography on silica gel (EtOAc/hexane, 20:80 to 30:70) to afford 19*k* (35.6 mg, 80%) as a white solid; $^1$H NMR (CDCl$_3$, 500 MHz) 8.56 (1H, d, J=2.3 Hz), 7.80 (1H, d, J=2.3 Hz), 7.62 (1H, d, J=8.6 Hz), 7.51 (2H, d, J=8.6 Hz), 7.07-7.05 (2H, m), 7.00 (2H, d, J=9.2 Hz), 6.93 (1H, s), 3.92 (3H, s), 3.61-3.59 (4H, m), 3.22-3.21 (4H, m), 3.12-3.08 (2H, m), 1.92-1.84 (2H, m), 1.48 (9H, s), 1.04 (3H, t, J=7.4 Hz); $^{13}$C NMR (CDCl$_3$, 125 MHz) 154.6, 151.3, 148.2, 147.2, 145.9, 137.1, 135.8, 135.5, 134.0, 127.7, 127.0, 126.5, 122.3, 119.1, 116.2, 111.9, 80.0, 56.0, 53.4, 48.6, 28.3, 17.2, 12.8.

tert-Butyl 4-(4-(6-chloro-5-(3-methoxy-5-(methylsulfonamido)phenyl)pyridin-3-yl)phenyl)piperazine-1-carboxylate (19*laa*)

Method K; purified by column chromatography on silica gel (EtOAc/hexane, 20:80 to 60:40) to give 19*laa* (83%) as a white solid; $^1$H NMR (CDCl$_3$, 400 MHz) 8.56 (1H, d, J=2.3 Hz), 7.79 (1H, d, J=2.3 Hz), 7.53 (1H, br), 7.49(2H, d, J=8.7 Hz), 6.98 (2H, d, J=8.7 Hz), 6.95-6.94 (1H, m), 6.91 (1H, t, J=2.3 Hz), 6.81-6.80 (1H, m), 3.84 (3H, s), 3.60-3.58 (4H, m), 3.21-3.19 (4H, m), 3.08 (3H, s), 1.48 (9H, s); $^{13}$C NMR (CDCl$_3$, 100 MHz) 160.4, 154.7, 151.3, 147.0, 146.2, 139.8, 138.2, 137.1, 135.7, 135.6, 127.8, 126.8, 116.5, 113.2, 111.7, 105.8, 80.1, 55.6, 48.6, 39.4, 28.4.

tert-Butyl 4-(4-(6-chloro-5-(3-(ethylsulfonamido)-5-methoxyphenyl)pyridin-3-yl)phenyl)piperazine-1-carboxylate (191ba)

Method K; purified by column chromatography on silica gel (EtOAc/hexane, 30:70 to 45:55) to give 191ba (99%) as a white solid; $^1$H NMR (CDCl$_3$, 600 MHz) 8.57 (1H, d, J=2.1 Hz), 7.79 (1H, d, J=2.1 Hz), 7.49 (2H, d, J=8.9 Hz), 7.47 (1H, s), 6.99 (2H, d, J=8.9 Hz), 6.94 (1H, s), 6.91 (1H, s), 6.78 (1H, s), 3.84 (3H, s), 3.59-3.59 (4H, m), 3.21-3.19 (6H, m), 1.48 (9H, s), 1.39 (3H, t, J=7.6 Hz); $^{13}$C NMR (CDCl$_3$, 150 MHz) 160.4, 154.6, 151.3, 147.0, 146.2, 139.8, 138.3, 137.0, 135.7, 135.5, 127.8, 126.9, 116.5, 113.0, 111.4, 105.5, 80.0, 55.6, 55.5, 48.6, 45.9, 28.4, 8.22.

tert-Butyl 4-(4-(6-chloro-5-(3-methoxy-5-(propylsulfonamido)phenyl)pyridin-3-yl)phenyl)piperazine-1-carboxylate (191ca)

Method K; purified by column chromatography on silica gel (EtOAc/hexane, 20:80 to 40:60) to give 191ca (95%) as a pale yellow solid; $^1$H NMR (CDCl$_3$, 500 MHz) 8.57 (1H, d, J=2.9 Hz), 7.79 (1H, d, J=2.9 Hz), 7.49 (2H, d, J=8.6 Hz), 7.47 (1H, br), 6.99 (2H, d, J=8.6 Hz), 6.93 (1H, s), 6.90 (1H, t, J=1.7 Hz), 6.78-6.77 (1H, m), 3.84 (3H, s), 3.60-3.58 (4H, m), 3.21-3.19 (4H, m), 3.16-3.13 (2H, m), 1.91-1.84 (2H, m), 1.48 (9H, s), 1.02 (3H, t, J=7.4 Hz); $^{13}$C NMR (CDCl$_3$, 125 MHz) 160.4, 154.7, 151.3, 147.0, 146.2, 139.8, 138.3, 137.0, 135.7, 135.5, 127.8, 126.9, 116.5, 112.9, 111.3, 105.5, 80.1, 55.5, 53.3, 48.6, 28.4, 24.8, 17.2, 12.8.

tert-Butyl 4-(4-(6-chloro-5-(3-methoxy-5-(1-methylethylsulfonamido)phenyl)pyridin-3-yl)phenyl)piperazine-1-carboxylate (191da)

Method K; purified by column chromatography on silica gel (EtOAc/hexane, 30:70 to 50:50) to give 191da (79%) as a white solid; $^1$H NMR (CDCl$_3$, 500 MHz) 8.57 (1H, d, J=2.7 Hz), 7.79 (1H, d, J=2.3 Hz), 7.49 (2H, d, J=8.6 Hz), 7.37 (1H, s), 6.99 (2H, d, J=8.6 Hz), 6.95 (1H, s), 6.92 (1H, t, J=2.3 Hz), 6.76-6.75 (1H, m), 3.83 (3H, s), 3.60-3.58 (4H, m), 3.39 (1H, sep, J=6.9 Hz), 3.21-3.20 (4H, m), 1.48 (9H, s), 1.42 (6H, d, J=6.9 Hz); $^{13}$C NMR (CDCl$_3$, 125 MHz) 160.4, 154.6, 151.3, 147.0, 146.2, 139.7, 138.6, 137.0, 135.8, 135.5, 127.8, 126.9, 116.5, 112.9, 111.2, 105.4, 80.0, 55.5, 52.6, 48.6, 30.9, 28.4, 16.5.

tert-Butyl 4-(4-(6-chloro-5-(3-(cyclopropanesulfonamido)-5-methoxyphenyl)pyridin-3-yl)phenyl)piperazine-1-carboxylate (191ea)

Method K; purified by column chromatography on silica gel (EtOAc/hexane, 30:70 to 50:50) to give 191ea (76%) as a white solid; $^1$H NMR (CDCl$_3$, 400 MHz) 8.57 (1H, d, J=2.7 Hz), 7.79 (1H, d, J=2.3 Hz), 7.50 (2H, d, J=8.7 Hz), 7.01-6.96 (4H, m), 6.92 (1H, t, J=1.8 Hz), 6.81 (1H, t, J=1.4 Hz), 3.85 (3H, s), 3.61-3.58 (4H, m), 3.22-3.20 (4H, m), 2.60-2.54 (1H, m), 1.48 (9H, s), 1.24-1.22 (2H, m), 1.02-0.99 (2H, m); $^{13}$C NMR (CDCl$_3$, 100 MHz) 160.3, 154.7, 151.3, 147.0, 146.2, 139.7, 138.1, 137.1, 135.7, 135.6, 127.8, 127.0, 116.5, 114.3, 111.9, 106.8, 80.1, 55.6, 48.6, 30.0, 28.4, 5.7.

tert-Butyl 4-(4-(6-chloro-5-(3-methoxy-5-(2-methylpropylsulfonamido)phenyl) pyridine-3-yl)phenyl) piperazine-1-carboxylate (191fa)

Method K; purified by column chromatography on silica gel (EtOAc/hexane, 30:70 to 50:50) to give 191fa (79%) as a white solid; $^1$H NMR (CDCl$_3$, 500 MHz) 8.57 (1H, d, J=2.3 Hz), 7.79 (1H, d, J=2.9 Hz), 7.49 (2H, d, J=9.2 Hz), 7.38 (1H, s), 6.99 (2H, d, J=8.6Hz), 6.92-6.91 (1H, m), 6.89-6.88 (1H, d, J=2.3, 1.7 Hz), 6.78-6.77 (1H, m), 3.84 (3H, s), 3.61-3.59 (4H, m), 3.21-3.20 (4H, m), 3.07 (2H, d, J=6.9 Hz), 2.32 (1H, sep, J=6.9 Hz), 1.48 (9H, s), 1.09 (6H, d, J=6.9 Hz); $^{13}$C NMR (CDCl$_3$, 125 MHz) 160.4, 154.7, 151.3, 147.0, 146.2, 139.8, 138.3, 137.0, 135.7, 135.5, 127.8, 126.9, 116.5, 112.8, 111.3, 105.3, 80.0, 59.3, 55.5, 48.6, 28.4, 24.8, 22.5.

tert-Butyl 4-(4-(6-chloro-5-(3-fluoro-4-methoxy-5-(propylsulfonamido)phenyl)pyridin-3-yl)phenyl) piperazine-1-carboxylate (19pa)

Method K; purified by column chromatography on silica gel (EtOAc/hexane, 20:80) to give 19pa (69%) as a white solid; $^1$H NMR (CDCl$_3$, 500 MHz) 8.57 (1H, d, J=2.3 Hz), 7.82 (1H, d, J=2.3 Hz), 7.51 (2H, d, J=8.6 Hz), 7.39 (1H, t, J=8.0 Hz), 7.07 (1H, dd, J=6.6, 1.7 Hz), 7.03, 7.02 (1H, d, J=2.3, 1.7 Hz), 7.01-6.99 (3H, m), 3.85 (3H, s), 3.61-3.59 (4H, m), 3.21 (4H, br), 1.49 (9H, s); $^{13}$C NMR (CDCl$_3$, 125 MHz) 154.6, 153.9 (d, $J_{CF}$=248.6 Hz), 151.4, 147.0, 146.4, 137.0, 136.4 (d, $J_{CF}$=12.3 Hz), 135.7, 134.6, 133.0 (d, $J_{CF}$=8.6 Hz), 131.0 (d, $J_{CF}$=4.9 Hz), 127.8, 126.9, 116.5, 114.8 (d, $J_{CF}$=2.5 Hz), 113.4 (d, $J_{CF}$=20.9 Hz), 80.0, 61.6 (d, $J_{CF}$=7.4 Hz), 53.6, 48.6, 28.4, 17.2, 12.9.

N-(3-(2-Chloro-5-(4-(piperazin-1-yl)phenyl)pyridin-3-yl)-5-methoxyphenyeethanesulfonamide (CSLP14)

To a solution of 191ba (24.8 mg, 0.04 mmol) in anhydrous CH$_2$Cl$_2$ (3 mL) was added trifluoroacetic acid (0.3 mL), and the mixture was stirred at room temperature for 16 h. After being quenched with saturated aqueous NaHCO$_3$ (5 mL), CH$_2$Cl$_2$ were added, and the layers were separated. The combined organic phases were washed with brine, dried over anhydrous Na$_2$SO$_4$, filtered, and concentrated. The residue was purified by column chromatography on silica gel (MeOH/CH$_2$Cl$_2$, 5:95 to 10:90) to give CSLP14 (18.4 mg, 90%) as a yellow solid; $^1$H NMR (CDCl$_3$, 500 MHz) 8.58 (1H, d, J=2.3 Hz), 7.79 (1H, d, J=1.7 Hz), 7.50 (2H, d, J=8.6 Hz), 7.00 (1H, d, J=8.6 Hz), 6.89 (1H, s), 6.88(1H, s), 6.80(1H, s), 3.85 (3H, s), 3.27-3.25 (4H, m), 3.21 (2H, q, J=7.4 Hz), 3.11-3.09 (4H, m), 1.40 (3H, t, J=7.4 Hz); $^{13}$C NMR (CDCl$_3$, 125 MHz) 160.5, 151.8, 146.9, 146.3, 140.0, 138.2, 137.0, 135.7, 135.6, 127.7, 126.5, 116.1, 113.1, 111.5, 105.6, 55.6, 49.4, 46.0, 45.8, 8.3.

General Procedure for the Preparation of 1-(4-(6-methyl-5-phenylpyridin-3-yl)phenyl)piperazines; N-(2-methoxy-4-(2-methyl-5-(4-(piperazin-1-yl)phenyl)pyridin-3-yl)phenyl)propane-1-sulfonamide (CSLP1), Method L To a mixture of 19k (35.0 mg, 0.06 mmol), K$_2$CO$_3$ (16.0 mg, 0.12 mmol), and Pd(PPh$_3$)$_4$ (13.4 mg, 0.01 mmol) was added anhydrous 1,4-dioxane (1.5 mL) and trimethylboraxine (0.03 mL, 0.23 mmol) under argon. The reaction was stirred at room temperature for 10 min then the mixture was refluxed for 16 h. After being quenched by the addition of water, the aqueous layer was extracted with EtOAc (2×15 mL). The combined organic extracts were washed with brine, dried over anhydrous $Na_2SO_4$, filtered, and concentrated. The residue was purified by column chromatography on silica gel (EtOAc/hexane, 20:80 to 70:30) to afford the methylated pyridine product then anhydrous $CH_2Cl_2$ (3 mL) and trifluoroacetic acid (0.3 mL) were added. The mixture was stirred at room temperature for 16 h. After being quenched with saturated aqueous $NaHCO_3$ (5 mL), $CH_2Cl_2$ were added, and the layers were separated. The combined organic phases were washed with brine, dried over anhydrous $Na_2SO_4$, filtered, and concentrated. The residue was purified by column chromatography on silica gel (MeOH/$CH_2Cl_2$, 5:95 to 15:85) to give CSLP1 (24.7 mg, 89%) as a yellow solid; $^1$H NMR (CDCl$_3$, 400 MHz) 8.70 (1H, d, J=1.8 Hz), 7.67 (1H, d, J=1.8 Hz), 7.60 (1H, d, J=8.2 Hz), 7.52 (2H, d, J=8.7 Hz), 7.00 (2H, d, J=8.7 Hz), 6.96 (2H, dd, J=8.2, 1.8 Hz), 6.88 (1H, d, J=1.4 Hz), 3.90 (3H, s), 3.24-3.22 (4H, m), 3.11-3.07 (5H, m), 2.53 (3H, s), 1.88 (2H, sex, J=7.8 Hz), 1.04 (3H, t, J=7.3 Hz); $^{13}$C NMR (CDCl$_3$, 100 MHz) 153.5, 151.3, 148.6, 145.8, 136.8, 136.0, 134.8, 133.7, 128.3, 127.6, 125.7, 122.0, 119.6, 116.2, 111.5, 55.9, 53.3, 49.6, 45.7, 23.0, 17.2, 12.9; Purity (method A) >99%, $t_R$=14.8 min.

N-(3-Methoxy-5-(2-methyl-5-(4-(piperazin-1-yl)phenyl)pyridin-3-yl)phenyl)methanesulfonamide (CSLP2)

Method L; purified by column chromatography on silica gel (MeOH/$CH_2Cl_2$, 5:95 to 20:80) to give CSLP2 (81%) as a yellow solid; $^1$H NMR (CDCl$_3$, 500 MHz) 8.71 (1H, d, J=2.3 Hz), 7.65 (1H, s), 7.50 (2H, d, J=8.6 Hz), 6.99 (2H, d, J=8.6 Hz), 6.86 (1H, s), 6.77 (1H, s), 6.70 (1H, s), 3.84 (3H, s), 3.24-3.22 (4H, m), 3.09-3.07 (7H, m), 2.52 (3H, s); $^{13}$C NMR (CDCl$_3$, 125 MHz) 160.6, 153.3, 151.4, 146.0, 142.6, 138.2, 135.9, 134.6, 133.7, 128.2, 127.6, 116.2, 113.0, 111.5, 105.1, 55.6, 49.6, 45.8, 39.6, 22.9; Purity (method A) 98%, $t_R$=13.2 min.

N-(3-Methoxy-5-(2-methyl-5-(4-(piperazin-1-yl)phenyl)pyridin-3-yl)phenyl)cyclopropanesulfonamide (CSLP9)

Method L; purified by column chromatography on silica gel (MeOH/$CH_2Cl_2$, 10:90 to 20:80) to give CSLP9 (86%) as a pale yellow solid; $^1$H NMR (CDCl$_3$, 400 MHz) 8.69 (1H, d, J=2.3 Hz), 7.64 (1H, d, J=2.3 Hz), 7.48 (2H, d, J=8.7 Hz), 6.97 (2H, d, J=9.2 Hz), 6.92 (1H, t, J=1.8 Hz), 6.84-6.83 (1H, m), 6.68 (1H, t, J=1.8 Hz), 4.87 (1H, br), 3.83 (3H, s), 3.26-3.24 (4H, m), 3.14-3.11 (4H, m), 2.59-2.53 (1H, m), 2.51 (1H, s), 1.22-1.18 (2H, m), 1.01-0.96 (2H, m); $^{13}$C NMR (CDCl$_3$, 100 MHz) 160.3, 153.4, 151.1, 145.9, 142.1, 138.4, 136.0, 134.6, 133.7, 128.4, 127.6, 116.4, 114.0, 111.4, 106.0, 55.5, 49.1, 45.4, 30.0, 22.9, 5.6; Purity (method A) 97%, $t_R$=14.3 min.

N-(3-Methoxy-5-(2-methyl-5-(4-(piperazin-1-yl)phenyl)pyridin-3-yl)phenyl)propane-1-sulfonamide (CSLP10)

Method L; purified by column chromatography on silica gel (MeOH/$CH_2Cl_2$, 10:90 to 20:80) to give CSLP10 (65%) as a yellow solid; $^1$H NMR (CDCl$_3$, 500 MHz) 8.71 (1H, d, J=2.3 Hz), 7.65 (1H, d, J=2.3 Hz), 7.50 (2H, d, J=8.6 Hz), 7.00 (2H, d, J=8.6 Hz), 6.85 (1H, t, J=2.3 Hz), 6.75 (1H, t, J=1.7 Hz), 6.68 (1H, t, J=2.3 Hz), 3.84 (3H, s), 3.23-3.21 (4H, m), 3.15-3.12 (2H, m), 3.08-3.06 (4H, m), 2.52 (3H, s), 1.92-1.84 (2H, m), 1.04 (3H, t, J=7.4 Hz); $^{13}$C NMR (CDCl$_3$, 125 MHz) 160.6, 153.3, 151.4, 146.0, 142.6, 138.2, 135.9, 134.6, 133.8, 128.2, 127.6, 116.2, 112.8, 111.2, 105.8, 55.5, 53.5, 49.8, 45.9, 22.9, 17.3, 12.9; Purity (method A) 98%, $t_R$=14.3 min.

N-(3-Methoxy-5-(2-methyl-5-(4-(piperazin-1-yl)phenyl)pyridin-3-yl)phenyl)ethanesulfonamide (CSLP15)

Method L; purified by column chromatography on silica gel (MeOH/$CH_2Cl_2$, 5:95 to 20:80) to give CSLP15 (62%) as a yellow solid; $^1$H NMR (CDCl$_3$, 400 MHz) 8.70 (1H, d, J=1.8 Hz), 7.64 (1H, d, J=1.8 Hz), 7.51 (2H, d, J=8.7 Hz), 7.00 (2H, d, J=8.7 Hz), 6.86 (1H, s), 6.77 (1H, s), 6.68 (1H, s), 3.84 (3H, s), 3.31-3.28 (4H, m), 3.22-3.16 (6H, m), 2.52 (3H, s), 1.40 (3H, t, J=7.3 Hz); $^{13}$C NMR (CDCl$_3$, 100 MHz) 160.6, 153.4, 151.0, 146.1, 142.5, 138.2, 135.9, 134.7, 133.7, 128.7, 127.7, 116.5, 112.8, 111.2, 104.8, 55.6, 49.0, 46.1, 45.3, 22.9, 8.3; Purity (method A) 98%, $t_R$=13.9 min.

N-(3-Methoxy-5-(2-methyl-5-(4-(piperazin-1-yl)phenyl)pyridin-3-yl)phenyl)propane-2-sulfonamide (CSLP16)

Method L; purified by column chromatography on silica gel (MeOH/$CH_2Cl_2$, 5:95 to 15:85) to give CSLP16 (96%) as a yellow solid; $^1$H NMR (CD$_3$OD, 500 MHz) 8.62 (1H, d, J=2.3 Hz), 7.81 (1H, d, J=2.3 Hz), 7.58 (2H, d, J=8.6 Hz), 7.08 (2H, d, J=9.2 Hz), 6.91 (1H, t, J=1.7 Hz), 6.84, (1H, t, J=1.7 Hz), 6.70 (1H, t, J=1.2 Hz), 3.82 (3H, s), 3.35-3.29 (1H, m), 3.23-3.21 (4H, m), 3.02-3.00 (4H, m), 2.48 (3H, s), 1.35 (6H, d, J=6.9 Hz); $^{13}$C NMR (CD$_3$OD, 125 MHz) 162.2, 154.1, 153.0, 145.9, 143.0, 141.2, 138.5, 136.3, 135.9, 129.1, 128.6, 117.6, 113.4, 111.2, 105.6, 56.0, 53.5, 50.3, 46.3, 22.4, 16.7; Purity (method B) 98%, $t_R$=15.8 min.

N-(3-Methoxy-5-(2-methyl-5-(4-(piperazin-1-yl)phenyl)pyridin-3-yl)phenyl)-2-methylpropane-1-sulfonamide (CSLP17)

Method L; purified by column chromatography on silica gel (MeOH/$CH_2Cl_2$, 5:95 to 15:85) to give CSLP17 (83%) as a yellow solid; $^1$H NMR (CDCl$_3$, 500 MHz) 8.71 (1H, d, J=2.3 Hz), 7.65 (1H, d, J=2.3 Hz), 7.51 (2H, d, J=8.6 Hz), 7.00 (2H, d, J=9.2 Hz), 6.84 (1H, t, J=1.7 Hz), 6.74 (1H, t, J=1.7 Hz), 6.69-6.68 (1H, m), 3.84 (3H, s), 3.28-3.26 (4H, m), 3.13-3.11 (4H, m), 3.05 (2H, d, J=6.3 Hz), 2.52 (3H, s), 2.32 (1H, sep, J=6.9 Hz), 1.10 (6H, d, J=6.9 Hz); $^{13}$C NMR (CDCl$_3$, 125 MHz) 160.6, 153.6, 150.6, 146.0, 142.5, 138.3, 135.9, 134.7, 133.6, 129.2, 127.7, 116.8, 112.7, 111.1, 104.7, 59.5, 55.6, 48.2, 44.6, 24.9, 22.9, 22.5; Purity (method A) 99%, $t_R$=15.8 min.

N-(3-Fluoro-2-methoxy-5-(2-methyl-5-(4-(piperazin-1-yl)phenyl)pyridin-3-yl)phenyl)propane-1-sulfonamide (CSLP53)

Method L; purified by column chromatography on silica gel (MeOH/$CH_2Cl_2$, 5:95 to 10:90) to give CSLP53 (90%) as a yellow solid; $^1$H NMR (CDCl$_3$, 600 MHz) 8.71 (1H, d, J=2.1 Hz), 7.63 (1H, d, J=2.1 Hz), 7.50 (2H, d, J=8.9 Hz), 7.34 (1H, s), 7.01 (2H, d, J=8.2 Hz), 6.88 (1H, dd, J=11.7, 1.4 Hz), 4.08 (3H, d, J=1.4 Hz), 3.23-3.22 (4H, m), 3.12-3.10 (2H, m), 3.08-3.06 (4H, m), 2.53 (3H, s), 1.87 (2H, sex, J=7.6 Hz), 1.04 (3H, t, J=7.6 Hz); $^{13}$C NMR (CDCl$_3$, 150 MHz) 154.1 (d, $J_{CF}$=246.9 Hz), 153.3, 151.5, 146.2 (d, $J_{CF}$=3.0 Hz), 135.9 (d, $J_{CF}$=10.4 Hz), 135.8 (d, $J_{CF}$=8.9 Hz), 134.8, 134. 6, 133.9, 131.0 (d, $J_{CF}$=5.9 Hz), 128.1, 127.6, 116.2, 114.8, 113.1 (d, $J_{CF}$=20.7 Hz), 61.6, 53.8, 49.8, 45.9, 23.0, 17.2, 12.9; Purity (method A) 97%, $t_R$=15.4 min.

General Procedure for the Preparation of 3-phenyl-5-(4-(piperazin-1-yl)phenyl)pyridin-2-amines; N-(3-(2-Amino-5-(4-(piperazin-1-yl)phenyl)pyridin-3-yl)-5-methoxyphenyemethanesulfonamide (CSLP3), Method M To a mixture of 141ab (26.0 mg, 0.07 mmol), 18 (29.8 mg, 0.08 mmol), and Pd(PPh$_3$)$_4$ (13.4 mg, 0.01 mmol) was added anhydrous DME (1.5 mL) under argon. The reaction was stirred at room temperature for 10 min then 1 M Na$_2$CO$_3$ (0.14 mL, 0.14 mmol) was added. The mixture was refluxed for 16 h. After being quenched by the addition of water, the aqueous layer was extracted with EtOAc (2×15 mL). The combined organic extracts were washed with brine, dried over anhydrous Na$_2$SO$_4$, filtered, and concentrated. The residue was purified by column chromatography on silica gel (EtOAc/hexane, 30:70 to 70:30) to afford the coupling product then anhydrous CH$_2$Cl$_2$ (3 mL), and trifluoroacetic acid (0.3 mL) were added. The mixture was stirred at room temperature for 16 h. After being quenched with saturated aqueous NaHCO$_3$ (5 mL), CH$_2$Cl$_2$ were added, and the layers were separated. The combined organic phases were washed with brine, dried over anhydrous Na$_2$SO$_4$, filtered, and concentrated. The residue was purified by column chromatography on silica gel (MeOH/CH$_2$Cl$_2$, 10:90 to 30:70) to give CSLP3 (9.9 mg, 31%) as a yellow solid; $^1$H NMR (CD$_3$OD, 500 MHz) 8.15 (1H, d, J=2.3 Hz), 7.62 (1H, d, J=2.3 Hz), 7.48 (2H, d, J=8.6 Hz), 7.06 (2H, d, J=8.6 Hz), 6.92 (1H, s), 6.89 (1H, t, J=1.7 Hz), 6.83 (1H, s), 3.84 (3H, s), 3.30-3.27 (4H, m), 3.17-3.15 (4H, m), 3.02 (3H, s); $^{13}$C NMR (CD$_3$OD, 125 MHz) 162.6, 156.4, 151.6, 144.9, 141.5, 141.4, 137.4, 131.2, 128.3, 127.8, 123.1, 118.1, 113.5, 111.2, 106.3, 66.9, 56.0, 45.7, 39.4; Purity (method A) 98%, $t_R$=13.2 min.

N-(3-(2-Amino-5-(4-(piperazin-1-yl)phenyl)pyridin-3-yl)-5-methoxyphenyepropane-1-sulfonamide (CSLP6)

Method M; purified by column chromatography on silica gel (MeOH/CH$_2$Cl$_2$, 5:95 to 15:85) to give CSLP6 (49%) as a yellow solid; $^1$H NMR (CD$_3$OD, 500 MHz) 8.15 (1H, d, J=2.3 Hz), 7.62 (1H, d, J=2.3 Hz), 7.48 (2H, d, J=8.6 Hz), 7.06 (2H, d, J=8.6 Hz), 6.92 (1H, t, J=1.7 Hz), 6.87 (1H, t, J=1.7 Hz), 6.81 (1H, t, J=1.7 Hz), 3.83 (3H, s), 3.33-3.29 (4H, m), 3.22-3.20 (4H, m), 3.14-3.10 (2H, m), 1.82 (2H, sex, J=7.4 Hz), 1.02 (3H, t, J=7.4 Hz); $^{13}$C NMR (CDCl$_3$, 125 MHz) 161.2, 154.2, 150.8, 145.1, 140.5, 139.1, 136.0, 129.1, 127.7, 126.9, 120.9, 116.4, 112.3, 110.1, 105.1, 55.6, 53.7, 50.0, 45.9, 17.3, 12.9; Purity (method A) 99%, $t_R$=14.6 min.

N-(3-(2-Amino-5-(4-(piperazin-1-yl)phenyl)pyridin-3-yl)-5-methoxyphenyeethanesulfonamide (CSLP7)

Method M; purified by column chromatography on silica gel (MeOH/CH$_2$Cl$_2$, 5:95 to 15:85) to give CSLP7 (30%) as a yellow solid; 41 NMR (CD$_3$OD, 500 MHz) 8.15 (1H, d, J=1.7 Hz), 7.61 (1H, d, J=2.3 Hz), 7.47(2H, d, J=8.6 Hz), 7.04 (2H, d, J=8.6 Hz), 6.92 (1H, t, J=1.7 Hz), 6.88 (1H, t, J=2.3 Hz), 6.80 (1H, t, J=2.3 Hz), 3.83 (3H, s), 3.25-3.23 (4H, m), 3.16 (2H, q, J=7.4 Hz), 3.10-3.08 (4H, m), 1.32 (3H, t, J=7.4 Hz); $^{13}$C NMR (CD$_3$OD, 125 MHz) 162.6, 156.3, 151.8, 144.9, 141.5, 137.4, 130.9, 128.4, 127.8, 123.1, 118.0, 113.2, 110.9, 106.0, 55.9, 50.0, 46.6, 46.0, 8.5; Purity (method A) 97%, $t_R$=13.7 min.

N-(3-(2-Amino-5-(4-(piperazin-1-yl)phenyl)pyridin-3-yl)-5-methoxyphenyepropane-2-sulfonamide (CSLP8)

Method M; purified by column chromatography on silica gel (MeOH/CH$_2$Cl$_2$, 5:95 to 15:85) to give CSLP8 (31%) as a yellow solid; $^1$H NMR (CD$_3$OD, 500 MHz) 8.14 (1H, d, J=1.7 Hz), 7.60 (1H, d, J=1.7 Hz), 7.45(2H, d, J=8.6 Hz), 7.02 (2H, d, J=8.6 Hz), 6.93 (1H, s), 6.89 (1H, s), 6.78 (1H, s), 3.82 (3H, s), 3.37-3.30 (1H, m), 3.21-3.19 (4H, m), 3.06-3.04 (4H, m), 1.35 (6H, d, J=6.9 Hz); $^{13}$C NMR (CD$_3$OD, 125 MHz) 162.5, 156.3, 152.0, 144.9, 141.7, 141.4, 137.4, 130.8, 128.4, 127.7, 123.1, 118.0, 113.0, 110.7, 105.9, 55.9, 53.4, 50.3, 46.2, 16.7; Purity (method A) >99%, $t_R$=14.3 min.

N-(3-(2-Amino-5-(4-(piperazin-1-yl)phenyl)pyridin-3-yl)-5-methoxyphenyl)cyclopropanesulfonamide (CSLP11)

Method M; purified by column chromatography on silica gel (MeOH/CH$_2$Cl$_2$, 5:95 to 15:85) to give CSLP11 (34%) as a yellow solid; $^1$H NMR (CD$_3$OD, 500 MHz) 8.15 (1H, s), 7.61 (1H, s), 7.45 (2H, d, J=8.6 Hz), 7.02 (2H, d, J=8.6 Hz), 6.95 (1H, s), 6.91 (1H, s), 6.82 (1H, s), 3.83 (3H, s), 3.18-3.16 (4H, m), 3.01-2.99 (4H, m), 2.64-2.61 (1H, m), 1.10-1.07 (2H, m), 0.99-0.97 (2H, m); $^{13}$C NMR (CD$_3$OD, 125 MHz) 162.4, 156.2, 152.2, 144.9, 141.5, 141.2, 137.4, 130.6, 128.5, 127.7, 123.1, 117.9, 114.3, 111.2, 107.1, 56.0, 50.7, 46.3, 30.6, 5.8; Purity (method A) 97%, $t_R$=13.9 min.

N-(3-(2-Amino-5-(4-(piperazin-1-yl)phenyl)pyridin-3-yl)-5-methoxyphenyl)-2-methylpropane-1-sulfonamide (CSLP12)

Method M; purified by column chromatography on silica gel (MeOH/CH$_2$Cl$_2$, 5:95 to 15:85) to give CSLP12 (29%) as a yellow solid; $^1$H NMR (CD$_3$OD, 500 MHz) 8.15 (1H, d, J=1.7 Hz), 7.61 (1H, d, J=2.3 Hz), 7.46(2H, d, J=8.6 Hz), 7.04 (2H, d, J=8.6 Hz), 6.90 (1H, s), 6.87 (1H, t, J=2.3 Hz), 6.81 (1H, s), 3.83 (3H, s), 3.22-3.20 (4H, m), 3.06-3.03 (6H, m), 2.24 (1H, sep, J=6.9 Hz), 1.07 (6H, d, J=6.9 Hz); $^{13}$C NMR (CD$_3$OD, 125 MHz) 162.6, 156.3, 152.0, 144.9, 141.5, 141.4, 137.4, 130.8, 128.4, 127.8, 123.1, 118.0, 113.2, 110.8, 106.0, 59.9, 56.0, 50.3, 46.2, 26.1, 22.8; Purity (method A) 99%, $t_R$=15.6 min.

N-(5-(2-Amino-5-(4-(piperazin-1-yl)phenyl)pyridin-3-yl)-2-methoxyphenyepropane-1-sulfonamide (CSLP18)

Method M; purified by column chromatography on silica gel (MeOH/CH$_2$Cl$_2$, 5:95 to 15:85) to give CSLP18 (39%) as a yellow solid; $^1$H NMR (CD$_3$OD, 500 MHz) 8.12 (1H, s), 7.60 (1H, d, J=1.7 Hz), 7.56 (1H, d, J=1.7 Hz), 7.46 (2H, d, J=8.6 Hz), 7.32 (1H, dd, J=8.6, 1.7 Hz), 7.16 (1H, d, J=8.6 Hz), 7.03 (2H, d, J=8.6 Hz), 3.94 (3H, s), 3.21-3.19 (4H, m), 3.06-3.03 (6H, m), 1.84 (2H, sex, J=8.0 Hz), 1.01 (3H, t, J=7.5 Hz); $^{13}$C NMR (CD$_3$OD, 125 MHz) 156.5, 152.7, 152.0, 144.4, 137.5, 131.6, 130.9, 128.6, 127.9, 127.8, 127.7, 125.7, 122.9, 118.0, 113.0, 56.5, 54.6, 50.4, 46.2, 18.3, 13.2; Purity (method A) 98%, $t_R$=14.1 min.

N-(5-(2-Amino-5-(4-(piperazin-1-yl)phenyl)pyridin-3-yl)-3-methoxy-2-methylphenyl)propane-1-sulfonamide (CSLP19)

Method M; purified by column chromatography on silica gel (MeOH/CH$_2$Cl$_2$, 5:95 to 15:85) to give CSLP19 (30%) as a yellow solid; $^1$H NMR (CD$_3$OD, 500 MHz) 8.19(1H, d, J=2.3 Hz), 7.54 (1H, d, J=2.3 Hz), 7.50 (2H, d, J=8.6 Hz), 7.08 (2H, d, J=9.2 Hz), 7.04 (1H, d, J=2.9 Hz), 6.73 (1H, d, J=2.9 Hz), 3.80 (3H, s), 3.41-3.39 (4H, m), 3.35-3.32 (4H, m), 3.16-3.13 (2H, m), 2.09 (3H, s), 1.88 (2H, sex, J=8.0 Hz), 1.07 (3H, t, J=7.4 Hz); $^{13}$C NMR (CD$_3$OD, 125 MHz) 159.7, 156.6, 150.8, 145.0, 140.3, 138.4, 137.6, 131.8, 127.9, 127.6, 125.4, 123.4, 118.4, 114.5, 112.6, 55.9, 55.2, 48.1, 45.0, 18.4, 14.7, 13.2; Purity (method B) 99%, $t_R$=15.9 min.

N-(3-(2-Amino-5-(4-(piperazin-1-yl)phenyl)pyridin-3-yl)-5-methoxyphenyl)benzenesulfonamide (CSLP20)

Method M; purified by column chromatography on silica gel (MeOH/CH$_2$Cl$_2$, 5:95 to 15:85) to give CSLP20 (24%) as a yellow solid; $^1$H NMR (CDCl$_3$, 500 MHz) 8.23 (1H, d, J=1.7 Hz), 7.85 (2H, d, J=7.4 Hz), 7.55 (1H, t, J=7.4 Hz), 7.47 (2H, t, J=7.4 Hz), 7.43 (1H, d, J=2.3 Hz), 7.38 (2H, d, J=8.6 Hz), 6.95 (2H, d, J=8.6 Hz), 6.78 (1H, t, J=1.7 Hz), 6.74 (1H, s), 6.69 (1H, s), 4.55 (2H, br), 3.78 (3H, s), 3.19-3.17 (4H, m), 3.08-3.06 (4H, m); $^{13}$C NMR (CDCl$_3$, 125 MHz) 160.9, 154.2, 150.8, 144.9, 140.0, 139.1, 138.6, 135.9, 133.1, 129.1, 129.0, 127.6, 127.3, 126.9, 120.8, 116.4, 113.4, 111.2, 106.4, 55.5, 50.0, 45.9; Purity (method A) 97%, $t_R$=15.7 min.

N-(5-(2-Amino-5-(4-(piperazin-1-yl)phenyl)pyridin-3-yl)-3-methoxy-2-methylphenyl)methanesulfonamide (CSLP21)

Method M; purified by column chromatography on silica gel (MeOH/CH$_2$Cl$_2$, 5:95 to 15:85) to give CSLP21 (50%) as a yellow solid; $^1$H NMR (CDCl$_3$, 500 MHz) 8.24 (1H, d, J=2.3 Hz), 7.46 (1H, d, J=2.3 Hz), 7.41 (2H, d, J=8.6 Hz), 7.09 (1H, d, J=2.3 Hz), 6.96 (2H, d, J=8.6 Hz), 6.66 (1H, d, J=2.9 Hz), 3.78 (3H, s), 3.22-3.20 (4H, m), 3.09-3.05 (6H, m), 2.05 (3H, s); $^{13}$C NMR (CDCl$_3$, 125 MHz) 158.4, 154.3, 150.4, 144.6, 138.9, 136.6, 136.2, 129.4, 127.0, 126.8, 121.3, 121.2, 116.6, 112.9, 109.0, 55.4, 49.4, 45.1, 40.0, 13.9; Purity (method A) 99%, $t_R$=13.1 min.

N-(3-(2-Amino-5-(4-(piperazin-1-yl)phenyl)pyridin-3-yl)-5-ethoxyphenyl)propane-2-sulfonamide (CSLP22)

Method M; purified by column chromatography on silica gel (MeOH/CH$_2$Cl$_2$, 5:95 to 15:85) to give CSLP22 (37%) as a yellow solid; $^1$H NMR (CD$_3$OD, 600 MHz) 8.14 (1H, d, J=2.1 Hz), 7.59 (1H, d, J=2.1 Hz), 7.44(2H, d, J=8.9 Hz), 7.02 (2H, d, J=8.9 Hz), 6.92 (1H, s), 6.88 (1H, t, J=2.1 Hz), 6.76 (1H, s), 4.05 (2H, q, J=6.9 Hz), 3.35-3.32 (1H, m), 3.24-3.22 (4H, m), 3.11-3.09 (4H, m), 1.39 (3H, t, J=6.9 Hz), 1.34 (6H, d, J=6.9 Hz); $^{13}$C NMR (CD$_3$OD, 125 MHz) 161.8, 156.3, 151.8, 144.9, 141.7, 141.3, 137.4, 130.9, 128.3, 127.8, 123.2, 118.0, 112.9, 111.2, 106.4, 64.8, 53.4, 49.3, 45.9, 16.7, 15.1; Purity (method A) 95%, $t_R$=15.2 min.

N-(3-(2-Amino-5-(4-(piperazin-1-yl)phenyl)pyridin-3-yl)-5-methoxyphenyl)-1-phenylmethanesulfonamide (CSLP24)

Method M; purified by column chromatography on silica gel (MeOH/CH$_2$Cl$_2$, 5:95 to 15:85) to give CSLP24 (29%) as a brown solid; $^1$H NMR (CD$_3$OD, 500 MHz) 8.16 (1H, d, J=2.3 Hz), 7.59 (1H, d, J=2.3 Hz), 7.50(2H, d, J=8.6 Hz), 7.32-7.29 (5H, m), 7.08 (2H, d, J=8.6 Hz), 6.81-6.80 (1H, m), 6.79-6.77 (2H, m), 4.47 (2H, s), 3.82 (3H, s), 3.31-3.29 (4H, m), 3.19-3.17 (4H, m); $^{13}$C NMR (CD$_3$OD, 125 MHz) 162.5, 156.4, 151.5, 144.9, 141.7, 141.2, 137.5, 132.2, 131.3, 130.7, 129.6, 129.5, 128.2, 127.9, 123.2, 118.2, 112.9, 110.7, 105.6, 58.6, 55.9, 49.6, 45.7; Purity (method A) 95%, $t_R$=15.9 min.

N-(5-(2-Amino-5-(4-(piperazin-1-yl)phenyl)pyridin-3-yl)-3-methoxy-2-methylphenyl)propane-2-sulfonamide (CSLP25)

Method M; purified by column chromatography on silica gel (MeOH/CH$_2$Cl$_2$, 5:95 to 15:85) to give CSLP25 (39%) as a yellow solid; $^1$H NMR (CD$_3$OD, 400 MHz) 8.17 (1H, d, J=2.3 Hz), 7.50 (1H, d, J=2.3 Hz), 7.43(2H, d, J=8.7 Hz), 7.07 (1H, d, J=2.3 Hz), 7.01 (2H, d, J=9.2 Hz), 6.69 (1H, d, J=2.8 Hz), 3.77 (3H, s), 3.37 (1H, sep, J=6.9 Hz), 3.21-3.18 (4H, m), 3.06-3.03 (4H, m), 2.09 (3H, s), 1.39 (6H, d, J=6.9 Hz); $^{13}$C NMR (CD$_3$OD, 100 MHz) 159.6, 156.4, 151.9, 144.9, 140.3, 138.8, 137.5, 130.8, 127.9, 127.7, 125.0, 123.4, 118.0, 114.1, 112.2, 55.9, 54.6, 50.2, 46.1, 17.0, 16.9, 14.8; Purity (method A) 98%, $t_R$=14.3 min.

N-(5-(2-Amino-5-(4-(piperazin-1-yl)phenyl)pyridin-3-yl)-2-methylphenyl)propane-1-sulfonamide (CSLP26)

Method M; purified by column chromatography on silica gel (MeOH/CH$_2$Cl$_2$, 5:95 to 15:85) to give CSLP26 (39%) as a pale yellow solid; $^1$H NMR (CD$_3$OD, 500 MHz) 8.13 (1H, d, J=2.3 Hz), 7.60 (1H, d, J=2.3 Hz), 7.48 (1H, d, J=1.7 Hz), 7.44 (2H, d, J=8.6 Hz), 7.36 (1H, d, J=8.0 Hz), 7.27 (1H, dd, J=7.7, 1.7 Hz), 7.01 (2H, d, J=8.6 Hz), 3.19-3.17 (4H, m), 3.13-3.10 (2H, m), 3.21-3.18 (4H, m), 3.04-3.02 (4H, m), 2.40 (3H, s), 1.89-1.81 (2H, m), 1.03 (3H, t, J=7.4 Hz); $^{13}$C NMR (CD$_3$OD, 125 MHz) 156.4, 152.0, 144.7, 137.6, 137.5, 137.3, 134.5, 133.0, 128.5, 127.7, 126.9, 122.8, 117.9, 55.4, 50.4, 46.2, 18.4, 18.3, 13.2; Purity (method A) 99%, $t_R$=14.5 min.

N-(5-(2-Amino-5-(4-(piperazin-1-yl)phenyl)pyridin-3-yl)-2-methoxyphenyl)propane-2-sulfonamide (CSLP28)

Method M; purified by column chromatography on silica gel (MeOH/CH$_2$Cl$_2$, 5:95 to 15:85) to give CSLP28 (33%) as a yellow solid; $^1$H NMR (CDCl$_3$, 400 MHz) 8.25 (1H, d, J=2.3 Hz), 7.68 (1H, d, J=1.8 Hz), 7.53 (1H, d, J=2.3 Hz), 7.44 (2H, d, J=8.7 Hz), 7.21 (1H, dd, J=8.2, 1.8 Hz), 7.00-6.97 (3H, m), 4.68 (2H, br), 3.94 (3H, s), 3.34-3.23 (5H, m), 3.13-3.12 (4H, m), 1.40 (6H, d, J=6.9 Hz); $^{13}$C NMR (CDCl$_3$, 100 MHz) 154.6, 150.4, 148.2, 144.7, 136.1, 131.0, 129.7, 127.6, 127.2, 127.0, 124.9, 120.8, 119.9, 116.6, 111.2, 56.0, 52.9, 49.6, 45.5, 16.5; Purity (method B) >99%, $t_R$=15.2 min.

N-(3-(2-Amino-5-(4-(piperazin-1-yl)phenyl)pyridin-3-yl)-5-isopropoxyphenyl)propane-2-sulfonamide (CSLP29)

Method M; purified by column chromatography on silica gel (MeOH/CH$_2$Cl$_2$, 5:95 to 15:85) to give CSLP29 (37%) as a yellow solid; 41 NMR (CD$_3$OD, 400 MHz) 8.21 (1H, d, J=2.3 Hz), 7.50-7.47 (3H, m), 6.97 (2H, d, J=9.2 Hz), 6.88 (1H, s), 6.77 (1H, s), 6.71 (1H, s), 5.64 (2H, br), 4.61 (1H, sep, J=6.3 Hz), 3.39-3.33 (1H, m), 3.12-3.10 (4H, m), 2.93-2.91 (4H, m), 1.28-1.24 (12H, m); $^{13}$C NMR (CDCl$_3$, 100 MHz) 159.3, 150.2, 144.5, 139.9, 139.6, 136.1, 129.6, 127.4, 126.9, 121.3, 116.7, 111.7, 111.6, 106.5, 70.2, 52.6, 49.1, 45.0, 21.9, 16.4; Purity (method A) >99%, $t_R$=17.0 min.

N-(5-(2-Amino-5-(4-(piperazin-1-yl)phenyl)pyridin-3-yl)-3-methoxy-2-methylphenyl)-1-phenylmethane-sulfonamide (CSLP31)

Method M; purified by column chromatography on silica gel (MeOH/CH$_2$Cl$_2$, 5:95 to 15:85) to give CSLP31 (46%) as a yellow solid; $^1$H NMR (CDCl$_3$, 500 MHz) 8.30 (1H, d, J=2.3 Hz), 7.46-7.44 (3H, m), 7.37-7.32 (3H, m), 7.28-7.26 (2H, m), 7.20 (1H, d, J=2.3 Hz), 6.98 (2H, d, J=8.6 Hz), 6.64 (1H, d, J=2.3 Hz), 4.46 (2H, s), 4.41 (2H, br), 3.80 (3H, s), 3.26-3.24 (4H, m), 3.13-3.11 (4H, m), 1.75 (3H, s); $^{13}$C NMR (CDCl$_3$, 125 MHz) 158.6, 154.4, 150.5, 145.1, 139.1, 137.2, 135.9, 130.6, 129.4, 129.0, 128.9, 128.4, 127.1, 126.9, 121.0, 118.6, 116.6, 111.8, 105.7, 57.8, 55.5, 49.4, 45.4, 13.4; Purity (method B) 98%, $t_R$=17.1 min.

N-(5-(2-Amino-5-(4-(piperazin-1-yl)phenyl)pyridin-3-yl)-2-methoxyphenyl)-1,1,1-trifluoromethane-sulfonamide (CSLP32)

Method M; purified by column chromatography on silica gel (MeOH/CH$_2$Cl$_2$, 5:95 to 15:85) to give CSLP32 (6%) as a yellow solid; $^1$H NMR (DMSO-d$_6$, 500 MHz) 8.87 (1H, s), 8.18 (1H, d, J=2.3 Hz), 7.52-7.49 (3H, m), 7.27 (1H, s), 7.04 (2H, d, J=8.6 Hz), 6.92 (1H, s), 3.73 (3H, s), 3.67-3.33 (4H, m), 3.22 (4H, br); HRMS (ESI-QTOF) m/z: [M+H]$^+$ calculated for C$_{23}$H$_{24}$F$_3$N$_5$O$_3$S 508.1613; found 508.1625.

N-(5-(2-Amino-5-(4-(piperazin-1-yl)phenyl)pyridin-3-yl)-3-chloro-2-methoxyphenyepropane-1-sulfonamide (CSLP35)

Method M; purified by column chromatography on silica gel (MeOH/CH$_2$Cl$_2$, 5:95 to 15:85) to give CSLP35 (62%) as a yellow solid; $^1$H NMR (CD$_3$OD, 500 MHz) 8.16 (1H, d, J=2.3 Hz), 7.60 (1H, d, J=2.3 Hz), 7.57(1H, d, J=1.7 Hz), 7.46 (2H, d, J=9.2 Hz), 7.31 (1H, d, J=1.7 Hz), 7.03 (2H, d, J=8.6 Hz), 3.93 (3H, s), 3.27-3.25 (4H, m), 3.20-3.12 (6H, m), 1.86 (2H, sex, J=8.0 Hz), 1.03 (3H, t, J=7.4 Hz); $^{13}$C NMR (CD$_3$OD, 125 MHz) 156.4, 151.6, 148.2, 145.3, 137.6, 136.2, 134.7, 130.9, 129.7, 128.4, 127.8, 127.2, 122.0, 121.6, 118.1, 61.7, 55.4, 49.6, 45.8, 18.4, 13.2; Purity (method B) 96%, $t_R$=16.4 min.

N-(5-(2-Amino-5-(4-(piperazin-1-yl)phenyl)pyridin-3-yl)-2-methoxybenzyl)propane-1-sulfonamide (CSLP36)

Method M; purified by column chromatography on silica gel (MeOH/CH$_2$Cl$_2$, 5:95 to 15:85) to give CSLP36 (39%) as a yellow solid; $^1$H NMR (CD$_3$OD, 500 MHz) 8.10 (1H, d, J=2.3 Hz), 7.57 (1H, d, J=2.3 Hz), 7.48 (1H, d, J=2.3 Hz), 7.45-7.40 (3H, m), 7.10 (1H, d, J=8.6 Hz), 7.02 (2H, d, J=9.2 Hz), 4.28 (2H, s), 3.91 (3H, s), 3.22-3.20 (4H, m), 3.08-3.06 (4H, m), 2.94-2.90 (2H, m), 1.77-1.69 (2H, m), 0.97 (3H, t, J=7.4 Hz); $^{13}$C NMR (CD$_3$OD, 125 MHz) 158.4, 156.6, 151.8, 144.2, 137.5, 131.1, 131.0, 130.8, 130.5, 128.5, 128.0, 127.7, 123.3, 118.0, 112.2, 56.1, 55.2, 50.1, 46.0, 42.8, 18.4, 13.3; Purity (method B) 98%, $t_R$=15.8 min.

N-(5-(2-Amino-5-(4-(piperazin-1-yl)phenyl)pyridin-3-yl)-3-fluoro-2-methoxyphenyl)propane-1-sulfonamide (CSLP37)

Method M; purified by column chromatography on silica gel (MeOH/CH$_2$Cl$_2$, 5:95 to 15:85) to give CSLP37 (52%) as a yellow solid; $^1$H NMR (CD$_3$OD, 500 MHz) 8.13 (1H, d, J=2.3 Hz), 7.58 (1H, d, J=2.3 Hz), 7.44-7.40 (3H, m), 7.10 (1H, dd, J=12.0, 2.3 Hz), 7.00 (2H, d, J=8.6 Hz), 4.01 (3H, d, J=1.7 Hz), 3.19-3.17 (4H, m), 3.14-3.11(2H, m), 3.04-3.02 (4H, m), 1.88-1.81(2H, m), 1.02 (3H, t, J=7.4 Hz); $^{13}$C NMR (CD$_3$OD, 125 MHz) 156.8 (d, $J_{CF}$=246.1 Hz), 156.2, 152.0, 145.1, 140.1 (d, $J_{CF}$=13.5 Hz), 137.5, 134.6 (d, $J_{CF}$=9.8 Hz), 133.6 (d, $J_{CF}$=4.9 Hz), 130.6, 128.4, 127.7, 121.8, 119.6, 117.9, 114.4, 62.1 (d, $J_{CF}$=7.4 Hz), 55.0, 50.3, 46.1, 18.4, 13.2; Purity (method B) 98%, $t_R$=15.9 min.

N-(3-(2-Amino-5-(4-(piperazin-1-yl)phenyl)pyridin-3-yl)-5-fluorophenyl)propane-1-sulfonamide (CSLP38)

Method M; purified by column chromatography on silica gel (MeOH/CH$_2$Cl$_2$, 5:95 to 15:85) to give CSLP38 (40%) as a yellow solid; $^1$H NMR (CD$_3$OD, 500 MHz) 8.16 (1H, d, J=2.8 Hz), 7.60 (1H, d, J=2.8 Hz), 7.44(2H, d, J=6.9 Hz), 7.13 (1H, s), 7.07 (1H, dt, J=10.3, 2.1 Hz), 7.02 (2H, d, J=8.9 Hz), 6.98 (1H, dt, J=10.0, 2.1 Hz), 3.21-3.19 (4H, m), 3.16-3.13 (2H, m), 3.06-3.04 (4H, m), 1.85-1.79 (2H, m), 1.02 (3H, t, J=7.6 Hz); $^{13}$C NMR (CD$_3$OD, 125 MHz) 165.0 (d, $J_{CF}$=245.4 Hz), 156.2, 152.0, 145.4 (d, $J_{CF}$=5.9 Hz), 142.4 (d, $J_{CF}$=11.8 Hz), 142.3 (d, $J_{CF}$=8.9 Hz), 137.5, 130.6, 128.4, 127.7, 122.0, 117.9, 116.4, 111.7 (d, $J_{CF}$=23.7 Hz), 106.6 (d, $J_{CF}$=26.6 Hz), 54.3, 50.2, 46.1, 18.4, 13.1; Purity (method B) >99%, $t_R$=15.9 min.

N-(3-(2-Amino-5-(4-(piperazin-1-yl)phenyl)pyridin-3-yl)-5-chlorophenyl)propane-1-sulfonamide (CSLP39)

Method M; purified by column chromatography on silica gel (MeOH/CH$_2$Cl$_2$, 5:95 to 15:85) to give CSLP39 (51%) as a yellow solid; $^1$H NMR (CD$_3$OD, 500 MHz) 8.16 (1H, d, J=2.3 Hz), 7.70 (1H, d, J=8.6 Hz), 7.62-7.61 (2H, m), 7.48 (2H, d, J=8.6 Hz), 7.45 (1H, dd, J=8.6, 1.7 Hz), 7.05 (2H, d, J=9.2 Hz), 3.31-3.28 (4H, m), 3.15-3.12 (6H, m), 1.92-1.84 (2H, m), 1.04 (3H, t, J=7.4 Hz); $^{13}$C NMR (CD$_3$OD, 150 MHz) 155.2, 150.0, 144.5, 135.4, 135.2, 135.1, 129.7, 128.3, 128.1, 127.9, 126.4, 126.2, 125.4, 118.7, 115.8, 54.0, 48.2, 44.8, 17.1, 12.8; Purity (method B) 99%, $t_R$=15.8 min.

N-(5-(2-Amino-5-(4-(piperazin-1-yl)phenyl)pyridin-3-yl)-3-chloro-2-methylphenyl)propane-1-sulfonamide (CSLP40)

Method M; purified by column chromatography on silica gel (MeOH/CH$_2$Cl$_2$, 10:90 to 15:85) to give CSLP40 (40%) as a yellow solid; $^1$H NMR (CD$_3$OD, 500 MHz) 8.17 (1H, d, J=2.3 Hz), 7.63 (1H, d, J=2.3 Hz), 7.50 (2H, d, J=9.2 Hz), 7.45 (2H, d, J=1.7 Hz), 7.07 (2H, d, J=8.6 Hz), 3.36-3.33 (4H, m), 3.27-3.24 (4H, m), 3.15-3.12 (2H, m), 2.46 (3H, s), 1.90-1.82 (2H, m), 1.05 (3H, t, J=7.4 Hz); $^{13}$C NMR (CD$_3$OD, 150 MHz) 156.5, 151.2, 145.4, 138.7, 138.3, 137.6, 137.1, 133.3, 131.3, 128.5, 128.4, 127.9, 126.3, 121.5, 118.2, 55.4, 45.3, 18.4, 15.8, 15.7, 13.2; Purity (method B) 98%, $t_R$=16.7 min.

N-(5-(2-Amino-5-(4-(piperazin-1-yl)phenyl)pyridin-3-yl)-3-fluoro-2-methylphenyl)propane-1-sulfonamide (CSLP41)

Method M; purified by column chromatography on silica gel (MeOH/CH$_2$Cl$_2$, 10:90 to 15:85) to give CSLP41(53%) as a pale yellow solid; $^1$H NMR (CD$_3$OD, 500 MHz) 8.16 (1H, d, J=2.3 Hz), 7.63 (1H, d, J=2.3 Hz), 7.47 (2H, d, J=8.6 Hz), 7.34 (1H, s), 7.14 (1H, dd, J=9.7, 1.2 Hz), 7.04 (2H, d, J=9.2 Hz), 3.23-3.21 (4H, m), 3.15-3.12 (2H, m), 3.08-3.06 (4H, m), 2.31 (3H, d, J=1.7 Hz), 1.90-1.82 (2H, m), 1.04 (3H, t, J=7.4 Hz); $^{13}$C NMR (CD$_3$OD, 125 MHz) 163.1 (d, $J_{CF}$=236.3 Hz), 156.3, 152.0, 145.2, 139.3 (d, $J_{CF}$=7.4 Hz), 138.3 (d, $J_{CF}$=9.8 Hz), 137.5, 130.7, 128.5, 127.8, 122.5, 121.9, 121.8 (d, $J_{CF}$=7.4 Hz), 118.0, 114.1 (d, $J_{CF}$=23.4 Hz), 55.3, 50.2, 46.1, 18.4, 13.2, 10.2 (d, $J_{CF}$=4.9 Hz) ; Purity (method B) >99%, $t_R$=15.9 min.

N-(5-(2-Amino-5-(4-(piperazin-1-yl)phenyl)pyridin-3-yl)-2-methoxy-3-methylphenyl)propane-1-sulfonamide (CSLP42)

Method M; purified by column chromatography on silica gel (MeOH/CH$_2$Cl$_2$, 10:90 to 15:85) to give CSLP42 (53%) as a yellow solid; $^1$H NMR (CD$_3$OD, 600 MHz) 8.13 (1H, d, J=2.1 Hz), 7.59 (1H, d, J=2.1 Hz), 7.46 (1H, d, J=8.9 Hz), 7.43 (1H, d, J=1.4 Hz), 7.11 (1H, s), 7.03 (2H, d, J=8.9 Hz), 3.82 (3H, s), 3.24-3.23 (4H, m), 3.18-3.16 (2H, m), 3.11-3.09 (4H, m), 2.36 (3H, s), 1.86 (2H, sex, J=7.6 Hz), 1.03 (3H, t, J=7.6 Hz); $^{13}$C NMR (CD$_3$OD, 150 MHz) 156.4, 151.8, 150.8, 144.6, 137.5, 135.1, 133.9, 132.7, 131.0, 128.7, 128.4, 127.8, 123.0, 121.2, 118.0, 61.2, 55.2, 49.9, 45.9, 18.4, 16.4, 13.2; Purity (method A) 97%, $t_R$=15.1 min.

N-(5-(2-Amino-5-(4-(piperazin-1-yl)phenyl)pyridin-3-yl)-2,3-dimethoxyphenyl)propane-1-sulfonamide (CSLP43)

Method M; purified by column chromatography on silica gel (MeOH/CH$_2$Cl$_2$, 5:95 to 15:85) to give CSLP43 (49%) as a yellow solid; 41 NMR (CD$_3$OD, 600 MHz) 8.14 (1H, d, J=2.1 Hz), 7.62 (1H, d, J=2.8 Hz), 7.47(2H, d, J=8.9 Hz), 7.20 (1H, d, J=1.4 Hz), 7.04 (2H, d, J=8.9 Hz), 6.94 (1H, d, J=2.1 Hz), 3.01 (3H, s), 3.90(3H, s), 3.26-3.24 (4H, m), 3.13-3.10 (6H, m), 1.84 (2H, sex, J=7.6 Hz), 1.02 (3H, t, J=7.6 Hz); $^{13}$C NMR (CD$_3$OD, 150 MHz) 156.4, 154.6, 151.7, 144.7, 141.2, 137.5, 134.8, 132.8, 131.1, 128.4, 127.8, 123.1, 118.1, 115.8, 110.6, 61.4, 56.6, 54.8, 49.7, 45.8, 18.4, 13.2; Purity (method A) 98%, $t_R$=14.9 min.

N-(5-(2-Amino-5-(4-(piperazin-1-yl)phenyl)pyridin-3-yl)-2,3-dimethylphenyl)propane-1-sulfonamide (CSLP45)

Method M; purified by column chromatography on silica gel (MeOH/CH$_2$Cl$_2$, 5:95 to 15:85) to give CSLP45 (44%) as a yellow solid; 41 NMR (CD$_3$OD, 500 MHz) 8.14 (1H, d, J=1.7 Hz), 7.62 (1H, d, J=2.3 Hz), 7.48(2H, d, J=8.6 Hz), 7.31 (1H, s), 7.24 (1H, s), 7.05 (2H, d, J=8.6 Hz), 3.27-3.25 (4H, m), 3.13-3.08 (6H, m), 2.37 (3H, s), 2.34 (3H, s), 1.90-1.84 (2H, m), 1.04 (3H, t, J=7.4 Hz); $^{13}$C NMR (CD$_3$OD, 125 MHz) 156.5, 151.7, 144.6, 140.5, 137.4, 136.9, 136.7, 134.3, 131.0, 129.6, 128.4, 127.8, 125.7, 122.9, 118.0, 55.2, 49.9, 45.9, 20.8, 18.4, 14.7, 13.3; Purity (method A) 98%, $t_R$=15.2 min.

5-(4-(Piperazin-1-yl)phenyl)-3-(1-(propylsulfonyl)indolin-6-yl)pyridin-2-amine (CSLP46)

Method M; purified by column chromatography on silica gel (MeOH/CH$_2$Cl$_2$, 5:95 to 10:90) to give CSLP46 (38%) as a yellow solid; 41 NMR (CDCl$_3$, 500 MHz) 8.27 (1H, d, J=2.3 Hz), 7.55 (1H, d, J=2.3 Hz), 7.47-7.43 (3H, m), 7.29 (1H, d, J=8.0 Hz), 7.13 (1H, dd, J=7.7, 1.2 Hz), 6.98 (2H, d, J=8.6 Hz), 4.66 (2H, br), 4.09 (2H, t, J=8.6 Hz), 3.22-3.18 (6H, m), 3.09-3.04 (6H, m), 1.94-1.86 (2H, m), 1.04 (3H, t, J=7.4 Hz); $^{13}$C NMR (CDCl$_3$, 125 MHz) 154.4, 150.7, 144.9, 143.0, 138.0, 136.1, 130.7, 129.4, 127.7, 127.0, 125.9, 123.6, 121.4, 116.5, 113.5, 51.3, 50.5, 49.9, 45.8, 27.8, 16.7, 13.1; Purity (method A) 98%, $t_R$=15.4 min.

5-(4-(Piperazin-1-yl)phenyl)-3-(4-(propylsulfonyl)-3,4-dihydro-2H-benzo[b][1,4]oxazin-6-yl)pyridin-2-amine (CSLP47)

Method M; purified by column chromatography on silica gel (MeOH/CH$_2$Cl$_2$, 5:95 to 15:85) to give CSLP47 (56%) as a pale yellow solid; 41 NMR (CD$_3$OD, 500 MHz) 8.13 (1H, d, J=2.3 Hz), 7.71 (1H, d, J=2.3 Hz), 7.60 (1H, d, J=2.3 Hz), 7.48 (2H, d, J=9.2 Hz), 7.19 (1H, dd, J=8.3, 2.3 Hz), 7.07-7.03 (3H, m), 4.34 (2H, t, J=4.6 Hz), 3.88 (2H, t, J=4.6 Hz), 3.30-3.24 (6H, m), 3.17-3.15 (4H, m), 1.85 (2H, sex, J=8.0 Hz), 1.04 (3H, t, J=7.4 Hz); $^{13}$C NMR (CD$_3$OD, 125 MHz) 156.5, 152.0, 147.6, 144.4, 137.4, 131.4, 130.8, 128.5, 127.7, 126.9, 126.0, 124.1, 123.0, 119.5, 117.9, 66.2, 54.9, 50.4, 46.2, 45.2, 18.2, 13.2; Purity (method A) >99%, $t_R$=15.5 min.

N-(5-(2-Amino-5-(4-(piperazin-1-yl)phenyl)pyridin-3-yl)-2-hydroxyphenyl)propane-1-sulfonamide (CSLP48)

Method M; purified by column chromatography on silica gel (MeOH/CH$_2$Cl$_2$, 5:95 to 15:85) to give CSLP48 (18%) as a yellow solid; 41 NMR (CD$_3$OD, 500 MHz) 8.11 (1H, s), 7.59 (1H, d, J=2.3 Hz), 7.50-7.48 (3H, m), 7.20(1H, dd, J=8.6, 2.3 Hz), 7.07 (2H, d, J=9.2 Hz), 7.00 (1H, d, J=8.0 Hz), 3.39-3.37 (4H, m), 3.30-3.29 (4H, m), 3.08-3.05 (2H, m), 1.91-1.84 (2H, m), 1.02 (3H, t, J=7.4 Hz); HRMS (ESI-QTOF) m/z: [M+M]$^+$ calculated for C$_{24}$H$_{29}$N$_5$O$_3$S 468.2064; found 468.2071; Purity (method A) 95%, $t_R$=13.2 min.

N-(5-(2-Amino-5-(4-(piperazin-1-yl)phenyl)pyridin-3-yl)-2,3-diethoxyphenye propane-1-sulfonamide (CSLP49)

Method M; purified by column chromatography on silica gel (MeOH/CH$_2$Cl$_2$, 5:95 to 15:85) to give CSLP49 (38%) as a yellow solid; 41 NMR (CDCl$_3$, 500 MHz) 8.25 (1H, s), 7.57 (1H, d, J=1.7 Hz), 7.46 (2H, d, J=8.6 Hz), 7.24 (1H, d, J=1.7 Hz), 6.99 7.57 (2H, d, J=8.6 Hz), 6.78 (1H, s), 4.85 (2H, br), 4.22(2H, q, J=6.9 Hz), 4.10 (2H, q, J=6.9 Hz), 3.45 (4H, br), 3.34 (4H, br), 3.13-3.10 (2H, m), 1.92-1.85 (2H, m), 1.47 (3H, t, J=6.9 Hz), 1.42 (3H, t, J=6.9 Hz), 1.03 (3H, t, J=7.4 Hz); HRMS (ESI-QTOF) m/z: [M+H]$^+$ calculated for $C_{28}H_{38}N_5O_4S$ 540.2639; found 540.26450; Purity (method A) 96%, $t_R$=17.0 min.

N-(5-(2-Amino-5-(4-(piperazin-1-yl)phenyl)pyridin-3-yl)-3-methoxy-2-methylphenyl)benzenesulfonamide (CSLP51)

Method M; purified by column chromatography on silica gel (MeOH/CH$_2$Cl$_2$, 5:95 to 15:85) to give CSLP51 (38%) as a yellow solid; 41 NMR (CD$_3$OD, 500 MHz) 8.15 (1H, s), 7.74 (2H, d, J=7.4 Hz), 7.62 (1H, t, J=7.4 Hz), 7.52 (1H, t, J=7.4 Hz), 7.48-7.44 (3H, m), 7.08 (2H, d, J=8.6 Hz), 6.72 (1H, d, J=2.9 Hz), 6.69 (1H, d, J=2.9 Hz), 3.69 (3H, s), 3.44-3.42 (4H, m), 3.38-3.36 (4H, m), 1.72 (3H, s); $^{13}$C NMR (CD$_3$OD, 125 MHz) 159.4, 156.4, 150.7, 144.9, 141.8, 140.1, 137.9, 137.5, 134.0, 131.8, 130.2, 128.2, 127.9, 127.6, 126.4, 123.2, 118.4, 115.4, 113.6, 55.8, 47.9, 44.9, 14.2; Purity (method A) 99%, $t_R$=15.9 min.

N-(7-(2-Amino-5-(4-(piperazin-1-yl)phenyl)pyridin-3-yl)-2,3-dihydrobenzo[b][1,4]dioxin-5-yl)propane-1-sulfonamide (CSLP52)

This compound was synthesized by using Method J followed by Method M; purified by column chromatography on silica gel (MeOH/CH$_2$Cl$_2$, 5:95 to 15:85) to give CSLP52 (37%) as a light brown solid; 41 NMR (CD$_3$OD, 600 MHz) 8.12 (1H, s), 7.58 (1H, d, J=1.4 Hz), 7.48 (2H, d, J=8.9 Hz), 7.12 (1H, s), 7.06 (2H, d, J=8.2 Hz), 6.85 (1H, s), 4.38-4.37 (2H, m), 4.32-4.31 (2H, m), 3.36-3.34 (4H, m), 3.27-3.25 (4H, m), 3.09 (2H, t, J=7.6 Hz), 1.86 (2H, sex, J=7.6 Hz), 1.03 (3H, t, J=7.6 Hz); $^{13}$C NMR (CD$_3$OD, 150 MHz) 156.5, 151.1, 145.8, 144.6, 137.4, 137.3, 131.6, 131.5, 128.2, 128.0, 127.9, 122.8, 118.3, 117.7, 115.5, 66.0, 65.6, 54.7, 45.3, 30.7, 18.4, 13.2; Purity (method A) 98%, $t_R$=14.2 min.

N-(5-(2-Amino-5-(4-(piperazin-1-yl)phenyl)pyridin-3-yl)-3-ethoxy-2-methylphenyl)-1-phenylmethanesulfonamide (CSLP54)

Method M; purified by column chromatography on silica gel (MeOH/CH$_2$Cl$_2$, 5:95 to 15:85) to give CSLP54 (63%) as a yellow solid; $^1$H NMR (CD$_3$OD, 500 MHz) 8.18 (1H, d, J=2.3 Hz), 7.51 (1H, d, J=2.3 Hz), 7.48 (2H, d, J=9.2 Hz), 7.40-7.37 (2H, m), 7.35-7.34 (3H, m), 7.05 (2H, d, J=8.6 Hz), 6.93 (1H, d, J=2.9 Hz), 6.65 (1H, d, J=2.9 Hz), 4.48 (2H, d, J=2.3 Hz), 3.97 (2H, q, J=6.9 Hz), 3.31-3.29 (4H, m), 3.19-3.17 (4H, m), 1.93 (3H, s), 1.37 (3H, t, J=6.9 Hz); $^{13}$C NMR (CDCl$_3$, 125 MHz) 158.1, 154.4, 150.3, 145.2, 139.0, 137.1, 135.9, 130.6, 129.7, 129.1, 128.9, 128.4, 127.1, 127.0, 121.0, 117.9, 116.8, 112.2, 105.6, 63.8, 57.6, 49.1, 45.2, 14.7, 13.3; Purity (method A) >99%, $t_R$=17.2 min.

N-(5-(2-Amino-5-(4-(piperazin-1-yl)phenyl)pyridin-3-yl)-3-ethoxy-2-methoxyphenyepropane-1-sulfonamide (CSLP56)

Method M; purified by column chromatography on silica gel (MeOH/CH$_2$Cl$_2$, 5:95 to 15:85) to give CSLP56 (52%) as a yellow solid; $^1$H NMR (CDCl$_3$, 600 MHz) 8.24 (1H, s), 7.70 (1H, d, J=2.1 Hz), 7.52 (2H, d, J=8.9 Hz), 7.10 (1H, s), 7.06 (2H, d, J=8.9 Hz), 6.91 (1H, s), 4.08 (2H, q, J=6.9 Hz), 3.88 (3H, s), 3.30-3.29 (4H, m), 3.18-3.17 (4H, m), 2.74-2.69 (1H, m), 2.67-2.62 (1H, m), 1.46-1.42 (1H, m), 1.41-1.36 (4H, m), 0.77 (3H, t, J=7.6 Hz); $^{13}$C NMR* (CD$_3$OD, 150 MHz) 156.7, 151.6, 151.0, 149.2, 145.2, 139.2, 131.0, 128.7, 128.6, 127.9, 127.8, 121.3, 118.1, 116.0, 113.7, 65.9, 56.6, 55.4, 45.6, 18.2, 15.1, 13.2; Purity (method A) 95%, $t_R$=14.5 min.

*One of $^{13}$C NMR peak was hidden in CD$_3$OD peaks due to low sample concentration.

3-(8-Fluoro-4-(propylsulfonyl)-3,4-dihydro-2H-benzo[b][1,4]oxazin-6-yl)-5-(4-(piperazin-1-yl)phenyl)pyridin-2-amine (CSLP57)

Method M; purified by column chromatography on silica gel (MeOH/CH$_2$Cl$_2$, 10:90 to 15:85) to give CSLP57 (50%) as a pale yellow solid; $^1$H NMR (CD$_3$OD, 500 MHz) 8.15 (1H, d, J=2.3 Hz), 7.61 (1H, d, J=2.3 Hz), 7.54 (1H, s), 7.48 (2H, d, J=8.6 Hz), 7.09 (1H, dd, J=10.9, 1.7 Hz), 7.05 (2H, d, J=9.2 Hz), 4.40 (2H, t, J=4.6 Hz), 3.93 (2H, t, J=4.6 Hz), 3.30-3.23 (6H, m), 3.11-3.09 (2H, m), 1.90-1.82 (2H, m), 1.06 (3H, t, J=7.4 Hz); $^{13}$C NMR (CDCl$_3$, 150 MHz) 154.4, 152.1 (d, $J_{CF}$=246.1 Hz), 150.6, 135.9, 134.6 (d, $J_{CF}$=13.5 Hz), 129.7 (d, $J_{CF}$=7.4 Hz), 129.4, 127.8, 127.0, 126.4, 119.8, 117.4, 116.5, 112.2 (d, $J_{CF}$=18.5 Hz), 65.3, 55.0, 49.7, 45.6, 44.0, 17.1, 12.9; Purity (method B) >99%, $t_R$=16.8 min.

N-(5-(2-Amino-5-(4-(piperazin-1-yl)phenyl)pyridin-3-yl)-3-fluoro-2-methoxyphenyl)propane-1-sulfonamide (CSLP58)

Method M; purified by column chromatography on silica gel (MeOH/CH$_2$Cl$_2$, 5:95 to 15:85) to give CSLP58 (48%) as a pale yellow solid; $^1$H NMR (CD$_3$OD, 500 MHz) 8.18 (1H, d, J=2.1 Hz), 7.64 (1H, d, J=2.1 Hz), 7.42 (1H, d, J=1.4 Hz), 7.30 (1H, t, J=7.6 Hz), 7.15-7.13 (2H, m), 7.07 (1H, d, J=7.7 Hz), 6.94(1H, dd, J=8.2, 2.1 Hz), 4.01 (3H, d, J=2.1 Hz), 3.28-3.27 (4H, m), 3.15-3.11 (6H, m), 1.89-1.82 (2H, m), 1.04 (3H, t, J=7.6 Hz); $^{13}$C NMR (CD$_3$OD, 150 MHz) 156.9, 156.8 (d, $J_{CF}$=246.9 Hz), 153.3, 145.8, 140.2 (d, $J_{CF}$=11.8 Hz), 140.0, 138.1, 134.5 (d, $J_{CF}$=8.9 Hz), 133.6 (d, $J_{CF}$=5.9 Hz), 130.8, 128.9, 121.7, 119.6, 119.5, 116.5, 115.6, 114.5 (d, $J_{CF}$=19.2 Hz), 62.1 (d, $J_{CF}$=7.4 Hz), 55.0, 50.1, 46.0, 18.4, 13.2; Purity (method B) >99%, $t_R$=16.5 min.

N-(5-(2-Amino-5-(3-(methylsulfonyl)phenyl)pyridin-3-yl)-2-methoxyphenyepropane-1-sulfonamide (CSLP30)

Method J; purified by column chromatography on silica gel (MeOH/CH$_2$Cl$_2$, 2.5:97.5 to 5:95) to give CSLP30 (60%) as a yellow solid; $^1$H NMR (CDCl$_3$, 500 MHz) 8.32 (1H, s), 8.08 (1H, s), 7.88 (1H, d, J=7.4 Hz), 7.82 (1H, d, J=8.0 Hz), 7.66-7.60 (3H, m), 7.24 (1H, dd, J=8.3, 2.9 Hz), 7.03 (1H, d, J=8.6 Hz), 6.95 (1H, s), 4.83 (2H, br), 3.95 (3H, s), 3.10-3.06 (5H, m), 1.91-1.84 (2H, m), 1.03 (3H, t, J=7.4 Hz); $^{13}$C NMR (CDCl$_3$, 125 MHz) 155.9, 148.8, 145.6, 141.2, 139.8, 136.4, 131.2, 130.4, 130.0, 126.9, 125.6, 125.4, 124.8, 121.0, 120.3, 120.3, 111.4, 50.0, 53.7, 44.5, 17.2, 12.9; Purity (method B) 96%, $t_R$=17.7 min.

N-(5-(2-Amino-5-(2-(methylsulfonyl)phenyl)pyridin-3-yl)-2-methoxyphenyl)propane-1-sulfonamide (CSLP33)

Method J; purified by column chromatography on silica gel (EtOAc/hexane, 50:50 to 80:20) to give CSLP33 (22%) as a yellow solid; $^1$H NMR (CDCl$_3$, 500 MHz) 8.24 (1H, dd, J=7.7, 1.7 Hz), 8.05 (1H, d, J=2.3 Hz), 7.69-7.66 (3H, m), 7.57 (1H, td, J=7.4, 1.2 Hz), 7.42 (1H, dd, J=7.4, 1.2 Hz), 7.29 (1H, dd, J=8.2, 2.3 Hz), 6.99 (1H, d, J=8.6 Hz), 6.83 (1H, s), 4.84 (2H, br), 3.93 (3H, s), 3.11-3.08 (2H, m), 2.79 (3H, s), 1.87 (2H, sex, J=8.0 Hz), 1.03 (3H, t, J=7.4 Hz); $^{13}$C NMR (CDCl$_3$, 125 MHz) 155.7, 148.6, 146.8, 140.4, 139.6, 138.3, 133.4, 133.2, 130.3, 129.0, 128.1, 126.8, 125.5, 125.0, 119.9, 119.3, 111.4, 56.0, 53.9, 43.5, 17.2, 12.8; Purity (method B) 95%, $t_R$=18.0 mM.

N-(5-(2-Amino-5-(4-(methylsulfonyl)phenyl)pyridin-3-yl)-2-methoxyphenyepropane-1-sulfonamide (CSLP34)

Method J; purified by column chromatography on silica gel (MeOH/CH$_2$Cl$_2$, 2.5:97.5 to 5:95) to give CSLP34 (83%) as a yellow solid; $^1$H NMR (CDCl$_3$, 500 MHz) 8.35 (1H, d, J=1.7 Hz), 7.98 (2H, d, J=8.6 Hz), 7.72(2H, d, J=8.0 Hz), 7.66 (1H, d, J=1.7 Hz), 7.60 (1H, d, J=2.3 Hz), 7.20-7.24 (1H, m), 7.03(1H, d, J=8.6 Hz), 6.90 (1H, s), 4.84 (2H, br), 3.95 (3H, s), 3.09-3.06 (5H, m), 1.88 (2H, sex, J=8.0 Hz), 1.03 (3H, t, J=7.4 Hz); $^{13}$C NMR (CDCl$_3$, 125 MHz) 156.1, 148.8, 145.9, 143.7, 138.5, 136.4, 130.4, 128.1, 127.0, 126.8, 125.6, 125.3, 120.9, 120.2, 111.3, 56.0, 53.8, 44.6, 17.2, 12.9; Purity (method B) 97%, $t_R$=17.5 mM.

N-(3-(2-Amino-5-(3-(methylsulfonyl)phenyl)pyridin-3-yl)-5-methoxyphenyl)propane-1-sulfonamide (CSLP44)

Method J; purified by column chromatography on silica gel (EtOAc/hexane, 40:60 to 80:20) to give CSLP44 (55%) as a white solid; $^1$H NMR (CDCl$_3$, 500 MHz) 8.35 (1H, d, J=1.4 Hz), 8.09 (1H, s), 7.88 (1H, d, J=8.2 Hz), 7.82 (1H, d, J=7.6 Hz), 7.64-7.62 (2H, m), 7.19 (1H, s), 6.88 (1H, d, J=4.8 Hz), 6.80 (1H, s), 4.87 (2H, br), 3.85 (3H, s), 3.16-3.14 (2H, m), 3.11 (3H, s), 1.89 (2H, sex, J=7.6 Hz), 1.04 (3H, t, J=7.6 Hz); $^{13}$C NMR (CDCl$_3$, 125 MHz) 161.3, 155.6, 145.9, 141.3, 139.8, 139.6, 139.1, 136.3, 131.2, 130.1, 125.6, 125.5, 124.8, 121.0, 112.2, 110.5, 105.3, 55.6, 53.8, 44.5, 17.3, 12.9; Purity (method B) 98%, $t_R$=17.4 min.

EXAMPLE 2

Receptor Interacting Protein Kinase 2 (RIPK2) Enzyme Assay

Recombinant RIPK2 protein (20 ng per reaction) is diluted in the reaction buffer consisting of 40 mM Tris (pH 7.5); 20 mM MgCl$_2$; 0.1 mg/ml BSA; 50 μM DTT. Diluted protein is added to low volume white 384 well plates (2 μL/well). Inhibitors are diluted in reaction buffer (final 25% DMSO), 1 μL is added to each well and incubated 5 min at room temperature. Reactions are initiated by the addition of 2 μL of 100 μM ATP and 1 mg/ml RS repeat peptide (SignalChem) in the reaction buffer. Plates are sealed with plastic coverslips and incubated at room temperature for 2 h. Reactions are stopped by the addition of 5 μL of ADP-Glo reagent (Promega) and ADP generation reaction is performed for 40 min at room temperature. Luminescence signal is generated by the addition of 10 μL of Kinase detection reagent (Promega) for 30 min at room temperature Luminescence signals are determined using appropriate luminescence plate-reader (typical integration time 0.3-1 sec). To calculate percent inhibition, average background signal is subtracted from test well and maximal signal wells. Inhibition, %=(1−(test signal/maximal signal))*100. The percent inhibition at a specified concentration is determined or IC$_{50}$ values are calculated based on a dose range of inhibitor concentrations using non-linear regression in GraphPad Prism software.

Activin-Like Kinase 2 (ALK2) Enzyme Assay

Enzyme inhibitory activity was evaluated in a standard kinase enzyme assay by incubating human ALK2 with the protein substrate casein (1 mg/mL) and γ-$^{33}$ATP (10 μM) in the presence of various concentrations of test compounds (10 nM-100 μM). After 30 min the amount of $^{33}$P-casein was determined. A plot of inhibitor concentration verses % activity was constructed and from this plot an IC$_{50}$ value was determined.

NOD2 Cell Signaling Assay.

HEK-Blue cells expressing human NOD2 and NFkB-SAEP reporter (Invivogen) are seeded into 96 well clear plates at 7.5×10$^3$ cells per well in 100 μL of DMEM media supplemented with 10% FBS and 1% antibiotic-antimycotic mix. Cells are allowed to attach for 48 h in 5% CO$_2$ tissue culture incubator at 37° C. On the morning of the experiment, media in the wells is replaced with 100 pt of HEK-Blue detection media (Invivogen). Cells are treated with the inhibitors, diluted in DMSO (0.5 μL per well) for 15 min in 5% CO$_2$ tissue culture incubator at 37° C. After that, cells are stimulated by the addition of 1 ng/well L18-MDP (Invivogen). Cells are incubated in 5% CO$_2$ tissue culture incubator at 37° C. for 8 h and absorbance, corresponding to the SEAP in the media, is determined in Wallac3V plate reader (Perkin Elmer). Inhibition, %=(1−((sample signal-unstimulated and DMSO treated cells)/(L18-MDP stimulated and DMSO treated cells−unstimulated and DMSO treated cells)))*100. IC$_{50}$ values are calculated based on a dose range of inhibitor concentrations using non-linear regression in GraphPad Prism software.

Inhibition of RIPK2 and ALK2 Enzyme Activities and NOD2 Cell Signaling by Compounds.

Prepared compounds were evaluated for their ability to inhibit RIPK2 and ALK2 enzyme activities and NOD2 cellular signaling using the methods described above. The percent inhibition at a specified concentration or IC$_{50}$ values for inhibition of RIPK2 enzyme and NOD2 cellular signaling by the compounds are shown in Table 1. IC$_{50}$ values for inhibition of ALK2 enzyme activity by the compounds are also shown in Table 1.

TABLE 1

| Compound | Conc. (nM) | % RIPK2 Inhibition | IC$_{50}$ (nM) Enzyme RIPK2 | IC$_{50}$ (nM) Enzyme ALK2 | HEKBlue RIPK2 |
|---|---|---|---|---|---|
| CSLP1 | 500 | NI$^a$ | NI | NI | >1000 |
| CSLP2 | 250 | 39 | >100 | >10 | >1000 |
| CSLP3 | | | >10 | >1 | >100 |
| CSLP6 | | | >10 | >1 | >100 |
| CSLP7 | | | >10 | | >100 |
| CSLP8 | | | >10 | >1 | >100 |
| CSLP9 | 500 | 76 | | | >1000 |
| CSLP10 | 500 | 84 | >100 | >10 | >1000 |
| CSLP11 | | | >10 | | >100 |
| CSLP12 | | | >10 | >1 | >100 |
| CSLP14 | 500 | 86 | >100 | >10 | >1000 |
| CSLP15 | 500 | 73 | >100 | >10 | >1000 |
| CSLP16 | 500 | 85 | >10 | >100 | >100 |
| CSLP17 | 500 | 86 | >10 | >10 | >1000 |
| CSLP18 | | | >10 | >1000 | >100 |
| CSLP19 | | | NI | >100 | >1000 |
| CSLP20 | | | >1 | >1 | >10 |
| CSLP21 | | | NI | >100 | >1000 |
| CSLP22 | | | >10 | >100 | >10 |

TABLE 1-continued

| Compound | Conc. (nM) | % RIPK2 Inhibition | IC$_{50}$ (nM) Enzyme RIPK2 | ALK2 | HEKBlue RIPK2 |
|---|---|---|---|---|---|
| CSLP24 | | | >100 | >1 | >100 |
| CSLP25 | | | NI | >1000 | >1000 |
| CSLP26 | | | >100 | >1000 | >1000 |
| CSLP28 | | | >10 | >1000 | >100 |
| CSLP29 | | | >100 | NI | >100 |
| CSLP30 | | | >100 | >10000 | >1000 |
| CSLP31 | | | NI | >10 | >100 |
| CSLP33 | | | NI | NI | NI |
| CSLP34 | | | >100 | >10000 | >1000 |
| CSLP35 | | | >10 | >100 | >10 |
| CSLP36 | | | >100 | >100 | >1000 |
| CSLP37 | | | >10 | >100 | >10 |
| CSLP38 | | | >10 | >10 | >100 |
| CSLP39 | | | >10 | >1000 | >1000 |
| CSLP40 | | | >100 | >100 | >1000 |
| CSLP41 | | | >100 | NI | >100 |
| CSLP42 | | | >10 | >100 | >100 |
| CSLP43 | | | >10 | >10 | >1 |
| CSLP44 | | | >10 | >100 | >1000 |
| CSLP45 | | | >100 | >100 | >100 |
| CSLP46 | | | >100 | NI | >1000 |
| CSLP47 | | | >10 | NI | >1000 |
| CSLP48 | | | >10 | >100 | >1000 |
| CSLP49 | | | NI | NI | NI |
| CSLP51 | | | NI | >1000 | >1000 |
| CSLP52 | | | >100 | NI | >1000 |
| CSLP53 | | | >1000 | NI | >1000 |
| CSLP54 | | | NI | >1000 | >1000 |
| CSLP55 | | | >10 | >10 | >100 |
| CSLP56 | | | NI | NI | NI |
| CSLP57 | | | >100 | >1000 | >100 |
| CSLP58 | | | >10 | >100 | >10 |

$^a$NI: no inhibition observed.

What is claimed is:

1. A compound demonstrating protein kinase inhibitory activity and having a structure of:

[structure of general formula with R1–R7 substituents]

wherein R$_1$ is H,

[piperazine, N-methylpiperazine, or dimethylaminoethoxy groups]

R$_2$ is H, SO$_2$Me, SO$_2$i—Pr, SO$_2$CF$_3$, or

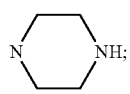

R$_3$ is H, Cl, Me, NH$_2$, NHMe, NHSO$_2$Me$_3$, or NMe$_2$;

R$_4$ is H, F, Cl, OMe, OEt, O-n-Pr, O-i-Pr, OPh, or OCF$_3$;

R$_5$ is H, Me, Et, Pr, i-Pr, OMe, OEt, O-n-Pr, O-i-Pr, OCF$_3$, Cl, or F;

R$_6$ is H, Me, or Et;

R$_7$ is Me, Et, n-Pr, i-Pr, CF$_3$, CF$_2$Et, CH$_2$Ph, or Ph;

n is 0 or 1; and wherein Me is methyl, Et is ethyl, i-Pr is isopropyl, and Ph is phenyl.

2. A pharmaceutical composition comprising a therapeutically effective amount of the compound of claim 1 and a pharmaceutically acceptable excipient, adjuvant, carrier, buffer, stabilizer, or mixture thereof.

3. The compound demonstrating protein kinase inhibitory activity of claim 1 wherein the compound has a structure of:

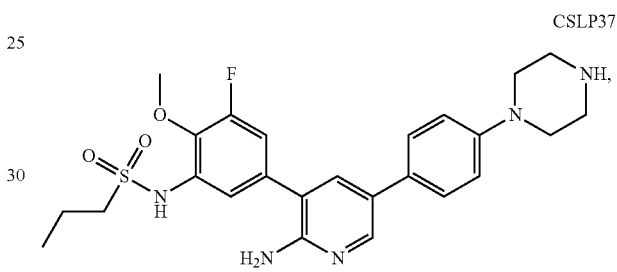

CSLP37

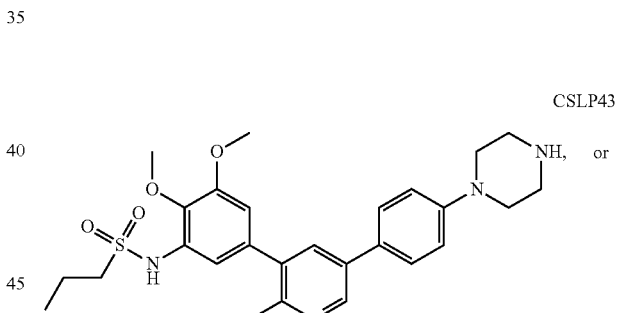

CSLP43 or

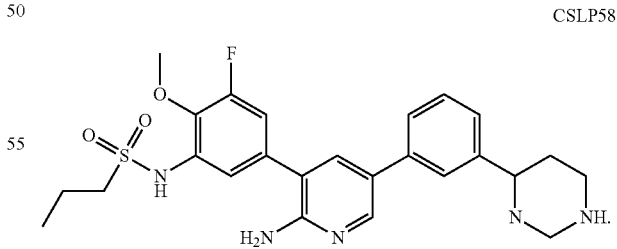

CSLP58

4. A pharmaceutical composition comprising a therapeutically effective amount of the compound of claim 3 and a pharmaceutically acceptable excipient, adjuvant, carrier, buffer, stabilizer, or mixture thereof.

5. A compound demonstrating NOD2 cellular signaling inhibitory activity and having a structure of:

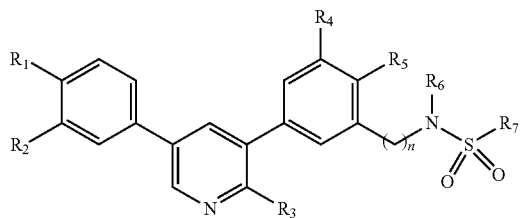

wherein R₁ is H,

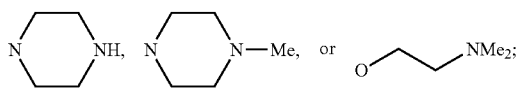

R₂ is H, SO₂Me, SO₂i-Pr, SO₂CF₃, or

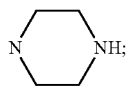

R₃ is H, Cl, Me, NH₂, NHMe, NHSO₂Me₃, or NMe₂;
R₄ is H, F, Cl, OMe, OEt, O-n-Pr, O-i-Pr, OPh, or OCF₃;
R₅ is H, Me, Et, Pr, i-Pr, OMe, OEt, O-n-Pr, O-i-Pr, OCF₃, Cl, or F;
R₆ is H, Me, or Et;
R₇ is Me, Et, n-Pr, i-Pr, CF₃, CF₂Et, CH₂Ph, or Ph;
n is 0 or 1; and
wherein Me is methyl, Et is ethyl, i-Pr is isopropyl, and Ph is phenyl.

6. A pharmaceutical composition comprising a therapeutically effective amount of the compound of claim 5 and a pharmaceutically acceptable excipient, adjuvant, carrier, buffer, stabilizer, or mixture thereof.

7. The compound demonstrating NOD2 cellular signaling inhibitory activity of claim 5 wherein the compound has a structure of:

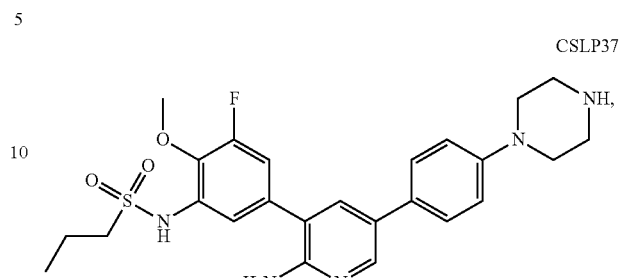

CSLP37

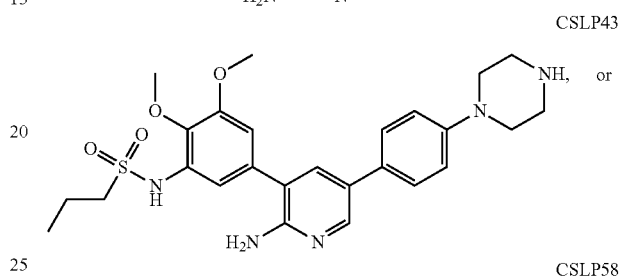

CSLP43

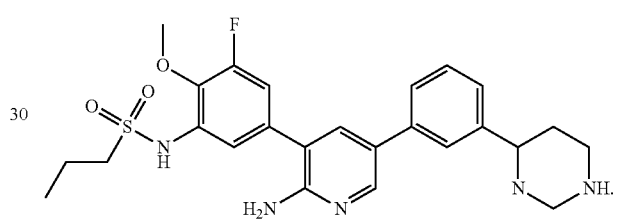

CSLP58

8. A pharmaceutical composition comprising a therapeutically effective amount of the compound of claim 7 and a pharmaceutically acceptable excipient, adjuvant, carrier, buffer, stabilizer, or mixture thereof.

* * * * *

UNITED STATES PATENT AND TRADEMARK OFFICE
CERTIFICATE OF CORRECTION

PATENT NO. : 11,135,209 B2
APPLICATION NO. : 16/496503
DATED : October 5, 2021
INVENTOR(S) : Gregory Cuny et al.

It is certified that error appears in the above-identified patent and that said Letters Patent is hereby corrected as shown below:

In the Specification

1. In Column 6, Line 57, delete "(6)" and insert -- ($\delta$) --, therefor.

2. In Column 17, Line 39, delete "41 NMR" and insert -- $^1$H NMR --, therefor.

3. In Column 21, Line 14, delete "4.26-4-.24" and insert -- 4.26-4.24 --, therefor.

4. In Column 30, Line 38, delete "41 NMR" and insert -- $^1$H NMR --, therefor.

5. In Column 45, Line 10, delete "41 NMR" and insert -- $^1$H NMR --, therefor.

6. In Column 45, Line 44, delete "[M+H[$^+$" and insert -- [M+H]$^+$ --, therefor.

7. In Column 48, Line 14, delete "41 NMR" and insert -- $^1$H NMR --, therefor.

8. In Column 48, Line 30, delete "41 NMR" and insert -- $^1$H NMR --, therefor.

9. In Column 48, Line 47, delete "41 NMR" and insert -- $^1$H NMR --, therefor.

10. In Column 48, Line 62, delete "41 NMR" and insert -- $^1$H NMR --, therefor.

11. In Column 49, Line 1, delete "[M+H[$^+$" and insert -- [M+H]$^+$ --, therefor.

12. In Column 49, Line 11, delete "41 NMR" and insert -- $^1$H NMR --, therefor.

13. In Column 49, Line 28, delete "41 NMR" and insert -- $^1$H NMR --, therefor.

14. In Column 52, Line 20, delete "100 pt" and insert -- 100 µL --, therefor.

Signed and Sealed this
Fourteenth Day of June, 2022

Katherine Kelly Vidal
*Director of the United States Patent and Trademark Office*

CERTIFICATE OF CORRECTION (continued)
U.S. Pat. No. 11,135,209 B2

In the Claims

15. In Column 56, Structure "CSLP58", in Claim 7, delete

" 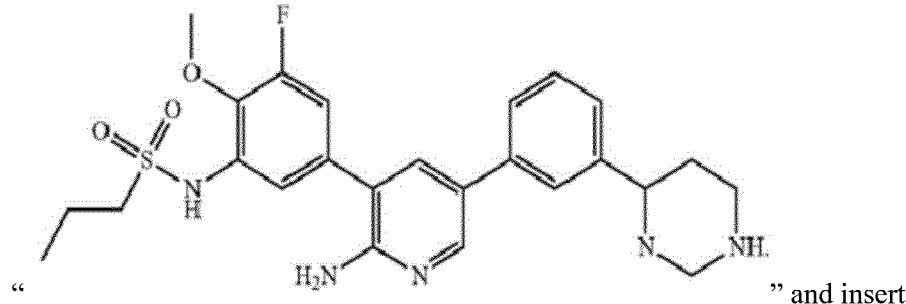 " and insert

-- 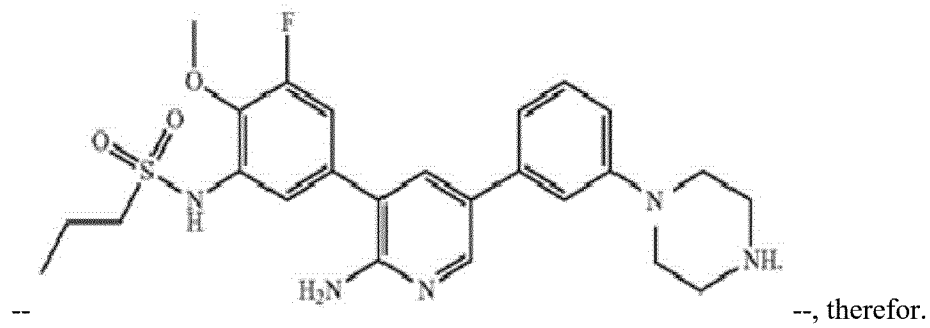 --, therefor.